United States Patent
Hagmann et al.

(10) Patent No.: US 9,527,875 B2
(45) Date of Patent: Dec. 27, 2016

(54) ANTIDIABETIC TRICYCLIC COMPOUNDS

(71) Applicant: Merck Sharp & Dohme Corp., Rahway, NJ (US)

(72) Inventors: William K. Hagmann, Westfield, NJ (US); Ravi P. Nargund, East Brunswick, NJ (US); Timothy A. Blizzard, Princeton, NJ (US); Hubert Josien, Jersey City, NJ (US); Purakkattle Biju, Piscataway, NJ (US); Christopher W. Plummer, Hoboken, NJ (US); Qun Dang, Westfield, NJ (US); Bing Li, Towaco, NJ (US); Derun Li, Scotch Plains, NJ (US); Linus S. Lin, Shanghai (CN); Mingxiang Cui, Shanghai (CN); Bin Hu, Shanghai (CN); Jinglai Hao, Shanghai (CN); Zhengxia Chen, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/418,147

(22) PCT Filed: Jul. 31, 2013

(86) PCT No.: PCT/US2013/052961
§ 371 (c)(1),
(2) Date: Jan. 29, 2015

(87) PCT Pub. No.: WO2014/022528
PCT Pub. Date: Feb. 6, 2014

(65) Prior Publication Data
US 2015/0191495 A1    Jul. 9, 2015

Related U.S. Application Data

(63) Continuation of application No. PCT/CN2012/079558, filed on Aug. 2, 2012.
(Continued)

(30) Foreign Application Priority Data

Aug. 2, 2012    (WO) ................ PCT/CN2012/079558

(51) Int. Cl.
C07D 417/12    (2006.01)
A61K 31/4353   (2006.01)
(Continued)

(52) U.S. Cl.
CPC ............ *C07F 9/582* (2013.01); *A61K 31/435* (2013.01); *A61K 31/444* (2013.01); *A61K 31/4412* (2013.01); *A61K 31/4427* (2013.01); *A61K 31/4433* (2013.01); *A61K 31/4439* (2013.01); *A61K 31/496* (2013.01); *A61K 31/506* (2013.01); *A61K 31/513* (2013.01);
*A61K 31/5377* (2013.01); *A61K 31/675* (2013.01); *A61K 45/06* (2013.01); *C07D 221/16* (2013.01); *C07D 401/12* (2013.01); *C07D 401/14* (2013.01);
(Continued)

(58) Field of Classification Search
CPC ... C07D 401/14; C07D 401/12; C07D 417/12; C07D 409/14; C07D 221/16
USPC ..................................... 546/79; 514/80, 290
See application file for complete search history.

(56) References Cited

U.S. PATENT DOCUMENTS 6,312,662 B1    11/2001  Erion et al.
6,489,476 B1    12/2002  Dang et al.
(Continued)

FOREIGN PATENT DOCUMENTS

CN    10106991 A    1/2014
EP    0126030 A2    11/1984
(Continued)

OTHER PUBLICATIONS

Medicinal Chemistry, Synopsis of some Recent Tactical Application of Bioisosteres in Drug Design by Nicholas Meanwell 2011.*
(Continued)

*Primary Examiner* — Rita Desai
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

(I)

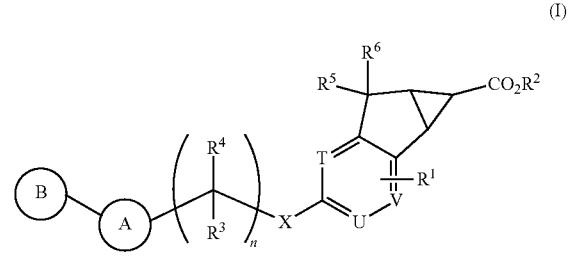

13 Claims, No Drawings

Related U.S. Application Data

(60) Provisional application No. 61/696,572, filed on Sep. 4, 2012.

(51) Int. Cl.

| | | |
|---|---|---|
| *C07F 9/58* | (2006.01) | |
| *C07D 401/14* | (2006.01) | |
| *C07D 221/16* | (2006.01) | |
| *C07D 401/12* | (2006.01) | |
| *A61K 31/435* | (2006.01) | |
| *A61K 31/444* | (2006.01) | |
| *A61K 45/06* | (2006.01) | |
| *A61K 31/4412* | (2006.01) | |
| *A61K 31/4427* | (2006.01) | |
| *A61K 31/4433* | (2006.01) | |
| *A61K 31/4439* | (2006.01) | |
| *A61K 31/496* | (2006.01) | |
| *A61K 31/506* | (2006.01) | |
| *A61K 31/513* | (2006.01) | |
| *A61K 31/5377* | (2006.01) | |
| *A61K 31/675* | (2006.01) | |
| *C07D 405/12* | (2006.01) | |
| *C07D 409/14* | (2006.01) | |

(52) U.S. Cl.
CPC ........... *C07D 405/12* (2013.01); *C07D 409/14* (2013.01); *C07D 417/12* (2013.01)

(56) References Cited

U.S. PATENT DOCUMENTS

| 2005/0148643 | A1 | 7/2005 | Rui et al. |
| 2007/0265332 | A1 | 11/2007 | Ge et al. |
| 2014/0045746 | A1 | 2/2014 | Hagmann et al. |

FOREIGN PATENT DOCUMENTS

| EP | 126030 A3 | 11/1984 |
| EP | 0128862 B1 | 12/1984 |
| EP | 0129506 B1 | 12/1984 |
| WO | WO9307124 A1 | 4/1993 |
| WO | WO9529897 A1 | 11/1995 |
| WO | WO 9839343 A1 | 9/1998 |
| WO | WO9839343 A1 | 9/1998 |
| WO | WO0003997 A1 | 1/2000 |
| WO | WO0014095 A1 | 3/2000 |
| WO | WO0153272 A1 | 7/2001 |
| WO | WO0153291 A1 | 7/2001 |
| WO | WO0240019 A1 | 5/2002 |
| WO | WO02092575 A1 | 11/2002 |
| WO | WO03018061 A1 | 3/2003 |
| WO | WO2004022551 A1 | 3/2004 |
| WO | WO2004041266 A1 | 5/2004 |
| WO | WO2005002520 A2 | 1/2005 |
| WO | WO2005002520 A3 | 1/2005 |
| WO | WO2005018672 A1 | 3/2005 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005086661 A3 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006094209 A2 | 9/2006 |
| WO | WO2006094209 A3 | 9/2006 |
| WO | WO2006127503 A2 | 11/2006 |
| WO | WO2006127503 A3 | 11/2006 |
| WO | WO2007013689 A1 | 2/2007 |
| WO | WO2007033002 A1 | 3/2007 |
| WO | WO2007106469 A2 | 9/2007 |
| WO | WO2007106469 A3 | 9/2007 |
| WO | WO2007123225 A1 | 11/2007 |
| WO | WO2007136572 A2 | 11/2007 |
| WO | WO2007136572 A3 | 11/2007 |
| WO | WO2007136573 A2 | 11/2007 |
| WO | WO2008001931 A2 | 1/2008 |
| WO | WO2008001931 A3 | 1/2008 |
| WO | WO2008030618 A1 | 3/2008 |
| WO | WO2008054674 A2 | 5/2008 |
| WO | WO2008054674 A3 | 5/2008 |
| WO | WO2008054675 A2 | 5/2008 |
| WO | WO2008054675 A3 | 5/2008 |
| WO | WO2008066097 A1 | 6/2008 |
| WO | WO2008130514 A1 | 10/2008 |
| WO | WO2009048527 A1 | 4/2009 |
| WO | WO2009005837 A1 | 5/2009 |
| WO | WO2009111056 A1 | 9/2009 |
| WO | WO2010036613 A1 | 4/2010 |
| WO | WO2010045258 A2 | 4/2010 |
| WO | WO2010045258 A3 | 4/2010 |
| WO | WO2010047982 A1 | 4/2010 |
| WO | WO2010051176 A1 | 5/2010 |
| WO | WO2010051206 A1 | 5/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2014019186 A1 | 2/2014 |
| WO | WO2014022528 A1 | 2/2014 |

OTHER PUBLICATIONS

Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.

Itoh, Y. et al., Free fatty acids regulate insulin secretion from pancreatic B cells through GPR40, Nature, 2003, 173-176, 422.

Kotarsky, K. et al., A human cell surface receptor activated by free fatty acids and thiazolidinedione drugs, Biochemical and Biophysical Research Communications, 2003, 406-410, 301.

PCT, International Search Report, PCT, May 2, 2013, p. 1-3, PCT/CN2012/079558.

PCT, PCT International Search Report, Patent Cooperation Treaty, Nov. 6, 2013, p. 1-3, PCT/US2013/052961.

PCT, Written Opinion of the International Searching Authority, Patent Cooperation Treaty, Nov. 6, 2013, p. 1-6, PCT-US2013/052961.

PCT, Written Opinion of the International Searching Authority, PCT, May 2, 2013, p. 1-6, PCT/CN2012/079558.

Chunyan, O., A Summary of Bioisostere and its Application in the Design of New Drugs, Journal of Zhanjiang Ocean University, 2004, p. 82-86, vol. 24, No. 4.

\* cited by examiner

ANTIDIABETIC TRICYCLIC COMPOUNDS

CROSS-REFERENCE TO RELATED APPLICATIONS

This application is a U.S. National Phase application under 35 U.S.C. §371 of PCT Application No. PCT/US2013/052961, filed on Jul. 31, 2013, which claims priority from and the benefit of PCT Application PCT/CN2012/079558, filed Aug. 2, 2012, and U.S. Provisional Application No. 61/696,572, filed Sep. 4, 2012.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic.

Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin, alogliptin, vildagliptin, linagliptin, denagliptin, and saxagliptin).

The biguanides are a class of drugs that are widely used to treat Type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of Type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of Type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) have been made and tested, but so far none have been approved by the regulatory authorities. The currently marketed PPAR gamma agonists are modestly effective in reducing plasma glucose and HemoglobinA1C. The currently marketed compounds do not greatly improve lipid metabolism and may actually have a negative effect on the lipid profile. Selective PPAR Gamma Partial Agonists (SPPARM's) are currently being developed and may be equally effective, with fewer side effects, such as weight gain and edema. Thus, the PPAR compounds represent an important advance in diabetic therapy.

Another widely used drug treatment involves the administration of insulin secretagogues, such as the sulfonylureas (e.g. tolbutamide, glipizide, and glimepiride). These drugs increase the plasma level of insulin by stimulating the pancreatic Iβ cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in Iβ-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase IV (DPP-4) inhibitors (e.g., sitagliptin, vildagliptin, alogliptin, linagliptin, denagliptin, and saxagliptin) provide a new route for increasing insulin secretion in response to food consumption. DPP-4 is a cell surface protein with broad tissue distribution that has been implicated in a wide range of biological functions. DPP-4 is identical to the T-cell activation marker CD26 and can cleave a number of immunoregulatory, endocrine, and neurological peptides in vitro. It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Studies with DPP-4(−/−)-deficient mice and clinical trials with DPP-4 inhibitors indicate that DPP-4 inhibition increases the steady state concentrations of GLP-1 and GIP, resulting in improved glucose tolerance. Inactivation of these peptides by DPP-4 may also play a role in glucose homeostasis. DPP-4 inhibitors therefore have utility in the treatment of Type 2 diabetes and in the treatment and prevention of the numerous conditions that often accompany Type 2 diabetes, including Metabolic Syndrome, reactive hypoglycemia, and diabetic dyslipidemia. GLP-1 has other effects that help to lower blood glucose and contribute to glucose homeostasis. GLP-1 inhibits glucagon secretion from the liver. Glucagon is a hormone that increases blood glucose levels by stimulating glucose production from glycogen stores in the liver. GLP-1 also delays stomach emptying, which helps to spread glucose absorption out over time, and thus limit hyperglycemia. Also, studies in animals have shown that GLP-1 can increase the number of beta cells, either through promoting growth or by inhibiting apoptosis. Thus, potentiation of GLP-1 action by preventing its degradation offers several mechanisms to attenuate hyperglycemia associated with Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion.

There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489, 476; US 2005/0148643; DE 3 316 095; JP 6 298 731; EP 0 126 030; EP 0 128 862; EP 0 129 506; and EP 0 120 403.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/

091176, WO 2004/041266, EP 2004/1630152, WO 2004/
022551, WO 2005/051890, WO 2005/051373, EP 2004/
1698624, WO 2005/086661, WO 2007/213364, WO 2005/
063729, WO 2005/087710, WO 2006/127503, WO 2007/
1013689, WO 2006/038738, WO 2007/033002, WO 2007/
106469, WO 2007/123225, WO 2008/001931, WO 2008/
030618, WO 2008/054674, WO 2008/054675, WO 2008/
066097, WO 2008/130514, WO 2009/048527, WO 2009/
111056, WO 2010/045258, WO 2010/085522, WO 2010/
085525, WO 2010/085528, WO 2010/091176, WO 2010/
143733 and WO 2012/0004187.

SUMMARY OF THE INVENTION

The present invention relates to novel substituted compounds of structural formula I:

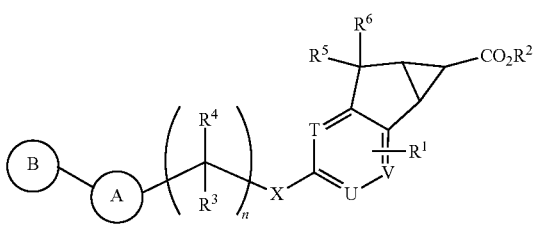

and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

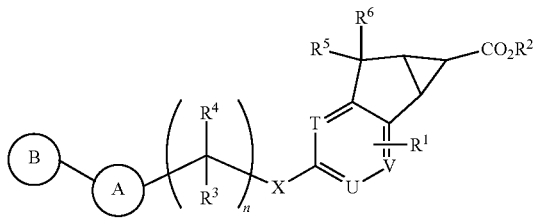

or a pharmaceutically acceptable salt thereof; wherein
X is selected from the group consisting of:
 (1) oxygen, and
 (2) NH;
T is selected from the group consisting of: CH, N and N-oxide;
U is selected from the group consisting of: CH, N and N-oxide;
V is selected from the group consisting of: CH, N and N-oxide;
provided that one or two of T, U and V is N or N-oxide;
A is selected from the group consisting of:
 (1) aryl, and
 (2) heteroaryl,
wherein A is unsubstituted or substituted with one to five substituents selected from $R^a$;
B is selected from the group consisting of:
 (1) aryl,
 (2) aryl-O—,
 (3) $C_{3-6}$cycloalkyl-,
 (4) $C_{3-6}$cycloalkyl-$C_{1-10}$alkyl-,
 (5) $C_{3-6}$cycloalkyl-$C_{1-10}$alkyl-O—,
 (6) $C_{2-5}$ cycloheteroalkyl-,
 (7) heteroaryl,
 (8) heteroaryl-O—,
 (9) aryl-$C_{1-10}$ alkyl-, and
 (10) heteroaryl-$C_{1-10}$ alkyl-;
wherein B is unsubstituted or substituted with one to five substituents selected from $R^b$;
$R^1$ is selected from the group consisting of:
 (1) halogen,
 (2) —$OR^e$,
 (3) —CN,
 (4) —$C_{1-6}$alkyl, and
 (5) —$C_{3-6}$ cycloalkyl,
wherein each —$C_{1-6}$alkyl and —$C_{3-6}$cycloalkyl is unsubstituted or substituted with one to three substituents selected from $R^i$;
$R^2$ is selected from the group consisting of:
 (1) hydrogen,
 (2) —$C_{1-6}$alkyl, and
 (3) —$C_{3-6}$ cycloalkyl,
wherein each —$C_{1-6}$alkyl and —$C_{3-6}$cycloalkyl is unsubstituted or substituted with one to three substituents selected from $R^j$;
$R^3$ is selected from the group consisting of:
 (1) hydrogen,
 (2) halogen,
 (3) —$OR^e$,
 (4) —$C_{1-6}$alkyl,
 (5) —$C_{2-6}$alkenyl,
 (6) —$C_{2-6}$alkynyl, and
 (7) —$C_{3-6}$cycloalkyl, wherein each $C_{1-6}$alkyl, $C_{2-6}$alkenyl, $C_{2-6}$alkynyl, and $C_{3-6}$cycloalkyl is unsubstituted or substituted with one to three substituents selected from $R^L$;

$R^4$ is selected from the group consisting of:
(1) hydrogen,
(2) halogen,
(3) —$OR^e$,
(4) —$C_{1-6}$alkyl,
(5) —$C_{2-6}$alkenyl,
(6) —$C_{2-6}$alkynyl, and
(7) —$C_{3-6}$cycloalkyl, wherein each —$C_{1-6}$alkyl, —$C_{2-6}$alkenyl, —$C_{2-6}$alkynyl, and —$C_{3-6}$cycloalkyl is unsubstituted or substituted with one to three substituents selected from $R^L$;

$R^5$ is selected from the group consisting of:
(1) hydrogen,
(2) —$C_{1-3}$alkyl, and
(3) halogen;

$R^6$ is selected from the group consisting of:
(1) hydrogen,
(2) —$C_{1-3}$alkyl, and
(3) halogen, or $R^5$ and $R^6$ can together form oxo;

$R^a$ is selected from the group consisting of:
(1) —$C_{1-6}$alkyl,
(2) halogen,
(3) —$OR^e$,
(4) —$NR^cS(O)_mR^e$,
(5) —$S(O)_mR^e$,
(6) —$S(O)_mNR^cR^d$,
(7) —$NR^cR^d$,
(8) —$C(O)R^e$,
(9) —$OC(O)R^e$,
(10) —$CO_2R^e$,
(11) —CN,
(12) —$C(O)NR^cR^d$,
(13) —$NR^cC(O)R^e$,
(14) —$NR^cC(O)OR^e$,
(15) —$NR^cC(O)NR^cR^d$,
(16) —$CF_3$,
(17) —$OCF_3$,
(18) —$OCHF_2$,
(19) —$C_{3-6}$cycloalkyl, and
(20) —$C_{2-5}$cycloheteroalkyl;

$R^b$ is independently selected from the group consisting of:
(1) —$C_{1-10}$alkyl,
(2) —$C_{2-10}$ alkenyl,
(3) halogen,
(4) —OH,
(5) —$OC_{1-10}$alkyl,
(6) —$OC_{2-10}$ alkenyl,
(7) —$O(CH_2)pOC_{1-10}$alkyl,
(8) —$O(CH_2)pC_{3-6}$cycloalkyl,
(9) —$O(CH_2)pC_{3-6}$cycloalkyl-$C_{1-10}$ alkyl-,
(10) —$O(CH_2)pC_{2-10}$cycloheteroalkyl,
(11) —$O(CH_2)pC_{2-5}$cycloheteroalkyl-$C_{1-10}$ alkyl-,
(12) —O-aryl,
(13) —O-heteroaryl,
(14) —O-aryl-$C_{1-10}$ alkyl-,
(15) —O-heteroaryl-$C_{1-10}$ alkyl-,
(16) —$NR^cS(O)_mR^e$,
(17) —$S(O)_mR^e$,
(18) —$S(O)_mNR^cR^d$,
(19) —$NR^cR^d$,
(20) —$C(O)R^e$,
(21) —$OC(O)R^e$,
(22) —$CO_2R^e$,
(23) —CN,
(24) —$C(O)NR^cR^d$,
(25) —$NR^cC(O)R^e$,
(26) —$NR^cC(O)OR^e$,
(27) —$NR^cC(O)NR^cR^d$,
(28) —$O(CH_2)pO$—$C_{3-6}$cycloalkyl,
(29) —$O(CH_2)pO$—$C_{2-10}$cycloheteroalkyl,
(30) —$CF_3$,
(31) —$OCF_3$,
(32) —$OCHF_2$,
(33) —$(CH_2)p$-$C_{3-6}$cycloalkyl,
(34) —$(CH_2)p$-$C_{2-10}$cycloheteroalkyl,
(35) aryl,
(36) heteroaryl,
(37) aryl-$C_{1-10}$ alkyl-, and
(38) heteroaryl-$C_{1-10}$ alkyl-, wherein each $R^b$ is unsubstituted or substituted with one to five substituents selected from $R^k$; $R^c$ and $R^d$ are each independently selected from the group consisting of:
(1) hydrogen,
(2) $C_{1-10}$alkyl,
(3) $C_{2-10}$alkenyl,
(4) $C_{3-6}$cycloalkyl,
(5) $C_{3-6}$ cycloalkyl-$C_{1-10}$alkyl-,
(6) cycloheteroalkyl,
(7) cycloheteroalkyl-$C_{1-10}$alkyl-,
(8) aryl,
(9) heteroaryl,
(10) aryl-$C_{1-10}$alkyl-, and
(11) heteroaryl-$C_{1-10}$alkyl-, or $R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$;

each $R^e$ is independently selected from the group consisting of:
(1) hydrogen,
(2) —$C_{1-10}$alkyl,
(3) —$C_{2-10}$ alkenyl,
(4) —$C_{3-6}$ cycloalkyl,
(5) —$C_{3-6}$ cycloalkyl-$C_{1-10}$alkyl-,
(6) —$C_{2-5}$cycloheteroalkyl,
(7) —$C_{2-5}$cycloheteroalkyl-$C_{1-10}$alkyl-,
(8) aryl,
(9) heteroaryl,
(10) aryl-$C_{1-10}$alkyl-, and
(11) hetero aryl-$C_{1-10}$alkyl-, wherein each $R^e$ is unsubstituted or substituted with one to three substituents selected from $R^h$;

each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$, wherein each $C_{1-10}$alkyl is unsubstituted or substituted with one to three substituents independently selected from: —OH, halogen, cyano, and —$S(O)_2CH_3$;

each $R^g$ is selected from the group consisting of:
(1) hydrogen,
(2) —C(O)$R^e$, and
(3) —C$_{1-10}$alkyl,
wherein —C$_{1-10}$alkyl is unsubstituted or substituted with one to five fluorines;
each $R^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each C$_{1-10}$ alkyl is unsubstituted or substituted with one to three substituents independently selected from: —OH, halogen, cyano, and —S(O)$_2$CH$_3$;
$R^i$ is independently selected from the group consisting of:
(1) —C$_{1-6}$alkyl,
(2) —O$R^e$,
(3) —N$R^c$S(O)$_m R^e$,
(4) halogen,
(5) —S(O)$_m R^e$,
(6) —S(O)$_m$N$R^c R^d$,
(7) —N$R^c R^d$,
(8) —C(O)$R^e$,
(9) —OC(O)$R^e$,
(10) —CO$_2 R^e$,
(11) —CN,
(12) —C(O)N$R^c R^d$,
(13) —N$R^c$C(O)$R^e$,
(14) —N$R^c$C(O)O$R^e$,
(15) —N$R^c$C(O)N$R^c R^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
$R^j$ is independently selected from the group consisting of:
(1) —C$_{1-6}$alkyl,
(2) —O$R^e$,
(3) —N$R^c$S(O)$_m R^e$,
(4) halogen,
(5) —S(O)$_m R^e$,
(6) —S(O)$_m$N$R^c R^d$,
(7) —N$R^c R^d$,
(8) —C(O)$R^e$,
(9) —OC(O)$R^e$,
(10) —CO$_2 R^e$,
(11) —CN,
(12) —C(O)N$R^c R^d$,
(13) —N$R^c$C(O)$R^e$,
(14) —N$R^c$C(O)O$R^e$,
(15) —N$R^c$C(O)N$R^c R^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each $R^k$ is independently selected from the group consisting of:
(1) halogen,
(2) —C$_{1-10}$ alkyl,
(3) —OH,
(4) oxo,
(5) halogen,
(6) —O—C$_{1-4}$ alkyl,
(7) —SO$_2$—C$_{1-6}$ alkyl,
(8) —C$_{1-6}$ alkyl-SO$_2$C$_{1-6}$ alkyl,
(9) —CN,
(10) —CF$_3$,
(11) —OCHF$_2$,
(12) —OCF$_3$,
(13) —NH$_2$,
(14) —NHSO$_2$C$_{1-6}$ alkyl,
(15) —NHCOC$_{1-6}$ alkyl,
(16) =N(OCH$_3$),
(17) —P(O)(OH)$_2$, and
(18) —P(O)(OC$_{1-6}$ alkyl)$_2$,
wherein each C$_{1-10}$alkyl is unsubstituted or substituted with one to three substituents independently selected from: —OH, —OC$_{1-6}$ alkyl, halogen, cyano, and —S(O)$_2$C$_{1-6}$alkyl;
$R^L$ is selected from the group consisting of:
(1) —C$_{1-6}$alkyl,
(2) halogen,
(3) —O$R^e$,
(4) —N$R^c$S(O)$_m R^e$,
(5) —S(O)$_m R^e$,
(6) —S(O)$_m$N$R^c R^d$,
(7) —N$R^c R^d$,
(8) —C(O)$R^e$,
(9) —OC(O)$R^e$,
(10) —CO$_2 R^e$,
(11) —CN,
(12) —C(O)N$R^c R^d$,
(13) —N$R^c$C(O)$R^e$,
(14) —N$R^c$C(O)O$R^e$,
(15) —N$R^c$C(O)N$R^c R^d$,
(16) —CF$_3$,
(17) —OCF$_3$,
(18) —OCHF$_2$,
(19) —C$_{3-6}$cycloalkyl, and
(20) —C$_{2-5}$cycloheteroalkyl;
each n is independently 0, 1, 2, 3 or 4;
each m is independently 0, 1 or 2; and
each p is independently selected from: 0, 1, 2, 3, 4, 5, 6, 7, 8, 9 or 10.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, X is selected from the group consisting of: oxygen, and —NH. In a class of this embodiment, X is oxygen. In another class of this embodiment, X is NH.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N.

In another embodiment of the present invention, U is selected from the group consisting of: CH, N and N-oxide. In a class of this embodiment, U is selected from the group consisting of: CH and N. In another class of this embodiment, U is CH. In another class of this embodiment, U is N or N-oxide. In another class of this embodiment, U is N.

In another embodiment of the present invention, V is selected from the group consisting of: CH, N and N-oxide. In a class of this embodiment, V is selected from the group consisting of: CH and N. In another class of this embodiment, V is CH. In another class of this embodiment, V is N or N-oxide. In another class of this embodiment, V is N.

In another embodiment of the present invention, T is CH, U is CH, and V is N or N-oxide. In a class of this embodiment, T is CH, U is CH, and V is N.

In another embodiment of the present invention, T is CH, U is N or N-oxide, and V is CH. In a class of this embodiment, T is CH, U is N, and V is CH.

In another embodiment of the present invention, T is N or N-oxide, U is CH, and V is CH. In a class of this embodiment, T is N, U is CH, and V is CH.

In another embodiment of the present invention, T is CH, U is N or N-oxide, and V is N or N-oxide. In a class of this embodiment, T is CH, U is N, and V is N.

In another embodiment of the present invention, T is N or N-oxide, U is CH, and V is N or N-oxide. In a class of this embodiment, T is N, U is CH, and V is N.

In another embodiment of the present invention, T is N or N-oxide, U is N or N-oxide, and V is CH. In a class of this embodiment, T is N, U is N, and V is CH.

In another embodiment of the present invention, A is selected from the group consisting of: aryl and heteroaryl, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, A is selected from the group consisting of: phenyl and pyridine, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, A is aryl, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, A is phenyl, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, A is heteroaryl, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, A is pyridine, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$.

In another embodiment of the present invention, B is selected from the group consisting of: aryl, aryl-O—, $C_{3-6}$cycloalkyl-, $C_{3-6}$cycloalkyl-$C_{1-10}$alkyl-, $C_{3-6}$cycloalkyl-$C_{1-10}$alkyl-O—, $C_{2-5}$cycloheteroalkyl-, heteroaryl, heteroaryl-O—, aryl-$C_{1-10}$ alkyl-, and heteroaryl-$C_{1-10}$ alkyl-, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is selected from the group consisting of: aryl, and heteroaryl, wherein B is unsubstituted or substituted with one to five substituents selected from $R^b$. In a class of this embodiment, B is selected from the group consisting of phenyl, pyridine, pyrimidine, thiazole, benzimidazole, benzthiazole, benzoxazole, and benzisoxazole, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is selected from the group consisting of: aryl, and heteroaryl, wherein B is unsubstituted or substituted with one to five substituents selected from $R^b$. In a class of this embodiment, B is selected from the group consisting of phenyl, pyridine, pyrimidine, thiazole and benzimidazole, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is aryl, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is phenyl, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is heteroaryl, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is selected from the group consisting of: pyridine, pyrimidine, thiazole, benzimidazole, benzthiazole, benzoxazole, and benzisoxazole, wherein B is unsubstituted or substituted with one to five substituents selected from $R^b$. In another embodiment of the present invention, B is selected from the group consisting of: pyridine, pyrimidine, thiazole, and benzimidazole, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, B is pyridine or benzimidazole, wherein B is unsubstituted or substituted with one to five substituents selected from $R^b$. In a class of this embodiment, B is unsubstituted or substituted with one to four substituents selected from $R^b$. In another class of this embodiment, B is unsubstituted or substituted with one to three substituents selected from $R^b$. In another class of this embodiment, B is unsubstituted or substituted with one to two substituents selected from $R^b$.

In another embodiment of the present invention, $R^1$ is selected from the group consisting of: halogen, —$OR^e$, —CN, —$C_{1-6}$alkyl, and $C_{3-6}$cycloalkyl, wherein each $C_{1-6}$alkyl and $C_{3-6}$cycloakyl is unsubstituted or substituted with one to three substituents selected from $R^i$. In a class of embodiment, $R^1$ is selected from the group consisting of: halogen, —$OR^e$, —CN, and —$C_{1-6}$alkyl, wherein each $C_{1-6}$alkyl is unsubstituted or substituted with one to three substituents selected from $R^i$. In another class of this embodiment, $R^1$ is selected from the group consisting of: halogen, —CN, and —$C_{1-6}$alkyl, wherein each $C_{1-6}$alkyl is unsubstituted or substituted with one to three substituents selected from $R^i$. In another class of this embodiment, $R^1$ is —$C_{1-6}$alkyl, wherein each $C_{1-6}$alkyl is unsubstituted or substituted with one to three substituents selected from $R'$.

In another embodiment of the present invention, $R^2$ is selected from the group consisting of: hydrogen, —$C_{1-6}$alkyl, and $C_{3-6}$cycloalkyl, wherein each $C_{1-6}$alkyl and $C_{3-6}$cycloalkyl is unsubstituted or substituted with one to three substituents selected from R. In a class of this embodiment, $R^2$ is selected from the group consisting of: hydrogen, and —$C_{1-6}$alkyl, wherein each $C_{1-6}$alkyl is unsubstituted or substituted with one to three substituents selected from R. In another class of this embodiment, $R^2$ is —$C_{1-6}$alkyl, wherein each $C_{1-6}$alkyl is unsubstituted or substituted with one to three substituents selected from R. In another class of this embodiment, $R^2$ is hydrogen.

In another embodiment of the present invention, $R^3$ is selected from the group consisting of: hydrogen, halogen, —$OR^e$, —$C_{1-6}$alkyl, —$C_{2-6}$alkenyl, —$C_{2-6}$alkynyl, and —$C_{3-6}$cycloalkyl, wherein each —$C_{1-6}$alkyl, —$C_{2-6}$alkenyl, —$C_{2-6}$alkynyl, and —$C_{3-6}$cycloalkyl is unsubstituted or substituted with one to three substituents selected from $R^L$. In a class of this embodiment, $R^3$ is selected from the group consisting of: hydrogen, halogen, —$OR^e$, —$C_{2-6}$alkenyl, and —$C_{2-6}$alkynyl, wherein each —$C_{1-6}$alkyl, —$C_{2-6}$alkenyl, and —$C_{2-6}$alkynyl is unsubstituted or substituted with one to three substituents selected from $R^L$. In another class of this embodiment, $R^3$ is selected from the group consisting of: hydrogen, halogen, and —$C_{1-6}$alkyl, wherein each $C_{1-6}$alkyl is unsubstituted or substituted with one to three substituents selected from $R^L$. In another embodiment of the present invention, $R^3$ is selected from the group consisting of: hydrogen, halogen, and —$C_{1-6}$alkyl, wherein each $C_{1-6}$alkyl is unsubstituted or substituted with one to three substituents selected from $R^L$. In a subclass of this class, $R^3$ is selected from the group consisting of: hydrogen, F and —$CH_3$. In another embodiment of the present invention, $R^3$ is hydrogen.

In another embodiment of the present invention, $R^4$ is selected from the group consisting of: hydrogen, halogen, —$OR^e$, —$C_{1-6}$alkyl, —$C_{2-6}$alkenyl, —$C_{2-6}$alkynyl, and —$C_{3-6}$cycloalkyl, wherein each —$C_{1-6}$alkyl, —$C_{2-6}$alkenyl, —$C_{2-6}$alkynyl, and —$C_{3-6}$cycloalkyl is unsubstituted or substituted with one to three substituents selected from $R^L$. In a class of this embodiment, $R^4$ is selected from the group consisting of: hydrogen, halogen, —$OR^e$, —$C_{2-6}$alkenyl, and —$C_{2-6}$alkynyl, wherein each —$C_{1-6}$alkyl, —$C_{2-6}$alkenyl, and —$C_{2-6}$alkynyl is unsubstituted or substituted with one to three substituents selected from $R^L$. In another class of this embodiment, $R^4$ is selected from the group consisting of: hydrogen, halogen, and —$C_{1-6}$alkyl, wherein each $C_{1-6}$alkyl is unsubstituted or substituted with one to three substituents selected from $R^L$. In another embodiment of the present invention, $R^4$ is selected from the group consisting of: hydrogen, halogen, and —$C_{1-6}$alkyl, wherein each $C_{1-6}$alkyl is unsubstituted or substituted with one to three substituents selected from $R^L$. In a subclass of this class, $R^4$ is selected from the group consisting of: hydrogen, F and —$CH_3$. In another embodiment of the present invention, $R^4$ is hydrogen.

In another embodiment of the present invention, $R^5$ is selected from the group consisting of: hydrogen, —$C_{1-3}$alkyl, and halogen. In a class of this embodiment, $R^5$ is selected from the group consisting of: hydrogen, —$C_{1-3}$ alkyl, and halogen. In another class of this embodiment, $R^5$ is selected from the group consisting of: hydrogen, and —$C_{1-3}$alkyl. In another class of this embodiment, $R^5$ is —$C_{1-3}$alkyl. In another class of this embodiment, $R^5$ is hydrogen.

In another embodiment of the present invention, $R^6$ is selected from the group consisting of: hydrogen, —$C_{1-3}$ alkyl, and halogen, or $R^5$ and $R^6$ can together form oxo. In a class of this embodiment, $R^6$ is selected from the group consisting of: hydrogen, —$C_{1-3}$alkyl, and halogen. In another class of this embodiment, $R^6$ is selected from the group consisting of: hydrogen, and —$C_{1-3}$alkyl. In another class of this embodiment, $R^6$ is —$C_{1-3}$alkyl. In another class of this embodiment, $R^6$ is hydrogen.

In another embodiment of the present invention, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl, provided that when A is phenyl, then $R^a$ is not selected from: —$C_{1-6}$alkyl and halogen. In a class of this embodiment, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl, provided that when A is phenyl, then $R^a$ is not selected from: —$CH_3$ and F.

In another embodiment of the present invention, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl, provided that when A is phenyl and B is phenyl or imidazopyridine, then $R^a$ is not selected from: —$C_{1-6}$alkyl and halogen. In a class of this embodiment, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl, provided that when A is phenyl and B is phenyl or imidazopyridine, then $R^a$ is not selected from: —$CH_3$ and F.

In another embodiment of the present invention, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl. In a class of this embodiment, $R^a$ is selected from the group consisting of: —$C_{1-6}$alkyl, halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, and —$OCHF_2$. In another class of this embodiment, $R^a$ is selected from the group consisting of: —$C_{1-6}$alkyl, halogen, —$OR^e$, —$S(O)_mR^e$, —$NR^cR^d$, —CN, —$CF_3$, —$OCF_3$, and —$OCHF_2$. In another class of this embodiment, $R^a$ is selected from the group consisting of: —$C_{1-6}$alkyl, halogen, —CN, —$CF_3$, —$OCF_3$, and —$OCHF_2$. In another class of this embodiment, $R^a$ is selected from the group consisting of: —$C_{1-6}$alkyl, halogen, and —$CF_3$. In a subclass of this class, $R^a$ is selected from the group consisting of: —$CH_3$, F, and —$CF_3$. In another class of this embodiment, $R^a$ is selected from the group consisting of: —$C_{1-6}$alkyl and halogen. In a subclass of this class, $R^a$ is selected from the group consisting of: —$CH_3$, and F. In another class of this embodiment, $R^a$ is —$C_{1-6}$alkyl. In a subclass of this class, $R^a$ is —$CH_3$. In another class of this embodiment, $R^a$ is halogen. In a subclass of this class, $R^a$ is F.

In another embodiment of the present invention, $R^a$ is selected from the group consisting of: halogen, —$OR^e$, —$NR^cS(O)_mR^e$, —$S(O)_mR^e$, —$S(O)_mNR^cR^d$, —$NR^cR^d$, —$C(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl. In a class of this embodiment, $R^a$ is selected from the group consisting of: halogen, —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, and —$OCHF_2$. In another class of this embodiment, $R^a$ is selected from the group consisting of: —$OR^e$, —$S(O)_mR^e$, —$NR^cR^d$, —CN, —$CF_3$, —$OCF_3$, and —$OCHF_2$. In another class of this embodiment, $R^a$ is selected from the group consisting of: halogen, —CN, —$CF_3$, —$OCF_3$, and —$OCHF_2$. In another class of this embodiment, $R^a$ is selected from the group consisting of: halogen, and —$CF_3$. In a subclass of this class, $R^a$ is selected from the group consisting of: F, and —$CF_3$. In a subclass of this class, $R^a$ is —$CF_3$. In another class of this embodiment, $R^a$ is F.

In another embodiment of the present invention, $R^a$ is selected from the group consisting of: —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl. In a class of this embodiment, $R^a$ is selected from the group consisting of: —$OR^e$, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, and —$OCHF_2$. In another class of this embodiment, $R^a$ is selected from the group consisting of: —$OR^e$, —$S(O)_mR^e$, —$NR^cR^d$, —CN, —$CF_3$, —$OCF_3$, and —$OCHF_2$. In another class of this embodiment, $R^a$ is selected from the group consisting of: —CN, —$CF_3$, —$OCF_3$, and —$OCHF_2$. In another class of this embodiment, $R^a$ is —$CF_3$.

In another embodiment of the present invention, $R^b$ is independently selected from the group consisting of: —$C_{1-10}$alkyl, —$C_{2-10}$ alkenyl, halogen, —OH, —$OC_{1-10}$alkyl, —$OC_{2-10}$ alkenyl, —$O(CH_2)pOC_{1-10}$alkyl, —$O(CH_2)pC_{3-6}$cycloalkyl, —$O(CH_2)pC_{3-6}$cycloalkyl-$C_{1-10}$ alkyl-, —$O(CH_2)pC_{2-10}$cycloheteroalkyl, —$O(CH_2)pC_{2-5}$cycloheteroalkyl-$C_{1-10}$ alkyl-, —O-aryl, —O-heteroaryl, —O-aryl-$C_{1-10}$ alkyl-, —O-heteroaryl-$C_{1-10}$ alkyl-, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$O(CH_2)pO$—$C_{3-6}$cycloalkyl, —$O(CH_2)pO$—$C_{2-10}$ cycloheteroalkyl, —$CF_3$, —$OCF_3$, —$OCHF_2$, —$(CH_2)p$-$C_{3-6}$ cycloalkyl, —$(CH_2)pO$—$C_{2-10}$ cycloheteroalkyl, aryl, heteroaryl, aryl-$C_{1-10}$ alkyl-, and heteroaryl-$C_{1-10}$ alkyl-, wherein each $R^b$ is unsubstituted or substituted with one to five substituents selected from $R^k$, provided that when B is phenyl or imidazopyridine, then $R^b$ is not selected from: halogen, —$OC_{1-10}$alkyl, —$O(CH_2)pO$—$C_{2-10}$cycloheteroalkyl, and —$CF_3$. In a class of this embodiment, $R^b$ is independently selected from the group consisting of: —$C_{1-10}$alkyl, —$C_{2-10}$ alkenyl, halogen, —OH, —$OC_{1-10}$ alkyl, —$OC_{2-10}$ alkenyl, —$O(CH_2)pOC_{1-10}$alkyl, —$O(CH_2)pC_{3-6}$cycloalkyl, —$O(CH_2)pC_{3-6}$ cycloalkyl-$C_{1-10}$ alkyl-, —$O(CH_2)pC_{2-10}$cycloheteroalkyl, —$O(CH_2)pC_{2-5}$cycloheteroalkyl-$C_{1-10}$ alkyl-, —O-aryl, —O-heteroaryl, —O-aryl-$C_{1-10}$ alkyl-, —O-heteroaryl-$C_{1-10}$ alkyl-, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$O(CH_2)pO$—$C_{3-6}$cycloalkyl, —$O(CH_2)pO$—$C_{2-10}$cycloheteroalkyl, —$CF_3$, —$OCF_3$, —$OCHF_2$, —$(CH_2)p$-$C_{3-6}$cycloalkyl, —$(CH_2)p$-$C_{2-10}$ cycloheteroalkyl, aryl, heteroaryl, aryl-$C_{1-10}$ alkyl-, and heteroaryl-$C_{1-10}$ alkyl-, wherein each $R^b$ is unsubstituted or substituted with one to five substituents selected from $R^k$, provided that when B is phenyl or imidazopyridine, then $R^b$ is not selected from: F, Cl, —$OCH_3$, —$OCH_2$-oxetane, and —$CF_3$.

In another embodiment of the present invention, $R^b$ is independently selected from the group consisting of: —$C_{1-10}$alkyl, —$C_{2-10}$ alkenyl, halogen, —OH, —$OC_{1-10}$alkyl, —$OC_{2-10}$ alkenyl, —$O(CH_2)pOC_{1-10}$alkyl, —O(CH₂)pC₃₋₆ cycloalkyl, —O(CH₂)pC₃₋₆cycloalkyl-C₁₋₁₀ alkyl-, —O(CH₂)pC₂₋₁₀cycloheteroalkyl, —O(CH₂)pC₂₋₅cycloheteroalkyl-C₁₋₁₀ alkyl-, —O-aryl, —O-heteroaryl, —O-aryl-C₁₋₁₀ alkyl-, —O-heteroaryl-C₁₋₁₀ alkyl-, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO₂R$^e$, —CN, —C(O)NR$^c$R$^d$, —NR$^c$C(O)R$^e$, —NR$^c$C(O)OR$^e$, —NR$^c$C(O)NR$^c$R$^d$, —O(CH₂)pO—C₃₋₆cycloalkyl, —O(CH₂)pO—C₂₋₁₀ cycloheteroalkyl, —CF₃, —OCF₃, —OCHF₂, —(CH₂)p-C₃₋₆ cycloalkyl, —(CH₂)p-C₂₋₁₀ cycloheteroalkyl, aryl, heteroaryl, aryl-C₁₋₁₀ alkyl-, and heteroaryl-C₁₋₁₀alkyl-, wherein each R$^b$ is unsubstituted or substituted with one to five substituents selected from R$^k$, provided that when B is phenyl or imidazopyridine, then R$^b$ is not selected from halogen, and —OC₁₋₁₀alkyl. In a class of this embodiment, R$^b$ is independently selected from the group consisting of: —C₁₋₁₀alkyl, —C₂₋₁₀ alkenyl, halogen, —OH, —OC₁₋₁₀ alkyl, —OC₂₋₁₀ alkenyl, —O(CH₂)pOC₁₋₁₀alkyl, —O(CH₂)pC₃₋₆cycloalkyl, —O(CH₂)pC₃₋₆cycloalkyl-C₁₋₁₀ alkyl-, —O(CH₂)pC₂₋₁₀-cycloheteroalkyl, —O(CH₂)pC₂₋₅cycloheteroalkyl-C₁₋₁₀ alkyl-, —O-aryl, —O-heteroaryl, —O-aryl-C₁₋₁₀ alkyl-, —O-heteroaryl-C₁₋₁₀ alkyl-, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO₂R$^e$, —CN, —C(O)NR$^c$R$^d$, —NR$^c$C(O)R$^e$, —NR$^c$C(O)OR$^e$, —NR$^c$C(O)NR$^c$R$^d$, —O(CH₂)pO—C₃₋₆cycloalkyl, —O(CH₂)pO—C₂₋₁₀cycloheteroalkyl, —CF₃, —OCF₃, —OCHF₂, —(CH₂)p-C₃₋₆ cycloalkyl, —(CH₂)p-C₂₋₁₀cycloheteroalkyl, aryl, heteroaryl, aryl-C₁₋₁₀ alkyl-, and heteroaryl-C₁₋₁₀ alkyl-, wherein each R$^b$ is unsubstituted or substituted with one to five substituents selected from R$^k$, provided that when B is phenyl or imidazopyridine, then R$^b$ is not selected from F, Cl, and —OCH₃.

In another embodiment of the present invention, R$^b$ is independently selected from the group consisting of: —C₁₋₁₀alkyl, —C₂₋₁₀ alkenyl, halogen, —OH, —OC₁₋₁₀ alkyl, —OC₂₋₁₀ alkenyl, —O(CH₂)pOC₁₋₁₀alkyl, —O(CH₂)pC₃₋₆cycloalkyl, —O(CH₂)pC₃₋₆cycloalkyl-C₁₋₁₀ alkyl-, —O(CH₂)pC₂₋₁₀cycloheteroalkyl, —O(CH₂)pC₂₋₅cycloheteroalkyl-C₁₋₁₀ alkyl-, —O-aryl, —O-heteroaryl, —O-aryl-C₁₋₁₀ alkyl-, —O-heteroaryl-C₁₋₁₀ alkyl-, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO₂R$^e$, —CN, —C(O)NR$^c$R$^d$, —NR$^c$C(O)R$^e$, —NR$^c$C(O)OR$^e$, —O(CH₂)pO—C₃₋₆ cycloalkyl, —O(CH₂)pO—C₂₋₁₀ cycloheteroalkyl, —CF₃, —OCF₃, —OCHF₂, —(CH₂)p-C₃₋₆ cycloalkyl, —(CH₂)p-C₂₋₁₀ cycloheteroalkyl, aryl, heteroaryl, aryl-C₁₋₁₀ alkyl-, and heteroaryl-C₁₋₁₀ alkyl-, wherein each R$^b$ is unsubstituted or substituted with one to five substituents selected from R$^k$, provided that when B is phenyl or imidazopyridine, then R$^b$ is not selected from: —OC₁₋₁₀alkyl. In a class of this embodiment, R$^b$ is independently selected from the group consisting of: —C₁₋₁₀alkyl, —C₂₋₁₀ alkenyl, halogen, —OH, —OC₁₋₁₀ alkyl, —OC₂₋₁₀ alkenyl, —O(CH₂)pO C₁₋₁₀alkyl, —O(CH₂)pC₃₋₆cycloalkyl, —O(CH₂)pC₃₋₆ cycloalkyl-C₁₋₁₀ alkyl-, —O(CH₂)pC₂₋₁₀ cycloheteroalkyl, —O(CH₂)pC₂₋₅cycloheteroalkyl-C₁₋₁₀ alkyl-, —O-aryl, —O-heteroaryl, —O-aryl-C₁₋₁₀ alkyl-, —O-heteroaryl-C₁₋₁₀ alkyl-, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO₂R$^e$, —CN, —C(O)NR$^c$R$^d$, —NR$^c$C(O)R$^e$, —NR$^c$C(O)OR$^e$, —NR$^c$C(O)NR$^c$R$^d$, —O(CH₂)pO—C₃₋₆cycloalkyl, —O(CH₂)pO—C₂₋₁₀cycloheteroalkyl, —CF₃, —OCF₃, —OCHF₂, —(CH₂)p-C₃₋₆ cycloalkyl, —(CH₂)p-C₂₋₁₀cycloheteroalkyl, aryl, heteroaryl, aryl-C₁₋₁₀ alkyl-, and heteroaryl-C₁₋₁₀ alkyl-, wherein each R$^b$ is unsubstituted or substituted with one to five substituents selected from R$^k$. In another class of this embodiment, R$^b$ is independently selected from the group consisting of: —C₁₋₁₀alkyl, halogen, —OH, —OC₁₋₁₀alkyl, —O(CH₂)pOC₁₋₁₀ alkyl, —O(CH₂)pC₃₋₆cycloalkyl, —O(CH₂)pC₂₋₁₀cycloheteroalkyl, —O(CH₂)pO—C₂₋₁₀cycloheteroalkyl, —CF₃, —OCF₃, —OCHF₂, —(CH₂)p-C₂₋₁₀cycloheteroalkyl, and —S(O)₂C₁₋₁₀alkyl, wherein each R$^b$ is unsubstituted or substituted with one to five substituents selected from R$^k$, or a pharmaceutically acceptable salt thereof. In another class of this embodiment, R$^b$ is independently selected from the group consisting of: —C₁₋₁₀alkyl, halogen, —OH, —OC₁₋₁₀alkyl, —O(CH₂)pC₂₋₁₀cycloheteroalkyl, —O(CH₂)pO—C₂₋₁₀cycloheteroalkyl, —CF₃, —(CH₂)p-C₂₋₁₀cycloheteroalkyl, wherein each R$^b$ is unsubstituted or substituted with one to five substituents selected from R$^k$, or a pharmaceutically acceptable salt thereof.

In another embodiment of the present invention, R$^b$ is independently selected from the group consisting of: —C₁₋₁₀alkyl, halogen, —OH, —OC₁₋₁₀alkyl, —O(CH₂)pOC₁₋₁₀ alkyl, —O(CH₂)pC₃₋₆cycloalkyl, —O(CH₂)p C₂₋₁₀cycloheteroalkyl, —CF₃, —OCF₃, —OCHF₂, —(CH₂)p-C₂₋₁₀ cycloheteroalkyl, —O—C₁₋₆alkyl-O-isosorbide and —O—C₁₋₆ alkyl-O-isomannide, wherein each R$^b$ is unsubstituted or substituted with one to five substituents selected from R$^k$. In a class of this embodiment, R$^b$ is independently selected from the group consisting of: —C₁₋₁₀alkyl, halogen, —OH, —OC₁₋₁₀ alkyl, —O(CH₂)pC₂₋₁₀cycloheteroalkyl, —CF₃, —(CH₂)p-C₂₋₁₀ cycloheteroalkyl, —O—C₁₋₆alkyl-O-isosorbide and —O—C₁₋₆alkyl-O-isomannide, wherein each R$^b$ is unsubstituted or substituted with one to five substituents selected from R$^k$.

In another embodiment of the present invention, R$^b$ is independently selected from the group consisting of: —CH₃, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OC$_{1-10}$ alkyl, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$cyclopropane, —O(CH$_2$)$_3$cyclopropane, —O—CH$_2$cyclobutane, —O(CH$_2$)$_2$cyclobutane, —O-cyclohexane, —O-cyclobutane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, —CH$_2$-oxetane, -piperazine, azetidine, pyrrolidine, morpholine, and spiro (indene-1,4-piperidine), —O—C$_{1-6}$alkyl-O-isosorbide and —O—C$_{1-6}$alkyl-O-isomannide, wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OC$_{1-10}$ alkyl, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$cyclopropane, —O(CH$_2$)$_3$cyclopropane, —O(CH$_2$)$_2$cyclobutane, —O-cyclohexane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, pyrrolidine, —O—C$_{1-6}$alkyl-O-isosorbide and —O—C$_{1-6}$alkyl-O-isomannide, wherein each R$^b$ is unsubstituted or substituted with one to five substituents selected from R$^k$. In another class of this embodiment, R$^b$ is independently selected from the group consisting of: —CH$_3$, —(CH$_2$)$_4$SO$_2$CH$_3$, F, I, —OH, —OC$_{1-10}$alkyl, —OCH$_2$C(CH$_3$)$_2$OH, —O(CH$_2$)$_2$C(CH$_3$)$_2$OH, —O(CH$_2$)$_3$C(CH$_3$)$_2$OH, —O(CH$_2$)$_2$CH(OH)CH$_3$, —O(CH$_2$)$_3$SO$_2$CH$_3$, —OCH$_2$C(CH$_2$OH)$_2$CH$_3$, —O(CH$_2$)$_3$C(CH$_3$)$_2$CN, —OCH$_2$-oxetane, —OCH$_2$-tetrahydropyran, —CF$_3$, and pyrrolidine, wherein each R$^b$ is unsubstituted or substituted with one to five substituents selected from R$^k$.

In another embodiment of the present invention, R$^b$ is independently selected from the group consisting of: —C$_{1-10}$alkyl, —C$_{2-10}$ alkenyl, halogen, —OH, —OC$_{1-10}$ alkyl, —OC$_{2-10}$ alkenyl, —O(CH$_2$)pOC$_{1-10}$alkyl, —O(CH$_2$)pC$_{3-6}$cycloalkyl, —O(CH$_2$)pC$_{3-6}$ cycloalkyl-C$_{1-10}$ alkyl-, —O(CH$_2$)pC$_{2-10}$cycloheteroalkyl, —O(CH$_2$)pC$_{2-5}$cycloheteroalkyl-C$_{1-10}$ alkyl-, —O-aryl, —O-heteroaryl, —O-aryl-C$_{1-10}$ alkyl-, —O-heteroaryl-C$_{1-10}$ alkyl-; —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$, —OCHF$_2$, —(CH$_2$)p-C$_{3-6}$cycloalkyl, —(CH$_2$)p-C$_{2-10}$cycloheteroalkyl, aryl, heteroaryl, aryl-C$_{1-10}$ alkyl-, and heteroaryl-C$_{1-10}$ alkyl-, wherein each R$^b$ is unsubstituted or substituted with one to five substituents selected from R$^k$.

In another embodiment of the present invention, R$^b$ is independently selected from the group consisting of: —C$_{1-10}$alkyl, halogen, —OH, —OC$_{1-10}$alkyl, —O(CH$_2$)pOC$_{1-10}$ alkyl, —O(CH$_2$)pC$_{3-6}$cycloalkyl, —O(CH$_2$)pC$_{2-10}$cycloheteroalkyl, —O-aryl, —O-heteroaryl, —CF$_3$, —OCF$_3$, —OCHF$_2$, —(CH$_2$)p-C$_{3-6}$ cycloalkyl, —(CH$_2$)p-C$_{2-10}$cycloheteroalkyl, aryl, and heteroaryl, wherein each R$^b$ is unsubstituted or substituted with one to five substituents selected from R$^k$.

In another embodiment of the present invention, R$^b$ is independently selected from the group consisting of: —C$_{1-10}$alkyl, —C$_{2-10}$ alkenyl, halogen, —OH, —OC$_{1-10}$ alkyl, —O(CH$_2$)pOC$_{1-10}$ alkyl, —O(CH$_2$)pC$_{3-6}$cycloalkyl, —O(CH$_2$)pC$_{2-10}$cycloheteroalkyl, —CF$_3$, —OCF$_3$, —OCHF$_2$, —(CH$_2$)p-C$_{3-6}$ cycloalkyl, —(CH$_2$)p-C$_{2-10}$cycloheteroalkyl, wherein each R$^b$ is unsubstituted or substituted with one to five substituents selected from R$^k$.

In another embodiment of the present invention, R$^b$ is independently selected from the group consisting of: —C$_{1-10}$alkyl, halogen, —OH, —OC$_{1-10}$alkyl, —O(CH$_2$)pOC$_{1-10}$ alkyl, —O(CH$_2$)pC$_{3-6}$cycloalkyl, —O(CH$_2$)pC$_{2-10}$cycloheteroalkyl, —CF$_3$, —OCF$_3$, —OCHF$_2$, —(CH$_2$)p-C$_{2-10}$cycloheteroalkyl, wherein each R$^b$ is unsubstituted or substituted with one to five substituents selected from R$^k$. In a class of this embodiment, R$^b$ is independently selected from the group consisting of: —C$_{1-10}$alkyl, halogen, —OH, —OC$_{1-10}$alkyl, —O(CH$_2$)pC$_{2-10}$ cycloheteroalkyl, —CF$_3$, —(CH$_2$)p-C$_{2-10}$cycloheteroalkyl, wherein each R$^b$ is unsubstituted or substituted with one to five substituents selected from R$^k$.

In another embodiment of the present invention, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OC$_{1-10}$alkyl, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$cyclopropane, —O(CH$_2$)$_3$cyclopropane, —O—CH$_2$cyclobutane, —O(CH$_2$)$_2$cyclobutane, —O-cyclohexane, —O-cyclobutane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, —CH$_2$-oxetane, -piperazine, azetidine, pyrrolidine, morpholine, and spiro (indene-1,4-piperidine), wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OC$_{1-10}$alkyl, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$cyclopropane, —O(CH$_2$)$_3$cyclopropane, —O(CH$_2$)$_2$cyclobutane, —O-cyclohexane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, and pyrrolidine, wherein each R$^b$ is unsubstituted or substituted with one to five substituents selected from R$^k$. In another class of this embodiment, R$^b$ is independently selected from the group consisting of: —CH$_3$, —(CH$_2$)$_4$SO$_2$CH$_3$, F, I, —OH, —OC$_{1-10}$alkyl, —OCH$_2$C(CH$_3$)$_2$OH, —O(CH$_2$)$_2$C(CH$_3$)$_2$OH, —O(CH$_2$)$_3$C(CH$_3$)$_2$OH, —O(CH$_2$)$_2$CH(OH)CH$_3$, —O(CH$_2$)$_3$SO$_2$CH$_3$, —OCH$_2$C(CH$_2$OH)$_2$CH$_3$, —O(CH$_2$)$_3$C(CH$_3$)$_2$CN, —OCH$_2$-oxetane, —OCH$_2$-tetrahydropyran, —CF$_3$, and pyrrolidine, wherein each R$^b$ is unsubstituted or substituted with one to five substituents selected from R$^k$.

In another embodiment of the present invention, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$ OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$-hydroxycyclopropane, —O(CH$_2$)$_3$cyanocyclopropane, —O—CH$_2$difluorocyclobutane, —O(CH$_2$)$_2$difluorocyclobutane, —O-hydroxycyclohexane, —O-cyano, methylcyclobutane, —OCH$_2$-methyloxetane, —OCH$_2$-fluorotetrahydropyran, —O(CH$_2$)$_3$difluoroazetidine, —O-dioxidotetrahydrothiopyran, —O(CH$_2$)$_3$-oxopyrrolidine, —CF$_3$, —OCF$_3$, —OCHF$_2$, spiro(indene-1,4-piperidine), (methylsulfonyl)-piperazine, (methylsulfonyl)methylazetidine, (methylsulfonyl)methylpyrrolidine, and (methylsulfonamido)pyrrolidine), wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, F, Cl, I, —OH, —OCH$_3$, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$-hydroxycyclopropane, —O(CH$_2$)$_3$cyanocyclopropane, —O(CH$_2$)$_2$difluorocyclobutane, —O-hydroxycyclohexane, —O-cyano, methylcyclobutane, —OCH$_2$-methyloxetane, —OCH$_2$-fluorotetrahydropyran, —O(CH$_2$)$_3$difluoroazetidine, —O-dioxidotetrahydrothiopyran, —O(CH$_2$)$_3$-oxopyrrolidine, —CF$_3$, —OCF$_3$, —OCHF$_2$, and (methylsulfonyl)methylpyrrolidine, wherein each R$^b$ is unsubstituted or substituted with one to five substituents selected from R$^k$. In another class of this embodiment, le is independently selected from the group consisting of: —CH$_3$, —(CH$_2$)$_4$SO$_2$CH$_3$, F, I, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —O(CH$_2$)$_2$CH(OH)CH$_3$, —O(CH$_2$)$_3$SO$_2$CH$_3$, —OCH$_2$C(CH$_2$OH)$_2$CH$_3$, —O(CH$_2$)$_3$C(CH$_3$)$_2$CN, —OCH$_2$-methyloxetane, —OCH$_2$-fluorotetrahydropyran, —CF$_3$, and (methylsulfonyl)methylpyrrolidine, wherein each R$^b$ is unsubstituted or substituted with one to five substituents selected from R$^k$.

In another embodiment of the present invention, R$^b$ is independently selected from the group consisting of: —C$_{1-10}$alkyl, —C$_{2-10}$ alkenyl, —OH, —OC$_{2-10}$alkyl, —OC$_{2-10}$ alkenyl, —O(CH$_2$)pOC$_{1-10}$alkyl, —O(CH$_2$)pC$_{3-6}$cycloalkyl, —O(CH$_2$)pC$_{3-6}$cycloalkyl-C$_{1-10}$ alkyl-, —O(CH$_2$)pC$_{2-10}$cycloheteroalkyl, —O(CH$_2$)pC$_{2-5}$ cycloheteroalkyl-C$_{1-10}$ alkyl-—O-aryl, —O— heteroaryl, —O-aryl-C$_{1-10}$ alkyl-, —O-heteroaryl-C$_{1-10}$ alkyl-, —NR$^c$S(O)$_m$R$^e$, —S(o)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —O(CH$_2$)pO—C$_{3-6}$cycloalkyl, —O(CH$_2$)pO—C$_{2-10}$ cycloheteroalkyl, —CF$_3$, —OCF$_3$, —OCHF$_2$, —(CH$_2$)p-C$_{3-6}$ cycloalkyl, —(CH$_2$)p-C$_{2-10}$ cycloheteroalkyl, aryl, heteroaryl, aryl-C$_{1-10}$ alkyl-, and heteroaryl-C$_{1-10}$ alkyl-, wherein each R$^b$ is unsubstituted or substituted with one to five substituents selected from R$^k$. In a class of this embodiment of the present invention, R$^b$ is independently selected from the group consisting of: —C$_{1-10}$alkyl, —C$_{2-10}$ alkenyl, —OH, —OC$_{2-10}$alkyl, —OC$_{2-10}$ alkenyl, —O(CH$_2$)pOC$_{1-10}$alkyl, —O(CH$_2$)pC$_{3-6}$cycloalkyl, —O(CH$_2$)pC$_{3-6}$ cycloalkyl-C$_{1-10}$ alkyl-, —O(CH$_2$)pC$_{2-10}$ cycloheteroalkyl, —O(CH$_2$)pC$_{2-5}$cycloheteroalkyl-C$_{1-10}$ alkyl-—O-aryl, —O-heteroaryl, —O-aryl-C$_{1-10}$ alkyl-, —O-heteroaryl-C$_{1-10}$ alkyl-, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —O(CH$_2$)pO—C$_{2-10}$cycloheteroalkyl, —CF$_3$, —OCF$_3$, —OCHF$_2$, —(CH$_2$)p-C$_{3-6}$ cycloalkyl, —(CH$_2$)p-C$_{2-10}$cycloheteroalkyl, aryl, heteroaryl, aryl-C$_{1-10}$ alkyl-, and heteroaryl-C$_{1-10}$alkyl-, wherein each R$^b$ is unsubstituted or substituted with one to five substituents selected from R$^k$. In another class of this embodiment, R$^b$ is independently selected from the group consisting of: —C$_{1-10}$alkyl, —OH, —OC$_{2-10}$alkyl, —O(CH$_2$)pOC$_{1-10}$alkyl, —O(CH$_2$)pC$_{3-6}$ cycloalkyl, —O(CH$_2$)pC$_{2-10}$cycloheteroalkyl, —O(CH$_2$)pO—C$_{2-10}$cycloheteroalkyl, —CF$_3$, —OCF$_3$, —OCHF$_2$, —(CH$_2$)p-C$_{2-10}$cycloheteroalkyl, and —S(O)$_2$C$_{1-10}$alkyl, wherein each R$^b$ is unsubstituted or substituted with one to five substituents selected from R$^k$, or a pharmaceutically acceptable salt thereof. In another class of this embodiment, R$^b$ is independently selected from the group consisting of: —C$_{1-10}$alkyl, halogen, —OH, —OC$_{1-10}$alkyl, —O(CH$_2$)pC$_{2-10}$ cycloheteroalkyl, —O(CH$_2$)pO—C$_{2-10}$cycloheteroalkyl, —CF$_3$, —(CH$_2$)p-C$_{2-10}$cycloheteroalkyl, wherein each R$^b$ is unsubstituted or substituted with one to five substituents selected from R$^k$, or a pharmaceutically acceptable salt thereof.

In another embodiment of the present invention, R$^b$ is independently selected from the group consisting of: —C$_{1-10}$alkyl, —OH, —OC$_{2-10}$alkyl, —O(CH$_2$)pOC$_{1-10}$ alkyl, —O(CH$_2$)pC$_{3-6}$ cycloalkyl, —O(CH$_2$)pC$_{2-10}$cycloheteroalkyl, —CF$_3$, —OCF$_3$, —OCHF$_2$, —(CH$_2$)p-C$_{2-10}$cycloheteroalkyl, —O—C$_{1-6}$alkyl-O-isosorbide and —O—C$_{1-6}$alkyl-O-isomannide, wherein each R$^b$ is unsubstituted or substituted with one to five substituents selected from R$^k$. In a class of this embodiment, R$^b$ is independently selected from the group consisting of: —C$_{1-10}$alkyl, —OH, —OC$_{2-10}$alkyl, —O(CH$_2$)pC$_{2-10}$cycloheteroalkyl, —CF$_3$, —(CH$_2$)p-C$_{2-10}$cycloheteroalkyl, —O—C$_{1-6}$alkyl-O-isosorbide and —O—C$_{1-6}$alkyl-O-isomannide, wherein each R$^b$ is unsubstituted or substituted with one to five substituents selected from R$^k$.

In another embodiment of the present invention, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$cyclopropane, —O(CH$_2$)$_3$cyclopropane, —O—CH$_2$cyclobutane, —O(CH$_2$)$_2$cyclobutane, —O-cyclohexane, —O-cyclobutane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, —CH$_2$-oxetane, -piperazine, azetidine, pyrrolidine, morpholine, and spiro(indene-1,4-piperidine), —O—C$_{1-6}$alkyl-O-isosorbide and —O—C$_{1-6}$alkyl-O-isomannide, wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$cyclopropane, —O(CH$_2$)$_3$cyclopropane, —O(CH$_2$)$_2$cyclobutane, —O-cyclohexane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, pyrrolidine, —O—C$_{1-6}$alkyl-O-isosorbide and —O—C$_{1-6}$alkyl-O-isomannide, wherein each R$^b$ is unsubstituted or substituted with one to five substituents selected from R$^k$. In another class of this embodiment, R$^b$ is independently selected from the group consisting of: —CH$_3$, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —O(CH$_2$)$_2$CH(OH)CH$_3$, —O(CH$_2$)$_3$SO$_2$CH$_3$, —OCH$_2$C(CH$_2$OH)$_2$CH$_3$, —O(CH$_2$)$_3$C(CH$_3$)$_2$CN, —OCH$_2$-oxetane, —OCH$_2$-tetrahydropyran, —CF$_3$, and pyrrolidine, wherein each R$^b$ is unsubstituted or substituted with one to five substituents selected from R$^k$.

In another embodiment of the present invention, R$^b$ is independently selected from the group consisting of: —C$_{1-10}$alkyl, —C$_{2-10}$ alkenyl, —OH, —OC$_{2-10}$alkyl, —OC$_{2-10}$ alkenyl, —O(CH$_2$)pOC$_{1-10}$alkyl, —O(CH$_2$)p C$_{3-6}$cycloalkyl, —O(CH$_2$)pC$_{3-6}$ cycloalkyl-C$_{1-10}$ alkyl-, —O(CH$_2$)pC$_{2-10}$cycloheteroalkyl, —O(CH$_2$)pC$_{2-5}$ cycloheteroalkyl-C$_{1-10}$ alkyl-, —O-aryl, —O— heteroaryl, —O-aryl-C$_{1-10}$ alkyl-, —O-heteroaryl-C$_{1-10}$ alkyl-; —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$, —OCHF$_2$, —(CH$_2$)p-C$_{3-6}$cycloalkyl, —(CH$_2$)p-C$_{2-10}$cycloheteroalkyl, aryl, heteroaryl, aryl-C$_{1-10}$ alkyl-, and heteroaryl-C$_{1-10}$ alkyl-, wherein each R$^b$ is unsubstituted or substituted with one to five substituents selected from R$^k$.

In another embodiment of the present invention, R$^b$ is independently selected from the group consisting of: —C$_{1-10}$alkyl, —OH, —OC$_{2-10}$alkyl, —O(CH$_2$)pOC$_{1-10}$alkyl, —O(CH$_2$)pC$_{3-6}$ cycloalkyl, —O(CH$_2$)pC$_{2-10}$cycloheteroalkyl, —O-aryl, —O-heteroaryl, —CF$_3$, —OCF$_3$, —OCHF$_2$, —(CH$_2$)p-C$_{3-6}$cycloalkyl, —(CH$_2$)p-C$_{2-10}$cycloheteroalkyl, aryl, and heteroaryl, wherein each R$^b$ is unsubstituted or substituted with one to five substituents selected from R$^k$.

In another embodiment of the present invention, R$^b$ is independently selected from the group consisting of: —C$_{1-10}$alkyl, —C$_{2-10}$ alkenyl, —OH, —OC$_{2-10}$alkyl, —O(CH$_2$)pOC$_{1-10}$alkyl, —O(CH$_2$)pC$_{3-6}$cycloalkyl, —O(CH$_2$)pC$_{2-10}$cycloheteroalkyl, —CF$_3$, —OCF$_3$, —OCHF$_2$, —(CH$_2$)p-C$_{3-6}$cycloalkyl, —(CH$_2$)p-C$_{2-10}$cycloheteroalkyl, wherein each R$^b$ is unsubstituted or substituted with one to five substituents selected from R$^k$.

In another embodiment of the present invention, R$^b$ is independently selected from the group consisting of: —C$_{1-10}$alkyl, —OH, —OC$_{2-10}$alkyl, —O(CH$_2$)pOC$_{1-10}$alkyl, —O(CH$_2$)pC$_{3-6}$ cycloalkyl, —O(CH$_2$)pC$_{2-10}$cycloheteroalkyl, —CF$_3$, —OCF$_3$, —OCHF$_2$, —(CH$_2$)p-C$_{2-10}$cycloheteroalkyl, wherein each R$^b$ is unsubstituted or substituted with one to five substituents selected from R$^k$. In a class of this embodiment, R$^b$ is independently selected from the group consisting of: —C$_{1-10}$alkyl, —OH, —OC$_{2-10}$alkyl, —O(CH$_2$)pC$_{2-10}$cycloheteroalkyl, —CF$_3$, —(CH$_2$)p-C$_{2-10}$cycloheteroalkyl, wherein each R$^b$ is unsubstituted or substituted with one to five substituents selected from R$^k$.

In another embodiment of the present invention, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$cyclopropane, —O(CH$_2$)$_3$cyclopropane, —O—CH$_2$cyclobutane, —O(CH$_2$)$_2$cyclobutane, —O-cyclohexane, —O-cyclobutane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, —CH$_2$-oxetane, -piperazine, azetidine, pyrrolidine, morpholine, and spiro(indene-1,4-piperidine), wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$cyclopropane, —O(CH$_2$)$_3$cyclopropane, —O(CH$_2$)$_2$cyclobutane, —O-cyclohexane, —OCH$_2$-oxetane, —OCH$_2$-tetrahydropyran, —O(CH$_2$)$_3$azetidine, —O-tetrahydrothiopyran, —O(CH$_2$)$_3$pyrrolidine, —CF$_3$, —OCF$_3$, —OCHF$_2$, and pyrrolidine, wherein each R$^b$ is unsubstituted or substituted with one to five substituents selected from R$^k$. In another class of this embodiment, R$^b$ is independently selected from the group consisting of: —CH$_3$, —(CH$_2$)$_4$SO$_2$CH$_3$, —OH, —OC$_{2-10}$alkyl, —OCH$_2$C(CH$_3$)$_2$OH, —O(CH$_2$)$_2$C(CH$_3$)$_2$OH, —O(CH$_2$)$_3$C(CH$_3$)$_2$OH, —O(CH$_2$)$_2$CH(OH)CH$_3$, —O(CH$_2$)$_3$SO$_2$CH$_3$, —OCH$_2$C(CH$_2$OH)$_2$CH$_3$, —O(CH$_2$)$_3$C(CH$_3$)$_2$CN, —OCH$_2$-oxetane, —OCH$_2$-tetrahydropyran, —CF$_3$, and pyrrolidine, wherein each R$^b$ is unsubstituted or substituted with one to five substituents selected from R$^k$.

In another embodiment of the present invention, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —OCH$_2$CF$_2$CF$_3$, —O(CH$_2$)$_3$C(CH$_3$)$_2$CN, —O(CH$_2$)$_3$C(=N—OCH$_3$)CH$_3$, —O—(CH$_2$)$_2$—O—CH$_2$C(CH$_3$)$_2$OH, —O(CH$_2$)$_2$-hydroxycyclopropane, —O(CH$_2$)$_3$cyanocyclopropane, —O—CH$_2$difluorocyclobutane, —O(CH$_2$)$_2$difluorocyclobutane, —O-hydroxycyclohexane, —O-cyano, methyl-cyclobutane, —OCH$_2$-methyloxetane, —OCH$_2$-fluorotetrahydropyran, —O(CH$_2$)$_3$difluoroazetidine, —O-dioxidotetrahydrothiopyran, —O(CH$_2$)$_3$-oxopyrrolidine, —CF$_3$, —OCF$_3$, —OCHF$_2$, spiro(indene-1,4-piperidine), (methylsulfonyl)-piperazine, (methylsulfonyl)methyl-azetidine, (methylsulfonyl)methyl-pyrrolidine, and (methylsulfonamido)-pyrrolidine, wherein each R$^b$ is unsubstituted or substituted with one to five substituents selected from R$^k$. In a class of this embodiment, R$^b$ is independently selected from the group consisting of: —CH$_3$, —CH$_2$CH$_3$, —(CH$_2$)$_2$C(CH$_3$)$_2$OH, —(CH$_2$)$_3$C(CH$_3$)$_2$OH, —(CH$_2$)$_4$SO$_2$CH$_3$, —OH, —OCH$_2$C(CH$_3$)$_2$OH, —O(CH$_2$)$_2$C(CH$_3$)$_2$OH, —O(CH$_2$)$_3$C(CH$_3$)$_2$OH, —OCH$_2$CH(OH)CH$_3$, —O(CH$_2$)$_2$CH(OH)CH$_3$, —O(CH$_2$)$_3$SO$_2$CH$_3$, —OCH$_2$CH(OH)CH$_2$OH, —OCH$_2$C(CH$_2$OH)$_2$CH$_3$, —O(CH$_2$)$_3$C(CH$_3$)$_2$CN, —O—(CH$_2$)$_2$—O—CH$_2$C(CH$_3$)$_2$OH, —O(CH$_2$)$_2$-hydroxycyclopropane, —O(CH$_2$)$_3$cyanocyclopropane, —O(CH$_2$)$_2$difluorocyclobutane, —O-hydroxycyclohexane, —O-cyano, methyl-cyclobutane, —OCH$_2$-methyloxetane, —OCH$_2$-fluorotetrahydropyran, —O(CH$_2$)$_3$difluoro-azetidine, —O-dioxidotetrahydrothiopyran, —O(CH$_2$)$_3$-oxopyrrolidine, —CF$_3$, —OCF$_3$, —OCHF$_2$, and (methylsulfonyl)methylpyrrolidine, wherein each R$^b$ is unsubstituted or substituted with one to five substituents selected from $R^k$. In another class of this embodiment, $R^b$ is independently selected from the group consisting of: —$CH_3$, —$(CH_2)_4SO_2CH_3$, —OH, —$OCH_2C(CH_3)_2OH$, —O$(CH_2)_2C(CH_3)_2OH$, —$O(CH_2)_3C(CH_3)_2OH$, —$O(CH_2)_2CH(OH)CH_3$, —$O(CH_2)_3SO_2CH_3$, —$OCH_2C(CH_2OH)_2CH_3$, —$O(CH_2)_3C(CH_3)_2CN$, —$OCH_2$-methyloxetane, —$OCH_2$-fluorotetrahydropyran, —$CF_3$, and (methylsulfonyl)methyl-pyrrolidine, wherein each $R^b$ is unsubstituted or substituted with one to five substituents selected from $R^k$.

In another embodiment of the present invention, $R^b$ is independently selected from the group consisting of: —$C_{1-10}$alkyl, —$C_{2-10}$ alkenyl, OH, —$OC_{2-10}$alkyl, —$OC_{2-10}$ alkenyl, —$O(CH_2)pOC_{1-10}$alkyl, —$O(CH_2)p C_{3-6}$cycloalkyl, —$O(CH_2)pC_{3-6}$cycloalkyl-$C_{1-10}$ alkyl-, —O-aryl, —O-heteroaryl, —O-aryl-$C_{1-10}$ alkyl-, —O-heteroaryl-$C_{1-10}$ alkyl-, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$O(CH_2)pO—C_{3-6}$cycloalkyl, —$O(CH_2)pO—C_{2-10}$ cycloheteroalkyl, —$OCF_3$, —$OCHF_2$, —$(CH_2)p$-$C_{3-6}$ cycloalkyl, —$(CH_2)p$-$C_{2-10}$ cycloheteroalkyl, aryl, heteroaryl, aryl-$C_{1-10}$ alkyl-, and heteroaryl-$C_{1-10}$ alkyl-, wherein each $R^b$ is unsubstituted or substituted with one to five substituents selected from $R^k$. In a class of this embodiment of the present invention, $R^b$ is independently selected from the group consisting of: —$C_{1-10}$alkyl, —$C_{2-10}$ alkenyl, OH, —$OC_{2-10}$alkyl, —$OC_{2-10}$ alkenyl, —$O(CH_2)pOC_{1-10}$alkyl, —$O(CH_2)p C_{3-6}$cycloalkyl, —$O(CH_2)pC_{3-6}$ cycloalkyl-$C_{1-10}$ alkyl-, —O-aryl, —O-heteroaryl, —O-aryl-$C_{1-10}$alkyl-, —O-heteroaryl-$C_{1-10}$ alkyl-, —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$O(CH_2)pO—C_{2-10}$cycloheteroalkyl, —$OCF_3$, —$OCHF_2$, —$(CH_2)p$-$C_{3-6}$ cycloalkyl, —$(CH_2)p$-$C_{2-10}$cycloheteroalkyl, aryl, heteroaryl, aryl-$C_{1-10}$ alkyl-, and heteroaryl-$C_{1-10}$alkyl-, wherein each $R^b$ is unsubstituted or substituted with one to five substituents selected from $R^k$. In another class of this embodiment, $R^b$ is independently selected from the group consisting of: —$C_{1-10}$alkyl, OH, —$OC_{2-10}$alkyl, —$O(CH_2)pOC_{1-10}$alkyl, —$O(CH_2)pC_{3-6}$ cycloalkyl, —$O(CH_2)pO—C_{2-10}$cycloheteroalkyl, —$OCF_3$, —$OCHF_2$, —$(CH_2)p$-$C_{2-10}$ cycloheteroalkyl, and —$S(O)_2C_{1-10}$alkyl, wherein each $R^b$ is unsubstituted or substituted with one to five substituents selected from $R^k$, or a pharmaceutically acceptable salt thereof. In another class of this embodiment, $R^b$ is independently selected from the group consisting of: —$C_{1-10}$ alkyl, —$OC_{2-10}$alkyl, —$O(CH_2)pO—C_{2-10}$cycloheteroalkyl, —$(CH_2)p$-$C_{2-10}$cycloheteroalkyl, wherein each $R^b$ is unsubstituted or substituted with one to five substituents selected from $R^k$, or a pharmaceutically acceptable salt thereof.

In another embodiment of the present invention, $R^b$ is independently selected from the group consisting of: —$C_{1-10}$alkyl, OH, —$OC_{2-10}$alkyl, —$O(CH_2)pOC_{1-10}$alkyl, —$O(CH_2)pC_{3-6}$ cycloalkyl, —$OCF_3$, —$OCHF_2$, —$(CH_2)p$-$C_{2-10}$cycloheteroalkyl, —O—$C_{1-6}$alkyl-O-isosorbide and —O—$C_{1-6}$alkyl-O-isomannide, wherein each $R^b$ is unsubstituted or substituted with one to five substituents selected from $R^k$. In a class of this embodiment, $R^b$ is independently selected from the group consisting of: —$C_{1-10}$alkyl, OH, —$OC_{2-10}$alkyl, —O—$C_{1-6}$alkyl-O-isosorbide and —O—$C_{1-6}$alkyl-O-isomannide, wherein each $R^b$ is unsubstituted or substituted with one to five substituents selected from $R^k$. In another embodiment of the present invention, $R^b$ is independently selected from the group consisting of: —$CH_3$, —$CH_2CH_3$, OH, —$(CH_2)_2C(CH_3)_2OH$, —$(CH_2)_3C(CH_3)_2OH$, —$(CH_2)_4SO_2CH_3$, —$OCH_2C(CH_3)_2OH$, —$O(CH_2)_2C(CH_3)_2OH$, —$O(CH_2)_3C(CH_3)_2OH$, —$OCH_2CH(OH)CH_3$, —$O(CH_2)_2CH(OH)CH_3$, —O$(CH_2)_3SO_2CH_3$, —$OCH_2CH(OH)CH_2OH$, —$OCH_2C(CH_2OH)_2CH_3$, —$OCH_2CF_2CF_3$, —$O(CH_2)_3C(CH_3)_2CN$, —$O(CH_2)_3C(=N—OCH_3)CH_3$, —O—$(CH_2)_2$—O—$CH_2C(CH_3)_2OH$, —$O(CH_2)_2$cyclopropane, —$O(CH_2)_3$cyclopropane, —O—$CH_2$cyclobutane, —$O(CH_2)_2$cyclobutane, —O-cyclohexane, —O-cyclobutane, —$OCF_3$, —$OCHF_2$, —$CH_2$-oxetane, -piperazine, azetidine, pyrrolidine, morpholine, and spiro(indene-1,4-piperidine), —O—$C_{1-6}$alkyl-O-isosorbide and —O—$C_{1-6}$alkyl-O-isomannide, wherein each $R^b$ is unsubstituted or substituted with one to five substituents selected from $R^k$. In a class of this embodiment, $R^b$ is independently selected from the group consisting of: —$CH_3$, —$CH_2CH_3$, OH, —$(CH_2)_2C(CH_3)_2OH$, —$(CH_2)_3C(CH_3)_2OH$, —$(CH_2)_4SO_2CH_3$, —$OCH_2C(CH_3)_2OH$, —$O(CH_2)_2C(CH_3)_2OH$, —O$(CH_2)_3C(CH_3)_2OH$, —$OCH_2CH(OH)CH_3$, —$O(CH_2)_2CH(OH)CH_3$, —$O(CH_2)_3SO_2CH_3$, —$OCH_2CH(OH)CH_2OH$, —$OCH_2C(CH_2OH)_2CH_3$, —$O(CH_2)_3C(CH_3)_2CN$, —O—$(CH_2)_2$—O—$CH_2C(CH_3)_2OH$, —$O(CH_2)_2$cyclopropane, —$O(CH_2)_3$cyclopropane, —$O(CH_2)_2$cyclobutane, —O-cyclohexane, —$OCF_3$, —$OCHF_2$, pyrrolidine, —O—$C_{1-6}$ alkyl-O-isosorbide and —O— $C_{1-6}$alkyl-O-isomannide, wherein each $R^b$ is unsubstituted or substituted with one to five substituents selected from $R^k$. In another class of this embodiment, $R^b$ is independently selected from the group consisting of: —$CH_3$, —$(CH_2)_4SO_2CH_3$, —$OCH_2C(CH_3)_2OH$, —$O(CH_2)_2C(CH_3)_2OH$, —$O(CH_2)_3C(CH_3)_2OH$, —$O(CH_2)_2CH(OH)CH_3$, —$O(CH_2)_3SO_2CH_3$, —$OCH_2C(CH_2OH)_2CH_3$, —$O(CH_2)_3C(CH_3)_2CN$, and pyrrolidine, wherein each $R^b$ is unsubstituted or substituted with one to five substituents selected from $R^k$.

In another embodiment of the present invention, $R^b$ is independently selected from the group consisting of: —$C_{1-10}$alkyl, —$C_{2-10}$ alkenyl, —$OC_{2-10}$alkyl, —$OC_{2-10}$ alkenyl, —$O(CH_2)pOC_{1-10}$alkyl, —$O(CH_2)pC_{3-6}$cycloalkyl, —$O(CH_2)pC_{3-6}$cycloalkyl-$C_{1-10}$ alkyl, —O-aryl, —O-heteroaryl, —O-aryl-$C_{1-10}$ alkyl-, —O-heteroaryl-$C_{1-10}$ alkyl-; —$NR^cS(O)_mR^e$, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$OCF_3$, —$OCHF_2$, —$(CH_2)p$-$C_{3-6}$cycloalkyl, —$(CH_2)p$-$C_{2-10}$cycloheteroalkyl, aryl, heteroaryl, aryl-$C_{1-10}$ alkyl-, and heteroaryl-$C_{1-10}$ alkyl-, wherein each $R^b$ is unsubstituted or substituted with one to five substituents selected from $R^k$.

In another embodiment of the present invention, $R^b$ is independently selected from the group consisting of: —$C_{1-10}$alkyl, —$OC_{2-10}$alkyl, —$O(CH_2)pOC_{1-10}$alkyl, —$O(CH_2)pC_{3-6}$cycloalkyl, —O-aryl, —O-heteroaryl, —$OCF_3$, —$OCHF_2$, —$(CH_2)p$-$C_{3-6}$ cycloalkyl, —$(CH_2)p$-$C_{2-10}$ cycloheteroalkyl, aryl, and heteroaryl, wherein each $R^b$ is unsubstituted or substituted with one to five substituents selected from $R^k$.

In another embodiment of the present invention, $R^b$ is independently selected from the group consisting of: —$C_{1-10}$alkyl, —$C_{2-10}$ alkenyl, —$OC_{2-10}$alkyl, —$O(CH_2)pOC_{1-10}$alkyl, —$O(CH_2)pC_{3-6}$cycloalkyl, —$OCF_3$, —$OCHF_2$, —$(CH_2)p$-$C_{3-6}$ cycloalkyl, —$(CH_2)p$-$C_{2-10}$cycloheteroalkyl, wherein each $R^b$ is unsubstituted or substituted with one to five substituents selected from $R^k$.

In another embodiment of the present invention, $R^b$ is independently selected from the group consisting of: —$C_{1-10}$alkyl, —$OC_{2-10}$alkyl, —$O(CH_2)pOC_{1-10}$alkyl, —$O(CH_2)pC_{3-6}$ cycloalkyl, —$OCF_3$, —$OCHF_2$, —$(CH_2)p$-$C_{2-10}$cycloheteroalkyl, wherein each $R^b$ is unsubstituted or substituted with one to five substituents selected from $R^k$. In a class of this embodiment, $R^b$ is independently selected from the group consisting of: —$C_{1-10}$alkyl, —$OC_{2-10}$ alkyl, —$(CH_2)p$-$C_{2-10}$cycloheteroalkyl, wherein each $R^b$ is unsubstituted or substituted with one to five substituents selected from $R^k$.

In another embodiment of the present invention, $R^b$ is independently selected from the group consisting of: —$CH_3$, —$CH_2CH_3$, —$(CH_2)_2C(CH_3)_2OH$, —$(CH_2)_3C(CH_3)_2OH$, —$(CH_2)_4SO_2CH_3$, —$OC_{2-10}$alkyl, —$OCH_2C(CH_3)_2OH$, —$O(CH_2)_2C(CH_3)_2OH$, —$O(CH_2)_3C(CH_3)_2OH$, —$OCH_2CH(OH)CH_3$, —$O(CH_2)_2CH(OH)CH_3$, —$O(CH_2)_3SO_2CH_3$, —$OCH_2CH(OH)CH_2OH$, —$OCH_2C(CH_2OH)_2CH_3$, —$OCH_2CF_2CF_3$, —$O(CH_2)_3C(CH_3)_2CN$, —$O(CH_2)_3C(=N—OCH_3)CH_3$, —$O—(CH_2)_2—O—CH_2C(CH_3)_2OH$, —$O(CH_2)_2$cyclopropane, —$O(CH_2)_3$cyclopropane, —$O—CH_2$cyclobutane, —$O(CH_2)_2$cyclobutane, —O-cyclohexane, —O-cyclobutane, —$OCF_3$, —$OCHF_2$, —$CH_2$-oxetane, -piperazine, azetidine, pyrrolidine, morpholine, and spiro(indene-1,4-piperidine), wherein each $R^b$ is unsubstituted or substituted with one to five substituents selected from $R^k$. In a class of this embodiment, $R^b$ is independently selected from the group consisting of: —$CH_3$, —$CH_2CH_3$, —$(CH_2)_2C(CH_3)_2OH$, —$(CH_2)_3C(CH_3)_2OH$, —$(CH_2)_4SO_2CH_3$, —$OC_{2-10}$alkyl, —$OCH_2C(CH_3)_2OH$, —$O(CH_2)_2C(CH_3)_2OH$, —$O(CH_2)_3C(CH_3)_2OH$, —$OCH_2CH(OH)CH_3$, —$O(CH_2)_2CH(OH)CH_3$, —$O(CH_2)_3SO_2CH_3$, —$OCH_2CH(OH)CH_2OH$, —$OCH_2C(CH_2OH)_2CH_3$, —$O(CH_2)_3C(CH_3)_2CN$, —$O—(CH_2)_2—O—CH_2C(CH_3)_2OH$, —$O(CH_2)_2$cyclopropane, —$O(CH_2)_3$cyclopropane, —$O(CH_2)_2$cyclobutane, —O-cyclohexane, —$OCF_3$, —$OCHF_2$, and pyrrolidine, wherein each $R^b$ is unsubstituted or substituted with one to five substituents selected from $R^k$. In another class of this embodiment, $R^b$ is independently selected from the group consisting of: —$CH_3$, —$(CH_2)_4SO_2CH_3$, —$OC_{2-10}$alkyl, —$OCH_2C(CH_3)_2OH$, —$O(CH_2)_2C(CH_3)_2OH$, —$O(CH_2)_3C(CH_3)_2OH$, —$O(CH_2)_2CH(OH)CH_3$, —$O(CH_2)_3SO_2CH_3$, —$OCH_2C(CH_2OH)_2CH_3$, —$O(CH_2)_3C(CH_3)_2CN$, and pyrrolidine, wherein each $R^b$ is unsubstituted or substituted with one to five substituents selected from $R^k$.

In another embodiment of the present invention, $R^b$ is independently selected from the group consisting of: —$CH_3$, —$CH_2CH_3$, —$(CH_2)_2C(CH_3)_2OH$, —$(CH_2)_3C(CH_3)_2OH$, —$(CH_2)_4SO_2CH_3$, —$OCH_2C(CH_3)_2OH$, —$O(CH_2)_2C(CH_3)_2OH$, —$O(CH_2)_3C(CH_3)_2OH$, —$OCH_2CH(OH)CH_3$, —$O(CH_2)_2CH(OH)CH_3$, —$O(CH_2)_3SO_2CH_3$, —$OCH_2CH(OH)CH_2OH$, —$OCH_2C(CH_2OH)_2CH_3$, —$OCH_2CF_2CF_3$, —$O(CH_2)_3C(CH_3)_2CN$, —$O(CH_2)_3C(=N—OCH_3)CH_3$, —$O—(CH_2)_2—O—CH_2C(CH_3)_2OH$, —$O(CH_2)_2$-hydroxycyclopropane, —$O(CH_2)_3$cyanocyclopropane, —$O—CH_2$difluorocyclobutane, —$O(CH_2)_2$difluorocyclobutane, —O-hydroxycyclohexane, —O-cyano, methyl-cyclobutane, —$OCF_3$, —$OCHF_2$, spiro(indene-1,4-piperidine), (methylsulfonyl)-piperazine, (methylsulfonyl)methylazetidine, (methylsulfonyl)methylpyrrolidine, and (methylsulfonamido)pyrrolidine), wherein each $R^b$ is unsubstituted or substituted with one to five substituents selected from $R^k$. In a class of this embodiment, $R^b$ is independently selected from the group consisting of: —$CH_3$, —$CH_2CH_3$, —$(CH_2)_2C(CH_3)_2OH$, —$(CH_2)_3C(CH_3)_2OH$, —$(CH_2)_4SO_2CH_3$, —$OCH_2C(CH_3)_2OH$, —$O(CH_2)_2C(CH_3)_2OH$, —$O(CH_2)_3C(CH_3)_2OH$, —$OCH_2CH(OH)CH_3$, —$O(CH_2)_2CH(OH)CH_3$, —$O(CH_2)_3SO_2CH_3$, —$OCH_2CH(OH)CH_2OH$, —$OCH_2C(CH_2OH)_2CH_3$, —$O(CH_2)_3C(CH_3)_2CN$, —$O—(CH_2)_2—O—CH_2C(CH_3)_2OH$, —$O(CH_2)_2$-hydroxycyclopropane, —$O(CH_2)_3$cyano-cyclopropane, —$O(CH_2)_2$difluorocyclobutane, —O-hydroxycyclohexane, —O-cyano, methyl-cyclobutane, —$OCF_3$, —$OCHF_2$, and (methylsulfonyl)-methylpyrrolidine, wherein each $R^b$ is unsubstituted or substituted with one to five substituents selected from $R^k$. In another class of this embodiment, $R^b$ is independently selected from the group consisting of: —$CH_3$, —$(CH_2)_4SO_2CH_3$, —$OCH_2C(CH_3)_2OH$, —$O(CH_2)_2C(CH_3)_2OH$, —$O(CH_2)_3C(CH_3)_2$ OH, —$O(CH_2)_2CH(OH)CH_3$, —$O(CH_2)_3SO_2CH_3$, —$OCH_2C(CH_2OH)_2CH_3$, —$O(CH_2)_3C(CH_3)_2CN$, and (methylsulfonyl)methylpyrrolidine, wherein each $R^b$ is unsubstituted or substituted with one to five substituents selected from $R^k$.

In another embodiment of the present invention, $R^b$ is —$OC_{1-10}$alkyl, wherein $R^b$ is unsubstituted or substituted with one to five substituents selected from $R^k$. In another embodiment of the present invention, $R^b$ is —$OC_{2-10}$alkyl, wherein $R^b$ is unsubstituted or substituted with one to five substituents selected from $R^k$. In another embodiment of the present invention, $R^b$ is —$OC_{3-10}$alkyl, wherein $R^b$ is unsubstituted or substituted with one to five substituents selected from $R^k$. In another embodiment of the present invention, $R^b$ is —$O(CH_2)_3SO_2CH_3$.

In another embodiment of the present invention, $R^c$ and $R^d$ are each independently selected from the group consisting of: hydrogen, —$C_{1-10}$alkyl, —$C_{2-10}$alkenyl, —$C_{3-6}$cycloalkyl, —$C_{3-6}$cycloalkyl-$C_{1-10}$alkyl-, —$C_{2-5}$cycloheteroalkyl, —$C_{2-5}$cycloheteroalkyl-$C_{1-10}$alkyl-, aryl, heteroaryl, aryl-$C_{1-10}$alkyl-, and heteroaryl-$C_{1-10}$alkyl-, or $R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$. In a class of this embodiment, $R^c$ and $R^d$ are each independently selected from the group consisting of: hydrogen, —$C_{1-10}$alkyl, —$C_{2-10}$ alkenyl, —$C_{3-6}$cycloalkyl, —$C_{2-5}$cycloheteroalkyl, aryl, and heteroaryl, or $R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$. In another class of this embodiment, $R^c$ and $R^d$ are each independently selected from the group consisting of: hydrogen, —$C_{1-10}$alkyl, and —$C_{2-10}$alkenyl, or $R^c$ and $R^d$ together with the atom(s) to which they are attached form a cycloheteroalkyl ring of 4 to 7 members containing 0-2 additional heteroatoms independently selected from oxygen, sulfur and N—$R^g$, and wherein each $R^c$ and $R^d$ is unsubstituted or substituted with one to three substituents independently selected from $R^f$.

In another embodiment of the present invention, $R^c$ and $R^d$ are each independently selected from the group consisting of: hydrogen, —$C_{1-10}$alkyl, —$C_{2-10}$alkenyl, —$C_{3-6}$cycloalkyl, —$C_{3-6}$cycloalkyl-$C_{1-10}$ alkyl-, —$C_{2-5}$cycloheteroalkyl, —$C_{2-5}$cycloheteroalkyl-$C_{1-10}$ alkyl-, aryl, heteroaryl, aryl-$C_{1-10}$alkyl-, and heteroaryl-$C_{1-10}$alkyl-, wherein each $R^c$ and $R^d$ is unsubstituted or substituted with one to three substituents independently selected from $R^f$. In a class of this embodiment, $R^c$ and $R^d$ are each independently selected from the group consisting of: hydrogen, —$C_{1-10}$alkyl, —$C_{2-10}$ alkenyl, —$C_{3-6}$cycloalkyl, —$C_{2-5}$cycloheteroalkyl, aryl, and heteroaryl, wherein each $R^c$ and $R^d$ is unsubstituted or substituted with one to three substituents independently selected from $R^f$. In another class of this embodiment, $R^c$ and $R^d$ are each independently selected from the group consisting of: hydrogen, —$C_{1-10}$alkyl, and —$C_{2-10}$ alkenyl, wherein each $R^c$ and $R^d$ is unsubstituted or substituted with one to three substituents independently selected from $R^f$.

In another embodiment of the present invention, $R^c$ is independently selected from the group consisting of: hydrogen, —$C_{1-10}$alkyl, —$C_{2-10}$alkenyl, —$C_{3-6}$cycloalkyl, —$C_{3-6}$cycloalkyl-$C_{1-10}$alkyl-, —$C_{2-5}$cycloheteroalkyl, —$C_{2-5}$cycloheteroalkyl-$C_{1-10}$alkyl-, aryl, heteroaryl, aryl-$C_{1-10}$ alkyl-, and heteroaryl-$C_{1-10}$alkyl-, wherein each $R^c$ is unsubstituted or substituted with one to three substituents independently selected from $R^f$. In a class of this embodiment, $R^c$ is independently selected from the group consisting of: hydrogen, —$C_{1-10}$alkyl, —$C_{2-10}$alkenyl, —$C_{3-6}$cycloalkyl, —$C_{2-5}$cycloheteroalkyl, aryl, and heteroaryl, wherein each $R^c$ is unsubstituted or substituted with one to three substituents independently selected from $R^f$. In another class of this embodiment, $R^c$ is independently selected from the group consisting of: hydrogen, —$C_{1-10}$alkyl, and —$C_{2-10}$ alkenyl, wherein each $R^c$ is unsubstituted or substituted with one to three substituents independently selected from $R^f$.

In another embodiment of the present invention, $R^d$ is independently selected from the group consisting of: hydrogen, —$C_{1-10}$ alkyl, —$C_{2-10}$ alkenyl, —$C_{3-6}$cycloalkyl, —$C_{3-6}$cycloalkyl-$C_{1-10}$alkyl-, —$C_{2-5}$cycloheteroalkyl, —$C_{2-5}$cycloheteroalkyl-$C_{1-10}$ alkyl-, aryl, heteroaryl, aryl-$C_{1-10}$ alkyl-, and heteroaryl-$C_{1-10}$ alkyl-, wherein each $R^d$ is unsubstituted or substituted with one to three substituents independently selected from $R^f$. In a class of this embodiment, $R^d$ is independently selected from the group consisting of: hydrogen, —$C_{1-10}$alkyl, —$C_{2-10}$ alkenyl, —$C_{3-6}$cycloalkyl, —$C_{2-5}$cycloheteroalkyl, aryl, and heteroaryl, wherein each $R^d$ is unsubstituted or substituted with one to three substituents independently selected from $R^f$. In another class of this embodiment, $R^d$ is independently selected from the group consisting of: hydrogen, —$C_{1-10}$alkyl, and —$C_{2-10}$ alkenyl, wherein each $R^d$ is unsubstituted or substituted with one to three substituents independently selected from $R^f$.

In another embodiment of the present invention, each $R^e$ is independently selected from the group consisting of: hydrogen, —$C_{1-10}$alkyl, —$C_{2-10}$ alkenyl, —$C_{3-6}$cycloalkyl, —$C_{3-6}$ cycloalkyl-$C_{1-10}$alkyl-, -cycloheteroalkyl, cyclohetroalkyl-$C_{1-10}$alkyl-, aryl, heteroaryl, aryl-$C_{1-10}$ alkyl-, and heteroaryl-$C_{1-10}$ alkyl-, wherein each $R^e$ is unsubstituted or substituted with one to three substituents selected from $R^h$. In a class of this embodiment, each $R^e$ is independently selected from the group consisting of: hydrogen, —$C_{1-10}$alkyl, —$C_{2-10}$ alkenyl, —$C_{3-6}$cycloalkyl, -cycloheteroalkyl, aryl, heteroaryl, wherein each $R^e$ is unsubstituted or substituted with one to three substituents selected from $R^h$. In another class of this embodiment, each $R^e$ is independently selected from the group consisting of: hydrogen, —$C_{1-10}$alkyl, and —$C_{2-10}$ alkenyl, wherein each $R^e$ is unsubstituted or substituted with one to three substituents selected from $R^h$. In another class of this embodiment, each $R^e$ is independently selected from the group consisting of: hydrogen, and —$C_{1-10}$alkyl, wherein each $R^e$ is unsubstituted or substituted with one to three substituents selected from $R^h$. In another class of this embodiment, each $R^e$ is —$C_{1-10}$alkyl, wherein each $R^e$ is unsubstituted or substituted with one to three substituents selected from $R^h$. In another class of this embodiment, each $R^e$ is —$C_{1-10}$alkyl. In another class of this embodiment, each $R^e$ is hydrogen.

In another embodiment of the present invention, each $R^f$ is selected from the group consisting of: halogen, —$C_{1-10}$alkyl, —OH, —O—$C_{1-4}$alkyl, —$S(O)_m$—$C_{1-4}$alkyl, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In a class of this embodiment, each $R^f$ is selected from the group consisting of: halogen, —$C_{1-10}$ alkyl, —OH, —O—$C_{1-4}$alkyl, —CN, —$CF_3$, —$OCHF_2$, and —$OCF_3$, wherein each $C_{1-10}$alkyl is unsubstituted or substituted with one to three substituents independently selected from: —OH, halogen, cyano, and —$S(O)_2CH_3$. In another class of this embodiment, each $R^f$ is selected from the group consisting of: halogen, —$C_{1-10}$alkyl, —OH, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In another class of this embodiment, each $R^f$ is selected from the group consisting of: halogen, and —$C_{1-10}$alkyl, wherein each $C_{1-10}$ alkyl is unsubstituted or substituted with one to three substituents independently selected from: —OH, halogen, cyano, and —$S(O)_2CH_3$.

In another embodiment of the present invention, each $R^g$ is selected from the group consisting of: hydrogen, —C(O)$R^e$, and —$C_{1-10}$alkyl, wherein —$C_{1-10}$ alkyl is unsubstituted or substituted with one to five fluorines.

In another embodiment of the present invention, each $R^h$ is selected from the group consisting of: halogen, —$C_{1-10}$alkyl, —OH, —O—$C_{1-4}$alkyl, —$S(O)_m$—$C_{1-4}$alkyl, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In a class of this embodiment, each $R^h$ is selected from the group consisting of: halogen, —$C_{1-10}$alkyl, —OH, —O—$C_{1-4}$alkyl, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In another class of this embodiment, each $R^h$ is selected from the group consisting of: halogen, —$C_{1-10}$alkyl, —OH, —CN, —$CF_3$, —$OCHF_2$, and —$OCF_3$, wherein each $C_{1-10}$ alkyl is unsubstituted or substituted with one to three substituents independently selected from: —OH, halogen, cyano, and —$S(O)_2CH_3$. In another class of this embodiment, each $R^h$ is selected from the group consisting of: halogen, and —$C_{1-10}$alkyl, wherein each $C_{1-10}$ alkyl is unsubstituted or substituted with one to three substituents independently selected from: —OH, halogen, cyano, and —$S(O)_2CH_3$.

In another embodiment of the present invention, $R^i$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl. In a class of this embodiment, $R^i$ is selected from the group consisting of: —$C_{1-6}$alkyl, halogen, —$OR^e$, —$NR^cR^d$, —$C(O)R^e$, —$OC(O)R^e$, —$CO_2R^e$, —CN, —$CF_3$, —$OCF_3$, and —$OCHF_2$. In another class of this embodiment, $R^i$ is selected from the group consisting of: —$C_{1-6}$alkyl, halogen, —CN, —$CF_3$, —$OCF_3$, and —$OCHF_2$. In another class of this embodiment, $R^i$ is —$CF_3$.

In another embodiment of the present invention, $R^j$ is independently selected from the group consisting of: —$C_{1-6}$alkyl, —$OR^e$, —$NR^cS(O)_mR^e$, halogen, —$S(O)_mR^e$, —$S(O)_mNR^cR^d$, —$NR^cR^d$, —$C(O)R^e$, —$OC(O)R^e$, —$CO_2R^e$, —CN, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{3-6}$cycloalkyl, and —$C_{2-5}$cycloheteroalkyl. In a class of this embodiment, $R^j$ is selected from the group consisting of: —$C_{1-6}$alkyl, halogen, —$OR^e$, —$NR^cR^d$, —$C(O)R^e$, —$OC(O)R^e$, —$CO_2R^e$, —CN, —$CF_3$, —$OCF_3$, and —$OCHF_2$. In another class of this embodiment, $R^j$ is selected from the group consisting of: —$C_{1-6}$alkyl, halogen, —CN, —$CF_3$, —$OCF_3$, and —$OCHF_2$. In another class of this embodiment, $R^j$ is —$CF_3$.

In another embodiment of the present invention, each $R^k$ is independently selected from the group consisting of: halogen, —$C_{1-10}$ alkyl, —OH, oxo, halogen, —O—$C_{1-4}$ alkyl, —$SO_2$—$C_{1-6}$ alkyl, —$C_{1-6}$ alkyl-$SO_2C_{1-6}$ alkyl, —CN, —$CF_3$, —$OCHF_2$, —$OCF_3$, —$NH_2$, —$NHSO_2C_{1-6}$ alkyl, —$NHCOC_{1-6}$alkyl, =$N(OCH_3)$, —$P(O)(OH)_2$, and —$P(O)(OC_{1-6}$alkyl$)_2$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: —$C_{1-10}$alkyl, —O—$C_{1-4}$ alkyl, —OH, halogen, —$SO_2$—$C_{1-6}$ alkyl, —$C_{1-6}$ alkyl-$SO_2C_{1-6}$ alkyl, —CN, —$NHSO_2C_{1-6}$ alkyl, and =$N(OCH_3)$, and —$P(O)(OC_{1-6}$alkyl$)_2$, wherein each $C_{1-10}$ alkyl is unsubstituted or substituted with one to three substituents independently selected from: —OH, —$OC_{1-6}$alkyl, halogen, cyano, and —$S(O)_2C_{1-6}$ alkyl; or a pharmaceutically acceptable salt thereof. In a subclass of this class, each $R^k$ is independently selected from the group consisting of: —$CH_3$, —$CH_2OH$, —OH, F, —$SO_2CH_3$, —$CH_2SO_2CH_3$, CN and —$P(O)(OCH_3)_2$, wherein each —$CH_3$ is unsubstituted or substituted with one to three substituents independently selected from: —OH, —$OC_{1-6}$alkyl, halogen, cyano, and —$S(O)_2C_{1-6}$alkyl. In another subclass of this class, each $R^k$ is independently selected from the group consisting of: —$CH_3$, —$CH_2OH$, —OH, F, —$SO_2CH_3$, —$CH_2SO_2CH_3$, CN and —$P(O)(OCH_3)_2$, wherein each —$CH_3$ is unsubstituted or substituted with one to three —OH. In another subclass of this class, each $R^k$ is independently selected from the group consisting of: —$CH_3$, —$CH_2OH$, —OH, F, —$SO_2CH_3$, —$CH_2SO_2CH_3$ and —$P(O)(OCH_3)_2$, In another embodiment of the present invention, each $R^k$ is independently selected from the group consisting of: halogen, —$C_{1-10}$ alkyl, —OH, oxo, halogen, —O—$C_{1-4}$ alkyl, —$SO_2$—$C_{1-6}$ alkyl, —$C_{1-6}$ alkyl-$SO_2C_{1-6}$alkyl, —CN, —$CF_3$, —$OCHF_2$, —$OCF_3$, —$NH_2$, —$NHSO_2C_{1-6}$alkyl, —$NHCOC_{1-6}$alkyl, and =$N(OCH_3)$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: —$C_{1-10}$ alkyl, —OH, halogen, —$SO_2$—$C_{1-6}$ alkyl, —$C_{1-6}$ alkyl-$SO_2C_{1-6}$alkyl, —CN, —$NH_2$, —$NHSO_2C_{1-6}$ alkyl, —$NHCOC_{1-6}$ alkyl, and =$N(OCH_3)$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl. In another class of this embodiment, each $R^k$ is independently selected from the group consisting of: —$C_{1-10}$ alkyl, —OH, halogen, —$SO_2$—$C_{1-6}$ alkyl, —$C_{1-6}$ alkyl-$SO_2C_{1-6}$alkyl, —CN, —$NHSO_2C_{1-6}$alkyl, and =$N(OCH_3)$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl. In another class of this embodiment, each $R^k$ is independently selected from the group consisting of: —$C_{1-10}$ alkyl, —OH, halogen, —$SO_2$—$C_{1-6}$ alkyl, —$C_{1-6}$ alkyl-$SO_2C_{1-6}$ alkyl, and —CN, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl. In a subclass of this class, each $R^k$ is independently selected from the group consisting of: —$CH_3$, —$CH_2OH$, —OH, F, —$SO_2CH_3$, —$CH_2SO_2CH_3$, and CN, wherein each —$CH_3$ is unsubstituted or substituted with one to three substituents independently selected from: —OH, —$OC_{1-6}$alkyl, halogen, cyano, and —$S(O)_2C_{1-6}$alkyl. In another subclass of this class, each $R^k$ is independently selected from the group consisting of: —$CH_3$, —$CH_2OH$, —OH, F, —$SO_2CH_3$, —$CH_2SO_2CH_3$, and CN, wherein each —$CH_3$ is unsubstituted or substituted with one to three —OH. In another subclass of this class, each $R^k$ is independently selected from the group consisting of: —$CH_3$, —$CH_2OH$, —OH, F, —$SO_2CH_3$, —$CH_2SO_2CH_3$.

In another embodiment of the present invention, each $R^k$ is independently selected from the group consisting of: —$C_{1-10}$alkyl, —O—$C_{1-4}$ alkyl, —OH, halogen, —$SO_2$—$C_{1-6}$ alkyl, —$C_{1-6}$ alkyl-$SO_2C_{1-6}$alkyl, —CN, —$NHSO_2C_{1-6}$alkyl, and =$N(OCH_3)$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl, or a pharmaceutically acceptable salt thereof. In a class of this embodiment, each $R^k$ is independently selected from the group consisting of: —$CH_3$, $OCH_3$, —$CH_2OH$, —OH, F, —$SO_2CH_3$, —$CH_2SO_2CH_3$, and CN, wherein each —$CH_3$ is unsubstituted or substituted with one to three —OH.

In another embodiment of the present invention, each $R^k$ is independently selected from the group consisting of: halogen, —$C_{1-10}$ alkyl, —OH, oxo, halogen, —O—$C_{1-4}$ alkyl, —$SO_2$—$C_{1-6}$ alkyl, —$C_{1-6}$ alkyl-$SO_2C_{1-6}$alkyl, —CN, —$CF_3$, —$OCHF_2$, —$OCF_3$, —$NH_2$, —$NHSO_2C_{1-6}$alkyl, —$NHCOC_{1-6}$ alkyl, =$N(OCH_3)$, —$P(O)(OH)_2$, and —$P(O)(OC_{1-6}$alkyl$)_2$, wherein each $C_{1-6}$ alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: —$C_{1-10}$alkyl, —O—$C_{1-4}$ alkyl, —OH, halogen, —$SO_2$—$C_{1-6}$ alkyl, —$C_{1-6}$ alkyl-$SO_2C_{1-6}$ alkyl, —CN, —$NHSO_2C_{1-6}$ alkyl, and =$N(OCH_3)$, and —$P(O)(OC_{1-6}$alkyl$)_2$, wherein each $C_{1-6}$ alkyl is unsubstituted or substituted with one to three substituents independently selected from: —OH, —$OC_{1-6}$alkyl, halogen, cyano, and —$S(O)_2C_{1-6}$ alkyl.

In another embodiment of the present invention, each $R^k$ is independently selected from the group consisting of: halogen, —$C_{1-10}$ alkyl, —OH, oxo, halogen, —O—$C_{1-4}$ alkyl, —$SO_2$—$C_{1-6}$ alkyl, —$C_{1-6}$ alkyl-$SO_2C_{1-6}$alkyl, —CN, —$CF_3$, —$OCHF_2$, —$OCF_3$, —$NH_2$, —$NHSO_2C_{1-6}$alkyl, —$NHCOC_{1-6}$ alkyl, and =$N(OCH_3)$, wherein each $C_{1-6}$ alkyl is unsubstituted or substituted with one to three substituents independently selected from: —OH, —$OC_{1-6}$alkyl, halogen, cyano, and —$S(O)_2C_{1-6}$alkyl. In a class of this embodiment, each $R^k$ is independently selected from the group consisting of: —$C_{1-10}$alkyl, —OH, halogen, —$SO_2$—$C_{1-6}$ alkyl, —$C_{1-6}$ alkyl-$SO_2C_{1-6}$alkyl, —CN, —$NH_2$, —$NHSO_2C_{1-6}$ alkyl, —$NHCOC_{1-6}$ alkyl, and =$N(OCH_3)$, wherein each $C_{1-6}$ alkyl is unsubstituted or substituted with one to three substituents independently selected from: —OH, —$OC_{1-6}$ alkyl, halogen, cyano, and —$S(O)_2C_{1-6}$alkyl. In another class of this embodiment, each $R^k$ is independently selected from the group consisting of: —$C_{1-10}$ alkyl, —OH, halogen, —$SO_2$—$C_{1-6}$ alkyl, —$C_{1-6}$ alkyl-$SO_2C_{1-6}$ alkyl, —CN, —$NHSO_2C_{1-6}$ alkyl, and =N(OCH₃), wherein each $C_{1-6}$ alkyl is unsubstituted or substituted with one to three substituents independently selected from: —OH, —OC$_{1-6}$alkyl, halogen, cyano, and —S(O)$_2$C$_{1-6}$alkyl. In another class of this embodiment, each $R^k$ is independently selected from the group consisting of: —C$_{1-10}$ alkyl, —OH, halogen, —SO$_2$—C$_{1-6}$ alkyl, —C$_{1-6}$ alkyl-SO$_2$C$_{1-6}$ alkyl, and —CN, wherein each C$_{1-6}$ alkyl is unsubstituted or substituted with one to three substituents independently selected from: —OH, —OC$_{1-6}$ alkyl, halogen, cyano, and —S(O)$_2$C$_{1-6}$alkyl.

In another embodiment of the present invention, each $R^k$ is independently selected from the group consisting of: —SO$_2$—C$_{1-6}$ alkyl, and —C$_{1-6}$ alkyl-SO$_2$C$_{1-6}$alkyl, wherein each C$_{1-6}$ alkyl is unsubstituted or substituted with one to three substituents independently selected from: —OH, —OC$_{1-6}$alkyl, halogen, cyano, and —S(O)$_2$C$_{1-6}$alkyl. In a class of this embodiment, each $R^k$ is independently selected from the group consisting of: —SO$_2$CH$_3$, and —CH$_2$SO$_2$CH$_3$, wherein each —CH$_3$ is unsubstituted or substituted with one to three —OH. In another class of this embodiment, each $R^k$ is independently selected from the group consisting of: —SO$_2$CH$_3$, and —CH$_2$SO$_2$CH$_3$.

In another embodiment of the present invention, $R^L$ is selected from the group consisting of: —C$_{1-6}$alkyl, halogen, —OR$^e$, —NR$^c$S(O)$_m$R$^e$, —S(O)$_m$R$^e$, —S(O)$_m$NR$^c$R$^d$, —NR$^c$R$^d$, —C(O)R$^e$, —OC(O)R$^e$, —CO$_2$R$^e$, —CN, —C(O)NR$^c$R$^d$, —NR$^c$C(O)R$^e$, —NR$^c$C(O)OR$^e$, —NR$^c$C(O)NR$^c$R$^d$, —CF$_3$, —OCF$_3$, —OCHF$_2$, —C$_{3-6}$cycloalkyl, and C$_{2-5}$cycloheteroalkyl. In a class of this embodiment, $R^L$ is selected from the group consisting of: —C$_{1-6}$alkyl, halogen, —OR$^e$, —NR$^c$R$^d$, —C(O)R$^e$, —OC(O)R$^e$, —CO$_2$R$^e$, —CN, —CF$_3$, —OCF$_3$, and OCHF$_2$. In another class of this embodiment, $R^L$ is selected from the group consisting of: —C$_{1-6}$alkyl, halogen, —CN, —CF$_3$, —OCF$_3$, and OCHF$_2$. In another class of this embodiment, $R^L$ is —CF$_3$.

In another embodiment of the present invention, n is 0, 1, 2, 3 or 4. In a class of this embodiment, n is 0, 1, 2 or 3. In another class of this embodiment, n is 0, 1 or 2. In a class of this embodiment, n is 0 or 1. In a class of this embodiment, n is 1, 2, 3 or 4. In another class of this embodiment, n is 1, 2 or 3. In another class of this embodiment, n is 1 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, p is 0, 1, 2, 3, 4, 5, 6, 7, 8, 9 or 10. In another embodiment of the present invention, p is 0, 1, 2, 3, 4, 5, 6, 7 or 8. In another embodiment of the present invention, p is 0, 1, 2, 3, 4, 5 or 6. In another embodiment of the present invention, p is 0, 1, 2, 3 or 4. a class of this embodiment, p is 0, 1, 2 or 3. In a class of this embodiment, p is 0, 1 or 2. In another embodiment of the present invention, p is 1, 2, 3, 4, 5, 6, 7, 8, 9 or 10. In another embodiment of the present invention, p is 1, 2, 3, 4, 5, 6, 7 or 8. In another embodiment of the present invention, p is 1, 2, 3, 4, 5 or 6. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6. In another class of this embodiment, p is 7. In another class of this embodiment, p is 8. In another class of this embodiment, p is 9. In another class of this embodiment, p is 10.

In another embodiment of the present invention, the invention relates to compounds of structural formula Ia:

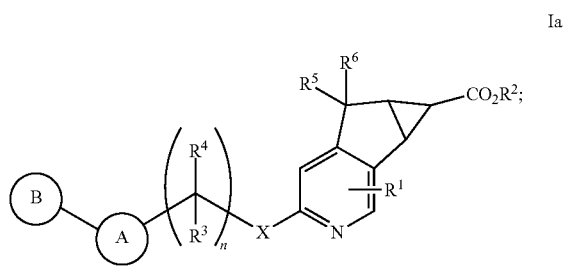

or a pharmaceutically acceptable salt thereof.

In another embodiment of the present invention, the invention relates to compounds of structural formula Ib:

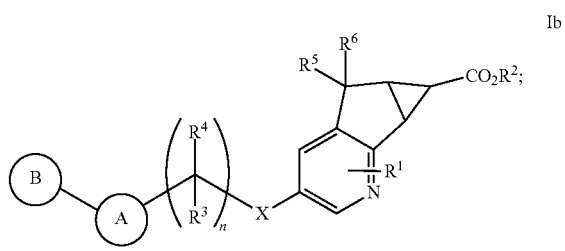

or a pharmaceutically acceptable salt thereof

In another embodiment of the present invention, the invention relates to compounds of structural formula Ic:

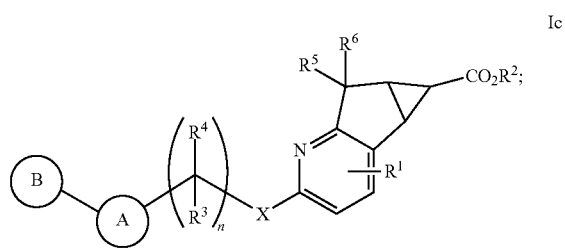

or a pharmaceutically acceptable salt thereof

In another embodiment of the present invention, the invention relates to compounds of structural formula Id:

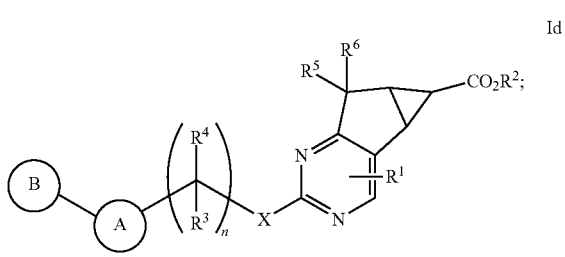

or a pharmaceutically acceptable salt thereof.

In another embodiment of the present invention, the invention relates to compounds of structural formula Ie:

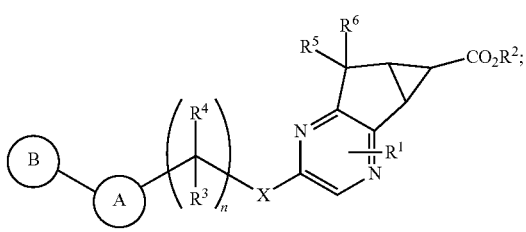

or a pharmaceutically acceptable salt thereof.

In another embodiment of the present invention, the invention relates to compounds of structural formula If:

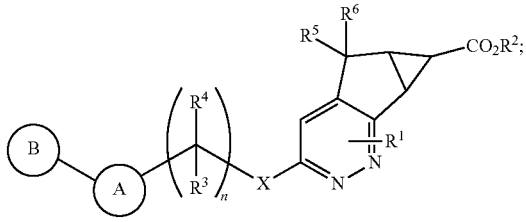

or a pharmaceutically acceptable salt thereof.

The compound of structural formula I, includes the compounds of structural formulas Ia, Ib, Ic, Id, Ie, If and Ig, and pharmaceutically acceptable salts, hydrates and solvates thereof.

Another embodiment of the present invention relates to compounds of structural formula I wherein:

n is 1;
X is oxygen;
T is CH;
U is N;
V is CH;
A is selected from the group consisting of: aryl and heteroaryl, wherein A is unsubstituted or substituted with one to five substituents selected from $R^a$;
B is selected from the group consisting of: aryl and heteroaryl, wherein B is unsubstituted or substituted with one to five substituents selected from $R^b$,
$R^1$, $R^2$, $R^5$ and $R^6$ are hydrogen; and
$R^3$ and $R^4$ are selected from the group consisting of: hydrogen, halogen, and —$C_{1-6}$alkyl, wherein each $C_{1-6}$alkyl is unsubstituted or substituted with one to three substituents selected from $R^L$;
or a pharmaceutically acceptable salt thereof Another embodiment of the present invention relates to compounds of structural formula I wherein:

n is 1;
X is oxygen;
T is CH;
U is N;
V is CH;
A is selected from the group consisting of: phenyl and pyridine, wherein A is unsubstituted or substituted with one to five substituents selected from $R^a$;
B is selected from the group consisting of phenyl, pyridine, pyrimidine, thiazole, benzimidazole, benzthiazole, benzoxazole, and benzisoxazole, wherein B is unsubstituted or substituted with one to five substituents selected from $R^b$;
$R^1$, $R^2$, $R^3$, $R^4$, $R^5$ and $R^6$ are hydrogen;
$R^a$ is selected from the group consisting of: —$C_{1-6}$alkyl, halogen, and —$CF_3$;
$R^b$ is independently selected from the group consisting of:
(1) —$C_{1-10}$alkyl,
(2) halogen,
(3) —OH,
(4) —$OC_{1-10}$alkyl,
(5) —$O(CH_2)pOC_{1-10}$alkyl,
(6) —$O(CH_2)pC_{3-6}$cycloalkyl,
(7) —$O(CH_2)pC_{2-10}$cycloheteroalkyl,
(8) —$O(CH_2)pO$—$C_{3-6}$cycloalkyl,
(9) —$O(CH_2)pO$—$C_{2-10}$cycloheteroalkyl,
(10) —$CF_3$,
(11) —$OCF_3$,
(12) —$OCHF_2$,
(13) $(CH_2)p$-$C_{2-10}$cycloheteroalkyl, and
(14) —$S(O)_2C_{1-10}$alkyl,
wherein each $R^b$ is unsubstituted or substituted with one to five substituents selected from $R^k$; and
each $R^k$ is independently selected from the group consisting of:
(1) —$C_{1-10}$alkyl,
(2) —O—$C_{1-4}$alkyl,
(3) —OH,
(4) halogen,
(5) —$SO_2$—$C_{1-6}$alkyl,
(6) —$C_{1-6}$ alkyl-$SO_2C_{1-6}$ alkyl,
(7) —CN,
(8) —$NHSO_2C_{1-6}$ alkyl,
(9) =$N(OCH_3)$, and
(10) —$P(O)(OC_{1-6}$alkyl$)_2$,
wherein each $C_{1-10}$alkyl is unsubstituted or substituted with one to three substituents independently selected from: —OH, —$OC_{1-6}$ alkyl, halogen, cyano, and —$S(O)_2C_{1-6}$ alkyl;
or a pharmaceutically acceptable salt thereof.

Another embodiment of the present invention relates to compounds of structural formula I wherein:

n is 1;
X is oxygen;
T is CH;
U is N;
V is CH;
A is phenyl, wherein phenyl is unsubstituted or substituted with one to five substituents selected from $R^a$;
B is selected from the group consisting of phenyl, and pyridine, wherein B is unsubstituted or substituted with one to five substituents selected from $R^b$;
$R^1$, $R^2$, $R^3$, $R^4$, $R^5$ and $R^6$ are hydrogen;
$R^a$ is selected from the group consisting of: —$C_{1-6}$alkyl, halogen, and —$CF_3$;
$R^b$ is independently selected from the group consisting of:
(1) —$C_{1-10}$alkyl,
(2) halogen,
(3) —OH,
(4) —$OC_{1-10}$alkyl,
(5) —$O(CH_2)pC_{2-10}$cycloheteroalkyl,
(6) —$CF_3$, and
(7) —$(CH_2)p$-$C_{2-10}$cycloheteroalkyl,
wherein each $R^b$ is unsubstituted or substituted with one to five substituents selected from $R^k$; and each $R^k$ is independently selected from the group consisting of:
- (1) —$C_{1-10}$ alkyl,
- (2) —OH,
- (3) halogen,
- (4) —$SO_2$—$C_{1-6}$ alkyl,
- (5) —$C_{1-6}$ alkyl-$SO_2C_{1-6}$ alkyl, and
- (6) —CN, wherein each $C_{1-10}$alkyl is unsubstituted or substituted with one to three substituents independently selected from: —OH, —$OC_{1-6}$ alkyl, halogen, cyano, and —$S(O)_2C_{1-6}$ alkyl; or a pharmaceutically acceptable salt thereof.

Illustrative, but non-limiting, examples of the compounds of the present invention that are useful as agonists of G-protein-coupled receptor 40 (GPR40) are the following compounds:

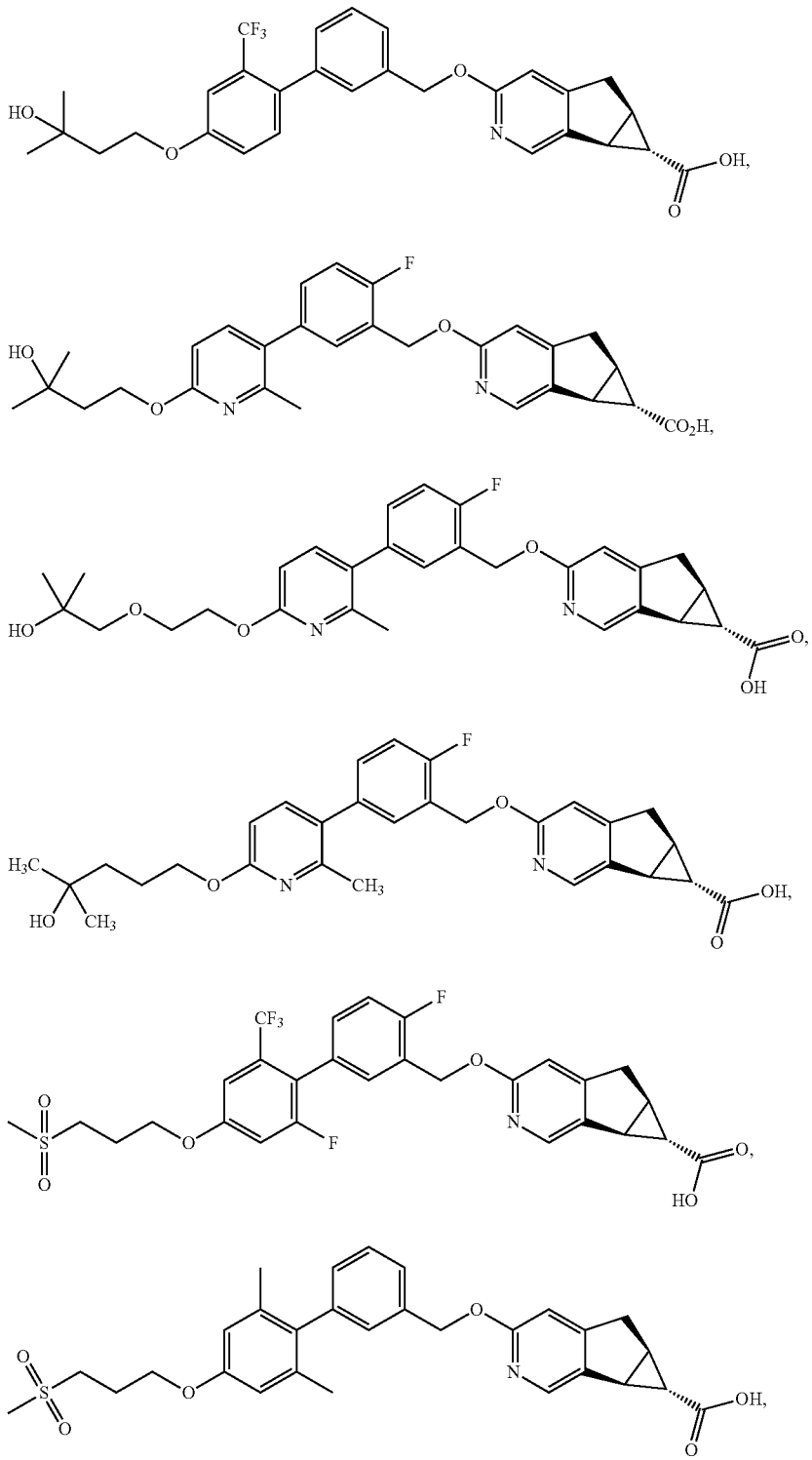

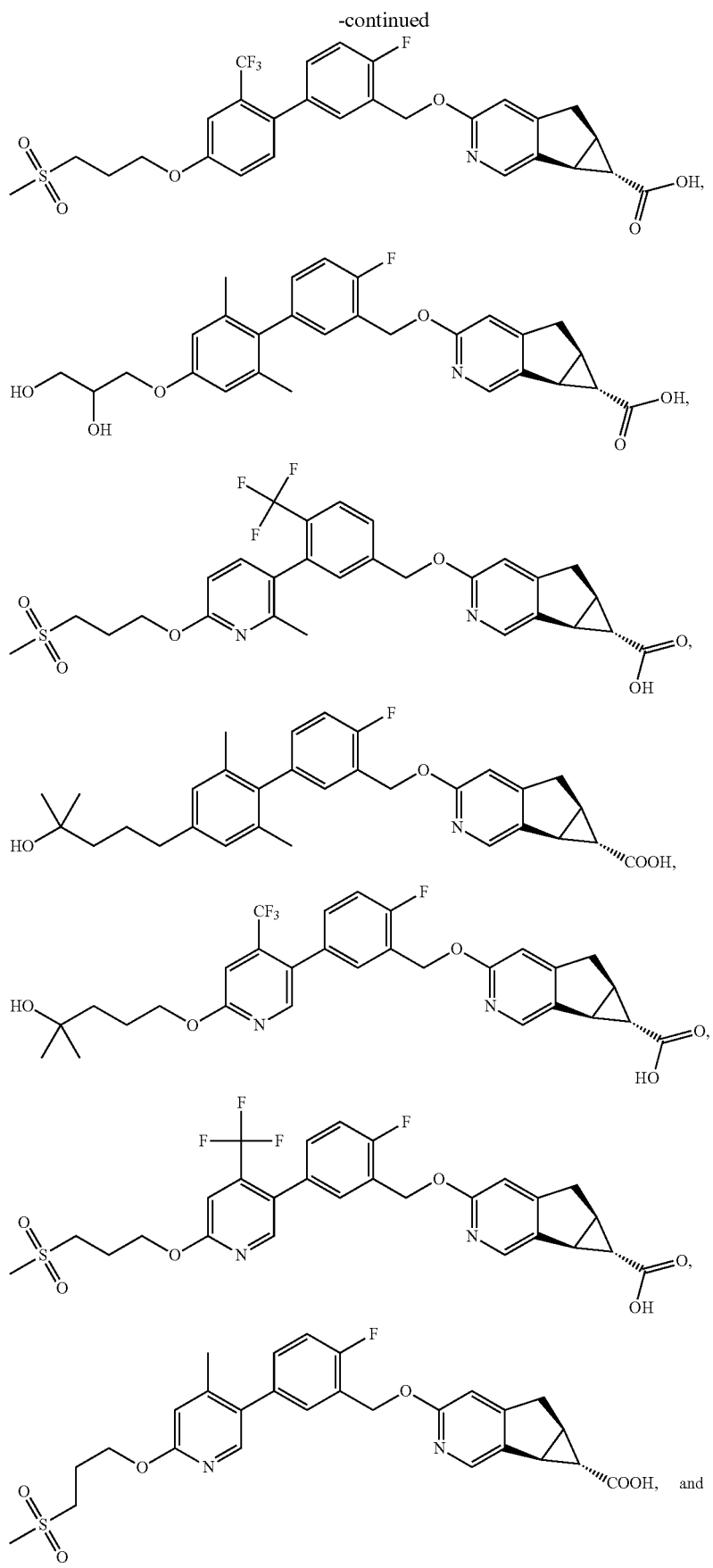

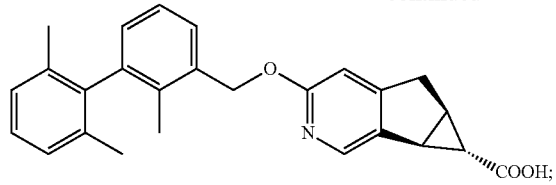

and pharmaceutically acceptable salts thereof.

In one embodiment of the present invention, the compounds of formula I have the absolute stereochemistry at the two stereogenic carbon centers as indicated in the compound of structural formula Ig:

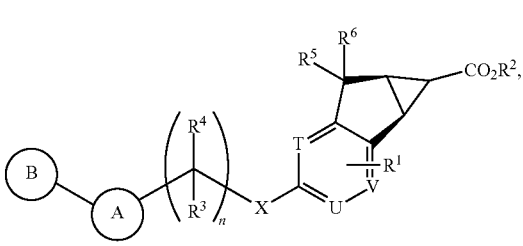

and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

DEFINITIONS

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropane, cyclobutane and cyclohexane.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated or partly unsaturated non-aromatic monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran, hexose, pentose, isosorbide and isomannide, dianhydromannitol, 1,4:3,6-dianhydromannitol, 1,4:3,6-dianhydro[D]mannitol, hexahydrofuro[3,2-b]furan, and 2,3,3a,5,6,6a-hexahydrofuro[3,2-b]furan. In one embodiment of the present invention, cycloheteroalkyl is selected from: hexose, pentose, isosorbide and isomannide. In another embodiment of the present invention, cycloheteroalkyl is selected from: isosorbide and isomannide. In another embodiment of the present invention, cycloheteroalkyl is selected from: oxetane, tetrahydropyran, azetidine, tetrahydrothiopyran and pyrrolidine. In another embodiment of the present invention cycloheteroalkyl is selected from: oxetane, -piperazine, azetidine, pyrrolidine, morpholine and spiro(indene-1,4-piperidine). In another embodiment of the present invention cycloheteroalkyl is oxetane.

"Cycloheteroalkenyl" means a nonaromatic monocyclic, bicyclic or bridged carbocyclic ring or ring system containing at least one double bond and containing at least one heteroatom selected from N, NH, S and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b) pyridyl, quinolyl, indolyl, isoquinolyl, quinazolinyl, dibenzofuranyl, and the like. In one embodiment of the present invention, heteroaryl is selected from: pyridine, pyrimidine, thiazole, benzimidazole, benzthiazole, benzoxazole, and benzisoxazole. In another embodiment of the present invention, heteroaryl is pyridine. In another embodiment of the present invention, heteroaryl is imidazopyridine.

"Halogen" includes fluorine, chlorine, bromine and iodine.

"Me" represents methyl.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$alkylcarbonylamino $C_{1-6}$alkyl substituent is equivalent to:

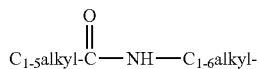

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases:

(1) non-insulin dependent diabetes mellitus (Type 2 diabetes);
(2) hyperglycemia;
(3) insulin resistance;
(4) Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapo-B-liproteinemia; and
(12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with Type 2 diabetes;
(2) Metabolic Syndrome;
(3) obesity; and
(4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The compounds of the present invention in which at least one of T, U and V is N or N-oxide, such as compounds A-1, A-2, A-3 and A-4 in Table A, have the unexpected benefit of increased intrinsic potency (2-20 fold) in the GPR40 Inositol Phosphate Turnover (IP1) Assay (+/−100% human serum) compared to the compounds in which T is CH, U is CH and V is CH, such as compounds B-1, B-2, B-3 and B-4 in Table A. Due to their increased potency in this assay, the compounds of the present invention are expected to exhibit glucose lowering efficacy at reduced plasma exposures, and can require a lower dose.

The compounds of the present invention, such as compounds A-1 and A-3 in Table A, also have the unexpected benefit of decreased binding (5-10-fold) to the ion channel, Kv11.1 compared to the compounds in which T is CH, U is CH and V is CH, such as compounds B-1 and B-3 in Table A. This ion channel, also called the hERG channel, is implicated in sometimes fatal cardiac arrythymias (QTc interval prolongation). This decreased off-target ion channel binding to ion channel Kv11.1, taken together with increased on-target GPR40 activity, results in the compounds of the present invention having an unexpected benefit of 20-100-fold improved selectivity, due to incorporating a single nitrogen atom into the molecule.

Additionally, the compounds of the present invention in which at least one of T, U and V is N or N-oxide, such as compounds A-1, A-2, A-3 and A-4 in Table A, have the unexpected benefit of greater solubility (2-5 fold) in aqueous media, such as Phosphate Buffered Saline (PBS) solution at pH 7, and/or biorelevant media, such as FaSSIF (Fasted State Simulated Intestinal Fluid) at pH 7, compared to the compounds in which T is CH, U is CH and V is CH, such as compounds B-1, B-2, B-3 and B-4 in Table A. Greater solubility in aqueous media and/or FaSSIF can result in the use of conventional formulation and formulation methods. Greater solubility can also improve exposure which can lead to a lower dose.

TABLE A

| Compound | Structure | Human GPR40 IP1, EC50, nM | | Kv11.1 ion channel (hERG) Ki, nM | Solubility pH 7, PBS μM |
| --- | --- | --- | --- | --- | --- |
| | | +0% human serum | +100% human serum | | |
| A-1 | 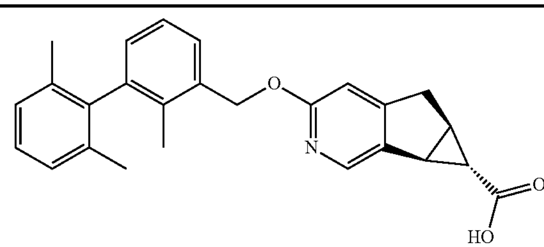 | 6 | 81 | 40,000 | 73 |
| B-1 | 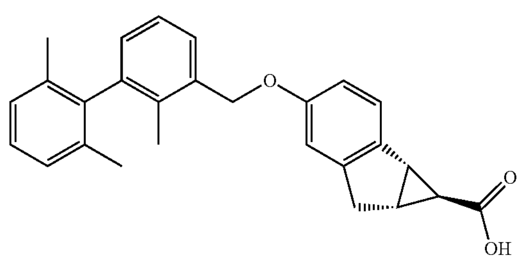 [SMILES: Cc1cccc(C)c1-c1cccc(COc2ccc3c(c2)C[C@H]2[C@H](C(=O)O)[C@@H]32)c1C] | 69 | 322 | 6000 | 56 |
| A-2 | 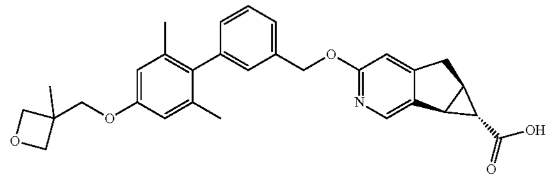 [SMILES: Cc1cc(OCC2(C)COC2)cc(C)c1-c1cccc(COc2cc3c(cn2)[C@H]2[C@@H](C3)[C@@H]2C(=O)O)c1] | 18 | 199 | Nd | 118 |
| B-2 | 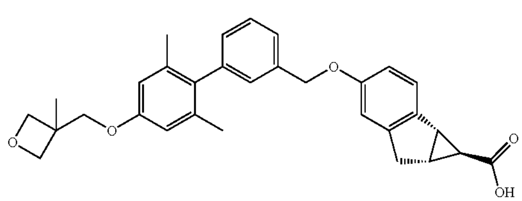 [SMILES: Cc1cc(OCC2(C)COC2)cc(C)c1-c1cccc(COc2ccc3c(c2)C[C@H]2[C@H](C(=O)O)[C@@H]32)c1] | 70 | 816 | 8600 | 21 |

TABLE A-continued

| Compound | Structure | Human GPR40 IP1, EC50, nM | | Kv11.1 ion channel (hERG) Ki, nM | Solubility pH 7, PBS μM |
|---|---|---|---|---|---|
| | | +0% human serum | +100% human serum | | |
| A-3 | 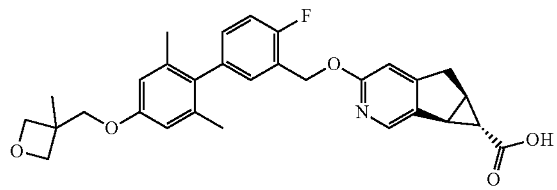 [SMILES: Cc1cc(OCC2(C)COC2)cc(C)c1-c1ccc(F)c(COc2cc3c(cn2)[C@H]2[C@@H](C3)[C@@H]2C(=O)O)c1] | 9 | 81 | 40,200 | 107 |
| B-3 | 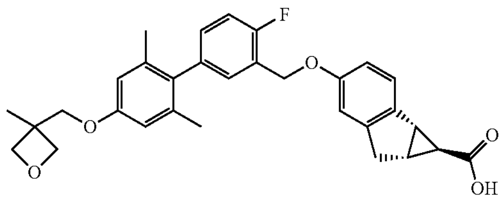 [SMILES: Cc1cc(OCC2(C)COC2)cc(C)c1-c1ccc(F)c(COc2ccc3c(c2)C[C@H]2[C@H](C(=O)O)[C@@H]32)c1] | 31 | 286 | 7800 | 49 |
| A-4 | 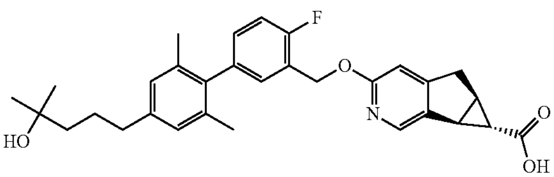 [SMILES: Cc1cc(CCCC(C)(C)O)cc(C)c1-c1ccc(F)c(COc2cc3c(cn2)[C@H]2[C@@H](C3)[C@@H]2C(=O)O)c1] | 5 | 124 | 7,500 | 143 |
| B-4 | 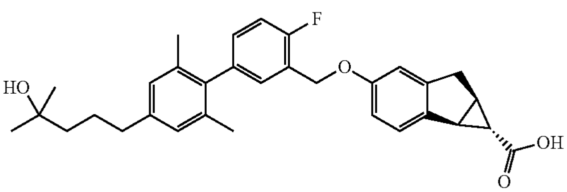 [SMILES: Cc1cc(CCCC(C)(C)O)cc(C)c1-c1ccc(F)c(COc2ccc3c(c2)C[C@H]2[C@H](C(=O)O)[C@@H]32)c1] | 100 | 348 | Nd | 66 |

Nd = not determined/not tested

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Additionally, in the treatment or prevention of conditions which require agonism of GPR40 receptor activity, an appropriate dosage level will generally be about 0.01 to 500 mg per kg patient body weight per week, which can be administered in single or multiple doses. Preferably, the dosage level will be about 0.1 to about 250 mg/kg per week; more preferably about 0.5 to about 100 mg/kg per week. A suitable dosage level may be about 0.01 to 250 mg/kg per week, about 0.05 to 100 mg/kg per week, or about 0.1 to 50 mg/kg per week. Within this range the dosage may be 0.05 to 0.5, 0.5 to 5 or 5 to 50 mg/kg per week. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may also be administered on a regimen of 1 to 4 times per week, preferably once or twice per week.

When treating or preventing diabetes mellitus and/or hyperglycemia or hypertriglyceridemia or other diseases for which compounds of the present invention are indicated, generally satisfactory results are obtained when the compounds of the present invention are administered at a weekly dosage of from about 0.1 mg to about 100 mg per kilogram of animal body weight, preferably given as a single weekly dose or in divided doses two to six times a week, or in sustained release form. For most large mammals, the total weekly dosage is from about 1.0 mg to about 1000 mg, preferably from about 1 mg to about 50 mg. In the case of a 70 kg adult human, the total weekly dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered separately or in the same pharmaceutical composition in combination with a compound of the formulas described herein include, but are not limited to:

(1) other dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS 1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACCT or ACC2);

(20) AMP-activated Protein Kinase (AMPK) activators, such as MB1055, ETC1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-lb antibodies, (e.g., XOMA052 and canakinumab);

(36) bromocriptine mesylate and rapid-release formulations thereof;

(37) GPR 120 agonists (such as KDT501.

Other suitable active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3)

protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methyl butoxy)-2-methylpyridine-3-yl]-2,3-dihydro-1H-indene-1-yl]oxy]phenyl]isothiazole-3-ol 1-oxide, 5-(4-((3-(2,6-di methyl-4-(3-(methyl sulfonyl)propoxy)phenyl)phenyl) methoxy)phenyl)iso, 5-(4-((3-(2-methyl-6-(3-hydroxypropoxy)pyridine-3-yl)-2-methyl phenyl)methoxy)phenyl) isothiazole-3-ol 1-oxide, and 5-[4-[[3-[4-(3-aminopropoxy)-2,6-di methyl phenyl]phenyl]methoxy]phenyl]isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532, 632, BAY63-2149 (Bayer), SC591, SC795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ □agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril, perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663$_1$ as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (*Vernalis*), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436, 272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) P3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 1113 HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TSO21, SSR 162369, GRC8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2- fluoro-2-methylpropyl]azetidin-1-yl}methyl)thiophene-3-carbonitrile, and pharmaceutically acceptable salts thereof as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5 S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5)N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; R067319; R1124; R1204; SSR146977; SSR240600; T-2328; and T2763; or a pharmaceutically acceptable salts thereof.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief. The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

Ac is acetyl; AcO is acetoxy; Alk is alkyl; APCI is atmospheric pressure chemical ionization; aq or aq. is aqueous; Ar is aryl; Boc is tert-butoxycarbonyl; Br is broad; t-BuOK is potassium tert-butoxide; ° C. is degrees celsius; Cbz is benzyloxycarbonyl; $CH_2Cl_2$ is dichloromethane; CO is carbon monoxide; conc or conc. is concentrated; d is doublet; DAST is (diethylamino)sulfur trifluoride; DIAD is diisopropyl azodicarboxylate; DCM is dichloromethane; DIPEA is N,N-diisopropylethylamine; DMAP is 4-dimethylaminopyridine; DMF is N,N-dimethylformamide; DMSO is dimethylsulfoxide; dppf is 1,1'-Bis(diphenyl-phosphino) ferrocene; ESI is electrospray ionization; EA or EtOAc is ethyl acetate; Et is ethyl; EtMgBr is ethyl magnesium bromide; EtOH is ethanol; g is gram(s); h or hr or hrs is hour(s); HPLC is high pressure liquid chromatography; HOAc or AcOH is acetic acid; kg is kilogram(s); KOH ispotassium hydroxide; KOAc is potassium acetate; L is liter; LC-MS is liquid chromatography-mass spectroscopy; LDA is lithium diisopropyl amide; LiOH is lithium hydroxide; m is multiplet; m-CPBA, MCPBA, or mCPBA is meta chloroperbenzoic acid; mL is milliliter; min or mins is minute(s); mol is mole(s); mmol is mmole(s); mg is milligram(s); MeMgBr is methyl magnesium bromide; MeOH is methyl alcohol; $MgSO_4$ is magnesium sulfate; MS is mass spectroscopy; MsCl or Ms-Cl is methane sulfonyl chloride; N is normal; $Na(AcO)_3BH$ is sodium triacetoxy borohydride; NaHMDS is sodium hexamethyldisilazide; NaOH is sodium hydroxide; $Na_2SO_4$ is sodium sulfate; $NH_4OAc$ is ammonium acetate; NBS is N-bromo succinamide; NIS is N-iodo succinamide; NMO is 4-methyl morpholine N-oxide; NMP is 1-methyl-2-pyrrolidinone; NMR is nuclear magnetic resonance spectroscopy; PE is petroleum ether; PG is protecting group; $P(Cy)_3$ is tricyclohexyl phosphine; $Pd_2(dba)_3$ is tris(dibenzylideneacetone)dipalladium(O); $Pd[P(t-Bu)_3]_2$ is bis(tri-tert-butylphosphine)palladium (O); Pd(dppf)$Cl_2$ is [1,1'-bis(diphenylphosphino)ferrocene]dichloropalladium (II); PMB is para-methoxybenzyl; PMBCl is para-methoxybenzyl chloride; prep is preparative; prep. TLC or prep-TLC, or prep TLC is preparative thin layer chromatography; RBF is round bottom flask; RCM is ring closing metathesis reaction; rt or r.t. or RT is room temperature; s is singlet; SFC is supercritical fluid chromatography; s-phos is 2-dicyclohexylphosphino-2',6'-dimethoxybiphenyl; t is triplet; TBTU is N,N,NW-Tetramethyl-O-(benzotriazol-1-yl)uronium tetrafluoroborate; TEA is triethyl amine; THF istetrahydrofuran; $Ti(OiPr)_4$ is titanium isopropoxide; TFA is trifluoroacetic acid; TLC is thin-layer chromatography; TMSCl is trimethyl silyl chloride; TsCl or TosCl is p-toluene sulfonyl chloride; TsOH is p-toluenesulfonic acid, and xphos is 2-Dicyclohexylphosphino-2',4',6'-triisopropylbiphenyl.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention. All temperatures are degrees Celsius unless otherwise noted.

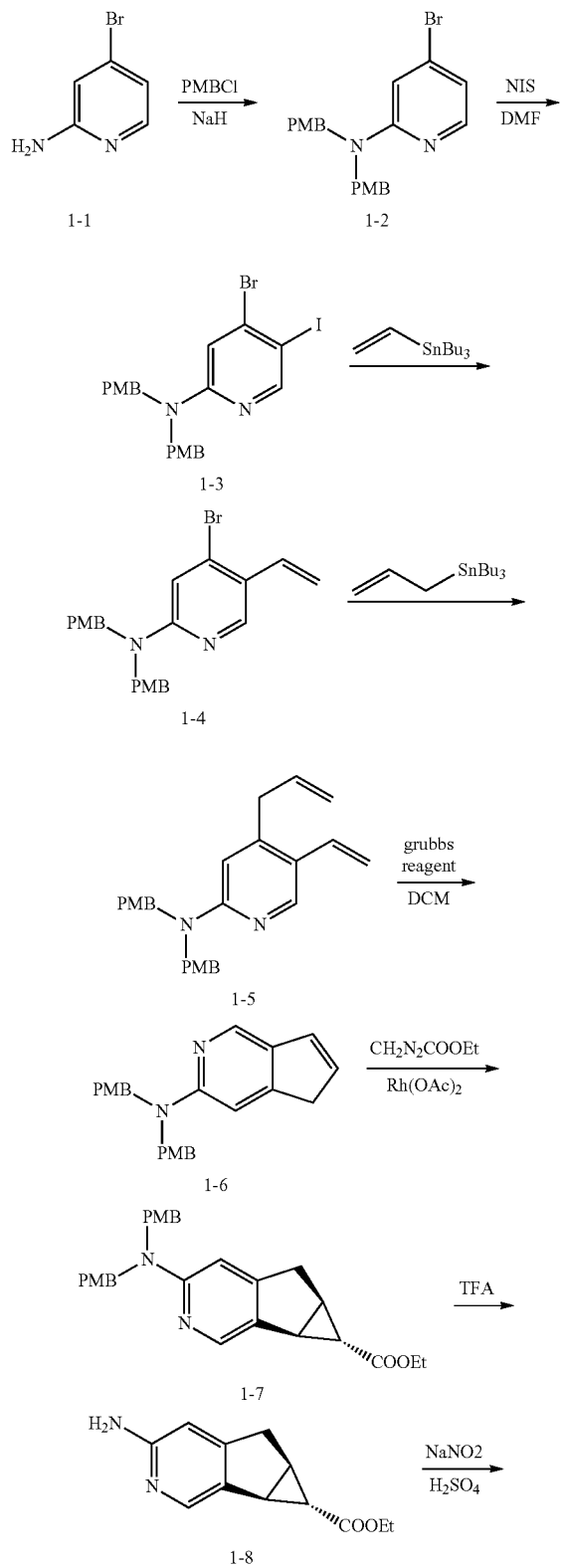

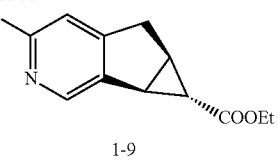

1-9

As outlined in Scheme 1, the amino group in 2-amino-4-bromopyridine (1-1) is protected by a bis-p-methoxybenzyl (PMB) group by reaction of (1-1) with PMB-Cl in the presence of strong base to afford (1-2). The protected pyridyl derivative (1-2) is reacted with N-iodosuccinimide (NIS) to yield the 5-iodopyridine (1-3). Under mild Suzuki reaction conditions with a vinyl-tin reagent, the iodo derivative (1-3) is converted to the 5-vinylpyridine (1-4). Under more vigorous Suzuki reaction conditions, (1-4) is reacted with tributyl-3-propenyl tin to afford the 4-allyl, 5-vinyl pyridyl compound (1-5). Under ring closure metathesis (RCM) conditions employing Grubbs catalyst, (1-5) is converted to the aza-indene derivative (1-6). Reaction of the double bond in (1-6) with ethyl diazoacetate in the presence of a rhodium catalyst affords the aza-tricyclic derivative (1-7). Removal of the PMB protecting groups in (1-7) and subsequent diazotization/hydrolysis yields the targeted hydroxyl-aza-tricyclic compound (1-9).

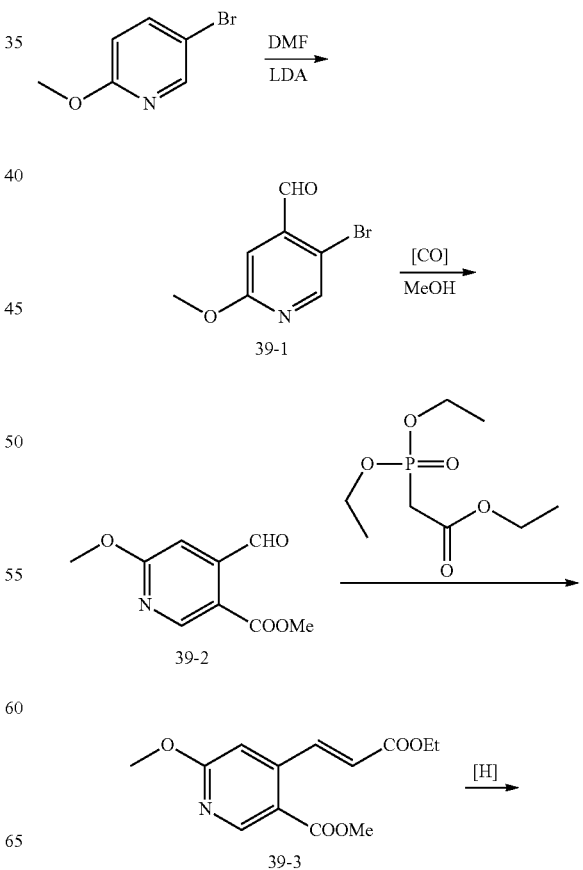

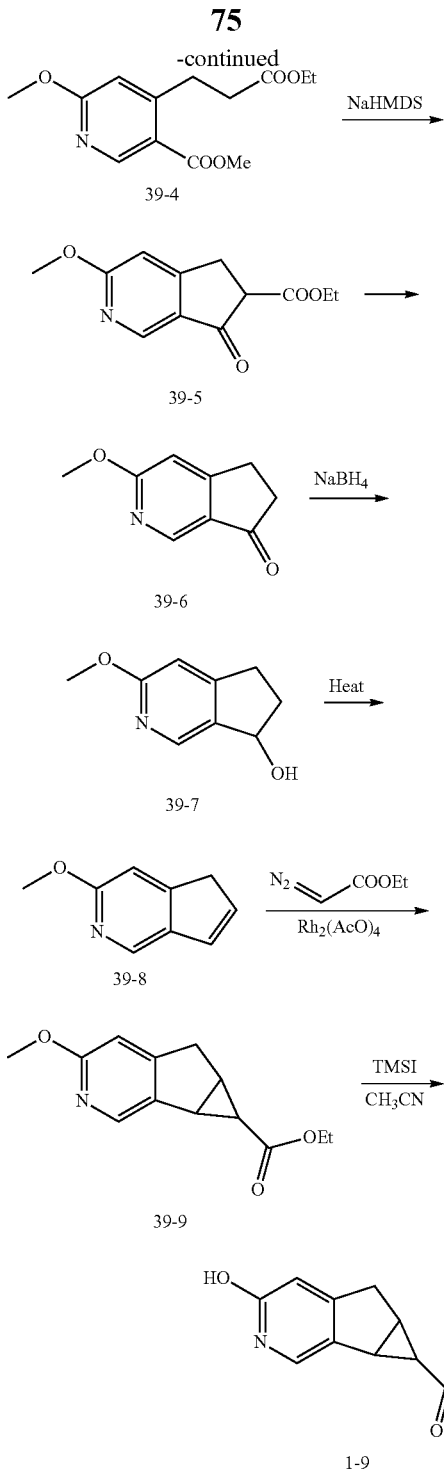

An alternative method for preparing compound 1-9 is outlined in Scheme 2. 2-Methoxy-5-bromopyridine is lithiated with LDA and quenched with DMF to afford aldehyde 39-1. Compound 39-1 in MeOH was reacted with Pd(dppf)Cl$_2$ under a CO atmosphere to yield ester 39-2. Homologation of the aldehyde in 39-2 gave vinyl ester 39-3. Hydrogenation of the double bond in 39-3 gave pyridyl-propionic acid diester 39-4. Treatment of 39-4 with sodium hexamethyldisilazide gave aza-indanone 39-6. Reduction of the ketone in 39-6 followed by elimination afforded aza-indene 39-8. Treatment of 39-8 with ethyl diazoacetate afforded the fused cyclopropyl derivative 39-9. Subsequent reaction of 39-9 with trimethylsilyl iodide gave compound 1-9.

Reference Example 1-9

4-Hydroxy-1,1a,6,6a-tetrahydro-3-aza-cyclopropa[a]indene-1-carboxylic acid ethyl ester (1-9)

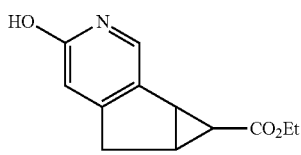 [SMILES: CCOC(=O)C1C2Cc3cc(O)ncc3C21]

Step A: 4-Bromo-pyridin-2-yl)-bis-(4-methoxy-benzyl)-amine (1-2)

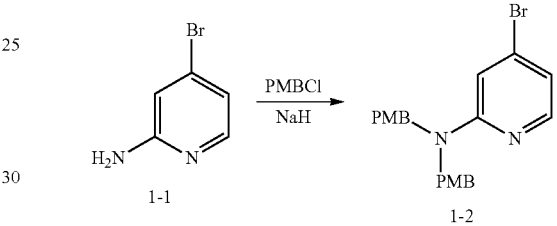

To a suspension of sodium hydride (60% in oil, 93 g, 2.32 mol) in DMF (1.8 L), was added compound 1-1 (100 g, 0.58 mol) in DMF (500 mL) slowly at 0° C. Then the resulting mixture was allowed to stir at r.t. for 0.5 h under N$_2$ protection. PMBCl (227 g, 1.45 mol) was added to the above mixture and the temperature was kept between 0-10° C. After addition, the mixture was allowed to stir at room temperature for 2 h. The mixture was carefully poured into ice water, and the resulting solid precipitate was collected, filtered and washed with PE (150 mL×3). The filtrate was concentrated to afford compound 1-2. MS (ESI) m/e (M+H$^+$) 414.1/416.1.

Step B: (4-Bromo-5-iodo-pyridin-2-yl)-bis-(4-methoxy-benzyl)-amine (1-3)

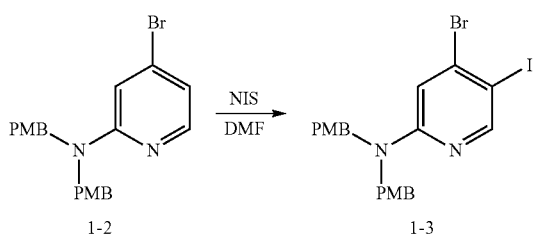

To a stirred solution of compound 1-2 (140 g, 0.34 mol) in DMF (2.8 L), was added NIS (115 g, 0.51 mmol) in portions. Then the resulting mixture was heated to 40° C. and stirred for 24 h. The mixture was cooled, poured into ice water and stirred constantly. The resulting solid precipitated was collected, filtered and washed with PE (100 mL×3). The filtrate was concentrated in vacuo to afford compound 1-3. MS (ESI) m/e (M+H⁺) 540,541 (M+H⁺)

Step C: (4-Bromo-5-vinyl-pyridin-2-yl)-bis-(4-methoxy-benzyl)-amine (1-4)

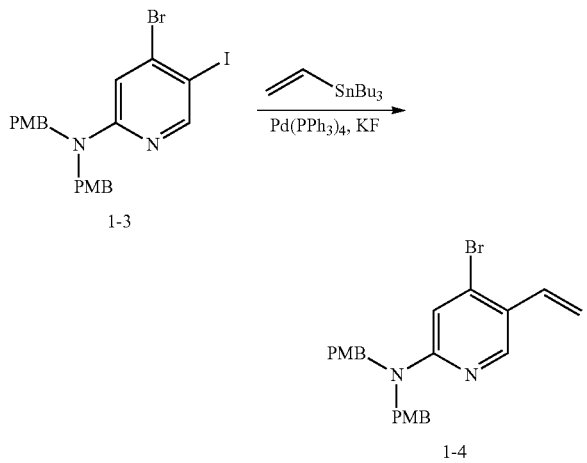

To a stirred solution of compound 1-3 (144 g, 267 mmol) in toluene (2 L) was added tributyl (vinyl) tin (85 g, 267 mmol), Pd(PPh₃)₄ (15.4 g, 13.4 mmol), and KF (31 g, 534 mmol). The resulting mixture was heated to reflux for 18 h under N₂. The mixture was cooled, KF (300 mL, 2 mol/L) was added and the mixture was stirred for 20 minutes. The mixture was then filtered and the filtrate was separated. The organic layer was collected and evaporated in vacuo to give crude product, which was purified by column chromatography on silica gel (PE:EA=20:1) to give compound 1-4. MS (ESI) m/e (M+H⁺) 439.8/441 8.

Step D: (4-Allyl-5-vinyl-pyridin-2-yl)-bis-(4-methoxy-benzyl)-amine (1-5)

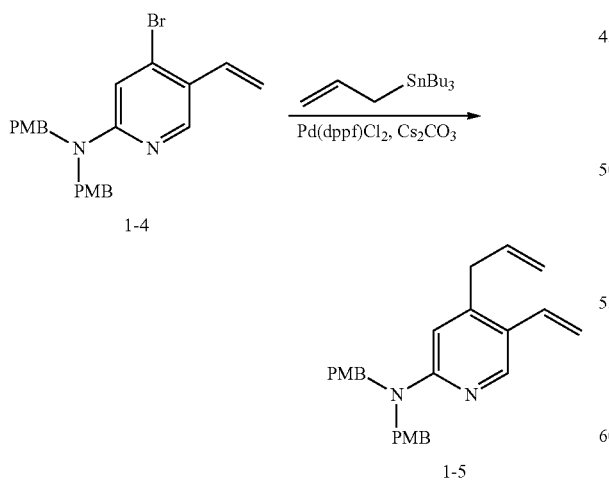

To a stirred solution of compound 1-4 (90 g, 205 mmol) in THF (2 L), was added Cs₂CO₃ (134 g, 410 mmol), Pd(dppf)Cl₂ (7.5 g, 10.3 mmol), and allyltributyltin (136 g, 410 mmol). Then the resulting mixture was heated to reflux for 18 h under N₂. The mixture was cooled, KF (300 mL, 2 mol/L) was added and the mixture was stirred for 20 min. The mixture was filtered and the filtrate was separated. The organic layer was collected and evaporated in vacuo to give crude product, which was purified by column chromatography on silica gel (PE:EA=30:1) to give compound 1-5. MS (ESI) m/e (M+H⁺): 440.1.

Step E: Bis-(4-methoxy-benzyl)-(5H-[2]pyrindin-3-yl)-amine (1-6)

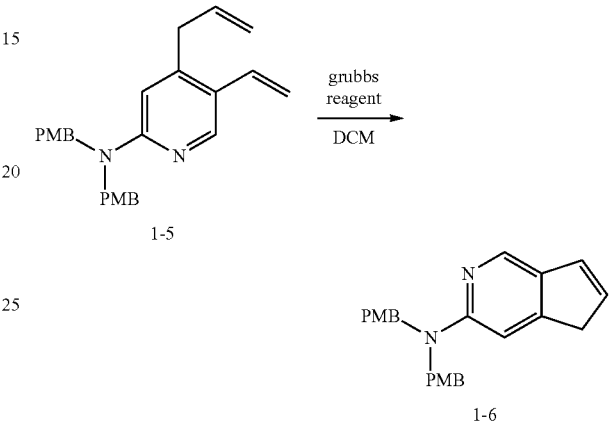

To a stirred solution of compound 1-5 (55 g, 138 mmol) in DCM (700 mL), was added Grubbs reagent (II) (3.5 g, 4.14 mmol) in one portion. The resulting mixture was heated at reflux for 3 h under N₂. The mixture was then cooled and used directly in the next step. MS (ESI) m/e (M+H⁺): 373.2.

Step F: 4-[Bis-(4-methoxy-benzyl)-amino]-1,1a,6,6a-tetrahydro-3-aza-cyclopropa[a]-indene-1-carboxylic acid ethyl ester (1-7)

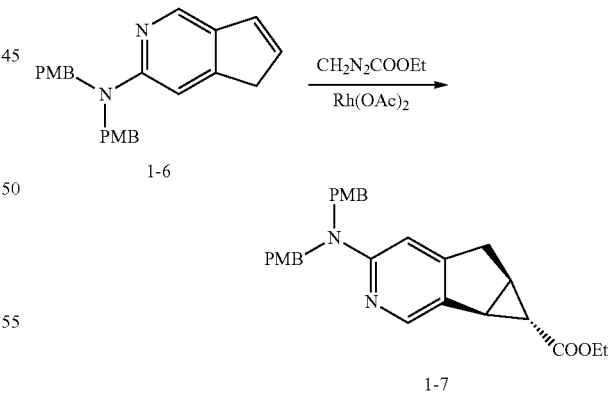

To a stirred solution of crude 1-6 (52 g, 138 mmol) in DCM (0.7 L) was added Rh(OAc)₂ (1.6 g, 6.9 mmol) in one portion. The mixture was stirred for 15 mins, then ethyl diazoacetate (126 g, 1.1 mol) was added slowly to the mixture under gentle reflux conditions over 3 h. The resulting mixture was allowed to stir at r.t for 1 h. The mixture evaporated in vacuo to give the crude product, which was purified by column chromatography on silica gel (PE:

EA=10:1) to give a trans-isomeric mixture of 1-7. The trans-isomeric mixture of 1-7 was separated by chiral column chromatography (SFC resolution conditions: Instrument: Thar 200; Column: AD 250 mm×50 mm, 10 um; Mobile Phase: A Supercritical $CO_2$, B EtOH (0.05% $NH_3$. $H_2O$), A/B=60/40 at 200 mL/min; Column Temp: 38° C.; Nozzle Pressure: 100 bar; Nozzle Temp: 60° C.; Evaporator Temp: 20° C.; Trimmer Temp: 25° C.; Wavelength: 220 nm) to give the desired enantiomer 1-7. MS (ESI) m/e (M+H$^+$): 459.1.

Step G: 4-Amino-1,1a,6,6a-tetrahydro-3-aza-cyclopropa[a]indene-1-carboxylic acid ethyl ester (1-8)

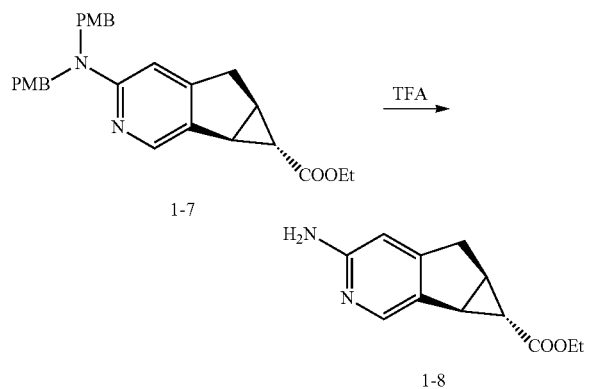

To a stirred solution of compound 1-7 (19 g, 41.4 mmol) in DCM (130 mL) was added TFA (130 mL) in one portion. The resulting mixture was stirred at r.t overnight. The mixture was evaporated in vacuo to give compound 1-8, which was used directly in next step. MS (ESI) m/e (M+H$^+$): 219.1.

Step H: 4-Hydroxy-1,1a,6,6a-tetrahydro-3-azacyclopropa[a]indene-1-carboxylic acid ethyl ester (1-9)

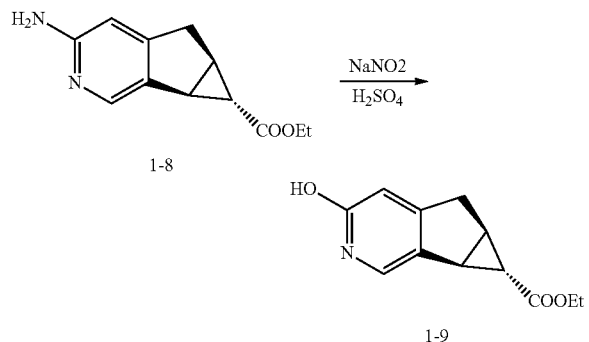

To a stirred solution of compound 1-8 (23 g, crude) in $H_2SO_4$ (200 mL, 15%) was added $NaNO_2$ (14.4 g, 209 mmol) in several portions at 0° C. The resulting mixture was allowed to stir at r.t for 2 h. The mixture was basified with 2N NaOH to pH=5-6, then aqueous $NaHCO_3$ was added to adjust the filtrate to pH=7. The suspension was then extracted with DCM (300 mL×3), the combined organic layers were washed with brine, dried over $Na_2SO_4$, and concentrated. The resulting residue was purified by column chromatography on silica gel (DCM/MeOH=50/1 to 20/1) to afford 1-9. MS (ESI) m/e (M+H$^+$): 220 (M+H$^+$). $^1$H-NMR (400 MHz, CDCl$_3$) δ: 12.52 (s, 1H), 7.28 (s, 1H), 6.38. (s, 1H), 4.14 (dd, 2H, J=7.2 and 14.4 Hz), 3.18 (dd, 1H, J=6.0 and 12.0 Hz), 2.94 (d, 1H, J=8.8 Hz), 2.77 (dd, 1H, J=2.4 and 6.4 Hz), 2.43-2.39 (m, 1H), 1.28-1.25 (m, 4H).

Alternative Method for the Preparation of Reference Compound 1-9

Step A: (5-bromo-2-methoxyisonicotinaldehyde (39-1)

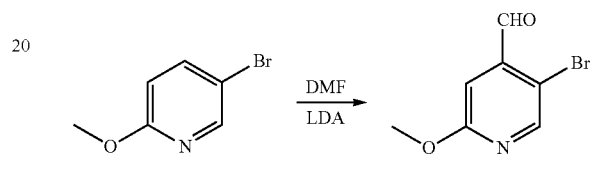

To a solution of diisopropylamine (63 g, 642 mmol) in anhydrous THF (500 ml) was added n-BuLi (2.5 M, in hexane, 256 mL, 642 mmol) dropwise under a $N_2$ atmosphere at −78° C., and the mixture was stirred for 30 min. To the reaction mixture was added a solution of 5-bromo-2-methoxypyridine (100 g, 535 mmol) in 100 mL of THF. The reaction mixture was stirred at −78° C. for 1 h, and then DMF (50 ml, 642 mmol) was added. After stirring for 30 min, the reaction mixture was quenched with water and extracted with EtOAc. The organic layer was washed with water and brine, and dried over $Na_2SO_4$. After filtration and concentration, the residue was purified by silica gel column chromatography (eluted with petroleum ether:ethyl acetate=10:1) to give solid 39-1. MS (ESI) m/e (M+H$^+$) 216.0/218.0.

Step B: methyl 4-formyl-6-methoxynicotinate (39-2)

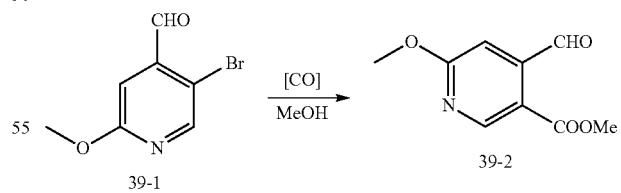

To a solution of compound 39-1 (30 g, 139 mmol) and Et$_3$N (27 g, 280 mmol) in 100 mL of methanol was added Pd(dppf)Cl$_2$ (10.5 g, 139 mmol). The resulting mixture was stirred under CO (50 Psi) at 70° C. for 12 hours. After cooling, filtration and concentration, the resulting residue was purified by column chromatography on silica gel (eluted with petroleum ether:ethyl acetate=3:1) to give 39-2. MS (ESI) m/e (M+H$^+$) 196.0.

Step C: (E)-methyl 4-(3-ethoxy-3-oxoprop-1-en-1-yl)-6-methoxynicotinate (39-3)

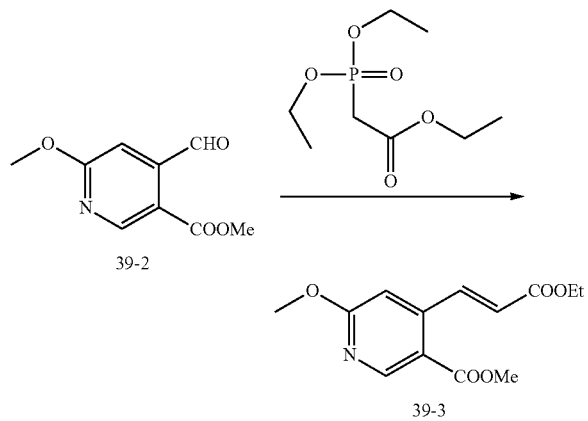

To a solution of NaH (5.6 g, 139 mmol) in 200 mL of THF was added ethyl 2-(diethoxyphosphoryl)acetate (31 g, 137 mmol) at room temperature The resulting mixture was stirred for 1 hour, and then 39-2 (22.5 g, 116 mmol) was added and the reaction mixture was stirred for 1 h. The reaction mixture was then partitioned between ethyl acetate and water. The organic layer was washed with brine and dried over Na$_2$SO$_4$. After concentration, the resulting residue was purified by column chromatography on silica gel (eluted with petroleum ether:ethyl acetate=10:1) to give 39-3. MS (ESI) m/e (M+H$^+$) 266.1.

Step D: methyl 4-(3-ethoxy-3-oxopropyl)-6-methoxynicotinate (39-4)

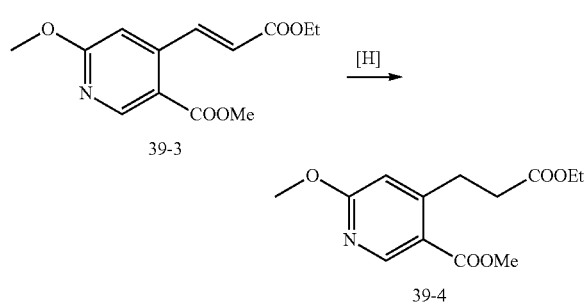

To a solution of 39-3 (24 g, 91 mmol) in MeOH (100 ml) was added Pd/C (2 g). The mixture was stirred at room temperature for 2.5 hours under a H$_2$ atmosphere (30 psi). After filtration, the filtrate was concentrated to give crude compound 39-4, which was used in next step without purification. MS (ESI) m/e (M+H$^+$): 268.1.

Step E: ethyl 3-methoxy-7-oxo-6,7-dihydro-5H-cyclopenta[c]pyridine-6-carboxylate (39-5)

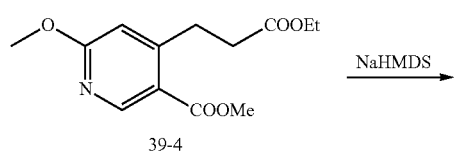

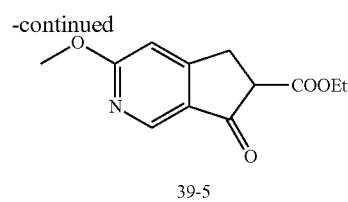

To a solution of 39-4 (18.8 g, 71 mmol) in THF (300 mL) was added NaHMDS (141 ml, 141 mmol) at −78° C. and the resulting mixture was stirred at this temperature for 2 h. The reaction mixture was quenched with water, and extracted with ethyl acetate. The organic layer was washed with brine, and dried over Na$_2$SO$_4$. After filtration and concentration, the residue was purified by column chromatography on silica gel (eluted with petroleum ether:ethyl acetate=10:1) to give 39-5. MS (ESI) m/e (M+H$^+$): 236.1

Step F: 3-methoxy-5H-cyclopenta[c]pyridin-7(6H)-one (39-6)

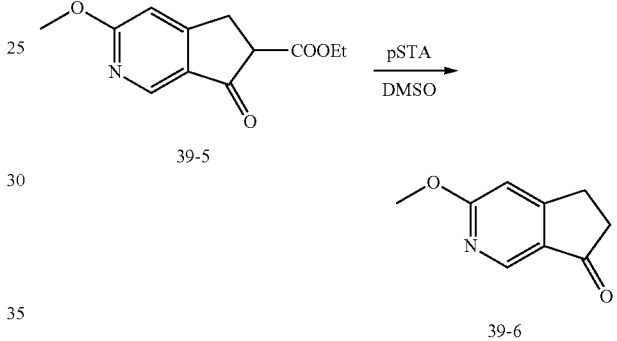

To the solution of compound 39-5 (12 g, 51 mmol) in DMSO/H$_2$O (15 mL/1 mL) was added p-TsOH (1 g). The resultant mixture was heated to 150° C. for 2 hours. After cooling, the reaction was quenched with water and extracted with ethyl acetate twice. The combined organic layers were washed with brine, and dried over Na$_2$SO$_4$. After filtration and concentration, the resulting residue was purified by column chromatography on silica gel to give 39-6. MS (ESI) m/e (M+H$^+$): 164.1.

Step G: 3-methoxy-6,7-dihydro-5H-cyclopenta[c]pyridin-7-ol (39-7)

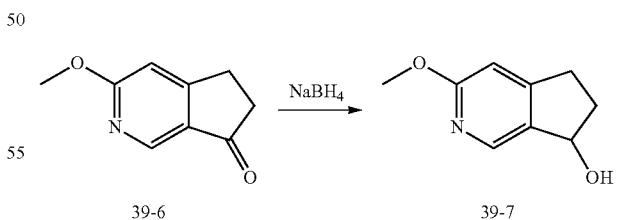

To a solution of 39-6 (8 g, 48 mmol) in MeOH (50 mL) was added NaBH$_4$ (1.8 g, 48 mmol) portionwise at 0° C. The mixture was stirred at room temperature for 2 hours. The reaction was quenched with water and extracted with ethyl acetate twice. The combined organic layers were washed with brine, and dried over Na$_2$SO$_4$. After filtration and concentration, the residue was purified by column chromatography on silica gel (eluted with petroleum ether:ethyl acetate=2:1) to give 39-7. MS (ESI) m/e (M+H$^+$): 166.1.

Step H: 3-methoxy-5H-cyclopenta[c]pyridine (39-8)

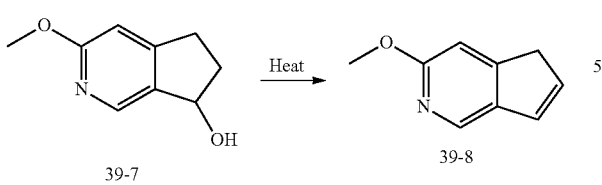

To a solution of 39-7 (7 g, 42.4 mmol) and MgSO₄ (11.6 g, 84.8 mmol) in 100 mL of toluene was added 1-Methanesulfonyl-4-methyl-benzene (0.73 g, 4.24 mmol). The resultant mixture was heated to 110° C. for 2 hours. After cooling to room temperature, the reaction was quenched with water and extracted with ethyl acetate twice. The combined organic layers were washed with brine, and dried over Na₂SO₄. After filtration and concentration, the resulting residue was purified by column chromatography on silica gel (eluted with petroleum ether:ethyl acetate=10:1) to give 39-8. MS (ESI) m/e (M+H⁺): 148.1.

Step I: ethyl 3-methoxy-5,5a,6,6a-tetrahydrocyclopropa[4,5]cyclopenta[1,2-c]pyridine-6-carboxylate (39-9)

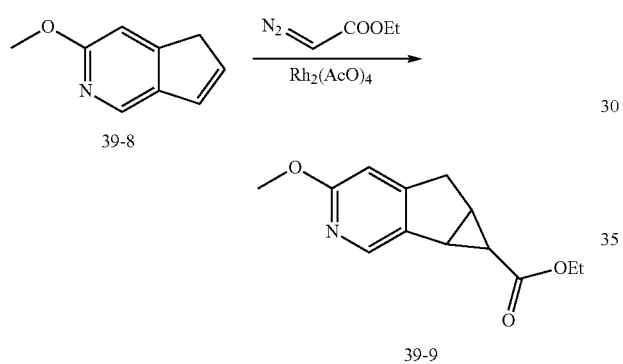

To a solution of the mixture of 39-8 (1.6 g, 10.7 mmol) in anhydrous DCM (30 mL) was added Rh₂(OAc)₄ (0.5 g, 1.07 mmol). Then a solution of ethyl diazoacetate (2.5 g, 21.4 mmol) in anhydrous DCM (10 mL) was added over 8 hours through a syringe pump. After addition, the reaction was quenched with water and the aqueous layer extracted with DCM twice. The combined organic layers were washed with brine, and dried over Na₂SO₄. After filtration and concentration, the resulting residue was purified by column chromatography on silica gel (eluted with petroleum ether:ethyl acetate=5:1) to give 39-9. MS (ESI) m/e (M+H⁺): 234.1.

Step J: ethyl 3-hydroxy-5,5a,6,6a-tetrahydrocyclopropa[4,5]cyclopenta[1,2-c]pyridine-6-carboxylate (1-9)

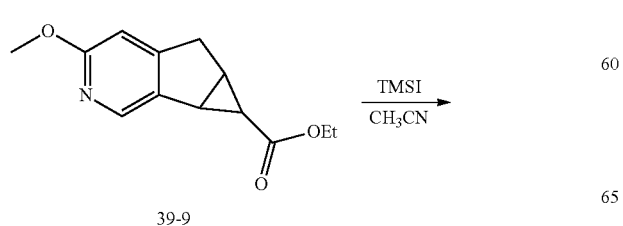

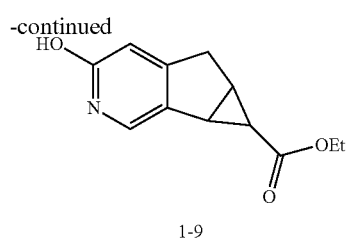

To a solution of 39-9 (0.2 g, 0.86 mmol) and NaI (0.17 g, 1.12 mmol) in 10 mL of CH₃CN was added TMSCl (0.47 g, 4.29 mmol) and the resultant mixture was refluxed for 2 hours. After cooling to room temperature, the reaction was quenched with water and the aqueous layer was extracted with ethyl acetate twice. The combined organic layers were washed with brine, and dried over Na₂SO₄. After filtration and concentration, the resulting residue was purified by column chromatography on silica gel (eluted with DCM:MeOH=30:1) to give compound 1-9. MS (ESI) m/e (M+H⁺): 220.1.

Reference Example 2-4

4-[2-Fluoro-5-(4,4,5,5-tetramethyl-[1,3,2]dioxaborolan-2-yl)-benzyloxy]-1,1a,6,6a-tetrahydro-3-azacyclopropa[a]indene-1-carboxylic acid ethyl ester (2-4)

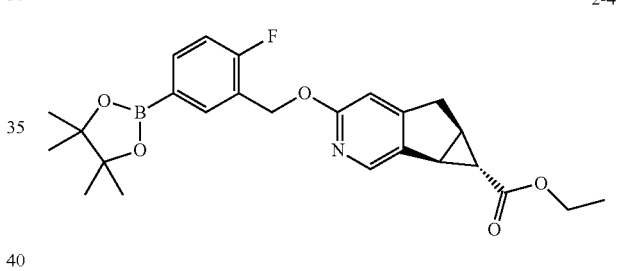

Step A: [2-Fluoro-5-(4,4,5,5-tetramethyl-[1,3,2]dioxaborolan-2-yl)-phenyl]-methanol (2-2)

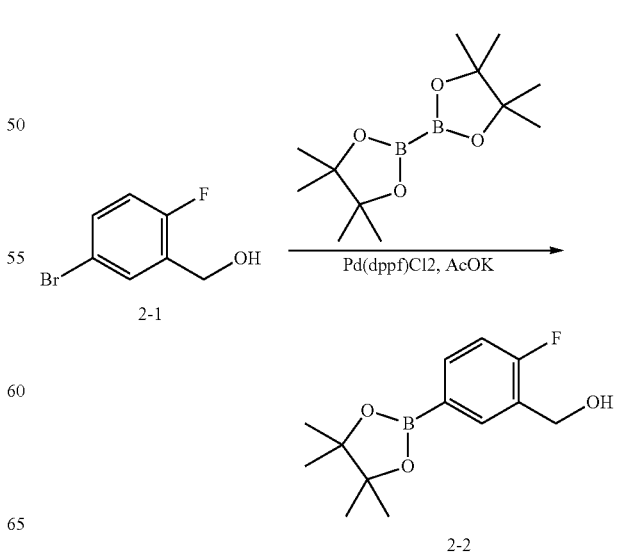

To a stirred solution of compound 2-1 (25 g, 120 mmol) in dioxane (400 mL), was added bis(pinacolato)diboron (45 g, 180 mmol), Pd(dppf)Cl$_2$ (4.4 g, 6.0 mmol) and KOAc (23.5 g, 240 mmol). The resulting mixture was heated to 110° C. under N$_2$ overnight. The mixture was then concentrated to afford the crude product, which was purified by column chromatography on silica gel (PE:EA=20:1) to give compound 2-2. MS (ESI) m/z: 253 (M+H$^+$).

Step B: 2-(3-Bromomethyl-4-fluoro-phenyl)-4,4,5,5-tetramethyl-[1,3,2]dioxaborolane (2-3)

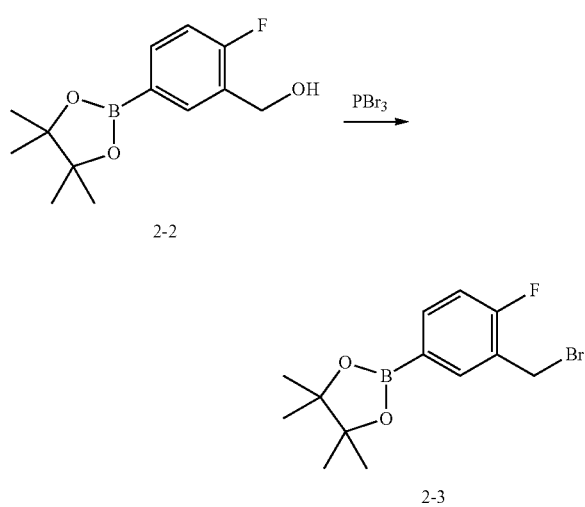

To a stirred solution of compound 2-2 (7 g, 28 mmol) in THF (80 mL), was added PBr$_3$ (7.6 g, 28 mmol) dropwise at 0° C. The resulting mixture was stirred at 0° C. for 1 h. H$_2$O (50 mL) was added to the mixture and the resulting mixture was extracted with EtOAc (50 mL×3). The combined organic layers were washed with brine, dried over Na$_2$SO$_4$, and concentrated to afford crude product, which was purified b by column chromatography on silica gel (PE:EA=20:1) to give compound 2-3. MS (ESI) m/z: 315, 316 (M+H$^+$).

Step C: 4-[2-Fluoro-5-(4,4,5,5-tetramethyl-[1,3,2]dioxaborolan-2-yl)-benzyloxy]-1,1a,6,6a-tetrahydro-3-aza-cyclopropa[a]indene-1-carboxylic acid ethyl ester (2-4)

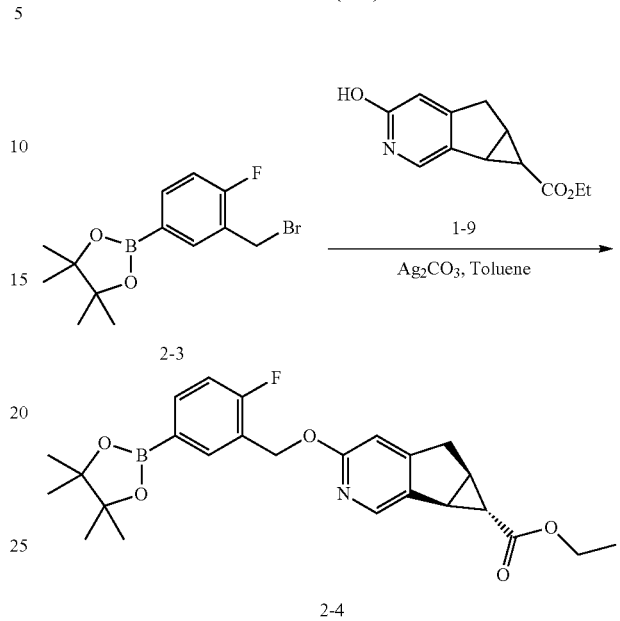

To a stirred solution of compound 2-3 (863 mg, 2.74 mmol) and 1-9 (500 mg, 2.28 mmol) in toluene (35 mL), was added Ag$_2$CO$_3$ (1.30 g, 4.56 mmol) in one portion. The resulting mixture was heated to 110° C. under N$_2$ protection overnight. TLC showed compound 2-3 was consumed. The mixture was filtered, the filtrate was concentrated to afford crude product which was purified b by column chromatography on silica gel (PE:EA=5:1) to give 2-4. MS (ESI) m/z: 454 (M+H$^+$). $^1$H-NMR (400 MHz, CDCl$_3$) δ: 8.10 (s, 1H), 7.93 (d, 1H, J=4.0 Hz), 7.72 (t, 1H, J=4.0 Hz), 7.06 (t, 1H, J=2.8 Hz), 6.61 (s, 1H), 5.36 (s, 2H), 4.12 (dd, 2H, J=2.0 and 7.2 Hz), 3.23 (dd, 1H, J=6.0 and 12.0 Hz), 2.98 (d, 1H, J=8.8 Hz), 2.88 (d, 1H, J=2.8 Hz), 2.43-2.39 (m, 1H), 1.33 (s, 12H), 1.26-1.23 (m, 4H).

Reference Example 2-5 was prepared in a similar manner to Reference Example 2-4 using the appropriate commercially available starting materials.

| Reference Example | Structure | M.W. | Compound Name | LC/MS (ESI) observed [M + 1]+ |
|---|---|---|---|---|
| 2-5 | 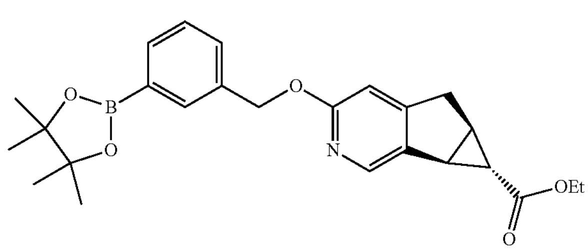 [SMILES: CCOC(=O)[C@H]1[C@@H]2Cc3cc(OCc4cccc(B5OC(C)(C)C(C)(C)O5)c4)ncc3[C@@H]21] | 435 | (5aR,6S,6aS)-ethyl 3-((3-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate | 436.1 |

Reference Example 2-5

$^1$H-NMR (400 MHz, CDCl$_3$) δ: 8.10 (s, 1H), 7.88 (s, 1H), 7.75 (d, 1H, J=4.0 Hz), 753 (d, 1H, J=4.0 Hz), 7.37 (t, 1H, J=8.0 Hz), 6.61 (s, 1H), 5.36 (s, 2H), 4.12 (dd, 2H, J=2.0 and 7.2 Hz), 3.23 (dd, 1H, J=6.0 and 12.0 Hz), 2.98 (d, 1H, J=8.8 Hz), 2.88 (d, 1H, J=2.8 Hz), 2.43-2.39 (m, 1H), 1.34 (s, 12H), 1.26-1.23 (m, 4H).

Reference Example 3-3

3-Bromo-2,4-dimethyl-6-(3-(methylsulfonyl)propoxy)pyridine (3-3)

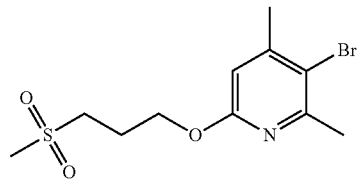

Step A: 3-Bromo-6-chloro-2,4-dimethylpyridine (3-1)

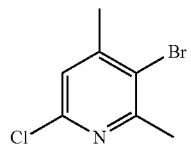

To a mixture of 2-amino-5-bromo-4,6-dimethylpyridine (5.03 g, 25 mmol) in conc. HCl (30 mL), which was cooled to −5° C., was added dropwise a solution of sodium nitrite (5.18 g, 75 mmol) in water (20 mL) over 30 min, while maintaining the reaction temperature between −5° C. and 5° C. After the addition was complete, the reaction was stirred for 1 h. Then the cooling bath was removed and the reaction was warmed to room temperature and stirred for 24 h. The reaction was then poured into ice and 5N NaOH was added to adjust the pH of resulting mixture to pH 7. The mixture was extracted with EtOAc three times. The combined organic layers were dried over anhydrous Na$_2$SO$_4$, filtered and concentrated. The resulting residue was purified by flash chromatography on silica gel with PE:EA=20:1 to afford 3-bromo-6-chloro-2,4-dimethylpyridine. MS (ESI) m/e (M+H$^+$): 222.0/220.0.

Step B: 3-bromo-2,4-dimethyl-6-(3-(methylthio)propoxy)pyridine (3-2)

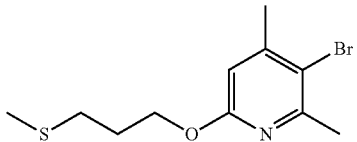

A mixture of 3-methylsulfanyl-propan-1-ol (212 mg, 2.0 mmol) and 3-bromo-6-chloro-2,4-dimethylpyridine (440 mg, 2.0 mmol) and t-BuOK (250 mg, 2.2 mmol) in anhydrous THF was heated to reflux for 2 h. The mixture was partitioned with water and EtOAc, then the aqueous and organic layers were separated and the aqueous solution was extracted with EtOAc two times. The combined organic layers were concentrated to afford a residue, which was purified by flash chromatography on silica gel to give 3-bromo-2,4-dimethyl-6-(3-(methylthio)propoxy)pyridine. MS (ESI) m/e (M+H$^+$): 292.0/290.0.

Step C: 3-bromo-2,4-dimethyl-6-(3-(methylsulfonyl)propoxy)pyridine (3-3)

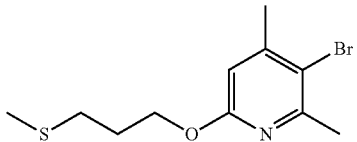

To a solution of 3-bromo-2,4-dimethyl-6-(3-(methylthio)propoxy)pyridine (378 mg, 1.3 mmol) in dry DCM (12 mL), cooled in an ice-bath, was added MCPBA (580 mg, 2.86 mmol). The resulting mixture was stirred at 0° C. for 2 h. Then the reaction was quenched with an aqueous solution of NaHSO$_3$. The DCM layer was separated, washed with Na$_2$CO$_3$ (aq.), water and brine, and then concentrated to give a residue, which was purified by flash chromatography on silica gel to give 3-bromo-2,4-dimethyl-6-(3-(methylsulfonyl)propoxy)pyridine. MS (ESI) m/e (M+H$^+$): 324.0/222.0. $^1$H-NMR (MeOH-d$_4$, 400 MHz): δ 6.59 (s, 1H), 4.36 (t, J=6.4 Hz, 2H), 3.25 (m, 2H), 2.98 (s, 3H), 2.52 (s, 3H), 2.34 (s, 3H), 2.25-2.20 (m, 2H).

Reference Examples 4-10 were prepared in a similar manner to Reference Example 3 using the appropriate commercially available starting materials:

| Reference Example | M.W. | Compound Name | LC/MS (ESI) observed [M + 1]+ |
|---|---|---|---|
| 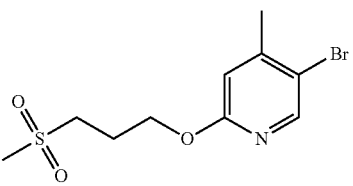 | 308.2 | 5-bromo-4-methyl-2-(3-(methylsulfonyl)propoxy)pyridine | 308.0/310.0 |

4

-continued

| Reference Example | M.W. | Compound Name | LC/MS (ESI) observed [M + 1]+ |
|---|---|---|---|
| 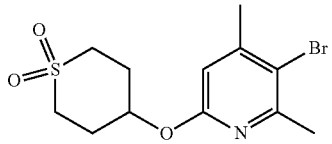<br>5 | 334.2 | 3-Bromo-6-(1,1-dioxo-hexahydro-1l6-thiopyran-4-yloxy)-2,4-dimethyl-pyridine | 334.2/336.2 |
| 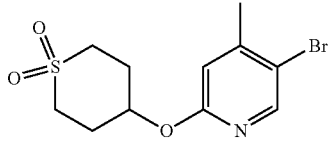<br>6 | 320.2 | 5-Bromo-2-(1,1-dioxo-hexahydro-1l6-thiopyran-4-yloxy)-4-methyl-pyridine | 320.2/322.2 |
| 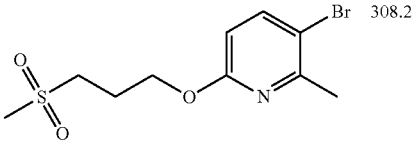<br>7 | 308.2 | 3-Bromo-6-(3-methanesulfonyl-propoxy)-2-methyl-pyridine | 308.0/310.0 |
| 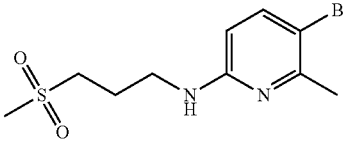<br>8 | 307.2 | (5-Bromo-6-methyl-pyridin-2-yl)-(3-methanesulfonyl-propyl)-amine | 307.0/309.0 |
| 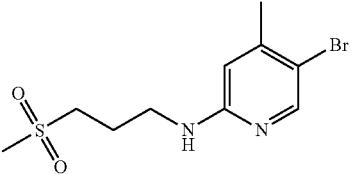<br>9 | 307.2 | (5-Bromo-4-methyl-pyridin-2-yl)-(3-methanesulfonyl-propyl)-amine | 307.0/309.0 |
| 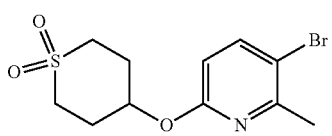<br>10 | 320.2 | 3-Bromo-6-(1,1-dioxo-hexahydro-1l6-thio-4-yloxy)-2-methyl-pyridine | 320.0/322.0 |

Reference Example 11

Compound 34-5

3'-(bromomethyl)-2,6-dimethyl-4-(3-(methylsulfonyl)propoxy)-1,1'-biphenyl (34-5)

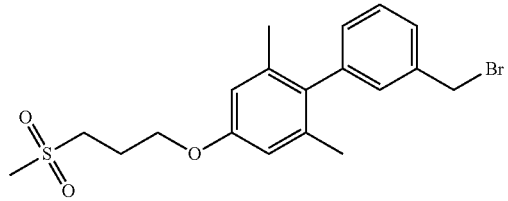

Step A: 3-(methylthio)propyl 4-methylbenzenesulfonate (34-1)

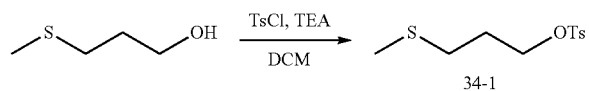

To a solution of the 3-(methylthio)propan-1-ol (50 g, 0.47 mol) and TEA (95 g, 0.94 mol) in DCM (500 mL) was added TsCl (90 g, 0.47 mol) portionwise at 0° C. After completion of addition, the reaction mixture was allowed to warm to room temperature slowly and stirred at this temperature for 16 h. Then the reaction was quenched with 1N HCl to adjust the pH to pH 7-8, and the mixture was extracted three times with ethyl acetate. The combined organic layers were washed with brine, dried over Na$_2$SO$_4$, filtered and concentrated in vacuo to give a residue. The residue was purified by chromatography on silica (petroleum ether:ethyl acetate 5/1) to afford compound 34-1.

Step B: 3-(methylsulfonyl)propyl 4-methylbenzenesulfonate (34-2)

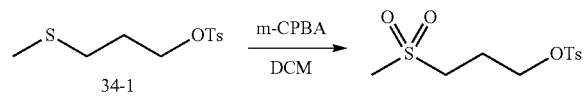

To a solution of 34-1 (35 g, 135 mmol) in dry DCM (400 mL) with ice-bath cooling was added MCPBA (46.5 g, 270 mmol) portionwise. The resulting mixture was stirred at 0° C. for 1 h, and then warmed to the room temperature and stirred for 20 h. The reaction was quenched by addition of aqueous solution of NaHSO$_3$ and the DCM layer was washed with Na$_2$CO$_3$ (aq.), water and brine, respectively, and concentrated to afford a residue, which was purified by chromatography on silica gel (petroleum ether:ethyl acetate=3/1) to give compound 34-2.

Step C: 2-bromo-1,3-dimethyl-5(3-(methylsulfonyl)propoxy)benzene (34-3)

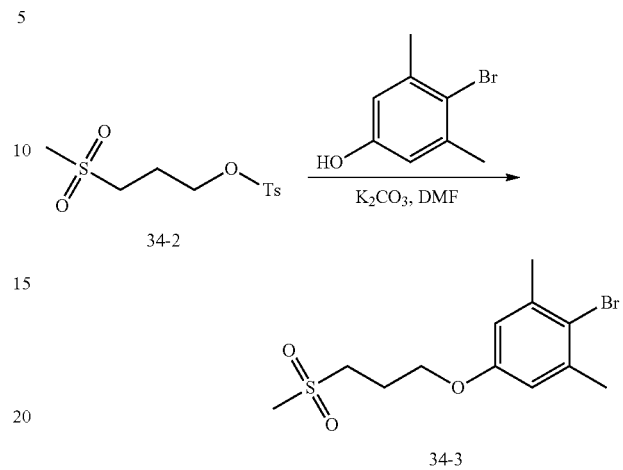

To a solution of compound 34-2 (32.1 g, 110 mmol) in DMF (300 mL) was added 4-bromo-3,5-dimethylphenol (20.1 g, 100 mmol), and K$_2$CO$_3$ (16.5 g, 120 mmol). The resulting mixture was stirred at 100° C. for 18 hours. Then water was added and the mixture was extracted with ethyl acetate (150 mL×3). The combined organic layers were washed with brine, dried and concentrated to give a residue. The residue was purified by chromatography on silica gel (petroleum ether:ethyl acetate=3/1) to give compound 34-3. MS (ESI) m/z (M+H)$^+$: 321.0/323.0.

Step D: (2',6'-dimethyl-4'-(3-(methylsulfonyl)propoxy)-[1,1'-biphenyl]-3-yl)methanol (34-4)

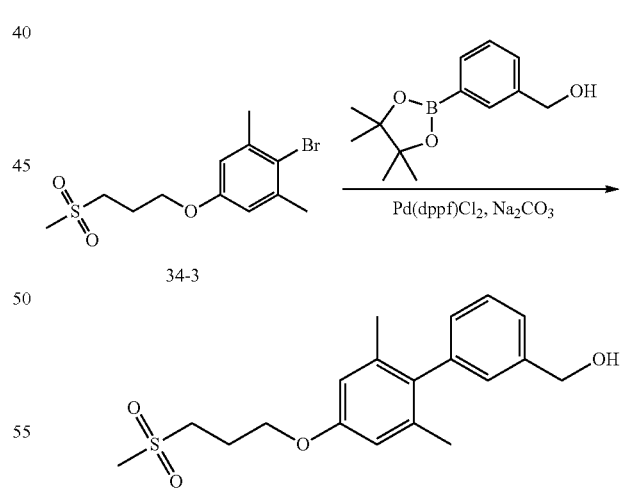

To a mixture of compound 34-3 (10 g, 31.1 mmol), (3-(4,4,5,5-tetramethyl-1,3,2-dioxaborolan-2-yl)phenyl)methanol (7.64 g, 32.6 mmol) and K$_3$PO$_4$ (15.7 g, 77.9 mmol) in a co-solvent of THF/H$_2$O (120/30 mL) was added Pd(dppf)$_2$Cl$_2$ (1.27 g, 1.56 mmol) under a nitrogen atmosphere. The resulting mixture was heated to reflux for 16 h. After cooling to room temperature, the mixture was filtered through a Celite™ pad and the filtrate was extracted with ethyl acetate twice. The combined organic layers were washed with water, dried and concentrated in vacuo to obtain a residue, which was purified by column chromatography on silica gel (petroleum ether:ethyl acetate=3/1) to give compound 34-4. MS (ESI) m/z (M+H)⁺: 349.1.

Step E: 3'-(bromomethyl)-2,6-dimethyl-4-(3-(methylsulfonyl)propoxy)-1,1'-biphenyl (34-5)

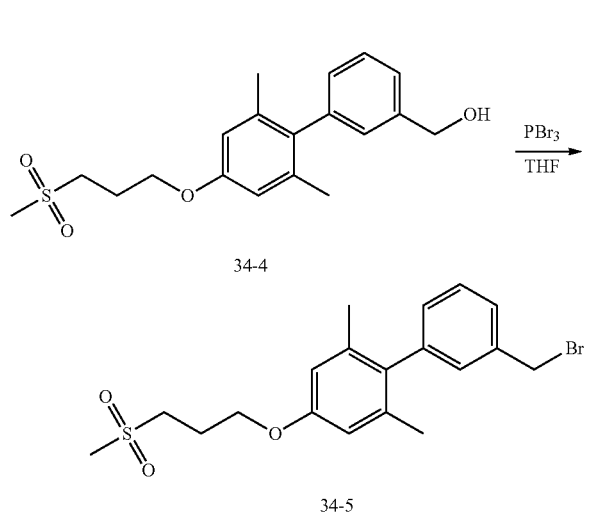

To a solution of crude compound 34-4 (20 g, 73 mmol) in dry THF (300 mL) with ice-cooling was added PBr₃ (6.8 g, 25.2 mmol) dropwise. And the reaction solution was stirred 0° C. for 1 h, then the mixture was warmed to 20° C. and stirred for 16 h. The mixture was then quenched with water, added to a saturated aqueous solution of NaHCO₃ to neutralize the mixture to pH 7. The organic layer was separated, washed with water, brine, dried over Na₂SO₄, and filtered. The filtrate was concentrated to afford a residue, which was purified by silica gel chromatography (PE/EA=5/1) to give 34-5. MS (ESI) m/e (M+H⁺): 341.1/343.1.

Example 1

Compound 3-4

(5aR,6S,6aS)-3-((2',6'-dimethyl-4'-((3-methyloxetan-3-yl)methoxy)-[1,1'-biphenyl]-3-yl) methoxy)-5,5a,6,6a-tetrahydrocyclopropa[4,5]cyclopenta[1,2-c]pyridine-6-carboxylic acid (3-4)

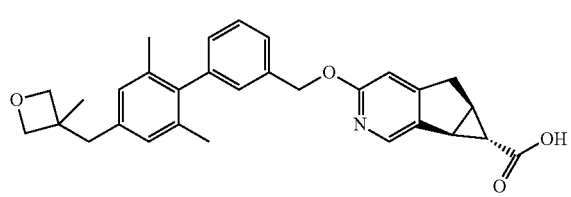

Step A: 3-((4-bromo-3,5-dimethylphenoxy)methyl)-3-methyloxetane (3-2)

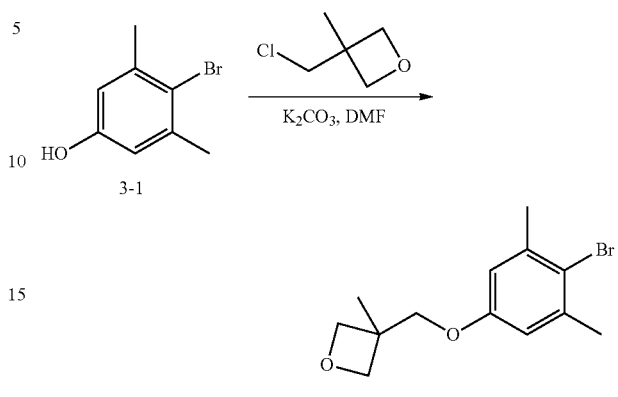

A solution of compound 3-1 (1 g, 5.0 mmol), 3-(Chloromethyl)-3-methyloxetane (1.2 g, 9.95 mmol) and K₂CO₃ (2.74 g, 19.9 mmol) in DMF (10 mL) was heated to 100° C. for 12 h. After the reaction was complete, the reaction mixture was treated with brine (100 mL), extracted with EtOAc (50 mL×3). The organic phase were combined, washed with water (50 mL), brine (50 mL), dried and concentrated to give crude compound 3-2, which would be used for the next step without further purification. MS (ESI) m/z: 285,287 (M+H).

Step B: (5aR,6S,6aS)-ethyl 3-((2',6'-dimethyl-4'-((3-methyloxetan-3-yl)methoxy)-[1,1'-biphenyl]-3-yl)methoxy)-5,5a,6,6a-tetrahydrocyclopropa[4,5]cyclopenta[1,2-c]pyridine-6-carboxylate (3-3)

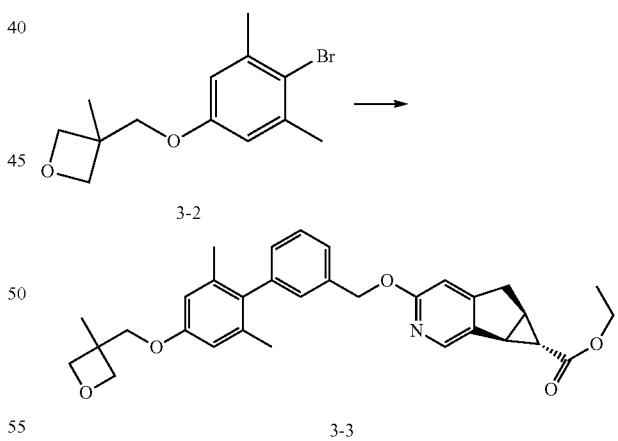

A mixture of compound 3-2 (90 mg, 0.31 mmol), boronate from Reference Example 2-4 (205 mg, 0.47 mmol), Pd₂(dba)₃ (27.48 mg, 0.03 mmol), P(Cy)₃ (16.8 mg, 0.06 mmol) and K₂CO₃ (86.94 mg, 0.63 mmol) in dioxane/H₂O (3 mL/0.6 mL) was stirred at 100° C. under N₂ for 10 min under microwave conditions. After the reaction finished, the mixture was filtered and concentrated. The resulting crude product was purified by preparative silica TLC on silica gel eluted with petroleum ether:ethyl acetate (3:1) to give ester 3-3. MS (ESI) m/z: 513 (M+H)⁺.

Step C: (5aR,6S,6aS)-3-((2',6'-dimethyl-4'-(3-methyloxetan-3-yl)methoxy)-[1,1'-biphenyl]-3-yl)methoxy)-5,5a,6,6a-tetrahydrocyclopropa[4,5]cyclopenta[1,2-c]pyridine-6-carboxylic acid (3-4)

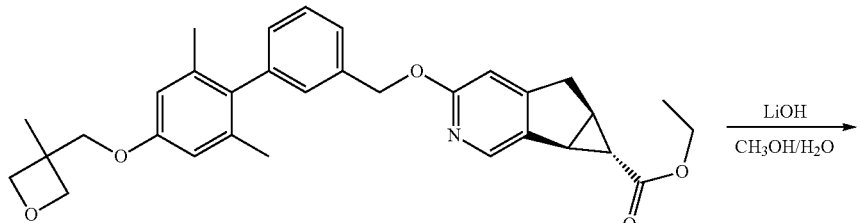

3-3

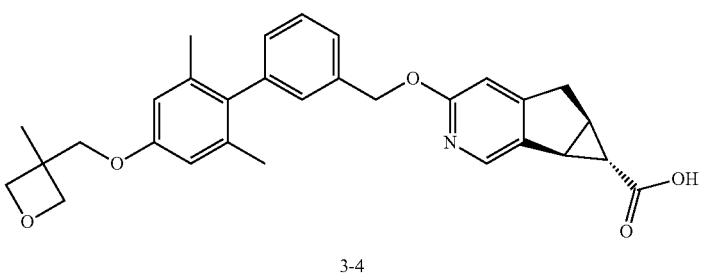

3-4

To a solution of compound 3-3 (130 mg, 0.25 mmol) in MeOH/H$_2$O (5/1 mL) was added LiOH (63 mg, 1.5 mmol). The solution was stirred at room temperature overnight. After the reaction finished, HCl (1 mol/L) was added to the solution to adjust the pH to pH 5. Then the solution was extracted with EtOAc (5 mL×3) and concentrated. The resulting crude compound was purified by preparative HPLC (preparative HPLC on a GILSON 281 instrument fitted with a YMC-Actus Triart 18 C (100×30 mm×4 um) using water and acetonitrile as the eluents. Mobile phase A: water (containing 0.1% TFA, v/v), mobile phase B: acetonitrile. Gradient: 36-66% B, 0-10 min; 100% B, 10.5-12.5 min; 5% B, 13-15 min) to give compound 3-4. MS (ESI) m/z: 486 (M+H)$^+$. $^1$H-NMR (400 MHz, CDCl$_3$) δ: 8.27 (s, 1H), 7.38-7.45 (m, 2H), 7.18 (s, 1H), 7.10-7.11 (d, 1H, J=7.3 Hz), 6.75 (s, 1H), 6.71 (s, 2H), 5.39 (s, 2H), 4.67-4.68 (d, 2H, J=5.9 Hz), 4.49-4.51 (d, 2H, J=6.0 Hz), 4.04 (s, 2H), 3.28-3.34 (dd, 2H, J$_1$=6.5 Hz, J$_2$=19.2 Hz), 3.05-3.07 (m, 1H), 2.55-2.58 (m, 1H), 1.93 (s, 6H), 1.25 (m, 1H).

The following Example 2 (compound 3-5) was prepared in a similar manner to compound 3-4 using the appropriate commercially available materials.

| Example | Structure | M.W. | Compound Name | LC/MS (ESI) observed [M + 1]+ |
|---|---|---|---|---|
| 2 | (Compound 3-5) | 503 | (5aR,6S,6aS)-3-((4-fluoro-2',6'-dimethyl-4'-((3-methyl-oxetan-3-yl)-methoxy)-[1,1'-biphenyl]-3-yl)-methoxy)-5,5a,6,6a-tetrahydrocyclopropa[4,5]cyclopenta[1,2-c]pyridine-6-carboxylic acid | 504 |

Compound 3-5: MS (ESI) m/z: 504 (M+H)'; $^1$H-NMR (400 MHz, MeOD) δ: 8.05 (s, 1H), 7.13-7.19 (m, 2H), 7.03-7.07 (m, 1H), 6.69-6.70 (d, 3H), 5.39 (s, 2H), 4.65-4.66 (d, 2H, J=5.8 Hz), 4.43-4.44 (d, 2H, J=6.0 Hz), 4.01 (s, 2H), 3.20-3.27 (dd, 1H, J$_1$=6.8 Hz, J$_2$=19.6 Hz), 2.98-3.05 (m, 1H), 2.90-2.91 (d, 1H, J=5.2 Hz), 2.85 (s, 1H), 2.40-2.44 (m, 1H), 1.918-1.924 (d, 6H, J=2.4 Hz), 1.42 (s, 3H), 1.11-1.13 (t, 1H, J=2.7 Hz).

Example 3

Compound 4-5

(5aR,6S,6aS)-3-((4'-(2-(1-hydroxycyclopropyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (4-5)

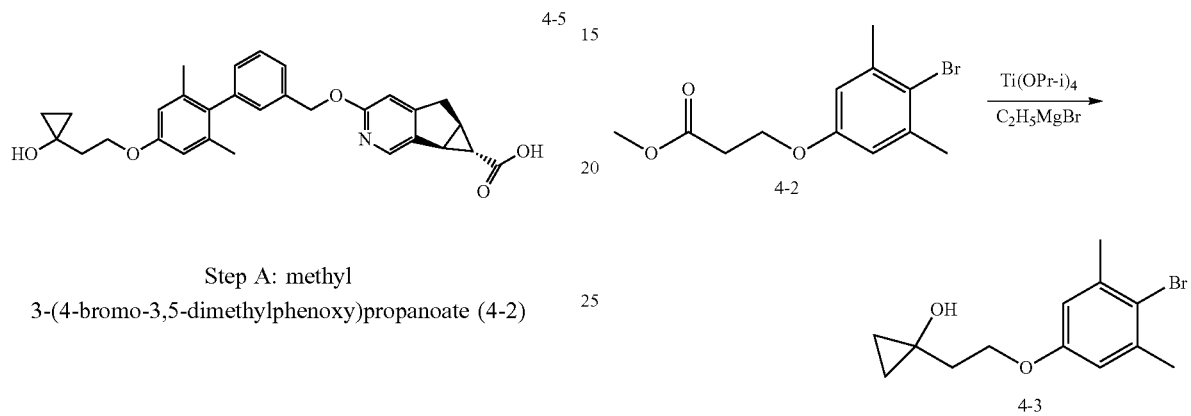

4-5

Step A: methyl 3-(4-bromo-3,5-dimethylphenoxy)propanoate (4-2)

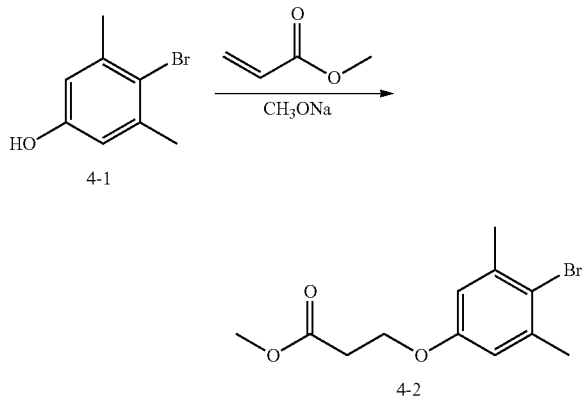

To a solution of compound 4-1 (2.0 g, 0.01 mol) in methyl acrylate (8.6 g, 0.1 mol) was added CH$_3$ONa (1.1 g, 0.02 mol). The resulting mixture was stirred at 50° C. for 20 hours. The solution was concentrated to remove the solvent, and H$_2$O was added. Then the solution was acidified with HCl (1M) to pH 2.5, and extracted with EtOAc (15 mL×3). The combined organic layers were washed with brine, dried, concentrated to give compound 4-2. MS (ESI) m/z: 287, 289 (M+H)$^+$.

Step B: 1-(2-(4-bromo-3,5-dimethylphenoxy)ethyl)cyclopropanol (4-3)

To a solution of compound 4-2 (0.5 g, 3.5 mmol) in THF (10 mL) was added titanium (IV) isopropoxide (0.04 g, 1.4 mmol). Then ethyl magnesium bromide (3.3 mL, 3M) was dissolved in THF (2 mL), and the solution was added dropwise to the reaction at 0° C. The reaction was quenched with HCl (1 M), and extracted with EtOAc (15 mL×3). The combined organic layers were washed with brine, dried, and concentrated to give the crude product, which was purified by preparative TLC on silica gel eluted with petroleum ether:ethyl acetate (5:1) to give compound 4-3.

Step C: (5aR,6S,6aS)-ethyl 3-((4'-(2-(1-hydroxycyclopropyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (4-4)

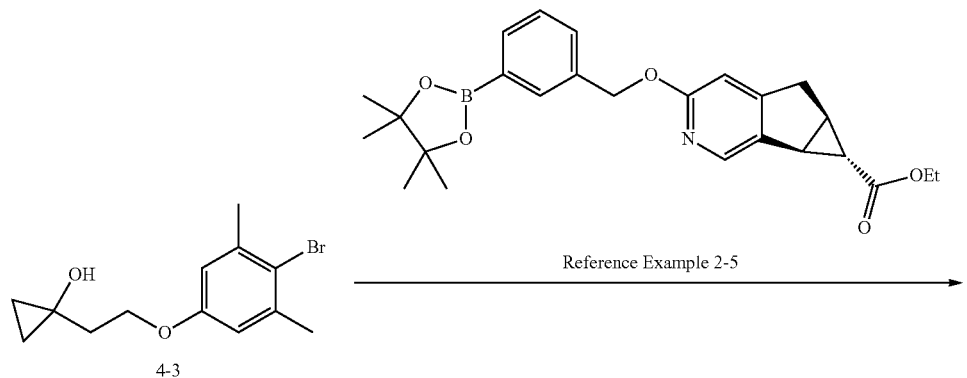

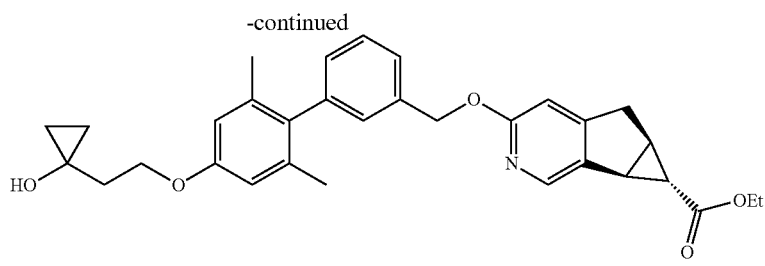

4-4

Compound 4-4 was prepared using a procedure similar to the procedure used to prepare compound 3-3. MS (ESI) m/z: 287, 289 (M+H)⁺.

Step D: (5aR,6S,6aS)-3-((4'-(2-(1-hydroxycyclopropyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (4-5)

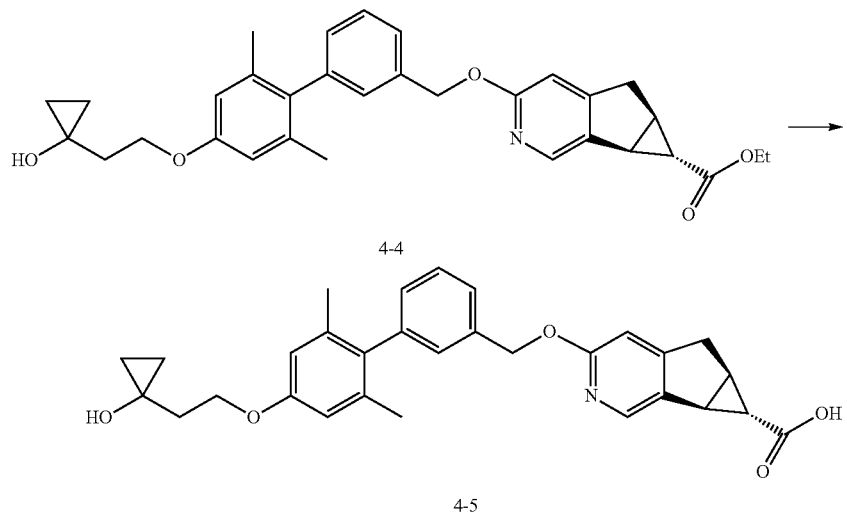

Compound 4-6 was prepared using a procedure similar to the procedure used to prepare compound 3-4. MS (ESI) m/z: 485 (M+H)⁺. ¹H-NMR (400 MHz, CDCl₃) δ: 8.36 (s, 1H), 7.42-7.45 (m, 1H), 7.37-7.39 (m, 1H), 7.11-7.16 (m, 2H), 6.83 (s, 1H), 6.69 (s, 2H), 5.40 (s, 2H), 4.27 (t, 2H, J=6.0 Hz), 3.31-3.38 (m, 1H), 3.09-3.16 (m, 2H), 2.60 (s, 1H), 2.06 (t, 2H, J=6.0 Hz), 1.98 (s, 6H), 1.29 (s, 1H), 0.82-0.85 (m, 2H), 0.53-0.56 (m, 2H).

The following Example 4 (compound 4-6) was prepared in a similar manner to Compound 4-5 using the appropriate commercially available starting materials.

| Example | Structure | M.W. | Compound Name | LC/MS (ESI) observed [M + 1]+ |
|---|---|---|---|---|
| 4 | (Compound 4-6) | 503 | (5aR,6S,6aS)-3-((4-fluoro-4'-(2-(1-hydroxycyclopropyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 504 |

Compound 4-6: ¹H-NMR (400 MHz, CDCl₃) δ: 8.31 (s, 1H), 7.20-7.26 (m, 1H), 7.10-7.17 (m, 2H), 6.83 (s, 1H), 6.67-6.68 (m, 2H), 5.45 (s, 2H), 4.26 (t, 2H, J=6.0 Hz), 3.32-3.39 (m, 1H), 3.08-3.17 (m, 2H), 2.61 (s, 1H), 2.06-2.07 (m, 2H), 1.97 (s, 6H), 1.30-1.34 (m, 2H), 0.83-0.85 (m, 2H), 0.54-0.57 (m, 2H).

Example 5

Compound 5-3

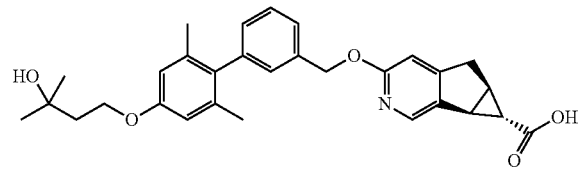

Step A: 4-(4-bromo-3,5-dimethylphenoxy)-2-methylbutan-2-ol (5-1)

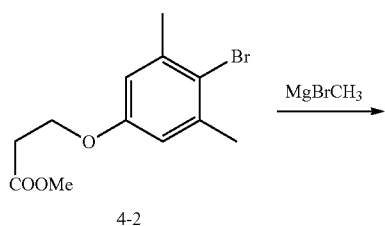

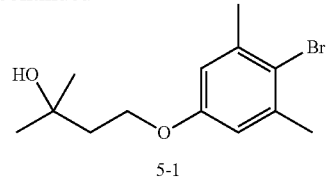

To a solution of compound 4-2 (3.4 g, 0.01 mol) in THF (20 mL) was added dropwise CH₃MgBr (3 M, 13 mL) slowly at 0° C. The reaction mixture was warmed to r.t. and stirred for 2 hours. The reaction was quenched with HCl (1 M), and extracted with EtOAc (15 mL×3). The combined organic layers were washed with brine, dried, concentrated to give compound 4-3.

Steps B and C: (5aR,6S,6aS)-3-((4'-(3-hydroxy-3-methylbutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (5-3)

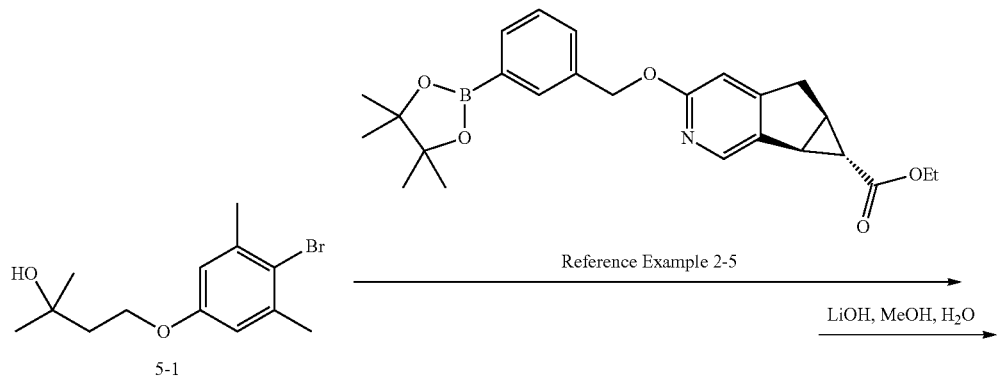

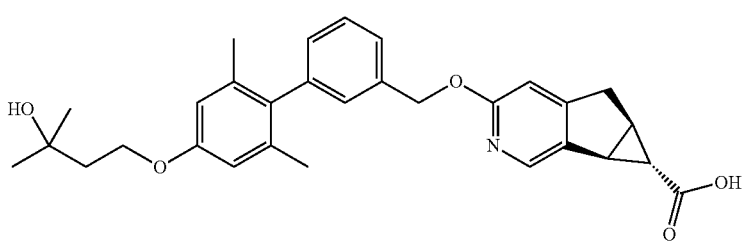

Compound 5-3 was prepared using procedures similar to the procedures used to prepare compounds 3-3 and 3-4. MS (ESI) m/z: 488 (M+H)+. $^1$H-NMR (400 MHz, CDCl$_3$) δ: 8.38 (s, 1H), 7.43-7.47 (m, 1H), 7.38-7.40 (m, 1H), 7.13-7.17 (m, 1H), 6.87 (s, 1H), 6.68 (s, 2H), 5.41 (s, 2H), 4.22 (t, 2H, J=6.0 Hz), 3.33-3.39 (m, 1H), 3.10-3.19 (m, 2H), 2.61 (s, 1H), 2.03 (t, 2H, J=6.0 Hz), 1.98 (s, 6H), 1.35 (s, 6H), 1.30-1.33 (m, 1H).

The following Examples 6-8 (compounds 5-4, 5-5 and 5-6) were prepared in a similar manner to compound 5-3 using the appropriate commercially available starting materials.

Example 8

Compound 5-6

$^1$H-NMR (400 MHz, MeOD) δ: 8.13 (s, 1H), 7.36-7.46 (m, 3H), 7.24-7.27 (m, 3H), 7.16-7.19 (m, 1H), 7.01 (s, 1H), 5.39 (s, 2H), 4.19-4.22 (t, 2H, J=6.8 Hz), 3.29-3.01 (m, 1H), 3.11-3.16 (d, 2H, J=19.2 Hz), 2.97-2.99 (dd, 1H, J$_1$=1.6 Hz, J$_2$=6.4 Hz), 2.47-2.51 (m, 1H), 1.98-2.01 (t, 2H, J=6.8 Hz), 1.29 (s, 6H), 1.22-1.23 (t, 1H, J=2.8 Hz)

| Example | Structure | M.W. | Compound Name | LC/MS (ESI) observed [M + 1]+ |
|---|---|---|---|---|
| 6 | (Compound 5-4) | 503 | (5aR,6S,6aS)-3-((4-fluoro-4'-(2-(1-hydroxycyclopropyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 504 |
| 7 | (Compound 5-5) | 545 | (5aR,6S,6aS)-3-((4-fluoro-4'-(3-hydroxy-3-methylbutoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 546 |
| 8 | (Compound 5-6) | 527 | (5aR,6S,6aS)-3-((4'-(3-hydroxy-3-methylbutoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 528 |

Example 6

Compound 5-4

$^1$H-NMR (400 MHz, CDCl3) δ: 8.30 (s, 1H), 7.20-7.26 (m, 1H), 7.10-7.17 (m, 2H), 6.82 (s, 1H), 6.67 (s, 2H), 5.45 (s, 2H), 4.21 (t, 2H, J=6.0 Hz), 3.32-3.38 (m, 1H), 3.08-3.17 (m, 2H), 2.61 (s, 1H), 2.00-2.03 (m, 2H), 1.97 (s, 6H), 1.34 (s, 6H), 1.25-1.29 (m, 1H).

Example 7

Compound 5-5

$^1$H-NMR (400 MHz, MeOD) δ: 8.09 (s, 1H), 7.38-7.41 (dd, 1H, J$_1$=1.6 Hz, J$_2$=6.8 Hz), 7.21-7.27 (m, 3H), 7.12-7.17 (m, 2H), 6.87 (s, 1H), 5.41 (s, 2H), 4.19-4.21 (t, 3H, J=7.2 Hz), 3.26-3.31 (m, 2H), 3.06-3.11 (d, 1H, J=18.8 Hz), 2.93-2.96 (dd, 1H, J$_1$=2.0 Hz, J$_2$=6.4 Hz), 2.43-2.47 (m, 1H), 1.97-2.01 (t, 2H, J=6.8 Hz), 1.28 (s, 6H), 1.18-1.19 (t, 1H, J=2.8 Hz)

Example 9

Compound 6-4

(5aR,6S,6aS)-3-((4-fluoro-4'-((S)-2-hydroxypropoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (6-4)

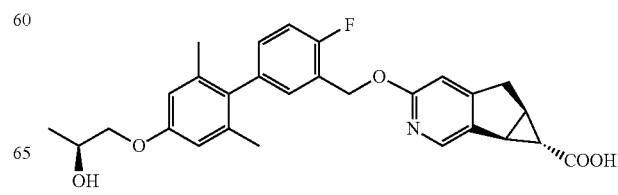

6-4

Step A: (S)-1-(4-bromo-3,5-dimethylphenoxy)pro-
pan-2-ol (6-2)

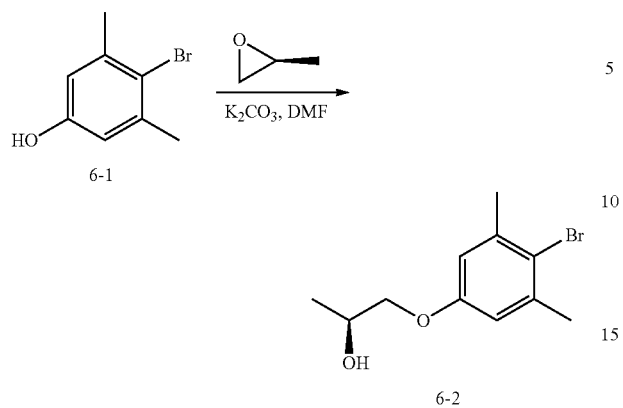

To a solution of compound 6-1 (100 mg, 0.5 mmol) and (S)-(−)-propylene oxide (120 mg, 2 mmol) in DMF (3 mL) was added $K_2CO_3$ (280 mg, 2 mmol). The mixture was heated at 100° C. overnight, and then filtered. The filtrate was concentrated in vacuo, the resulting residue was purified by preparative TLC on silica gel eluted with petroleum ether:ethyl acetate (2:1) to give compound 6-2. MS (ESI) m/z: 241 (M+H-18)$^+$.

Step B: (5aR,6S,6aS)-ethyl 3-((4-fluoro-4'-((S)-2-hydroxypropoxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylate (6-3)

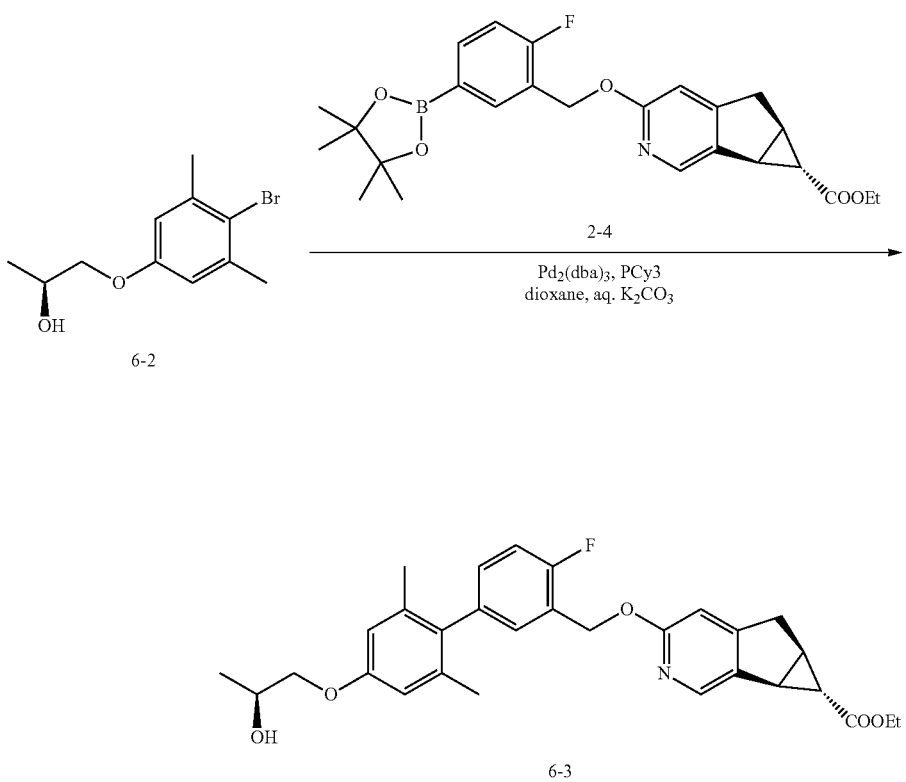

To a suspension of compound 6-2 (15.5 mg, 0.06 mmol) and Reference Example 2-4 (30 mg, 0.066 mmol) in dioxane (2 mL) and 2M $K_2CO_3$ aq. solution (1 mL) was added $Pd_2(dba)_3$ (10 mg, 0.01 mmol) and tricyclohexylphosphine (8.4 mg, 0.03 mmol) under $N_2$. The reaction was heated to 130° C. for 10 minutes in a microwave reactor, then the dioxane layer was separated and purified by preparative TLC on silica gel eluted with petroleum ether:ethyl acetate (2:1) to give compound 6-3. MS (ESI) m/z: 506 (M+H)$^+$.

Step C: (5aR,6S,6aS)-3-((4-fluoro-4'4'S)-2-hydroxy-propoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (6-4)

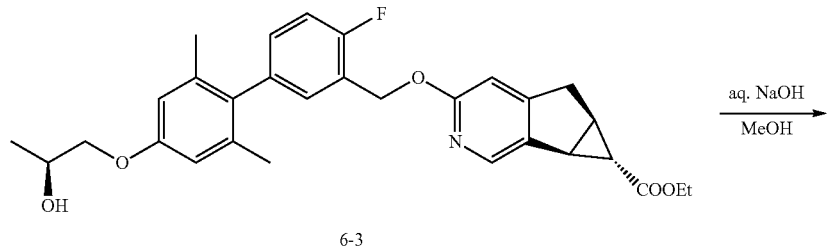

6-3

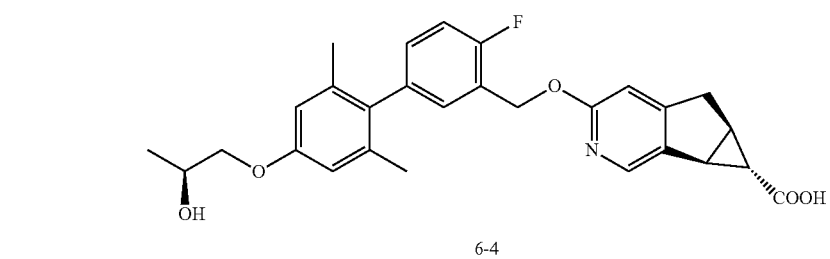

6-4

To a solution of compound 6-3 (10 mg, 0.02 mmol) in MeOH (2 mL) was added 2 M aq. NaOH solution (1 mL). The mixture was heated to 50° C. for 30 minutes, then poured into 10 mL of water, and acidified to pH 4 with diluted HCl. The mixture was extracted with ethyl acetate (5 mL×3), and the ethyl acetate layer was separated and concentrated in vacuo to give compound 6-4. MS (ESI) m/z: 478 (M+H)$^+$. $^1$H-NMR J000197236 H14692-1227-1 (400 MHz, CD$_3$OD) δ: 8.09 (s, 1H), 7.15-7.21 (m, 2H), 7.06-7.09 (m, 1H), 6.89 (s, 1H), 6.66 (s, 2H), 5.42 (s, 2H), 4.05-4.09 (m, 1H), 3.82-3.85 (m, 2H), 3.29-3.33 (m, 1H), 3.09 (d, 1H, J=18.8 Hz), 2.95 (d, 1H, J=4.8 Hz), 2.44-2.48 (m, 1H), 1.91 (s, 6H), 1.24 (d, 3H, J=6.4 Hz), 1.17 (t, 1H, J=2.0 Hz).

Example 10

Compound 7-4

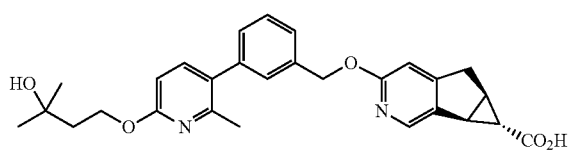

7-4

Step A: 4-((5-bromo-6-methylpyridin-2-yl)oxy)-2-methylbutan-2-ol (7-2)

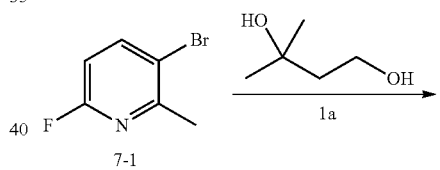

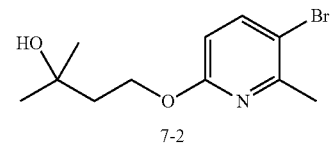

7-2

To a stirred solution of compound 1a (4 g, 38 mmol) in DMF (30 mL) was added NaH (3.3 g, 8.4 mmol, 60% in mineral oil) at 0° C. over 10 mins. The mixture was stirred for half an hour at r.t., and then cooled to 0° C. Then compound 7-1 (6 g, 32 mmol) in DMF (20 mL) was added to the reaction, and the reaction was stirred at r.t. for 12 h. The reaction was poured into water (100 mL), and the resulting mixture was stirred for 10 min. The mixture was then was extracted with EtOAc (60 mL×3). The organic layers were combined, washed with water (60 mL), brine (60 mL), dried and concentrated to give crude product, which was used directly for the next step without further purification. MS (ESI) m/z: 274.1.

Step B: (5aR,6S,6aS)-ethyl 34(3-(6-(3-hydroxy-3-methylbutoxy)-2-methylpyridin-3-yl) benzyl)oxyl-5,a,6,6a-tetrahydrocyclopropa[4,5]cyclopenta[1,2-c]pyridine-6-carboxylate (7-3)

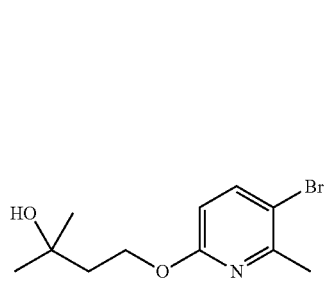

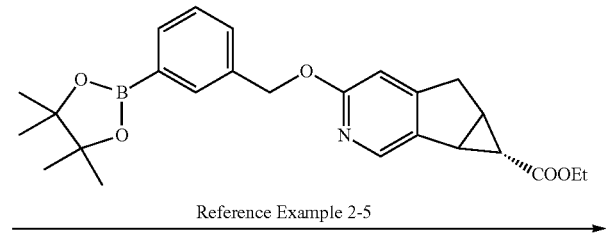

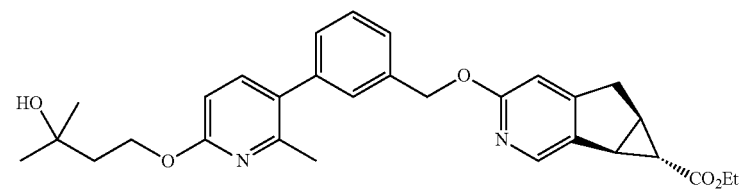

To a stirred solution of compound 7-2 (22 mg, 0.08 mmol) Reference Example 2-5 (35 mg, 0.08 mmol) $Na_2CO_3$ (40 mg) and $Pd(PPh_3)_4$ (5 mg) in dioxane (3 mL), was added $H_2O$ (1 mL). The resulting mixture was heated to 100° C. under $N_2$ for 2 h. Then the mixture was filtered, and the filtrate was concentrated to afford crude product, which was purified preparative TLC on silica gel eluted with petroleum ether:ethyl acetate (2:1) to give compound 7-3. MS (ESI) m/z: 503 (M+H)$^+$.

Step C: (5aR,6S,6aS)-34(3-(6-(3-hydroxy-3-methylbutoxy)-2-methylpyridin-3-yl)benzyl)oxy)-5, 5a,6, 6a-tetrahydrocyclopropa[4,5]cyclopenta[1,2-c]pyridine-6-carboxylic acid

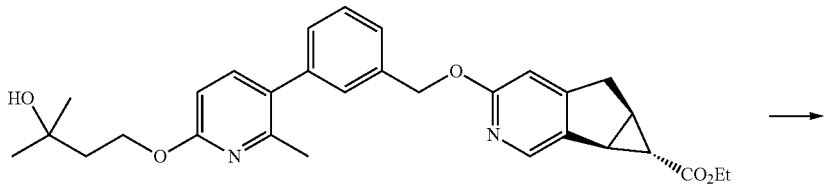

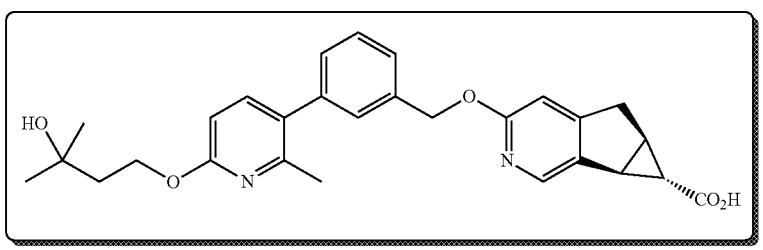

Compound 7-4 was prepared using a procedure similar to the procedure used to prepare Example 1 (compound 3-4). MS (ESI) m/z: 475 (M+H⁺). $^1$H-NMR (400 MHz, CD$_3$OD) δ: 8.11 (s, 1H), 7.90 (d, 1H, J=4.0 Hz), 7.48 (d, 2H, J=2.8 Hz), 7.35 (s, 1H), 7.33-7.31 (m, 1H), 7.08 (d, 1H, J=4.0 Hz), 6.94 (s, 1H), 5.40 (s, 2H), 4.52 (t, 2H, J=7.2 Hz), 3.35-3.32 (m, 1H), 3.12 (d, 1H, J=7.2 Hz), 2.96 (d, 1H, J=2.4 Hz), 2.49-2.45 (m, 4H), 2.01 (t, 2H, J=7.2 Hz), 1.29 (s, 6H), 1.17-1.15 (m, 1H).

The following Examples 11-14 (compounds 7-5, 7-6, 7-7 and 7-8) were prepared in a similar manner to Compound 7-4 using the appropriate commercially available starting materials and Reference Example 2-4.

| Example | Structure | M.W. | Compound Name | LC/MS (ESI) observed [M + 1]+ |
|---|---|---|---|---|
| 11 | 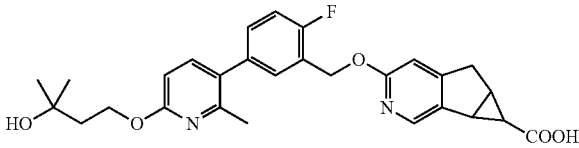 (Compound 7-5) | 492 | 3-((2-fluoro-5-(6-(3-hydroxy-3-methylbutoxy)-2-methylpyridin-3-yl)benzyl)oxy)-5,5a,6,6a-tetrahydrocyclopropa[4,5]cyclopenta[1,2-c]pyridine-6-carboxylic acid | 493 |
| 12 | 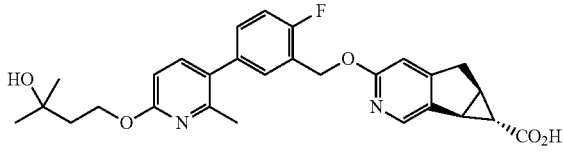 (Compound 7-6) | 492.6 | (5aR,6S,6aS)-3-((2-fluoro-5-(6-(3-hydroxy-3-methylbutoxy)-2-methylpyridin-3-yl)benzyl)oxy)-5,5a,6,6a-tetrahydrocyclopropa[4,5]cyclopenta[1,2-c]pyridine-6-carboxylic acid | 493 |
| 13 | 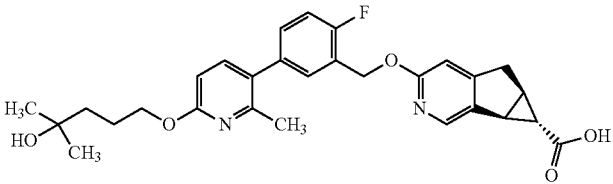 (Compound 7-7) | 506 | (5aR,6S,6aS)-3-((2-fluoro-5-(6-((4-hydroxy-4-methylpentyl)oxy)-2-methylpyridin-3-yl)benzyl)oxy)-5,5a,6,6a-tetrahydrocyclopropa[4,5]cyclopenta[1,2-c]pyridine-6-carboxylic acid | 507 |
| 14 | 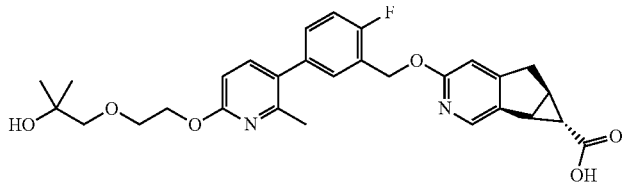 (Compound 7-8) | 552.6 | (5aR,6S,6aS)-3-((2-fluoro-5-(6-(2-(2-hydroxy-2-methylpropoxy)ethoxy)-2-methylpyridin-3-yl)benzyl)oxy)-5,5a,6,6a-tetrahydrocyclopropa[4,5]cyclopenta[1,2-c]pyridine-6-carboxylic acid | 533.4 |

Example 11

Compound 7-5

¹H-NMR (400 MHz, CD₃OD) δ: 8.06 (s, 1H), 7.45 (d, 1H, J=8.4 Hz), 7.40 (m, 1H), 7.24-7.28 (m, 1H), 7.16 (t, 1H, J=8.4 Hz), 6.69 (s, 1H), 6.64 (d, 1H, J=8.4 Hz), 5.39 (s, 2H), 4.40 (t, 2H, J=7.2 Hz), 3.21-3.26 (m, 1H), 3.03 (d, 1H, J=18.8 Hz), 2.91-2.92 (m, 1H), 2.40-2.44 (m, 1H), 2.28 (s, 3H), 1.96 (t, 2H, J=7.2 Hz), 1.27 (s, 6H), 1.13 (t, 1H, J=2.8 Hz).

Example 12

Compound 7-6

¹H-NMR (400 MHz, CD₃Cl) δ: 8.08 (s, 1H), 7.41-7.07 (m, 4H), 6.61-6.58 (m, 2H), 5.43 (s, 2H), 4.52 (t, 2H, J=7.2 Hz), 3.22 (dd, 1H, J=6.0 and 12.0 Hz), 2.99 (d, 2H, J=8.8 Hz), 2.48 (s, 1H), 2.32 (s, 3H), 1.99 (t, 2H, J=5.6 Hz), 1.29 (s, 6H), 1.23-1.17 (m, 7H).

Example 13

Compound 7-7

¹HNMR (400 MHz, CDCl₃) δ: 8.11 (s, 1H), 7.37-7.41 (m, 2H), 7.18-7.20 (m, 1H), 7.11 (t, 1H, J=8.8 Hz), 6.58-6.63 (m, 2H), 5.45 (s, 2H), 4.34 (t, 2H, J=6.4 Hz), 3.21-3.27 (m, 1H), 3.00-3.05 (m, 4H), 2.50-2.53 (m, 1H), 2.34 (s, 3H), 1.85-1.91 (m, 2H), 1.63-1.67 (m, 2H), 1.23-1.27 (m, 8H).

Example 14

Compound 7-8

¹HNMR (400 MHz, MeOH) δ: 8.11 (s, 1H), 7.80 (D, 1H, J=8.8 Hz), 7.49 (D, 1H, J=5.2 Hz), 7.36-7.33 (m, 1H), 7.23 (t, 1H, J=9.2 Hz), 7.02 (D, 1H, J=8.4 Hz), 6.91 (s, 1H), 5.44 (s, 2H), 4.53 (t, 2H, J=4.4 Hz), 3.87 (t, 2H, J=4.4 Hz), 3.35-3.33 (m, 3H), 3.10 (D, 1H, J=19.2 Hz), 2.95 (D, 1H, J=5.2 Hz), 2.46 (m, 1H), 2.37 (s, 3H), 1.18 (m, 1H), 1.16 (s, 6H).

Example 15

Compound 8-5

(5aR,6S,6aS)-3-((4-fluoro-4'-(2-(1-hydroxycyclopropyl)ethoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid (8-5)

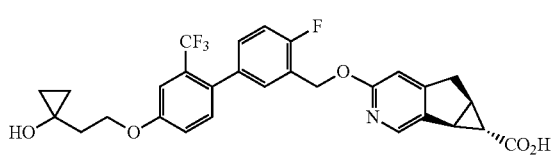

Step A: methyl 3-(4-bromo-3-(trifluoromethyl)phenoxy)propanoate (8-2)

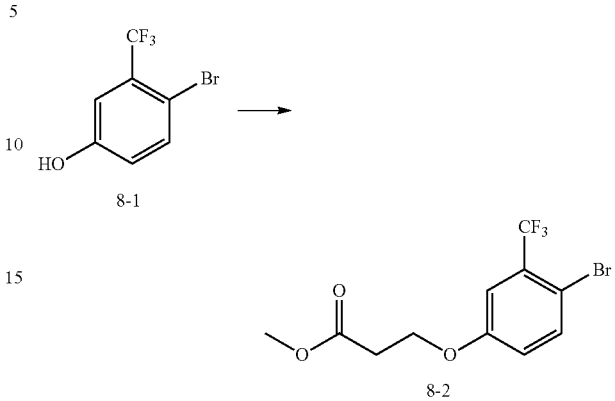

To a stirred solution of compound 8-1 (3 g, 12.4 mmol) in methylacrylate (25 mL) was added MeONa (2.1 g, 37.2 mmol) in portions. The mixture heated to reflux overnight under N₂. HCl (2N, 30 mL) was added to the mixture. Then the mixture was extracted with EA, washed with brine, dried and concentrated to afford the crude product, which was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 50-80% B, 0-10 min; 100% B, 10.5-12.5 min; 5% B, 13-15 min) to give compound 8-2. MS (ESI) m/z: no MS was observed.

Step B: 1-(2-(4-bromo-3-(trifluoromethyl)phenoxy)ethyl)cyclopropanol (8-3)

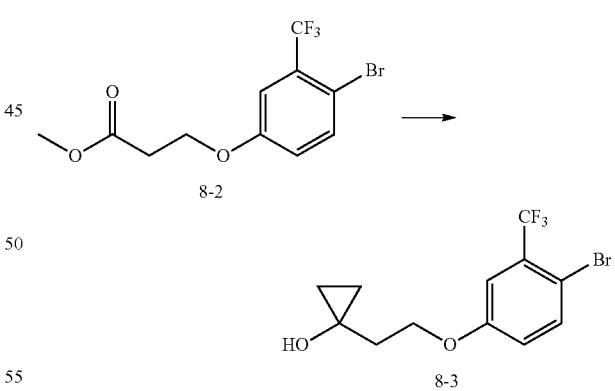

To a stirred solution of compound 8-2 (250 mg, 0.76 mmol) in THF (10 mL) was added Ti(OiPr)₄ (86 mg, 0.31 mmol) in one portion. The mixture stirred for 10 mins, then EtMgBr (0.31 mL, 0.93 mmol) was added dropwise to the mixture at 0° C. The resulting mixture was stirred at r.t for 1 h. The mixture was then quenched with 2 N HCl, extracted with EtOAc (20 mL×3), washed with brine, dried over Na₂SO₄, and concentrated to afford crude product, which was purified by preparative TLC on silica gel eluted with petroleum ether:ethyl acetate (3:1) to give compound 8-3.

Step C: (5aR,6S,6aS)-ethyl 3-((4-fluoro-4'-(2-(1-hydroxycyclopropyl)ethoxy)-2'-(trifluoromethyl)-[1,1'-biphenyl]-3-yl)methoxy)-5,5a,6,6a-tetrahydrocyclopropa[4,5]-cyclopenta[1,2-c]pyridine-6-carboxylate (8-4)

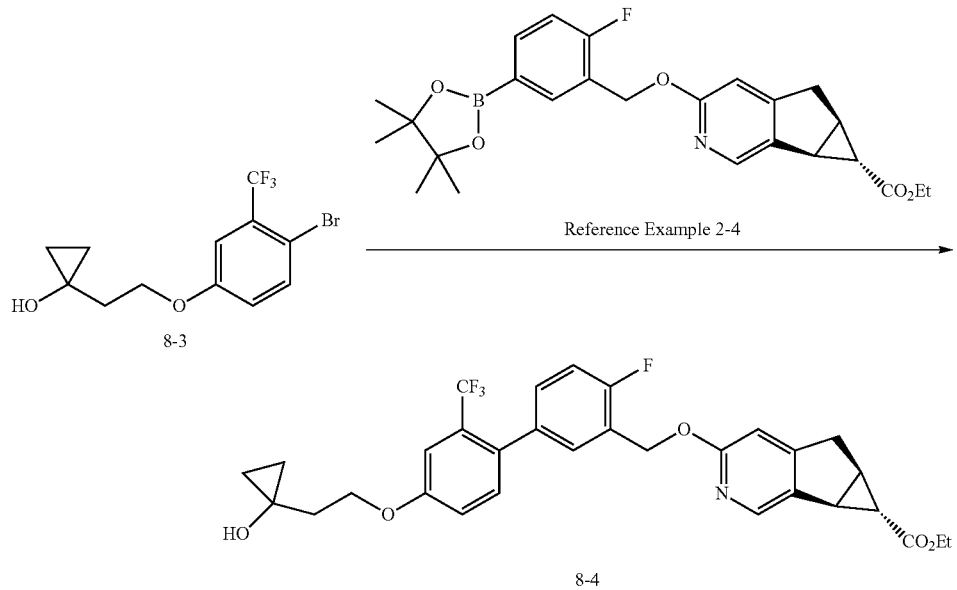

A microwave vessel charged with compound 8-3 (20 mg, 0.06 mmol), Reference Example 2-4 (33 mg, 0.07 mmol), Pd(dppf)Cl$_2$ (5 mg), K$_3$PO$_4$ (25 mg, 0.12 mmol), THF (2 mL) and H$_2$O (0.5 mL) was heated to 100° C. for 30 mins in the microwave. The reaction mixture was cooled and filtered. The filtrate was concentrated and the resulting residue was purified by preparative silica TLC (PE/EA=1/1) to give compound 8-4. MS (ESI) m/z: 572 (M+H$^+$).

Step D: (5aR,6S,6aS)-3-((4-fluoro-4'-(2-(1-hydroxycyclopropyl)ethoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid (8-5)

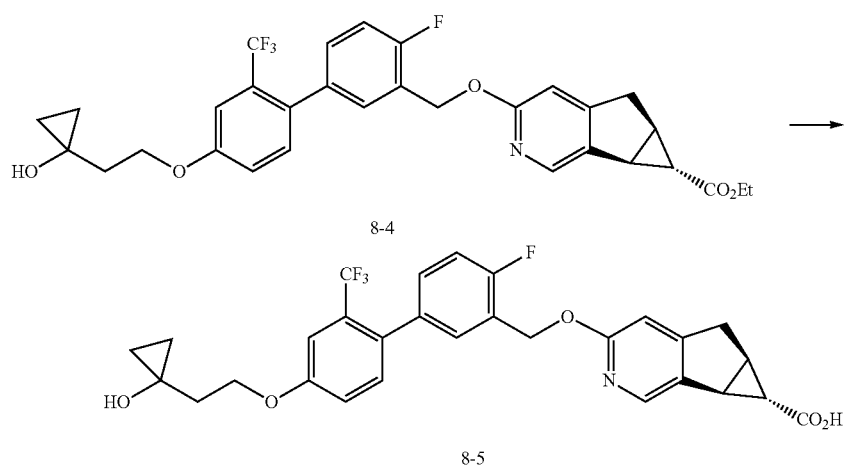

To a stirred solution of compound 8-4 (12 mg) in MeOH (2 mL) and H$_2$O (2 mL) was added LiOH (100 mg) in one portion. The reaction mixture stirred at r.t for 1 h. The reaction mixture was poured into 10 mL of water, and acidified to pH 4 with 1N aq. HCl. The mixture was extracted with ethyl acetate (5 mL×3), and the combined ethyl acetate layer was separated and concentrated in vacuo to give the crude compound, which was purified by prep.

HPLC (preparative HPLC on a GILSON 281 instrument fitted with a YMC-Actus Triart C18 (150×30 min×4 um) using water and acetonitrile as the eluents. Mobile phase A: water (containing 0.1% TFA, v/v), mobile phase B: acetonitrile. Gradient: 45-65% B, 0-10 min; 100% B, 10.5-12.5 min; 5% B, 13-15 min) to give compound 8-5. MS (ESI) m/z: 544 (M+H$^+$). $^1$H-NMR (400 MHz, CD$_3$OD) δ: 8.13 (s, 1H), 7.41 (d, 1H, J=2.8 Hz), 7.28-7.14 (m, 5H), 7.03 (s, 1H), 5.45 (s, 2H), 4.29 (t, 2H, J=6.8 Hz), 3.40 (dd, 1H, J=6.0 and 12.0 Hz), 3.19 (d, 1H, J=8.8 Hz), 3.02 (d, 1H, J=2.8 Hz), 2.55-2.51 (m, 1H), 2.05 (t, 2H, J=6.8 Hz), 1.27-1.26 (m, 1H), 0.72-0.69 (m, 2H), 0.58-0.55 (m, 2H).

The following Example 16 (Compound 8-6) was prepared in a similar manner to Compound 8-5 using the appropriate commercially available starting materials.

Step A: 4-((ethylperoxy)methyl)-4-fluorotetrahydro-2H-pyran (9-2)

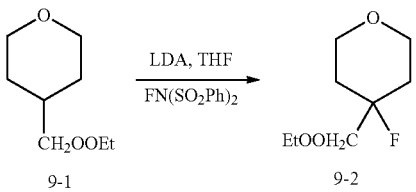

| Example | Structure | M.W. | Compound Name | LC/MS (ESI) observed [M + 1]+ |
|---|---|---|---|---|
| 16 | (Compound 8-6) | 525 | (5aR,6S,6aS)-3((4'-(2-(1-hydroxycyclopropyl)ethoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 526 |

Example 16

Compound 8-6

$^1$H-NMR (400 MHz, CD$_3$OD) δ: 8.18 (s, 1H), 7.49-7.38 (m, 3H), 7.28-7.20 (m, 4H), 7.14 (s, 1H), 5.42 (s, 2H), 4.30 (t, 2H, J=6.8 Hz), 3.40 (dd, 1H, J=6.0 and 12.0 Hz), 3.19 (d, 1H, J=8.8 Hz), 3.02 (d, 1H, J=2.8 Hz), 2.55-2.51 (m, 1H), 2.05 (t, 2H, J=6.8 Hz), 1.27-1.26 (m, 1H), 0.74-0.71 (m, 2H), 0.58-0.55 (m, 2H).

Example 17

Compound 9-7

(5aR,6S,6aS)-3-((4-fluoro-4'-((4-fluorotetrahydro-2H-pyran-4-yl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (9-7)

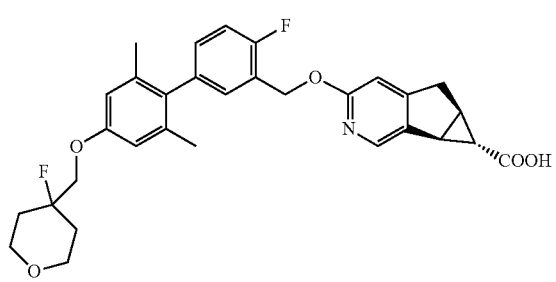

To a solution of compound 9-1 (2 g, 14 mmol) in THF (20 mL) at −78° C. was added dropwise LDA (2M, 14 mL). The reaction mixture was stirred at rt for 1 h. Then a solution of FN(SO$_2$Ph)$_2$ (446 mg, 11.7 mmol) in THF (10 mL) was added dropwise at −78° C., and the mixture was stirred at rt for 12 h. The reaction mixture was then quenched with saturated NH$_4$Cl and extracted with EtOAc (10 mL×3). The organic layers were combined, dried over Na$_2$SO$_4$, filtered and concentrated to give compound 9-2, which was used directly for the next step.

Step B: (4-fluorotetrahydro-2H-pyran-4-yl)methanol (9-3)

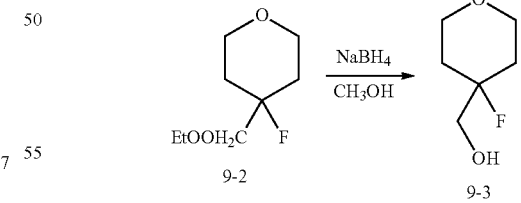

To a solution of compound 9-2 (500 mg, 3.1 mmol) in CH$_3$OH in 0° C. was added NaBH$_4$ (352 mg, 9.3 mmol). The reaction mixture was stirred at rt for 3 h. The reaction mixture was then concentrated in vacuo and the resulting residue was treated with brine (20 mL), and extracted with EtOAc (5 mL×4). The organic layers were combined, dried over Na$_2$SO$_4$, filtered and concentrated to give compound 9-3 as a solid.

Step C: (4-fluorotetrahydro-2H-pyran-4-yl) methyl 4-methylbenzenesulfonate (9-4)

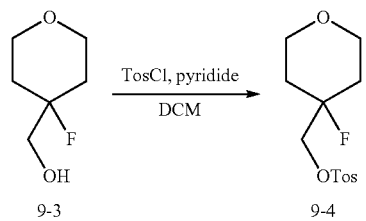

To a solution of compound 9-3 (320 mg, 2.4 mmol) in pyridine (2 mL) at 0° C. was added TosCl (1.36 g, 7.2 mmol) in several portions and the reaction stirred at rt for 1 h. The reaction mixture was then concentrated in vacuo, treated with brine (30 mL), and extracted with EtOAc (10 mL×3). The organic layers were combined, dried over Na₂SO₄, filtered and concentrated to give compound 9-4 as a solid. MS (ESI) m/z: 298 (M+H)⁺.

Step D: 4-((4-bromo-3,5-dimethylphenoxy)methyl)-4-fluorotetrahydro-2H-pyran (9-5)

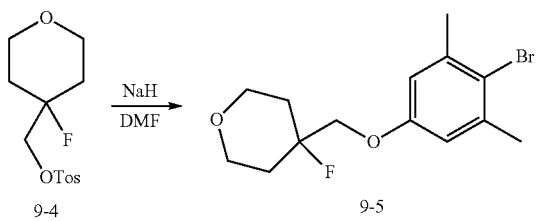

To a solution of compound 9-4 (150 mg, 0.52 mmol) and 4-bromo-3,5-dimethyl-phenol (210 mg, 1.04 mmol) in DMF (2 mL) was added NaH (72 mg, 3 mmol). The reaction mixture was stirred at rt for 3 h. After the reaction finished, H₂O (5 mL) was added and the mixture was extracted with EtOAc (3 mL×3). The organic layer were combined, washed with brine, dried over Na₂SO₄ and concentrated. The resulting residue was purified by preparative TLC on silica gel eluted with petroleum ether:ethyl acetate (5:1) to give compound 9-5. MS (ESI) m/z: 318 and 320 (M+H)⁺.

Step E: ethyl 3-((4-fluoro-4'-((4-fluorotetrahydro-2H-pyran-4-yl)methoxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylate (9-6)

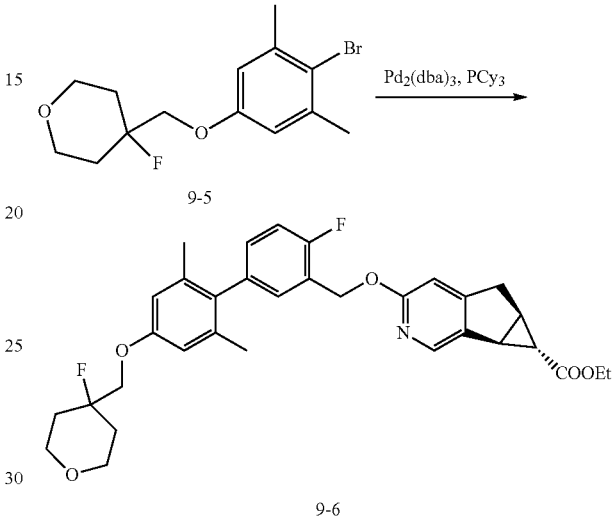

A solution of compound 9-5 (30 mg, 0.092 mmol), boronate from Reference Example 2-4 (62 mg, 0.138 mmol), Pd₂(dba)₃ (11 mg, 0.0092 mmol), P(Cy)₃ (5 mg, 0.0018 mmol) and K₂CO₃ (25 mg, 0.184 mmol) in dioxane (2 mL) and H₂O (0.4 mL) was heated to reflux for 1 h. Then the solvent was removed and the resulting residue was preparative TLC on silica gel eluted with petroleum ether: ethyl acetate (5:1) to give compound 9-6. MS (ESI) m/z: 564 (M+H)⁺.

Step F: (5aR,6S,6aS)-3-((4-fluoro-4'-((4-fluorotetrahydro-2H-pyran-4-yl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (9-7)

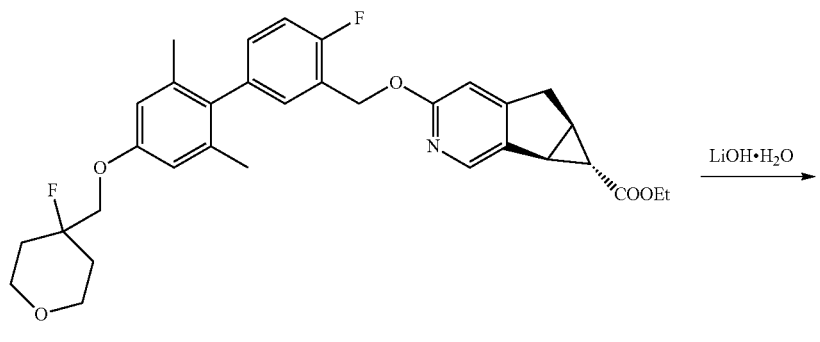

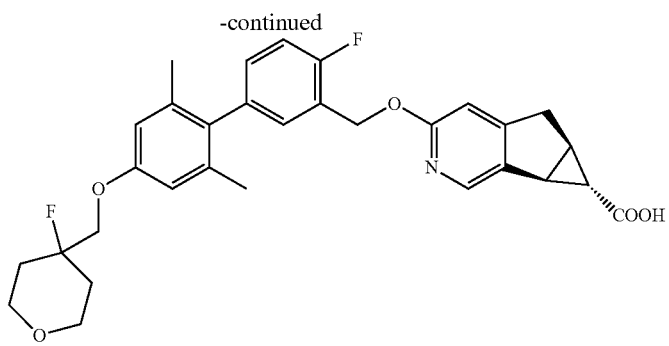

9-7

To a solution of compound 9-6 (20 mg, 0.035 mmol) in CH$_3$OH and H$_2$O (2 mL/0.5 mL) was added LiOH.H$_2$O (4 mg, 0.1 mmol) and the mixture was heated to 40° C. for 2 h. Then the reaction mixture was concentrated in vacuo to give a residue, which was purified by preparative TLC on silica gel eluted with DCM:MeOH (2:1) to give compound 9-7. MS (ESI) m/z: 535 (M+H)$^+$. $^1$H-NMR (400 MHz, CDCl$_3$)$^1$H NMR (400 MHz, CDCl$_3$) δ: 7.10-7.31 (m, 3H), 6.91 (s, 1H), 6.67 (s, 2H), 5.45 (s, 2H), 3.98 (d, 2H, J=17.6 Hz), 3.90-4.01 (m, 2H), 3.75-3.85 (m, 2H), 3.38 (dd, 1H, J=6.0 and 18 Hz), 3.07-3.20 (m, 2H), 2.51 (t, 1H, J=2.8 Hz), 1.85-2.05 (m, 9H), 1.31 (s, 1H).

The following Example 18 (Compound 9-8) was prepared in a similar manner to Compound 9-7 using the appropriate commercially available starting materials and boronate from Reference Example 2-5

Example 19

Compound 10-5

(5aR,6S,6aS)-3((2', 4-difluoro-4'-(3-(methylsulfonyl)propoxy)-6'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid (10-5)

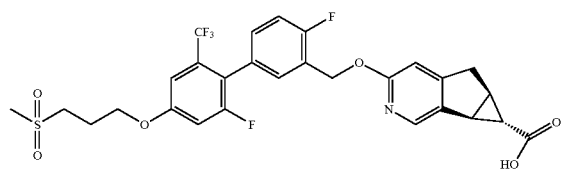

10-5

| Example | Structure | M.W. | Compound Name | LC/MS (ESI) observed [M + 1]+ |
|---|---|---|---|---|
| 18 | 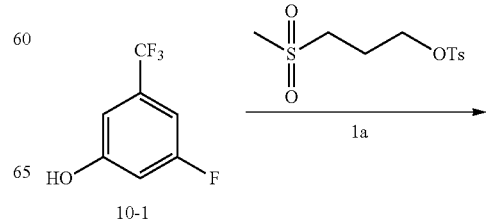(Compound 9-8) | 517 | (5aR,6S,6aS)-3-((4'-((4-fluorotetrahydro-2H-pyran-4-yl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 518 |

Example 18

Compound 9-8

$^1$H-NMR (400 MHz, MeOD) δ: 8.14 (s, 1H), 7.38-7.44 (m, 2H), 7.17-7.20 (d, 2H, J=7.6 Hz), 7.05-7.07 (d, 1H, J=6.4 Hz), 6.65 (s, 2H), 5.39 (s, 2H), 3.94-3.98 (d, 2H, J=18.8 Hz), 3.77-3.81 (m, 2H), 3.66-3.73 (m, 2H), 3.34-3.40 (dd, 1H, J$_1$=6.4 Hz, J$_2$=20 Hz), 3.15-3.20 (d, 1H, J=19.6 Hz), 2.97-2.99 (m, 1H), 2.47-2.51 (m, 1H), 1.83-1.92 (m, 10H), 1.23-1.25 (m, 1H).

Step A: 1-fluoro-3-(3-(methylsulfonyl)propoxy)-5-(trifluoromethyl)benzene (10-2)

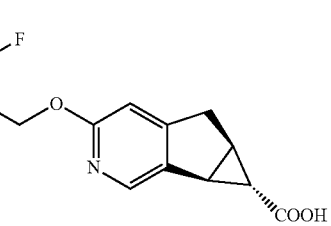

10-1

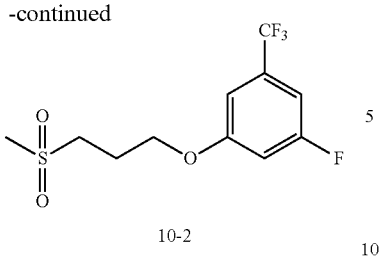

10-2

To a solution of compound 10-1 (400 mg, 2.22 mmol) in DMF (5.0 mL) was added compound 1a (973 mg, 3.33 mmol), and K$_2$CO$_3$ (613 mg, 4.44 mmol). The resulting mixture was stirred at 100° C. for 18 hours. H$_2$O was added and the resulting mixture was extracted with EtOAc (15 mL×3). The combined organic layers were washed with brine, dried and concentrated to give a residue, which was purified by preparative TLC on silica gel eluted with petroleum ether:ethyl acetate (5:1) to give compound 10-2.

Step B: 2-bromo-1-fluoro-5-(3-(methylsulfonyl)propoxy)-3-(trifluoromethyl)benzene (10-3)

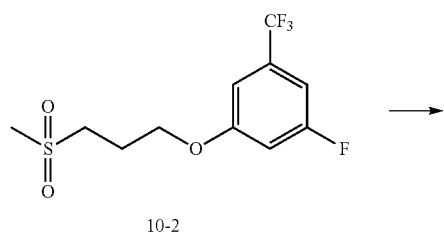

10-2

10-3

To a solution of compound 10-2 (300 mg, 1.0 mmol) in HOAc (5.0 mL) was added Br$_2$ (2.0 mL). The resulting mixture was stirred at rt. for 4 hours. Then the solution was basified with NaHCO$_3$, quenched with saturated Na$_2$SO$_3$, extracted with EtOAc (10 mL×3). The combined organic layers were washed with brine, dried and concentrated to give a residue, which was purified by preparative TLC on silica gel eluted with petroleum ether:ethyl acetate (3:1) to give compound 10-3. MS (ESI) m/z: 378, 380 (M+H)$^+$.

Step C: 2 (5aR,6S,6aS)-ethyl 3-((2',4-difluoro-4'-(3-(methylsulfonyl)propoxy)-6'-(trifluoromethyl)-[1,1'-biphenyl]-3-yl)methoxy)-5,5a,6,6a-tetrahydrocyclopropa[4,5]-cyclopenta[1,2-c]pyridine-6-carboxylate (10-4)

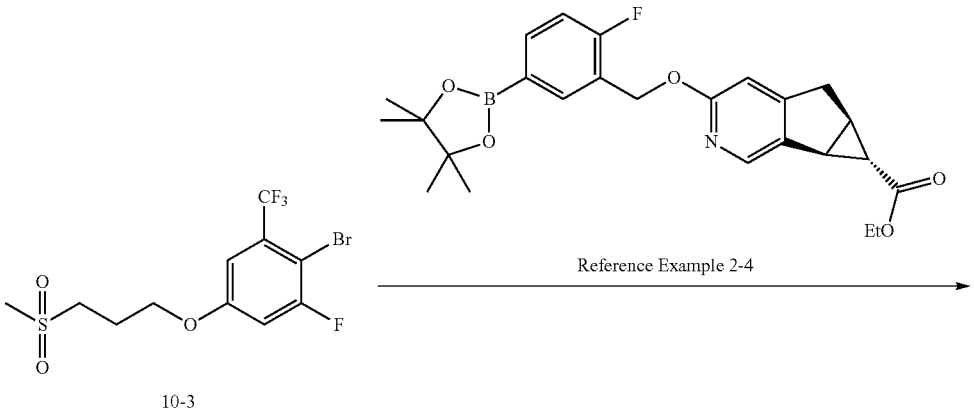

10-3

Reference Example 2-4

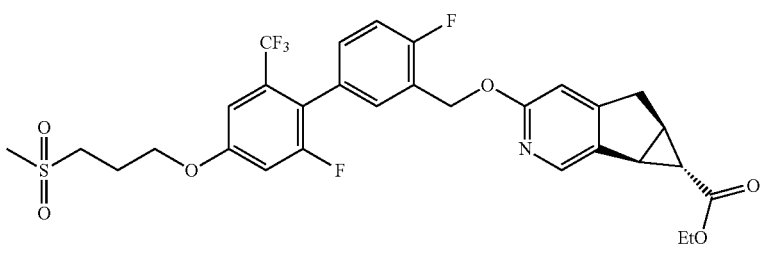

10-4

To a solution of compound 10-3 (40 mg, 0.11 mmol) in THF (9.0 mL) and H$_2$O (3.0 mL) was added boronate from Reference Example 2-4 (57 mg, 0.13 mmol), K$_3$PO$_4$ (70 mg, 0.33 mmol) and Pd(dppf)$_2$Cl$_2$ (8 mg, 0.01 mmol) in N$_2$. The resulting mixture was sealed and heated to 100° C. with microwaves for 10 mins. The solution was then filtered and the filtrate was concentrated to give a residue, which was purified by preparative TLC on silica gel eluted with petroleum ether:ethyl acetate (1:1) to give compound 10-4. MS (ESI) m/z: 626 (M+H)$^+$.

Step D: (5aR,6S,6aS)-3-((2',4-difluoro-4'-(3-(methylsulfonyl)propoxy)-6'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid (10-5)

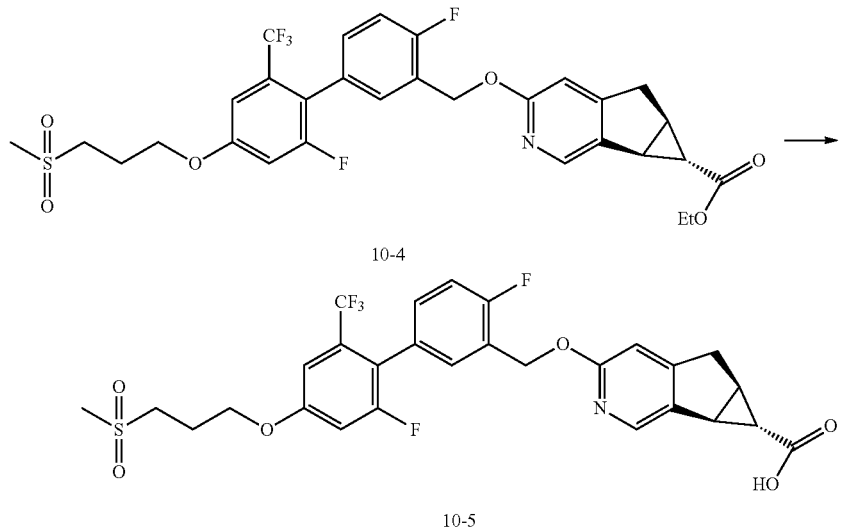

To a solution of compound 10-4 (30 mg, 0.05 mmol) in THF (9.0 mL), MeOH (3.0 mL) and H$_2$O (3.0 mL) was added LiOH.H$_2$O (8 mg, 0.20 mmol). The resulting mixture was stirred at rt. for 4 hours. H$_2$O was added, then the solution was acidified with HCl (1 M) to pH 2.5, and extracted with EtOAc (10 mL×3). The combined organic layer were washed with brine, dried and concentrated to give a residue, which was purified by preparative HPLC (preparative HPLC on a GILSON 281 instrument fitted with a YMC-Actus Triart C18 (150×30 mm×4 um) using water and acetonitrile as the eluents. Mobile phase A: water (containing 0.1% TFA, v/v), mobile phase B: acetonitrile. Gradient: 35-65% B, 0-10 min; 100% B, 10.5-12.5 min; 5% B, 13-15 min) to give compound 10-5. MS (ESI) m/z: 598 (M+H)$^+$.
$^1$H-NMR (400 MHz, CDCl$_3$) δ: 8.32 (s, 1H), 7.96 (d, 1H, J=6.8 Hz), 7.11-7.16 (m, 1H), 7.06 (s, 1H), 6.80-6.85 (m, 1H), 5.45 (s, 2H), 4.18 (t, 2H, J=6.0 Hz), 3.33-3.36 (m, 1H), 3.24-3.31 (m, 2H), 3.07-316 (m, 2H), 2.98 (s, 3H), 2.59-2.63 (m, 1H), 2.36-2.42 (m, 2H), 1.19 (s, 1H).

Example 20

Compound 10-6 and

Example 21

Compound 10-7

(Compound 10-6)

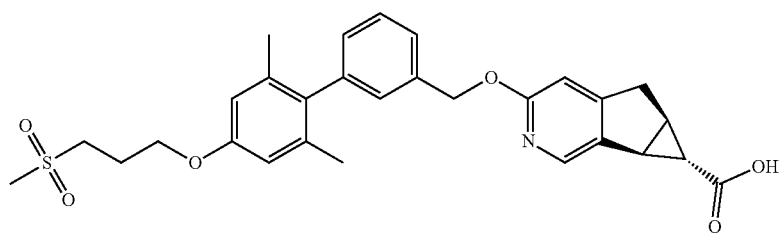

(Compound 10-7)
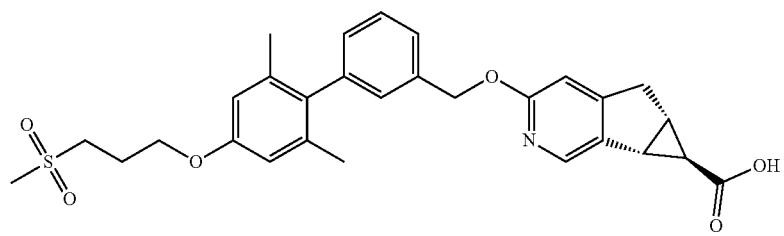
Step A: (5aR,6S,6aS)-ethyl 3-((2',6'-dimethyl-4'-(3-(methylsulfonyl)propoxy)-[1,1'-biphenyl]-3-yl)methoxy)-5,5a,6,6a-tetrahydrocyclopropa[4,5]cyclopenta[1,2-c]pyridine-6-carboxylate (34-6) and its enantiomer (34-6a)
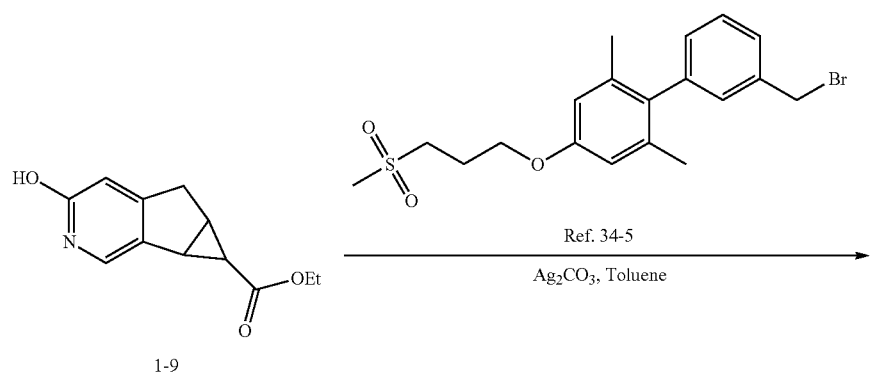
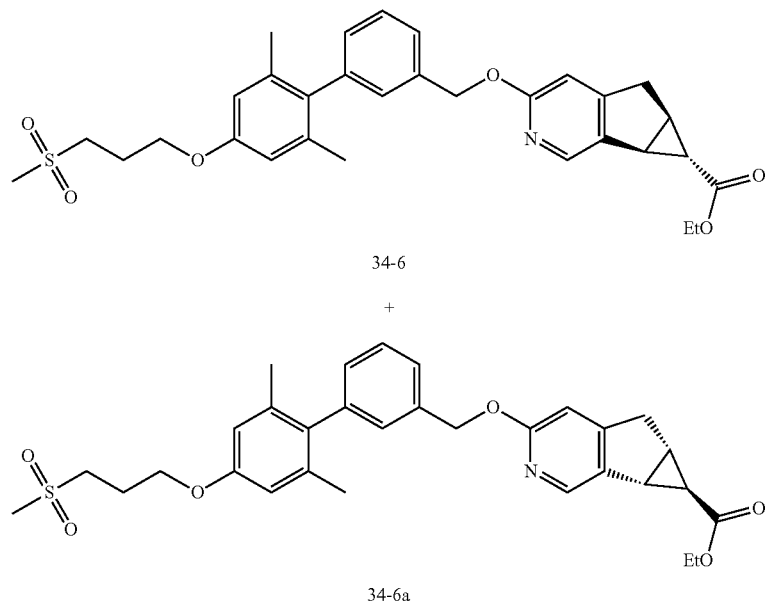

To a suspension of Reference Example 1-9 (0.12 g, 0.55 mmol) and Ag$_2$CO$_3$ (0.4 g, 1.46 mmol) in 3 mL of toluene was added Compound 34-5 from Reference Example 11 (0.3 g, 0.73 mmol) and the resultant mixture was heated at 110° C. for 3 hours. After cooling to room temperature, the reaction was quenched with water and the aqueous layer extracted twice with ethyl acetate. The combined organic layers were washed with brine and dried over Na$_2$SO$_4$. After filtration and concentration, the resulting residue was purified by column chromatography on silica gel (eluted with DCM: MeOH=30:1) to give a mixture of enantiomers. The mixture of enantiomers was resolved by SFC to give compound 34-6 and its enantiomer compound 34-6a, under the following SFC separation conditions: instrument: Thar 80, column: AD 250 mm×20 mm, 20 um; mobile phase: A: supercritical CO$_2$, B: ethanol (0.05% NH$_3$H$_2$O, A:B=60:40 at 80 mL/min; column temperature: 38° C., nozzle pressure: 100 bar, nozzle temperature: 60° C., evaporator temperature: 20° C., trimmer temperature: 25° C., wavelength: 220 nm. MS (ESI) m/e (M+H$^+$): 550.2.

Step B: (5aR,6S,6aS)-3-((2',6'-dimethyl-4'-(3-(methylsulfonyl)propoxy)-[1,1'-biphenyl]-3-yl)methoxy)-5,5a,6,6a-tetrahydrocyclopropa[4,5]cyclopenta[1,2-c]pyridine-6-carboxylic acid (10-6)

0.9 mmol). The resulting mixture was stirred at room temperature for 2 h. After adjusting the pH to pH-3 with 1N HCl, the reaction mixture was partitioned between ethyl acetate and water. The aqueous layer was separated, and extracted by ethyl acetate twice. The combined organic layers were washed with brine, dried over Na$_2$SO$_4$ and concentrated. The resulting residue was purified by preparative HPLC (preparative HPLC on a GILSON 281 instrument fitted with a Phenomenex Synergi C18 column (150×30 mm×5 um) using water and acetonitrile as the eluents: mobile phase A: water (containing 0.1% TFA, v/v), mobile phase B: acetonitrile; Gradient: 20-60% B, 0-10 min; 100% B, 10.5-12.5 min; 5% B, 13-15 min) to give compound 10-6. MS (ESI) m/e (M+H$^+$): 522.2. $^1$H-NMR: MeOD 400 MHz δ: 8.02 (s, 1H, ArH), 7.37 (m, 2H, ArH), 7.11 (s, 1H, ArH), 7.01 (m, 1H, ArH), 6.66 (m, 3H, ArH), 5.30 (s, 2H, CH$_2$), 4.08 (m, 2H, CH), 3.32~3.23 (m, 4H, CH$_2$), 3.18 (m, 1H, CH$_2$), 2.99 (s, 3H, CH$_3$), 2.87 (m, 1H, CH$_2$), 2.41~2.37 (m, 1H, CH$_2$), 2.29~2.22 (m, 2H, CH$_2$), 1.91 (s, 6H, CH$_3$).

Likewise, compound 34-6a was reacted with lithium hydroxide as described in Step B to give (5aS,6R,6aR)-3-((2',6'-dimethyl-4'-(3-(methylsulfonyl)-propoxy)-[1,1'-biphenyl]-3-yl)methoxy)-5,5a,6,6a-tetrahydrocyclopropa[4,5]cyclopenta[1,2-c]pyridine-6-carboxylic acid (Example 21,

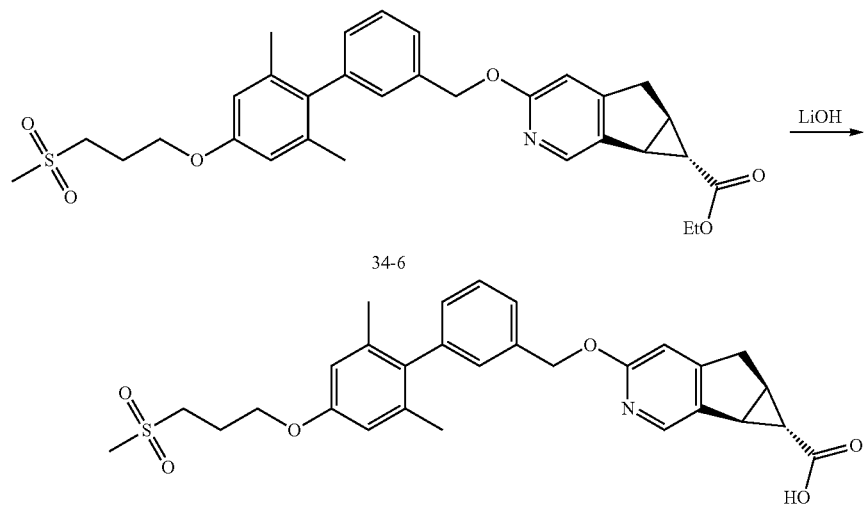

34-6

Example 20 (Compound 10-6)

To a solution of compound 34-6 (100 mg, 0.182 mmol) in methanol (3 mL) and water (1 mL) was added LiOH (36 mg, Compound 10-7), which exhibited identical spectral properties to those of compound 10-6.

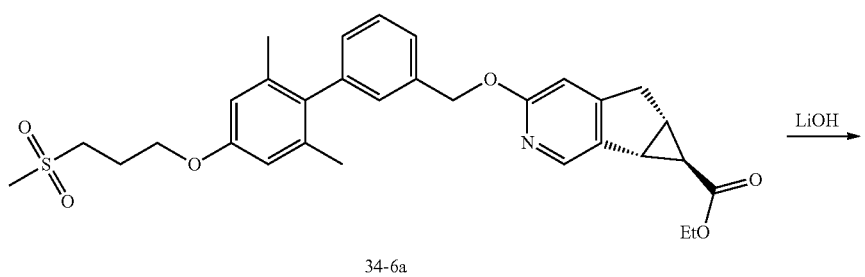

34-6a

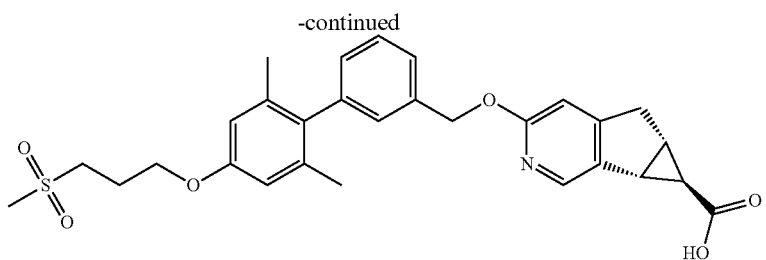

Example 21 (Compound 10-7)

The following Examples 22-26 (Compounds 10-8 to 10-12) were prepared in a similar manner to Example 19 (compound 10-5) using the appropriate starting materials and a boronate from either Reference Example 2-4 or Reference Example 2-5.

| Example | Structure | M.W. | Compound Name | LC/MS (ESI) observed [M + 1]+ |
|---|---|---|---|---|
| 22 | (Compound 10-8) | 539.6 | (5aR,6S,6aS)-3-((4-fluoro-2',6'-dimethyl-4'-(3-(methylsulfonyl)propoxy)-[1,1'-biphenyl]-3-yl)methoxy)-5,5a,6,6a-tetrahydrocyclopropa[4,5]cyclopenta[1,2-c]pyridine-6-carboxylic acid | 540.3 |
| 23 | (Compound 10-9) | 579.6 | 3-((4-fluoro-4'-(3-(methylsulfonyl)propoxy)-2'-(trifluoromethyl)[1,1'-biphenyl]-3-yl)methoxy)-5,5a,6,6a-tetrahydrocyclopropa[4,5]cyclopenta[1,2-c]pyridine-6-carboxylic acid | 580.4 |
| 24 | (Compound 10-10) | 579.6 | (5aR,6S,6aS)-3-((4-fluoro-4'-(3-(methylsulfonyl)propoxy)-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 580.4 |

| Example | Structure | M.W. | Compound Name | LC/MS (ESI) observed [M + 1]+ |
|---|---|---|---|---|
| 25 | (Compound 10-11) | 595.6 | (5aR,6S,6aS)-3-((4-fluoro-5'-(3-(methylsulfonyl)-propoxy)-2'-(trifluoro-methoxy)-[1,1'-biphenyl]-3-yl)methoxy)-5,5a,6,6a-tetrahydrocyclopropa[4,5]cyclopenta[1,2-c]pyridine-6-carboxylic acid | 596.4 |
| 26 | (Compound 10-12) | 647.5 | 3-((3'-iodo-2',6'-dimethyl-4'-(3-(methylsulfonyl)-propoxy)-[1,1'-biphenyl]-3-yl)methoxy)-5,5a,6,6a-tetrahydrocyclopropa[4,5]cyclopenta[1,2-c]pyridine-6-carboxylic acid | 648.3 |

Example 27

Compound 11-6

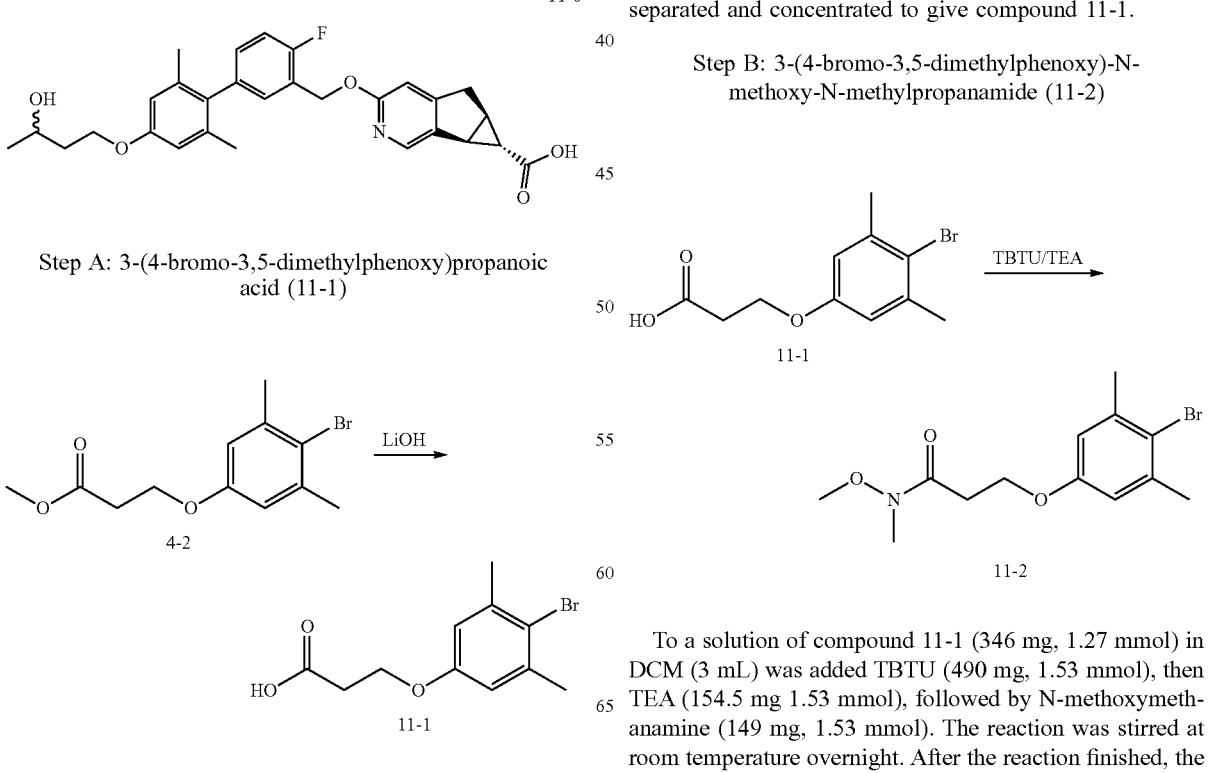

Step A: 3-(4-bromo-3,5-dimethylphenoxy)propanoic acid (11-1)

To a solution of compound 4-2 (330 mg, 1.15 mmol) in MeOH/H$_2$O (4/1 mL) was added LiOH (144.8 mg, 3.45 mmol). The solution was stirred at 100° C. for 2 h. After the reaction finished, HCl (1 mol/L, 1 mL) was added to the solution to adjust the pH to 5. Then the solution was extracted with EtOAc (5 mL×3) and the organic layers were separated and concentrated to give compound 11-1.

Step B: 3-(4-bromo-3,5-dimethylphenoxy)-N-methoxy-N-methylpropanamide (11-2)

To a solution of compound 11-1 (346 mg, 1.27 mmol) in DCM (3 mL) was added TBTU (490 mg, 1.53 mmol), then TEA (154.5 mg 1.53 mmol), followed by N-methoxymeth-anamine (149 mg, 1.53 mmol). The reaction was stirred at room temperature overnight. After the reaction finished, the reaction mixture was washed with water and extracted with DCM (5 mL×3). The organic layers were separated, combined and concentrated to give the crude product, which was purified by preparative TLC on silica gel eluted with petroleum ether:ethyl acetate (5:1) to give compound 11-2. MS (ESI) m/z: 316,318 (M+H)⁺.

Step C: 4-(4-bromo-3,5-dimethylphenoxy)butan-2-one (11-3)

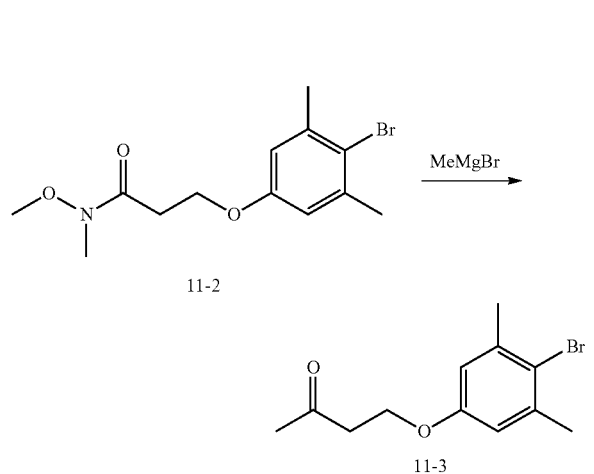

To a solution of compound 11-2 (100 mg, 0.317 mmol) in THF (2 mL), cooled in an ice bath, was added dropwise MeMgBr (1 mL). The reaction was stirred at room temperature for 2 h. After the reaction finished, the reaction mixture was quenched with 2 mol/L HCl at 0° C. The reaction mixture was washed with water and extracted with EtOAc (5 mL×3). The organic layers were combined and concentrated to give a crude product, which was by column chromatography on silica gel (petroleum ether:ethyl acetate (5:1) to give compound 11-3. MS (ESI) m/z: 271 (M+H)⁺.

Step D: 4-(4-bromo-3,5-dimethylphenoxy)butan-2-ol (11-4)

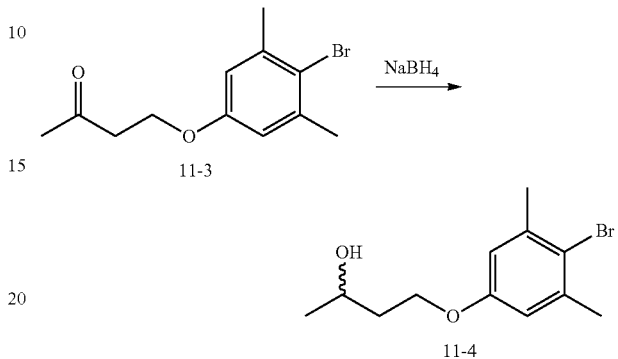

To a solution of compound 11-3 (80 mg, 0.332 mmol) in MeOH (1 mL) was added NaBH₄ (61.44 mg, 1.66 mmol). The solution was stirred at room temperature for 20 min. After the reaction was finished, the reaction was extracted with EtOAc (5 mL×3) and the combined organic layers were concentrated to give compound 11-4. MS (ESI) m/z: 273, 275 (M+H)⁺; 255,257 (M+H—H₂O)'; 314,316 (M+H+HCN)⁺.

Step E: (5aR,6S,6aS)-ethyl 3-((4-fluoro-4'-(3-hydroxybutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (11-5)

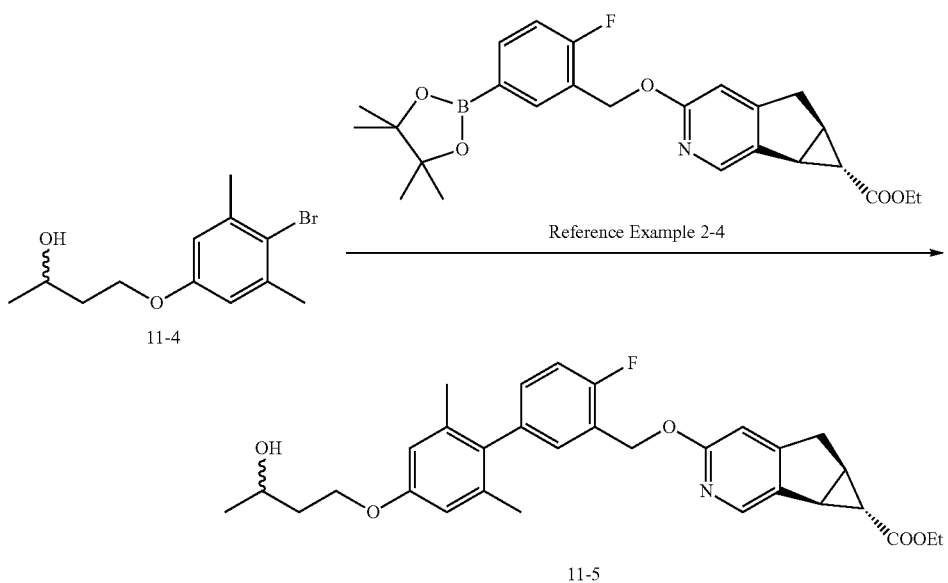

Compound 11-5 was prepared using a procedure similar to the procedure used to prepare compound 10-4. MS (ESI) m/z: 520 (M+H)⁺.

Step F: (5aR,6S,6aS)-3-((4-fluoro-4'-(3-hydroxybutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (11-6)

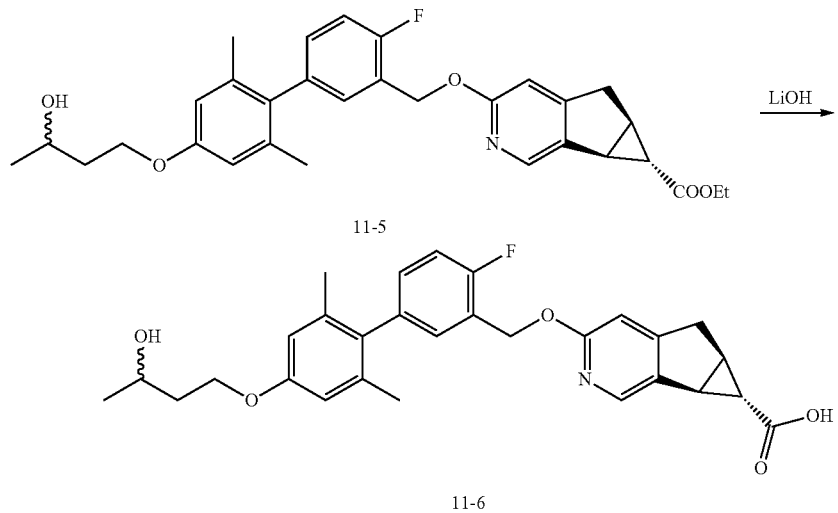

Compound 11-6 was prepared using a procedure similar to the procedure used to prepare Compound 10-5. MS (ESI) m/z: 492 (M+H)+. $^1$H-NMR (400 MHz, MeOD) δ: 8.16 (s, 1H), 7.17-7.26 (m, 3H), 7.10-7.14 (m, 1H), 6.63 (s, 2H), 5.47 (s, 2H), 3.94-4.10 (m, 3H), 3.36-3.42 (dd, 1H, $J_1$=6.0 Hz, $J_2$=20.0 Hz), 3.17-3.22 (d, 1H, J=19.6 Hz), 2.99-3.02 (dd, 1H, $J_1$=2.0 Hz, $J_2$=6.4 Hz), 2.50-2.54 (m, 1H), 1.92 (s, 6H), 1.82-1.92 (m, 2H), 1.25-1.27 (t, 1H, J=2.9 Hz), 1.21-1.22 (d, 1H, J=6.3 Hz).

Example 28

Compound 12-7

(5aR,6S,6aS)-3-((3-(2-methoxypyridin-4-yl)-4-methylbenzyl)oxy)-5,5a,6,6a-tetrahydrocyclopropa[4,5]cyclopenta[1,2-c]pyridine-6-carboxylic acid (12-7)

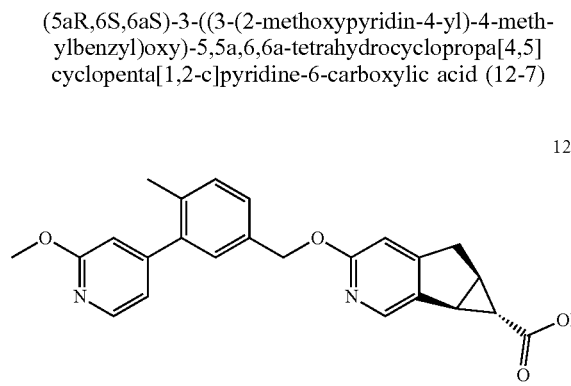

Step A: (3-bromo-4-methylphenyl) methanol (12-2)

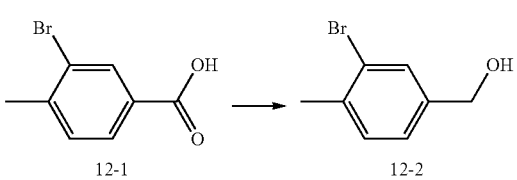

To a solution of compound 12-1 (5.0 g, 0.02 mol) in THF (40 mL) was added dropwise BH$_3$—(CH$_3$)$_2$S (14 mL, 10M) slowly at 0° C. The resulting mixture was stirred at rt. for 18 hours. The solution was quenched with HCl (1M), and extracted with EtOAc (30 mL×3). The combined organic layers were washed with brine, dried, and concentrated to give a residue, which was purified by column chromatography on silica gel (petroleum ether:ethyl acetate (8:1) to give compound 12-2.

Step B: (4-methyl-3-(4,4,5,5-tetramethyl-1,3,2-dioxaborolan-2-yl)phenyl)methanol (12-3)

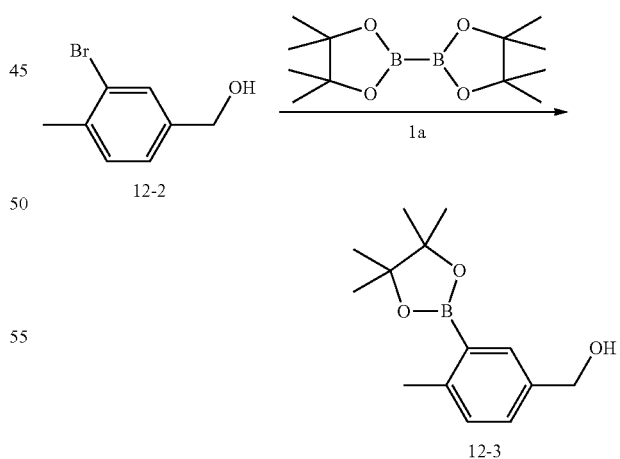

To a solution of compound 12-2 (200 mg, 1.0 mmol) in dioxane (5.0 mL) was added compound 1a (381 mg, 1.5 mmol), KOAc (196 mg, 2.0 mmol) and Pd(dppf)$_2$Cl$_2$ (146 mg, 2.0 mmol) in an N$_2$ atmosphere. The resulting mixture was stirred at 100° C. for 18 hours. Then the solution was filtered and the filtrate was concentrated to give the residue, which was purified by preparative TLC on silica gel eluted with petroleum ether:ethyl acetate (5:1) to give compound 12-3.

Step C: (3-(2-methoxypyridin-4-yl)-4-methylphenyl)methanol (12-4)

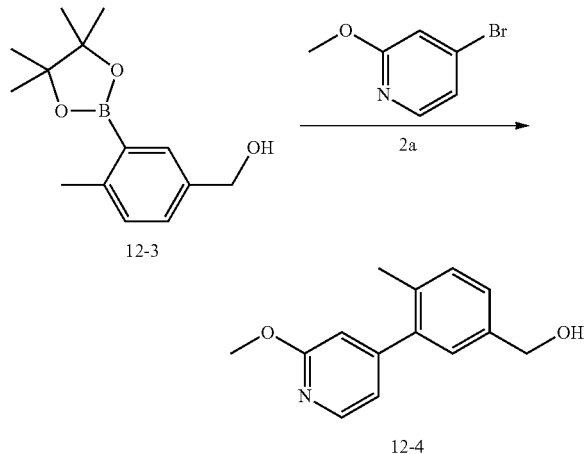

To a solution of compound 12-3 (220 mg, 0.89 mmol) in dioxane (9.0 mL) and H$_2$O (3.0 mL) was added compound 2a (139 mg, 0.74 mmol), Na$_2$CO$_3$ (204 mg, 1.48 mmol) and Pd(PPh$_3$)$_2$Cl$_2$ (54 mg, 0.07 mmol) in N$_2$. The resulting mixture was sealed and heated to 100° C. with microwaves for 10 mins. The mixture was filtered, and the filtrate concentrated to give a residue, which was purified by preparative TLC on silica gel eluted with petroleum ether:ethyl acetate (3:1) to give compound 12-4. MS (ESI) m/z: 230 (M+H)$^+$.

Step D: 4-(5-(bromomethyl)-2-methylphenyl)-2-methoxypyridine (12-5)

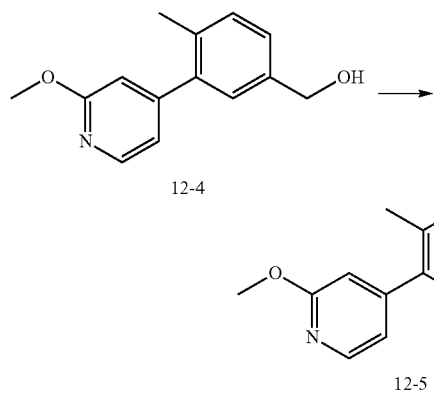

To a solution of compound 12-4 (80 mg, 0.35 mmol) in THF (5.0 mL) was added PBr$_3$ (95 mg, 0.35 mmol) slowly at 0° C. The resulting mixture was stirred for 1 hour. Then H$_2$O was added and the solution was extracted with EtOAc (10 mL×3). The combined organic layers were washed with brine, dried and concentrated to give a residue, which was purified by preparative TLC on silica gel eluted with petro-leum ether:ethyl acetate (5:1) to give the compound 12-5. MS (ESI) m/z: 292, 294 (M+H)$^+$.

Step E: (5aR,6S,6aS)-ethyl 3-((3-(2-methoxypyridin-4-yl)-4-methylbenzyl)oxy)-5,5a,6,6a-tetrahydrocyclopropa[4,5]cyclopenta[1,2-c]pyridine-6-carboxylate (12-6)

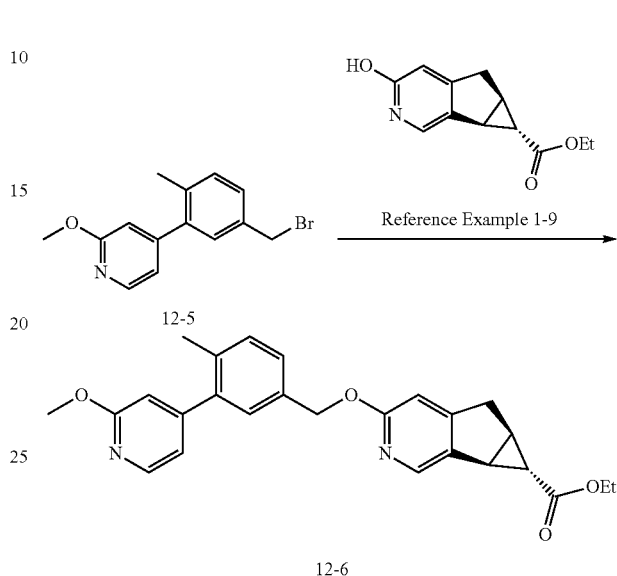

To a solution of compound 12-5 (67 mg, 0.23 mmol) in toluene (5 mL) was added Reference Example 1-9 (60 mg, 0.28 mmol), and Ag$_2$CO$_3$ (127 mg, 0.46 mmol). The resulting mixture was stirred at 100° C. for 20 hours. Then the mixture was filtered, and the filtrate was extracted with EtOAc (10 mL×3). The combined organic layers were washed with brine, dried, concentrated to give a residue, which was by column chromatography on silica gel eluted with petroleum ether:ethyl acetate (3:1) to give compound 12-6. MS (ESI) m/z: 431 (M+H)$^+$.

Step F: (5aR,6S,6aS)-3-((3-(2-methoxypyridin-4-yl)-4-methylbenzyl)oxy)-5,5a,6,6a-tetrahydrocyclopropa[4,5]cyclopenta[1,2-c]pyridine-6-carboxylic acid (12-7)

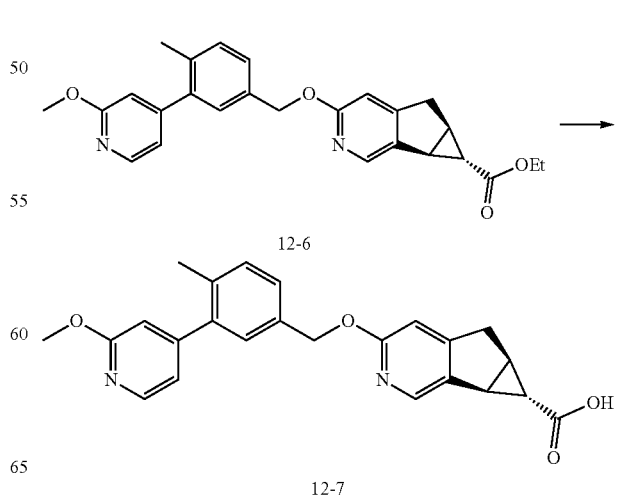

To a solution of compound 12-6 (80 mg, 0.19 mmol) in THF (9.0 mL), MeOH (3.0 mL) and H$_2$O (3.0 mL) was added LiOH.H$_2$O (32 mg, 0.76 mmol). The resulting mixture was stirred at rt. for 4 hours. Then H$_2$O was added, then the solution was acidified with HCl (1 M) to pH 2.5, and extracted with EtOAc (10 mL×3). The combined organic layers were washed with brine, dried and concentrated to give a residue, which was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 35-65% B, 0-10 min; 100% B, 10.5-12.5 min; 5% B, 13-15 min) to give compound 12-7. MS (ESI) m/z: 403 (M+H)$^+$. $^1$H-NMR (400 MHz, Methanol-d$_4$) δ: 8.18-8.21 (m, 2H), 7.43-7.45 (m, 1H), 7.35-7.36 (m, 2H), 7.21 (s, 1H), 7.07 (dd, 1H, J$_1$=J$_2$=0.8 Hz), 6.95 (s, 1H), 5.39 (s, 2H), 4.01 (s, 3H), 3.40-3.45 (m, 1H), 3.19-3.38 (m, 1H), 3.02 (dd, 1H, J$_1$=J$_2$=1.6 Hz), 2.50-2.54 (m, 1H), 2.29 (s, 3H), 1.22-1.26 (m, 1H).

The following Examples 29-31 (Compounds 12-8, 12-9 and 12-10) were prepared in a similar manner to Compound 10-5 using the appropriate commercially available starting materials and boronates.

Example 32

Compound 13-7

(5aR,6S,6aS)-3-((3-(6-(2-hydroxy-2-methyl-propoxy)-4-(trifluoromethyl)pyridin-3-yl)benzyl)oxy)-5,5a,6,6a-tetrahydrocyclopropa[4,5]cyclopenta[1,2-c]pyridine-6-carboxylic acid (13-7)

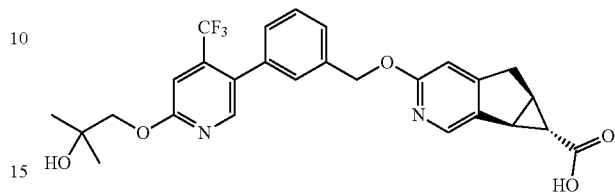

Step A: 4-(trifluoromethyl) pyridin-2-ol (13-2)

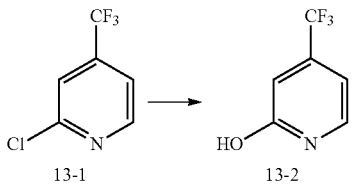 [SMILES: FC(F)(F)c1ccnc(Cl)c1 ; Oc1cc(C(F)(F)F)ccn1]

| Example | Structure | M.W. | Compound Name | LC/MS (ESI) observed [M + 1]+ |
|---|---|---|---|---|
| 29 | (Compound 12-8) | 576.6 | (5aR,6S,6aS)-3-((3-(2-methyl-6-(3-(methylsulfonyl)propoxy)pyridin-3-yl)-5-(trifluoromethyl)benzyl)oxy)-5,5a,6,6a-tetrahydrocyclopropa[4,5]cyclopenta[1,2-c]pyridine-6-carboxylic acid | 577.4 |
| 30 | (Compound 12-9) | 557.6 | (5aR,6S,6aS)-3-((4,6-difluoro-2',6'-dimethyl-4'-(3-(methylsulfonyl)-propoxy)-[1,1'-biphenyl]-3-yl)methoxy)-5,5a,6,6a-tetrahydrocyclopropa[4,5]cyclopenta[1,2-c]pyridine-6-carboxylic acid | 558.4 |
| 31 | (Compound 12-10) | 576.6 | (5aR,6S,6aS)-3-((3-(2-methyl-6-(3-(methylsulfonyl)propoxy)-pyridin-3-yl)-4-(trifluoromethyl)benzyl)oxy)-5,5a,6,6a-tetrahydrocyclopropa[4,5]cyclopenta[1,2-c]pyridine-6-carboxylic acid | 577.4 |

To a solution of compound 13-1 (8.0 g, 0.04 mol) in H₂O (20 mL) was added concentrated HCl (20 mL). The resulting mixture was stirred at 110° C. for 20 hours. Then the solution was basified with NaHCO₃, and extracted with EtOAc (40 mL×3). The combined organic layers were washed with brine, dried, and concentrated to give compound 13-2.

Step B: ethyl 2-((4-(trifluoromethyl) pyridin-2-yl) oxy)acetate (13-3)

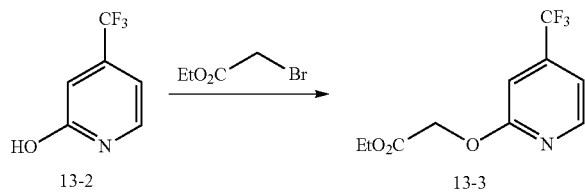 [SMILES: Oc1cc(C(F)(F)F)ccn1 ; CCOC(=O)CBr ; CCOC(=O)COc1cc(C(F)(F)F)ccn1]

To a solution of compound 13-2 (1.0 g, 6.1 mmol) in toluene (10 mL) was added ethyl bromoacetate (3.1 g, 0.02 mol) and Ag₂CO₃ (5.1 g, 0.02 mol). The resulting mixture was stirred at 100° C. for 20 hours. Then the solution was filtered and the filtrate was extracted with EtOAc (15 mL×3). The combined organic layers were washed with brine, dried, concentrated to give a residue, which was purified by column chromatography on silica gel eluted with petroleum ether:ethyl acetate (5:1) to give compound 13-3. MS (ESI) m/z: 250 (M+H)⁺.

Step C: 2-methyl-1-((4-(trifluoromethyl)pyridin-2-yl)oxy)propan-2-ol (13-4)

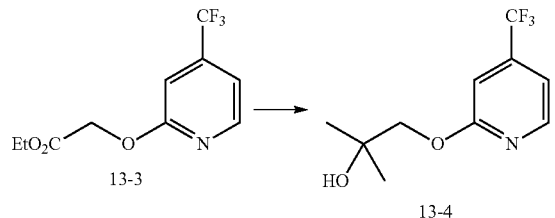 [SMILES: CCOC(=O)COc1cc(C(F)(F)F)ccn1 ; CC(C)(O)COc1cc(C(F)(F)F)ccn1]

To a solution of compound 13-3 (1.0 g, 4.02 mmol) in THF (10 mL) was added dropwise CH₃MgBr (3 M, 8 mL) slowly at 0° C. The reaction mixture was warmed to rt. and stirred for 2 hours. Then the reaction was quenched with HCl (1M), and extracted with EtOAc (15 mL×3). The combined organic layers were washed with brine, dried, and concentrated to give compound 13-4.

Step D: 1-((5-bromo-4-(trifluoromethyl)pyridin-2-yl)oxy)-2-methylpropan-2-ol (13-5)

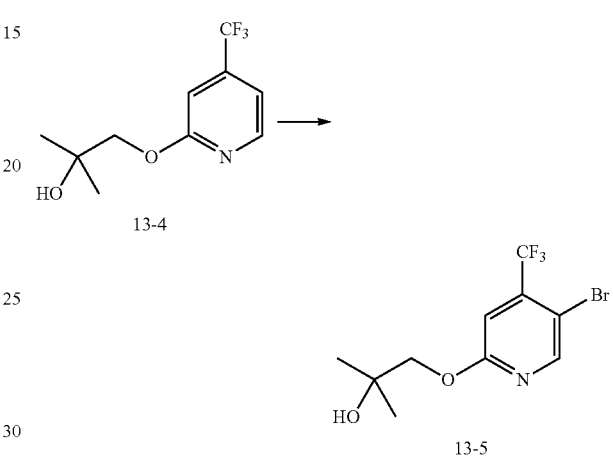

To a solution of compound 13-4 (200 mg, 0.85 mmol) in HOAc (5.0 mL) was added Br₂ (5.0 mL). The resulting mixture was stirred at rt. for 2 hours. Then the mixture was basified with NaHCO₃, quenched with saturated Na₂SO₃, and extracted with EtOAc (10 mL×3). The combined organic layers were washed with brine, dried and concentrated to give a residue, which was purified by preparative TLC on silica gel eluted with petroleum ether:ethyl acetate (4:1) to give compound 13-5. MS (ESI) m/z: 313, 315 (M+H)⁺.

Step E: (5aR,6S,6aS)-ethyl 3-((3-(6-(2-hydroxy-2-methylpropoxy)-4-(trifluoromethyl)pyridin-3-yl)benzyl)oxy)-5,5a,6,6a-tetrahydrocyclopropa[4,5]cyclopenta[1,2-c]pyridine-6-carboxylate (13-6)

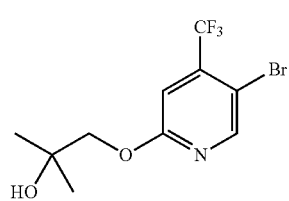

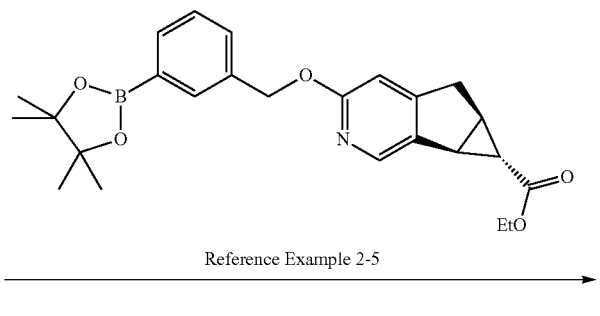

Reference Example 2-5

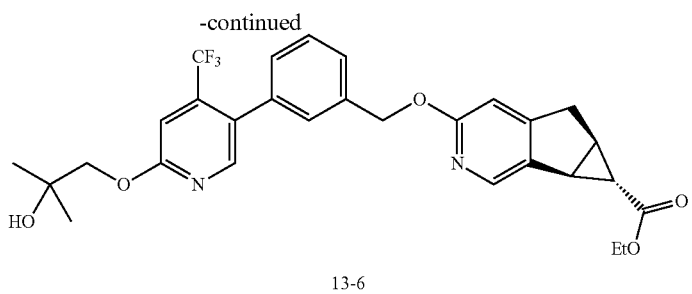

13-6

To a solution of compound 13-5 (40 mg, 0.14 mmol) in THF (9.0 mL) and H$_2$O (3.0 mL) was added Reference Example 2-5 (72 mg, 0.16 mmol), K$_3$PO$_4$ (89 mg, 0.42 mmol) and Pd(dppf)$_2$Cl$_2$ (7 mg, 0.01 mmol) in N$_2$. The resulting mixture was sealed and heated to 100° C. with microwaves for 10 mins. The mixture was filtered and the filtrate was concentrated to give a residue, which was purified by preparative TLC on silica gel eluted with petroleum ether:ethyl acetate (1:1) to give compound 13-6. MS (ESI) m/z: 543 (M+H)$^+$.

Step F: (5aR,6S,6aS)-3-((3-(6-(2-hydroxy-2-methyl-propoxy)-4-(trifluoromethyl)pyridin-3-yl) benzyl)oxy)-5,5a,6,6a-tetrahydrocyclopropa[4,5]cyclopenta[1,2-c]pyridine-6-carboxylic acid (13-7)

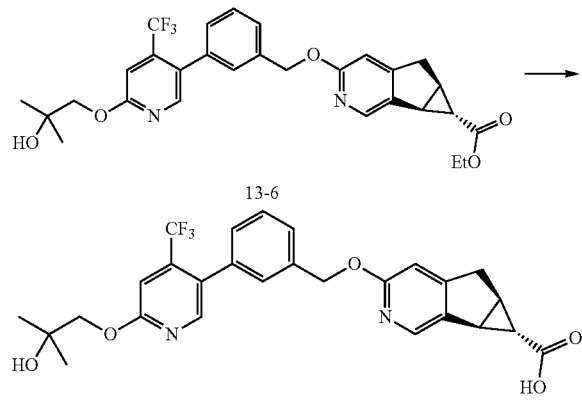

To a solution of compound 13-6 (40 mg, 0.07 mmol) in THF (9.0 mL), MeOH (3.0 mL) and H$_2$O (3.0 mL) was added LiOH.H$_2$O (12 mg, 0.28 mmol). The resulting mixture was stirred at rt. for 4 hours. Then H$_2$O was added and the solution was acidified with HCl (1M) to pH 2.5, and extracted with EtOAc (5 mL×3). The combined organic layers were washed with brine, dried and concentrated to give a residue, which was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 47-67% B, 0-10 min; 100% B, 10.5-12.5 min; 5% B, 13-15 min) to give compound 13-7. MS (ESI) m/z: 515 (M+H)$^+$. $^1$H-NMR (400 MHz, CDCl$_3$): δ 8.05 (d, 2H, J=10.0 Hz), 7.45-7.47 (m, 1H), 7.39-7.41 (m, 1H), 7.34 (s, 1H), 7.21-7.23 (m, 1H), 7.13 (s, 1H), 6.62 (s, 1H), 5.34 (s, 2H), 4.22 (s, 2H), 3.17-3.24 (m, 1H), 3.01 (s, 1H), 2.91-2.96 (m, 1H), 2.44 (s, 1H), 1.32 (s, 6H), 1.17-1.22 (m, 2H).

The following Example 33 (Compound 13-8) was prepared in a similar manner to Compound 13-7 using the appropriate commercially available starting materials.

| Example | Structure | M.W. | Compound Name | LC/MS (ESI) observed [M + 1]+ |
|---|---|---|---|---|
| 33 | (Compound 13-8) | 532 | (5aR,6S,6aS)-3-((2-fluoro-5-(6-(2-hydroxy-2-methylpropoxy)-4-(trifluoromethyl)pyridin-3-yl)benzyl)oxy)-5,5a,6,6a-tetrahydrocyclopropa[4,5]cyclopenta[1,2-c]pyridine-6-carboxylic acid | 533 |

Example 33

Compound 13-8

$^1$H-NMR (400 MHz, Methanol-d$_4$): δ 8.12 (d, 2H, J=7.2 Hz), 7.46 (d, 1H, J=5.6 Hz), 7.34 (s, 1H), 7.19-7.24 (m, 2H), 7.00 (s, 1H), 5.46 (s, 1H), 4.22 (s, 2H), 3.33-3.38 (m, 1H), 3.11-3.29 (m, 1H), 2.97-2.99 (m, 1H), 2.48-2.51 (m, 1H), 1.32 (s, 6H), 1.17-1.22 (m, 1H).

Example 34

Compound 14-4

(5aR,6S,6aS)-3-((4'-(2,3-dihydroxypropoxy)-4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (4-4)

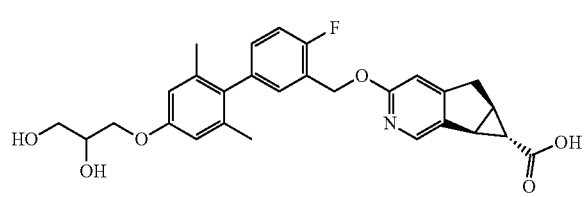

Step A: 3-(4-bromo-3,5-dimethylphenoxy)propane-1,2-diol (14-2)

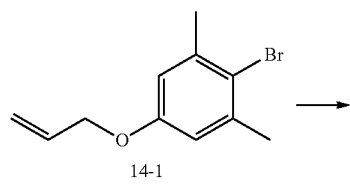

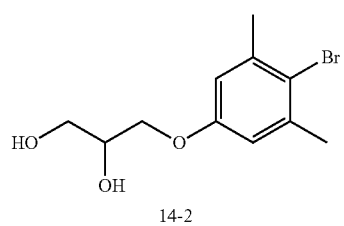

To a solution of compound 14-1 (200 mg, 0.83 mmol) and OsO$_4$ (21.1 mg, 0.083 mmol) in acetone (2 mL) was added NMO (116.5 mg, 0.996 mmol) at 0° C. in batches. The reaction mixture was then stirred at 0° C. for 0.5 h. After the reaction finished, the reaction mixture was quenched with EtOH (4 mL), and extracted with EtOAc (5 mL×3). The combined organic layers were washed with water (10 mL), brine (10 mL), dried and concentrated to give compound 14-2. MS (ESI) m/z: 275,277 (M+H).

Step B: (5aR,6S,6aS)-ethyl 3-((4'-(2,3-dihydroxypropoxy)-4-fluoro-2',6'-dimethyl-[1,1'-biphenyl]-3-yl) methoxy)-5,5a,6,6a-tetrahydrocyclopropa[4,5]cyclopenta[1,2-c]pyridine-6-carboxylate (14-3)

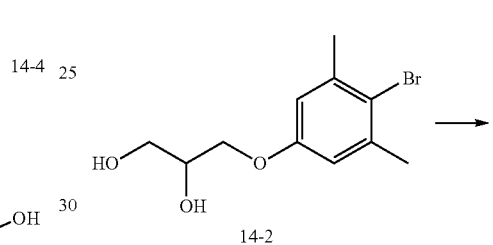

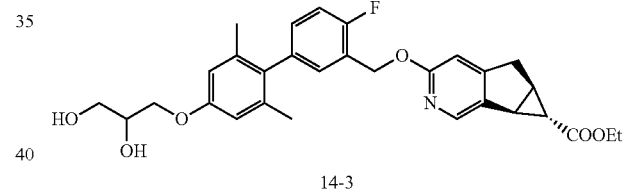

Compound 14-3 was prepared using a procedure is similar to the procedure used to prepare compound 13-6. MS (ESI) m/z: 522 (M+H)$^+$.

Step C: (5aR,6S,6aS)-3-((4'-(2,3-dihydroxypropoxy)-4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

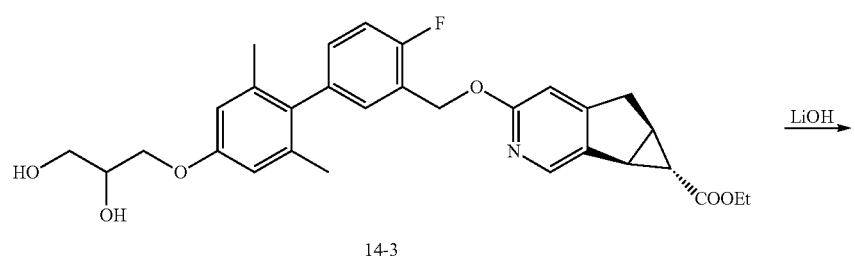

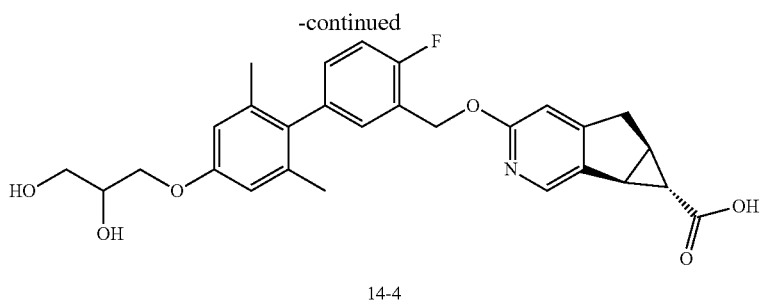

14-4

Compound 14-4 was prepared using a procedure is similar to the procedure used to prepare compound 13-7. MS (ESI) m/z: 494 (M+H)⁺. ¹H-NMR (400 MHz, MeOD) δ: 8.14 (s, 1H), 7.17-7.25 (m, 2H), 7.10-7.13 (m, 2H), 6.68 (s, 2H), 5.46 (s, 2H), 4.00-4.03 (m, 1H), 3.92-3.98 (m, 2H), 3.61-3.70 (m, 2H), 3.34-3.40 (dd, 1H, J1=6.4 Hz, J2=19.6 Hz), 3.14-3.19 (d, 1H, J=19.6 Hz), 2.98-3.00 (m, 1H), 2.48-2.52 (m, 1H), 1.92 (s, 6H), 1.23-1.24 (t, 1H, J=2.8 Hz).

Example 35

Compound 15-5

(5aR,6S,6aS)-3-((4'-(3-hydroxy-2-(hydroxymethyl)-2-methylpropoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (15-5)

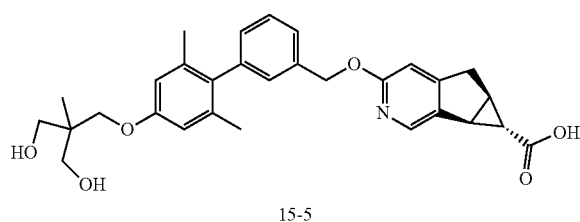 [SMILES: Cc1cc(OCC(C)(CO)CO)cc(C)c1-c1cccc(COc2cc3c(cn2)[C@H]2[C@@H](C3)[C@@H]2C(=O)O)c1]

15-5

Step A: 3-((4-bromo-3,5-dimethylphenoxy)methyl)-3-methyloxetane (15-2)

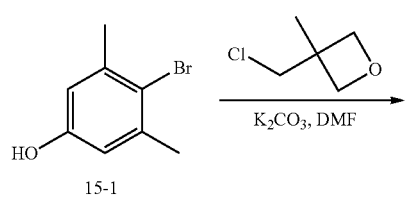

15-1

A solution of compound 15-1 (1 g, 5.0 mmol), 3-(chloromethyl)-3-methyloxetane (1.2 g, 9.95 mmol) and K₂CO₃ (2.74 g, 19.9 mmol) in DMF (10 mL) was heated to 100° C. for 12 h. After the reaction finished, the reaction mixture was treated with brine (100 mL), and extracted with EtOAc (50 mL×3). The combined organic layers were washed with water (10 mL), brine (10 mL), dried and concentrated to give compound 15-2. MS (ESI) m/z: 285,287 (M+H).

Step B: 2-((4-bromo-3,5-dimethylphenoxy)methyl)-2-methylpropane-1,3-diol (15-3)

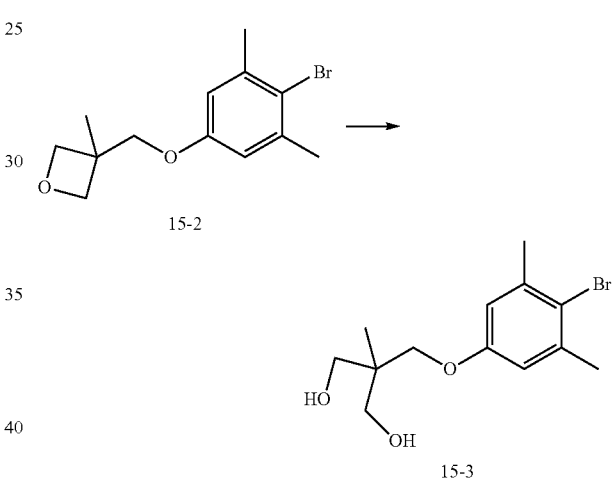

15-2

15-3

To a solution of HCl (5 mL, 2 mol/L) was added compound 15-2 (100 mg, 0.35 mmol). The solution was stirred at reflux for 3 h. After the reaction finished, the solution was extracted with EtOAc (10 mL×3) and concentrated to give compound 15-3. MS (ESI) m/z: 303,305 (M+H)⁺.

Step C: (5aR,6S,6aS)-ethyl 3-((4'-(3-hydroxy-2-(hydroxymethyl)-2-methylpropoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (15-4)

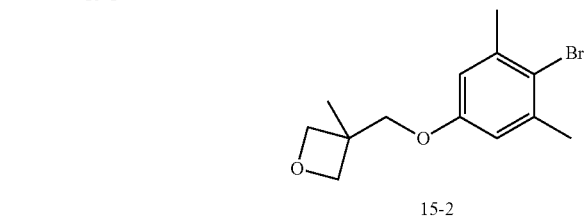

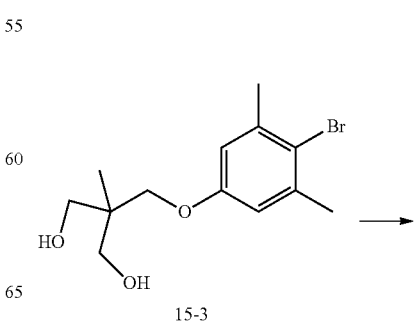

15-3

-continued

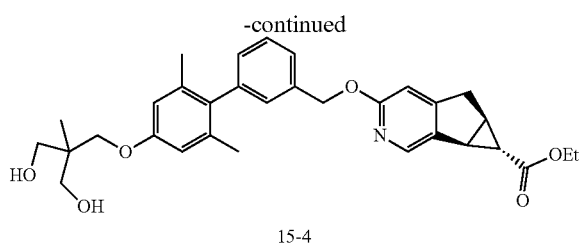

15-4

Compound 15-4 was prepared using a procedure similar to the procedure used to prepare compound 13-6. MS (ESI) m/z: 532 (M+H)+

Step D: (5aR,6S,6aS)-3-((4'-(3-hydroxy-2-(hydroxymethyl)-2-methylpropoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (15-5)

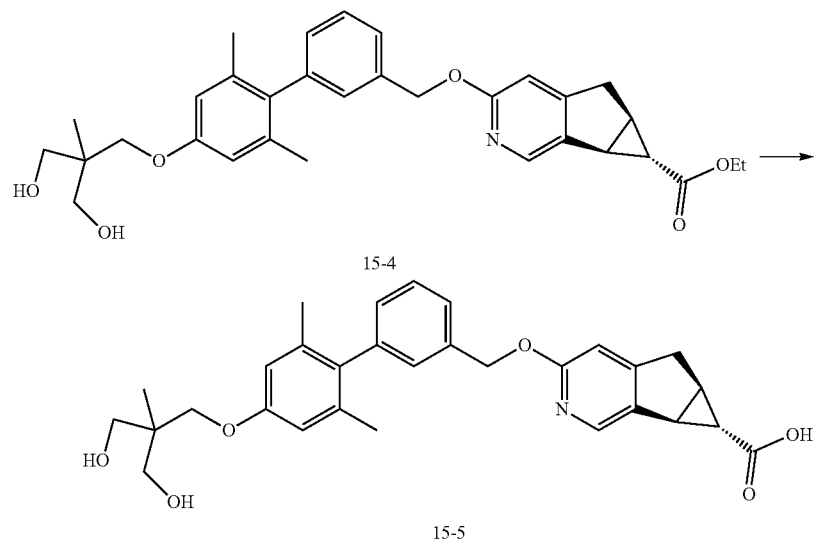 [SMILES: CCOC(=O)[C@H]1[C@@H]2Cc3cc(OCc4cccc(-c5c(C)cc(OCC(C)(CO)CO)cc5C)c4)ncc3[C@@H]21 ; Cc1cc(OCC(C)(CO)CO)cc(C)c1-c1cccc(COc2cc3c(cn2)[C@H]2[C@@H](C3)[C@@H]2C(=O)O)c1]

Compound 15-5 was prepared using a procedure similar to the procedure used to prepare compound 13-7. MS (ESI) m/z: 522 (M+H+H$_2$O)+. $^1$H-NMR (400 MHz, MeOD) δ: 8.14 (s, 1H), 7.38-7.44 (m, 2H), 7.18 (s, 2H), 7.06-7.08 (d, 1H, J=6.8 Hz), 6.63 (s, 2H), 5.39 (s, 2H), 3.79-3.84 (m, 2H), 3.62-3.70 (m, 2H), 3.52-3.60 (m, 2H), 3.34-3.41 (dd, 1H, J$_1$=6.4 Hz, J$_2$=19.6 Hz), 3.16-3.20 (d, 1H, J=19.6 Hz), 2.98-2.99 (d, 1H, J=6.4 Hz), 2.48-2.52 (m, 1H), 1.90 (s, 6H), 1.24 (s, 1H), 1.06 (s, 3H).

The following Example 36 (Compound 15-6) was prepared in a similar manner to Compound 15-5 using the appropriate starting materials and the boronate from Reference Example 2-4.

| Example | Structure | M.W. | Compound Name | LC/MS (ESI) observed [M + 1]+ |
|---|---|---|---|---|
| 36 | ![Compound 15-6 structure] (Compound 15-6) | 521 | (5aR,6S,6aS)-3-((4-fluoro-4'-(3-hydroxy-2-(hydroxymethyl)-2-methylpropoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 540 |

Compound 15-6: $^1$H-NMR (400 MHz, MeOD) δ: 8.16 (s, 1H), 7.13-7.26 (m, 4H), 6.66 (s, 2H), 5.47 (s, 2H), 3.82-3.87 (m, 2H), 3.62-3.70 (m, 2H), 3.58 (s, 2H), 3.36-3.42 (dd, 1H, $J_1$=6.0 Hz, $J_2$=19.6 Hz), 3.17-3.22 (d, 1H, J=19.6 Hz), 3.00-3.01 (d, 1H, J=4.0 Hz), 2.51-2.52 (d, 1H, J=2.8 Hz), 1.93 (s, 6H), 1.26 (s, 1H), 1.09 (s, 3H).

Example 37

Compound 16-8

(5aR,6S,6aS)-3-((4'-((3,3-difluorocyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (16-8)

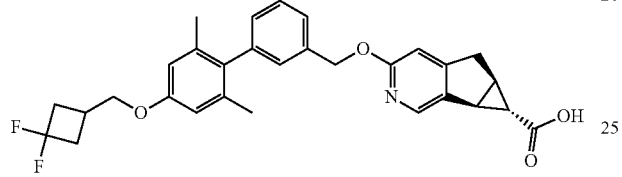

Step A: 3-(hydroxymethyl)cyclobutanol (16-2)

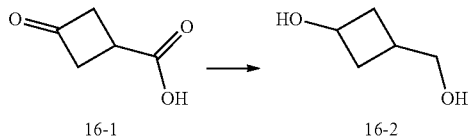 [SMILES: O=C1CC(C(=O)O)C1 ; OCC1CC(O)C1]

To a solution of compound 16-1 (500 mg, 4.24 mmol) in THF (5 mL) was added dropwise BH$_3$—(CH$_3$)$_2$S (0.6 mL, 10M) slowly at −78° C. The resulting mixture was warmed to rt. and stirred for 18 hours. The solution was quenched with HCl (1 M), and extracted with EtOAc (30 mL×3). The combined organic layers were washed with brine, dried, and concentrated to give the compound 16-2.

Step B: (3-hydroxycyclobutyl)methyl 4-methylbenzenesulfonate (16-3)

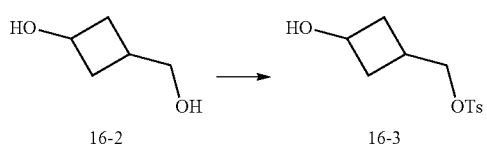 [SMILES: OCC1CC(O)C1 ; Cc1ccc(S(=O)(=O)OCC2CC(O)C2)cc1]

To a solution of compound 16-2 (300 mg, 3.0 mmol) in DCM (5 mL) was added Et$_3$N (606 mg, 6.0 mmol) and TosCl (573 mg, 3.0 mmol) slowly at 0° C. The resulting mixture was warmed to rt. and stirred for 4 hours. The solution was quenched with HCl (1 M), and extracted with EtOAc (30 mL×3). H$_2$O was added and the solution was extracted with DCM (10 mL×3). The combined organic layers were dried and concentrated to give a residue, which was purified by preparative TLC on silica gel eluted with petroleum ether:ethyl acetate (5:1) to give compound 16-3. MS (ESI) m/z: 257 (M+H)$^+$.

Step C: 3-((4-bromo-3,5-dimethylphenoxy)methyl)cyclobutanol (16-4)

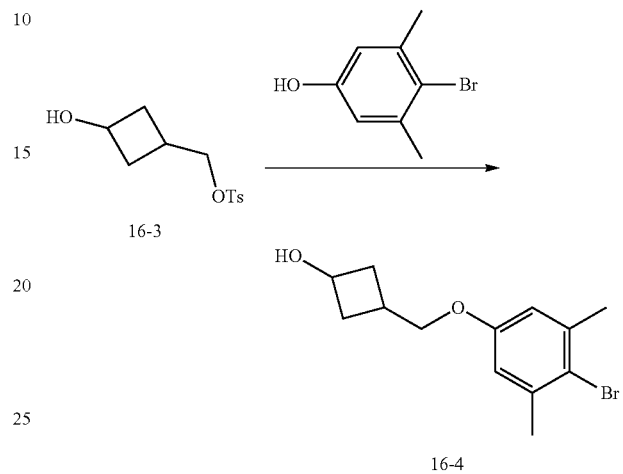

To a solution of compound 16-3 (330 mg, 1.64 mmol) in DMF (10.0 mL) was added 4-bromo-3,5-dimethylphenol (350 mg, 1.37 mmol) and K$_2$CO$_3$ (378 mg, 2.74 mmol). The resulting mixture was stirred at 100° C. for 18 hours. Then H$_2$O was added and the solution was extracted with EtOAc (15 mL×3). The combined organic layers were washed with brine, dried and concentrated to give a residue, which was purified by preparative TLC on silica gel eluted with petroleum ether:ethyl acetate (3:1) to give compound 16-4.

Step D: 3-((4-bromo-3,5-dimethylphenoxy)methyl)cyclobutanone (16-5)

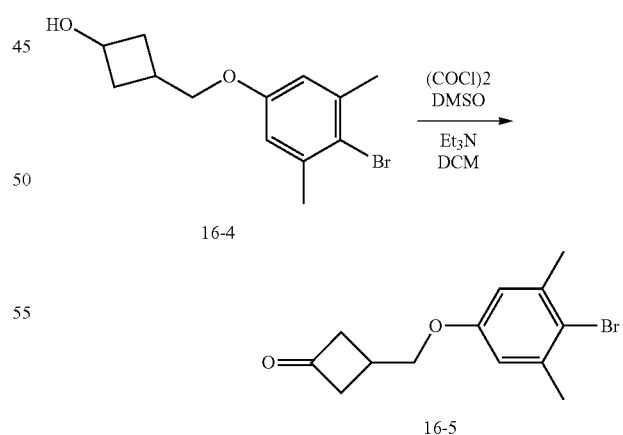

To a solution of oxalyl dichloride (170 mg, 1.34 mmol) in DCM (5.0 mL) was added DMSO (209 mg, 2.68 mmol) at −78° C. The solution was stirred at −78° C. for 15 mins, then compound 16-4 (190 mg, 0.67 mmol) in DCM (2 mL) was added slowly at −78° C. and the reaction was stirred for 15 mins, followed by addition of Et$_3$N (338 mg, 3.35 mmol)

and the reaction was allowed to react at room temperature for additional 2 h. Then H₂O was added and the reaction was extracted with DCM (15 mL×3). The combined organic layers were washed with brine, dried and concentrated to give a residue, which was purified by preparative TLC on silica gel eluted with petroleum ether:ethyl acetate (5:1) to give compound 16-5.

Step E: 2-bromo-5-((3,3-difluorocyclobutyl) methoxy)-1,3-dimethylbenzene (16-6)

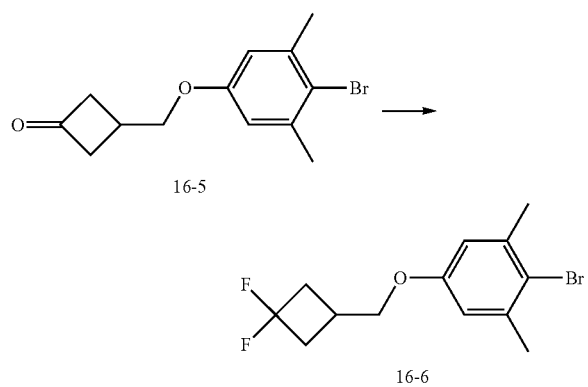

The solution of compound 16-5 (90 mg, 0.32 mmol) dissolved in DAST (2 mL) was stirred for 2 hours. The reaction was quenched with ice-water and extracted with EtOAc. The combined organic layers were washed with brine, dried and concentrated to give a residue, which was purified by preparative TLC on silica gel eluted with petroleum ether:ethyl acetate (5:1) to give compound 16-6.

Step F: (5aR,6S,6aS)-3-((4'-((3,3-difluorocyclobutyl)methoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (16-8)

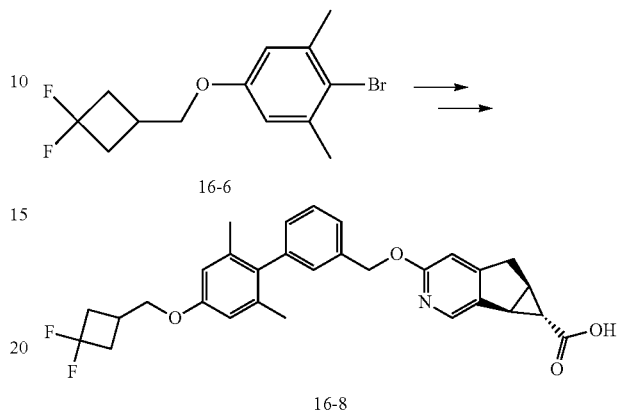

Compound 16-8 was obtained via a Suzuki reaction with Reference Example 2-5 and subsequent ester hydrolysis; the procedure was similar to the procedure used to prepare compound 13-7. ¹H-NMR (400 MHz, Methanol-d₄) δ: 8.05 (s, 1H), 7.38-7.40 (m, 2H), 7.13 (s, 1H), 7.02 (d, 1H, J=6.4 Hz), 6.70 (s, 1H), 6.65 (s, 2H), 5.32 (s, 2H), 4.00 (d, 2H, J=6.4 Hz), 3.21-3.28 (m, 1H), 3.01-3.05 (m, 1H), 2.90-2.92 (m, 1H), 2.47-2.58 (m, 3H), 2.42-2.45 (m, 3H), 1.95 (s, 6H), 1.08 (s, 1H).

The following Examples 38-40 (compounds 16-9 to 16-11) were prepared in a similar manner to Compound 16-8 using the appropriate starting materials and boronate from Reference Example 2-4 or Reference Example 2-5.

| Example | Structure | M.W. | Compound Name | LC/MS (ESI) observed [M + 1]+ |
|---|---|---|---|---|
| 38 | (Compound 16-9) | 537.6 | (5aR,6S,6aS)-3-((4'-(2-(3,3-difluorocyclobutyl)ethoxy)-4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 538.4 |
| 39 | (Compound 16-10) | 519.5 | (5aR,6S,6aS)-3-((4'-(2-(3,3-difluorocyclobutyl)ethoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 520.3 |

Example 40

Compound 17-5

(5aR,6S,6aS)-3-((4'-(((E)-4-(methoxyimino)pentyl)oxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylic acid (17-5)

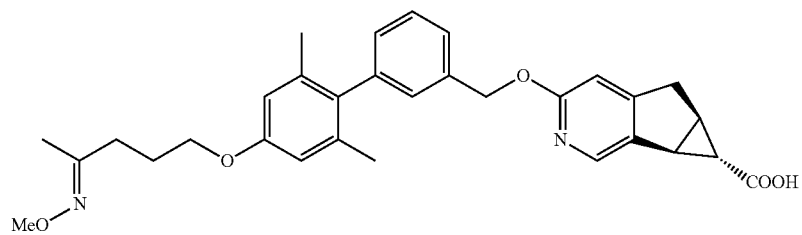

17-5

Step A: 5-(4-bromo-3,5-dimethylphenoxy)pentan-2-one (17-2)

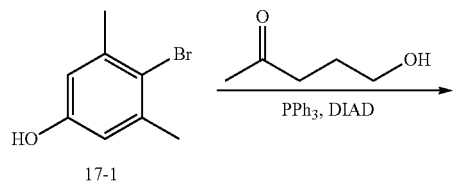

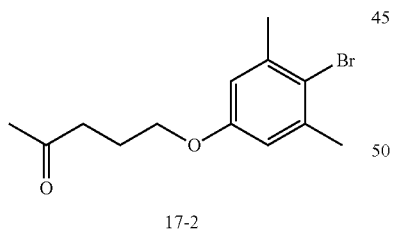

17-2

Under N$_2$, to a solution of compound 17-1 (100 mg, 0.5 mmol), 5-hydroxy-n-pentan-2-one (100 mg, 1 mmol) and triphenyl-phosphane (262 mg, 1 mmol) in THF (5 mL) was added DIAD (200 mg, 1 mmol) dropwise at 0° C. The mixture was stirred at room temperature for 2 hours. The reaction was quenched with water and extracted with EtOAc. The combined organic layers were washed with brine, dried and concentrated. The crude product was purified by preparative TLC on silica gel eluted with petroleum ether:ethyl acetate (3:1) to give compound 17-2.

Step B: 5-(4-bromo-3,5-dimethylphenoxy)pentan-2-one O-methyl oxime (17-3)

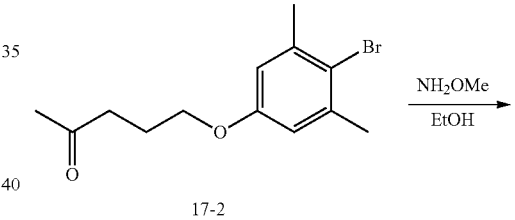

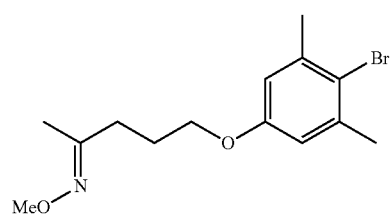

17-3

To a solution of compound 17-2 (50 mg, 0.17 mmol) in EtOH (2 mL) was added O-methyl-hydroxylamine (25 mg, 0.3 mmol). The reaction mixture was heated to reflux for 1 hour. The mixture was then poured into water (10 mL), and extracted with ethyl acetate (5 mL×2). The ethyl acetate layer was separated and concentrated in vacuo to give compound 17-3. MS (ESI) m/z: 314 (M+H)$^+$.

Step C: (5aR,6 S,6aS)-3-((4'-(((E)-4-(methoxy-imino)pentyl)oxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (7-5)

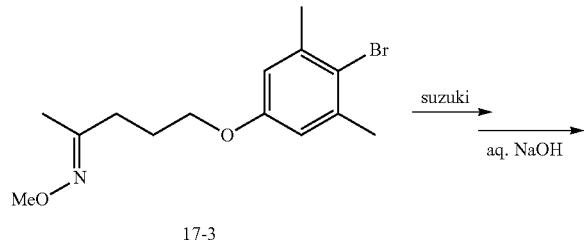

17-3

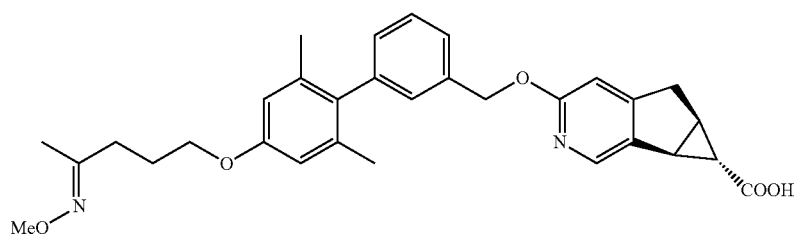

17-5

Compound 17-5 was prepared via a Suzuki reaction with the boronate from Reference Example 2-5 and subsequent ester hydrolysis; the procedure was similar to the procedure used to prepare compound 13-7. MS (ESI) m/z: 515 (M+H)$^+$. $^1$H-NMR (400 MHz, CD$_3$OD) δ 8.04 (s, 1H), 7.35-7.41 (m, 2H), 7.12 (s, 1H), 7.01 (d, 1H, J=6.8 Hz), 6.70 (s, 1H), 6.62 (s, 2H), 5.31 (s, 2H), 3.94-3.99 (m, 2H), 3.74-3.76 (m, 3H), 3.20-3.25 (m, 1H), 3.02 (d, 1H, J=18.4 Hz), 2.91 (d, 1H, J=6.0 Hz), 2.34-2.49 (m, 3H), 1.92-1.99 (m, 8H), 1.85-1.87 (m, 3H), 1.12 (t, 1H, J=2.4 Hz).

The following Example 41 (Compound 17-6) was prepared in a similar manner to Compound 17-5 using the appropriate starting materials.

| Example | Structure | M.W. | Compound Name | LC/MS (ESI) observed [M + 1]+ |
|---|---|---|---|---|
| 41 | 17-6 (Compound 17-6) | 501.59 | (5aR,6S,6aS)-3-((4'-(((E)-4-(methoxyimino)pentyl)oxy)-2'-methyl-[1,1'-biphenyl]-3-yl)methoxy)-5,5a,6,6a-tetrahydrocyclopropa[4,5]cyclopenta[1,2-c]pyridine-6-carboxylic acid | 502 |

Example 42

Compound 18-4

(5aR,6S,6aS)-3-((4'-(3-(3,3-difluoroazetidin-1-yl)propoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (18-4)

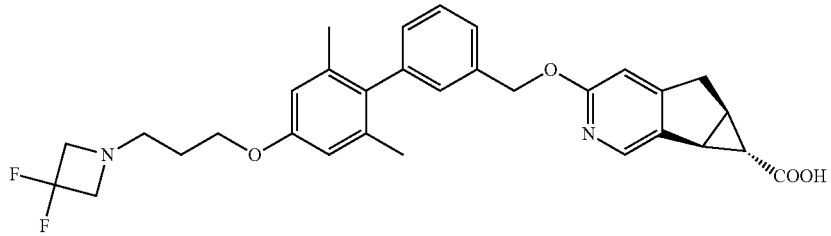

18-4

Step A: 3-(4-bromo-3,5-dimethylphenoxy)-1-(3,3-difluoroazetidin-1-yl)propan-1-one (18-1)

Step B: 1-(3-(4-bromo-3,5-dimethylphenoxy)propyl)-3,3-difluoroazetidine (18-2)

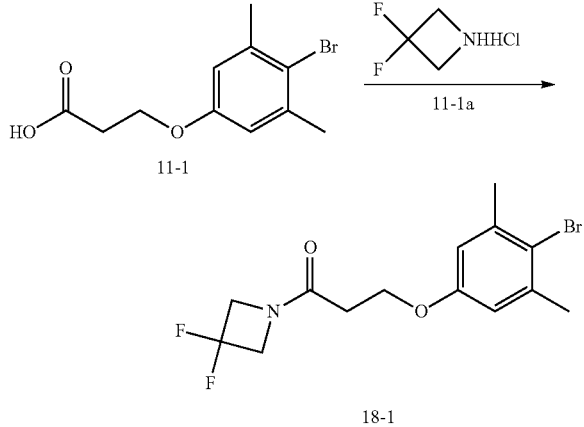

To a stirred solution of compound 11-1 (500 mg, 1.85 mmol) and compound 11-1a (715 mg, 5.55 mmol) in DMF (10 mL) was added Et$_3$N (0.52 mL, 3.7 mmol). The reaction was stirred for 15 mins, then TBTU (900 mg, 2.8 mmol) was added to the reaction in portions. The resulting mixture was allowed to stir at 40° C. overnight. Then H$_2$O was added and the mixture was extracted with EtOAc (20 mL×2), dried over Na$_2$SO$_4$, and concentrated to afford crude product, which was purified by preparative TLC on silica gel eluted with petroleum ether:ethyl acetate (3:1) to give compound 18-1. MS (ESI) m/z: 348,350 (M+H)$^+$.

To a stirred solution of compound 18-1 (50 mg, 0.14 mmol) in THF (5 mL) was added BH$_3$THF (0.42 mL, 1 mol/L) dropwise. The reaction mixture was heated to reflux for 10 h, then cooled and quenched with MeOH (0.1 mL) and NaOH (0.2 mL, 2 mol/L). The organic layer was separated, and purified by preparative TLC on silica gel eluted with petroleum ether:ethyl acetate (3:1) to give compound 18-2. MS (ESI) m/z: 334,336 (M+H)

Step C: (5aR,6S,6aS)-ethyl 3-((4'-(3-(3,3-difluoroazetidin-1-yl)propoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (18-3)

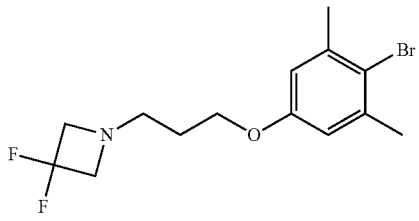

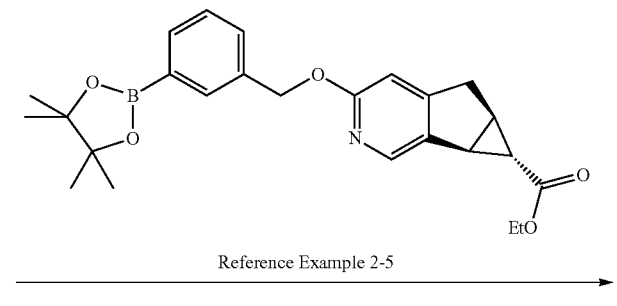

Reference Example 2-5

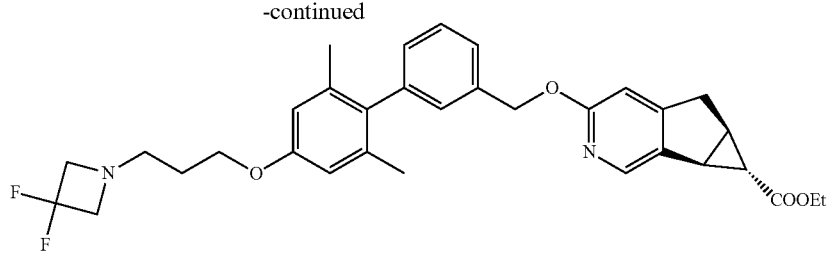

18-3

A microwave vessel charged with compound 18-2 (40 mg, 0.12 mmol), Reference Example 2-5 (52 mg, 0.12 mmol), Pd(dppf)Cl$_2$ (5 mg), K$_3$PO$_4$ (51 mg, 0.24 mmol), THF (2 mL) and H$_2$O (0.5 mL) was heated to 100° C. for 30 mins with microwaves. The reaction was cooled and the organic layer was separated and purified by preparative TLC on silica gel eluted with DCM:MeOH (20:1) to give compound 18-3. MS (ESI) m/z: 563 (M+H$^+$).

Step D: (5aR,6S,6aS)-3-((4'-(3-(3,3-difluoroazetidin-1-yl)propoxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylic acid (18-4)

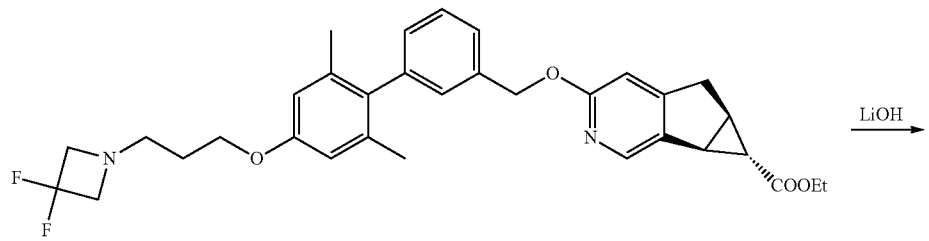

18-3

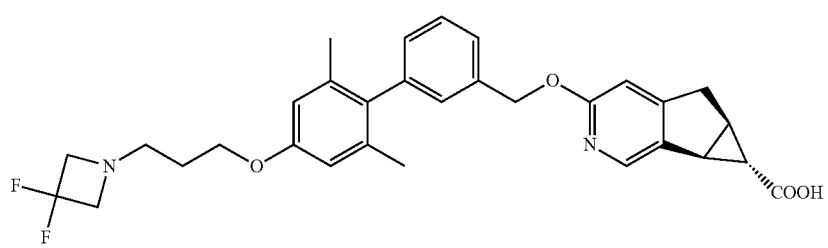

18-4

Compound 18-4 was prepared using a procedure similar to the procedure used to prepare compound 13-7. MS (ESI) m/z: 535 (M+H). $^1$HNMR (400 MHz, CDCl$_3$) δ: 8.07 (s, 1H), 7.41-7.39 (m, 2H), 7.13 (s, 1H), 7.03 (d, 1H, J=4.0 Hz), 6.81 (s, 1H), 6.68 (s, 2H), 5.34 (s, 2H), 4.78 (t, 2H, J=10.4 Hz), 4.09 (t, 2H, J=5.6 Hz), 3.58 (t, 2H, J=7.2 Hz), 3.26 (dd, 1H, J=6.0 and 12.0 Hz), 3.06 (d, 1H, J=8.8 Hz), 2.93 (d, 1H, J=1.2 Hz), 2.45-2.44 (m, 1H), 2.13-2.10 (m, 2H), 1.93 (s, 6H), 1.15-1.14 (m, 1H).

Example 43

Compound 19-6

(5aR,6S,6aS)-3-((4-fluoro-4'-(3-hydroxy-3-methyl-butyl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (9-6)

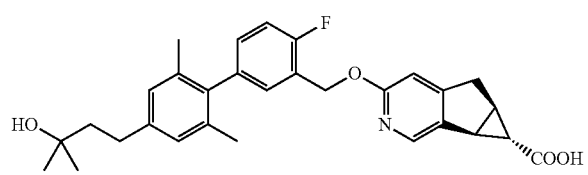

Step A: (E)-ethyl 3-(4-bromo-3,5-dimethylphenyl)acrylate (19-2)

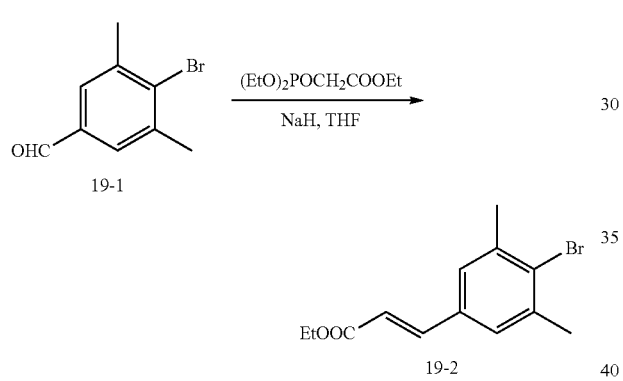

To a solution of triethyl phosphonoacetate (2.1 g, 9.4 mmol) in THF (20 mL) was added NaH (0.38 g, 9.4 mmol) in portions at 0° C. The mixture was stirred at 0° C. for 30 minutes, then compound 19-1 (1 g, 4.7 mmol) was added and the reaction was stirred at 0° C. for another 30 minutes. The reaction mixture was poured into 100 mL of water, and extracted with ethyl acetate (50 ml×2). The ethyl acetate layer was concentrated in vacuo, and the resulting residue was purified by column chromatography on silica gel eluted with petroleum ether:ethyl acetate (10:1) to give compound 19-2. MS (ESI) m/z: 283 (M+H)⁺.

Step B: ethyl 3-(4-bromo-3,5-dimethylphenyl)propanoate (19-3)

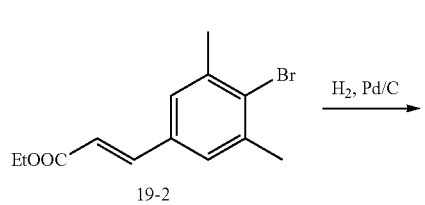

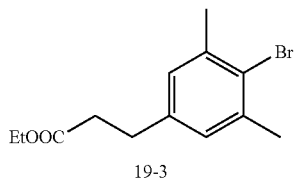

To a solution of compound 19-2 (140 mg, 0.5 mmol) in THF (5 mL) was added Pd/C (20 mg), and the mixture was degassed in vacuo and purged with H₂ several times. The mixture was stirred under a H₂ balloon for one hour at room temperature. Then the mixture was filtered, and the filtrate was concentrated to give compound 19-3. MS (ESI) m/z: 285 (M+H)⁺.

Step C: 4-(4-bromo-3,5-dimethylphenyl)-2-methylbutan-2-ol (19-4)

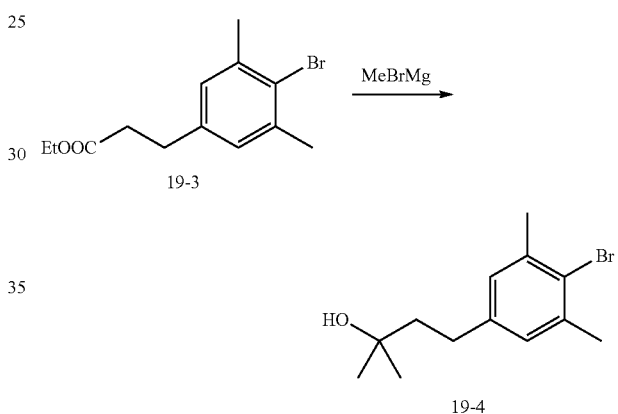

To a solution of compound 19-3 (130 mg, 0.46 mmol) in THF (3 mL) was added MeBrMg (0.5 mL, 1.5 mmol) dropwise at −60° C. The mixture was stirred at room temperature for one hour, then poured into 20 mL of ice water, and extracted with ethyl acetate (5 mL×4). The ethyl acetate layer was separated and concentrated in vacuo to give compound 19-4. MS (ESI) m/z: 253 (M-18+H)⁺.

Step D: (5aR,6S,6aS)-3-((4-fluoro-4'-(3-hydroxy-3-methylbutyl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (19-6)

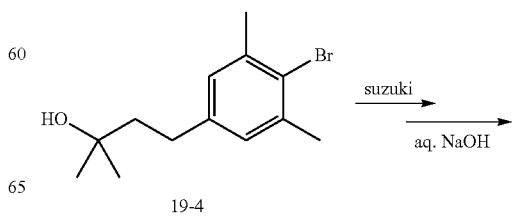

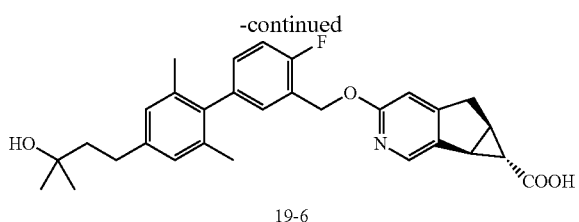

19-6

Compound 19-6 was obtained via a Suzuki reaction and the hydrolyzation; the procedure was similar to the procedure used to prepare compound 6-4. MS (ESI) m/z: 490 (M+H)$^+$. $^1$H-NMR (400 MHz, CD$_3$OD) δ: 8.04 (s, 1H), 7.12-7.17 (m, 2H), 7.02-7.06 (m, 1H), 6.89 (s, 2H), 6.67 (s, 1H), 5.38 (s, 2H), 3.22 (dd, 1H, J=6.4 Hz, J=18.4 Hz), 3.01 (d, 1H, J=18.4 Hz), 2.90 (d, 1H, J=4.8 Hz), 2.57-2.62 (m, 2H), 2.39-2.43 (m, 1H), 1.89 (s, 6H), 1.70-1.74 (m, 2H), 1.24 (s, 6H), 1.12 (t, 1H, J=2.8 Hz).

Example 44

Compound 19-16

(5aR,6S,6aS)-3-((4-fluoro-2',6'-dimethyl-4'-((4-(methylsulfonyl)butyl)-[1,1'-biphenyl]-3-yl)methoxy)-5,5a,6,6a-tetrahydrocyclopropa[4,5]cyclopenta[1,2-c]pyridine-6-carboxylic acid (9-16)

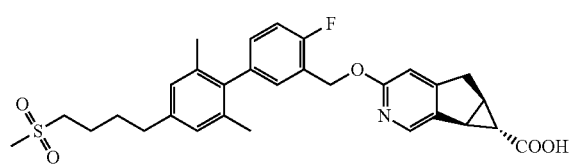

19-16

Step A: 3-(4-bromo-3,5-dimethylphenyl)propan-1-ol (19-7)

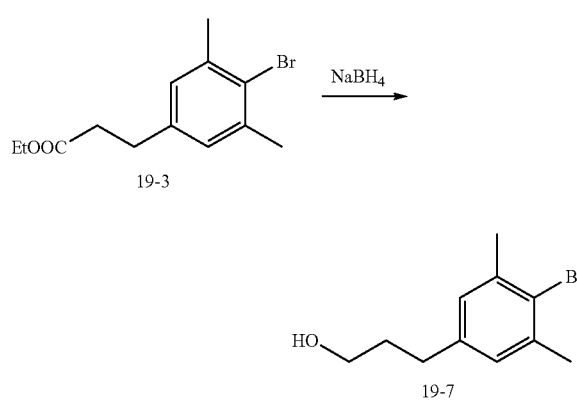

To a solution of compound 19-3 (1.4 g, 4.9 mmol) in MeOH (30 mL) was added NaBH$_4$ (0.57 g, 15 mmol) in portions. The mixture was stirred at room temperature for 2 hours. Then 50 mL of water was added to the mixture and MeOH was removed in vacuo. The aqueous layer was extracted with ethyl acetate (20 mL×3). The ethyl acetate layers were combined, washed with brine, dried over Na$_2$SO$_4$, and concentrated to give compound 19-7. MS (ESI) m/z: 243 (M+H)$^+$.

Step B: 3-(4-bromo-3,5-dimethylphenyl)propyl methanesulfonate (19-8)

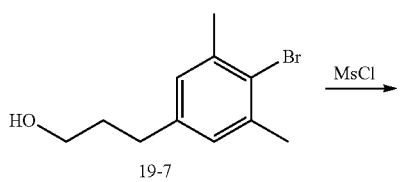

To a solution of compound 19-7 (100 mg, 0.4 mmol) and TEA (120 mg, 1.2 mmol) in DCM (3 mL) was added dropwise MsCl (68 mg, 0.6 mmol). The mixture was stirred at room temperature for 2 hours. Then 3 mL of water were added, and the DCM layer was separated and concentrated in vacuo to give compound 19-8.

Step C: 4-(4-bromo-3,5-dimethylphenyl)butanenitrile (19-9)

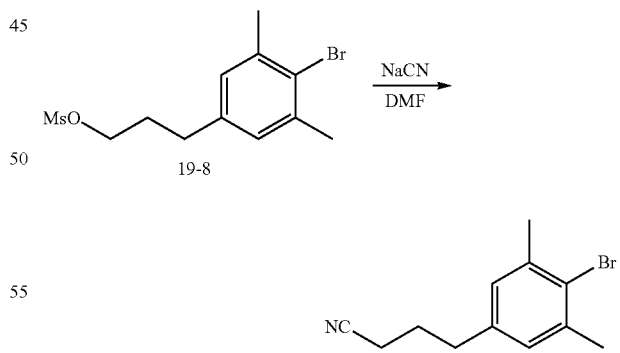

To a solution of compound 19-8 (32 mg, 0.37 mmol) in DMF (1 mL) was added NaCN (10 mg, 0.2 mmol), and the mixture was heated to 80° C. for 2 hours. Then 10 mL of water were added, and the mixture was extracted with ethyl acetate (3 mL×3). The ethyl acetate layers were combined, and concentrated in vacuo to give compound 19-9.

Step D: methyl
4-(4-bromo-3,5-dimethylphenyl)butanoate (19-10)

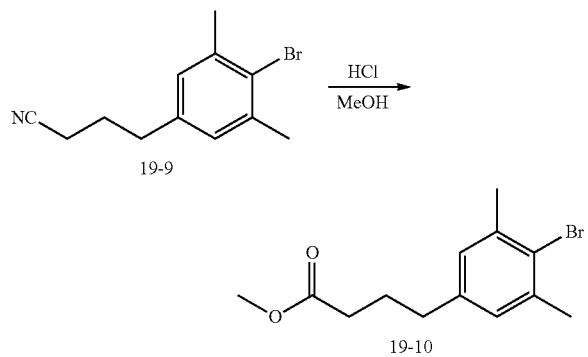

Compound 19-9 (0.5 g, 2 mmol) was dissolved in 4 M HCl/MeOH solution (5 mL) and heated to reflux for 1 hour. Then the solvent was removed in vacuo to give compound 19-10. MS (ESI) m/z: 285 (M+H)$^+$.

Step E: 4-(4-bromo-3,5-dimethylphenyl)butan-1-ol (19-11)

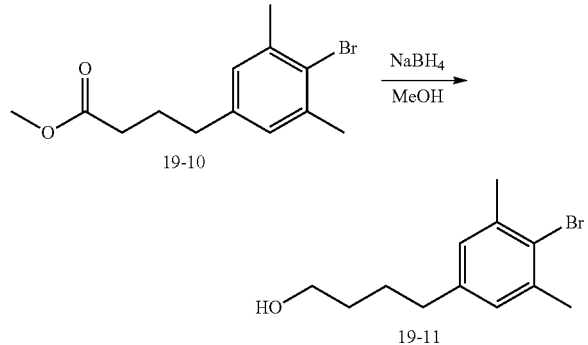

To a solution of compound 19-10 (0.3 g, 1.05 mmol) in MeOH (10 mL) was added NaBH$_4$ (0.19 g, 5 mmol) in portions, and the mixture was stirred at room temperature for 2 hours. Then 20 mL of water were added and the MeOH was removed in vacuo. The aqueous layer was extracted with ethyl acetate (10 mL×3). The combined ethyl acetate layers were washed with brine, dried over Na$_2$SO$_4$, and concentrated to give compound 19-11. MS (ESI) m/z: 257 (M+H)$^+$.

Step F: 4-(4-bromo-3,5-dimethylphenyl)butyl methanesulfonate (19-12)

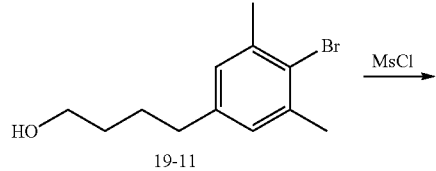

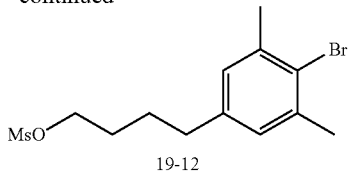

To a solution of compound 19-11 (50 mg, 0.2 mmol) and TEA (60 mg, 0.6 mmol) in DCM (2 mL) was added dropwise MsCl (34 mg, 0.3 mmol). The mixture was stirred at room temperature for 2 hours, then 10 mL of water were added. The aqueous layer was extracted with DCM (3 mL×3), and the DCM layers were concentrated in vacuo to give compound 19-12.

Step G: (4-(4-bromo-3,5-dimethylphenyl)butyl)(methyl)sulfane (19-13)

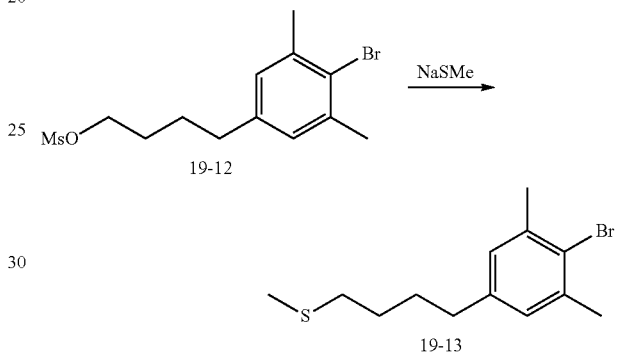

To a solution of compound 19-12 (300 mg, 0.89 mmol) in MeOH (10 mL) was added NaSMe (140 mg, 2 mmol), the mixture was stirred at room temperature for 2 hours. Then 30 mL of water were added. The aqueous layer was extracted with ethyl acetate (10 mL×2), and the ethyl acetate layer was concentrated in vacuo to give compound 19-13.

Step H: 2-bromo-1,3-dimethyl-5-(4-(methylsulfonyl)butyl)benzene (19-4)

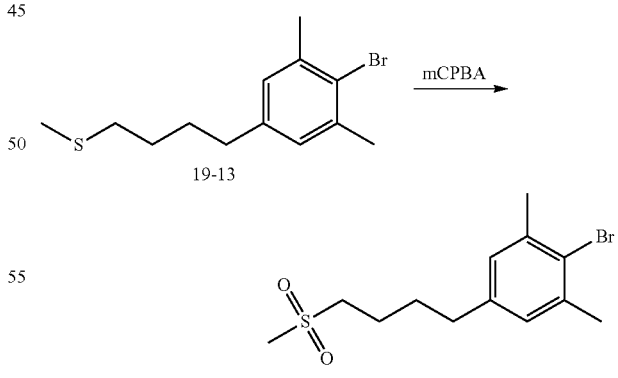

To a solution of compound 19-13 (100 mg, 0.35 mmol) in DCM (5 mL) was added m-CPBA (215 mg, 1 mmol), and the mixture was stirred at room temperature for 2 hours. Then 2 mL of 10% aq. NaOH was added. The DCM layer was separated and purified by preparative TLC on silica gel eluted with petroleum ether:ethyl acetate (1:1) to give compound 19-14.

Step I: (5aR,6S,6aS)-3-((4-fluoro-2',6'-dimethyl-4'-((4-(methylsulfonyl)butyl)-[1,1'-biphenyl]-3-yl)methoxy)-5,5a,6,6a-tetrahydrocyclopropa[4,5]cyclopenta[1,2-c]pyridine-6-carboxylic acid (19-16)

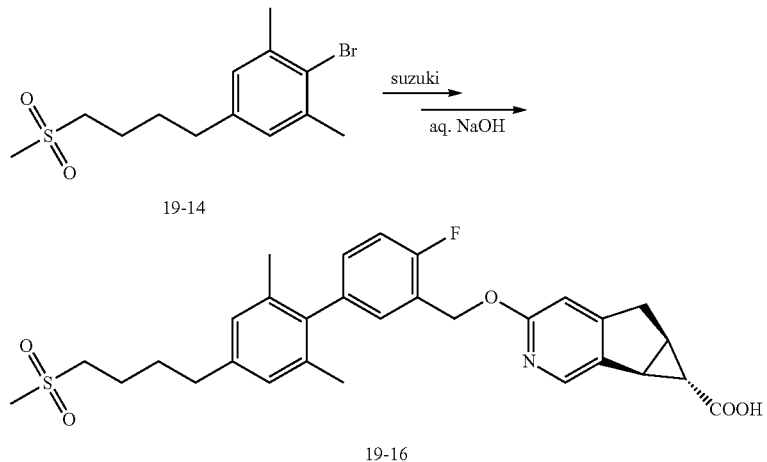

Compound 19-16 was obtained via a Suzuki reaction of compound 19-14 with Reference Example 2-4 and the subsequent hydrolyzation; the procedure was similar to the procedure used to prepare compound 6-4. MS (ESI) m/z: 538 (M+H)$^+$. $^1$H-NMR (400 MHz, CD$_3$OD) δ 8.04 (s, 1H), 7.13-7.17 (m, 2H), 7.02-7.06 (m, 1H), 6.91 (s, 2H), 6.67 (s, 1H), 5.38 (s, 2H), 3.22 (dd, 1H, J=6.4 Hz, J=18.8 Hz), 3.13 (t, 2H, J=6.8 Hz), 3.01 (d, 1H, J=18.8 Hz), 2.89-2.92 (m, 4H), 2.60 (t, 2H, J=7.2 Hz), 2.39-2.43 (m, 1H), 1.90 (s, 6H), 1.75-1.85 (m, 4H), 1.11 (t, 1H, J=2.8 Hz).

Example 45

Compound 19-19

(5aR,6S,6aS)-3-((4-fluoro-4'-((4-hydroxy-4-methylpentyl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (9-19)

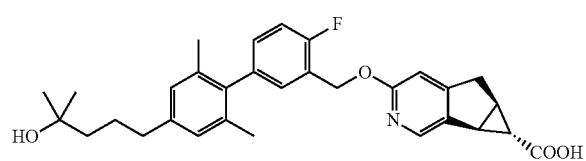

Step A: 5-(4-bromo-3,5-dimethylphenyl)-2-methylpentan-2-ol (19-17)

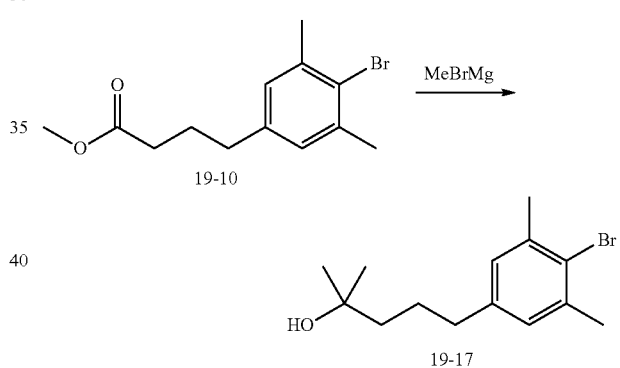

To a solution of compound 19-10 (100 mg, 0.35 mmol) in THF (3 mL) was added dropwise MeBrMg (1 mL, 3 mmol) at -70° C. The mixture was stirred at room temperature for 30 minutes, then poured into 10 mL of ice water, and extracted with ethyl acetate (5 mL×3). The ethyl acetate layers were combined and concentrated in vacuo to give compound 19-17.

Step B: (5aR,6S,6aS)-3-((4-fluoro-4'-((4-hydroxy-4-methylpentyl)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (9-19)

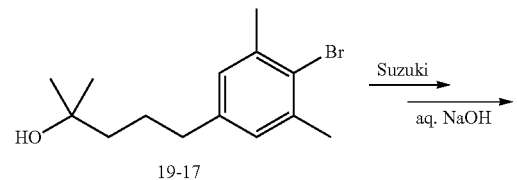

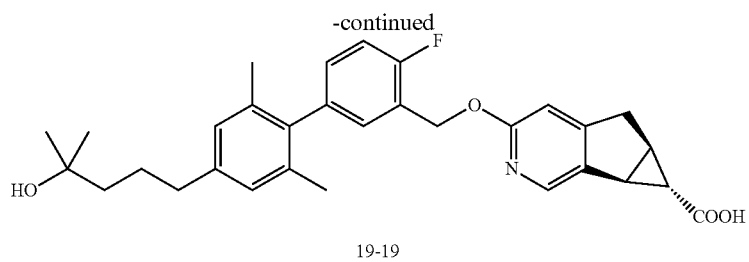

19-19

Compound 19-19 was obtained via a Suzuki reaction of compound 19-17 with Reference Example 2-4 and a subsequent hydrolysis, the procedure was similar to the procedure used to prepare compound 6-4. MS (ESI) m/z: 504 (M+H)⁺. ¹H-NMR (400 MHz, CD₃OD) δ: 8.05 (s, 1H), 7.13-7.18 (m, 2H), 7.03-7.07 (m, 1H), 6.89 (s, 2H), 6.70 (s, 1H), 5.39 (s, 2H), 3.19-3.22 (m, 1H), 3.02 (d, 1H, J=18.8 Hz), 2.91 (d, 1H, J=5.2 Hz), 2.54 (t, 2H, J=7.2 Hz), 2.40-2.44 (m, 1H), 1.91 (s, 3H), 1.90 (s, 3H), 1.63-1.71 (m, 2H), 1.46-1.50 (m, 2H), 1.16 (s, 6H), 1.12 (t, 1H, J=2.8 Hz).

Example 46

Compound 20-5

3-((2-fluoro-5-(6-(3-hydroxy-3-methylbutoxy)-4-(trifluoromethyl) pyridin-3-yl)benzyl)oxy)-5,5a,6,6a-tetrahydrocyclopropa[4,5]cyclopenta[1,2-c]pyridine-6-carboxylic acid (20-5)

20-5

Step A: 2-methyl-4-((4-(trifluoromethyl)pyridin-2-yl)oxy)butan-2-ol (20-2)

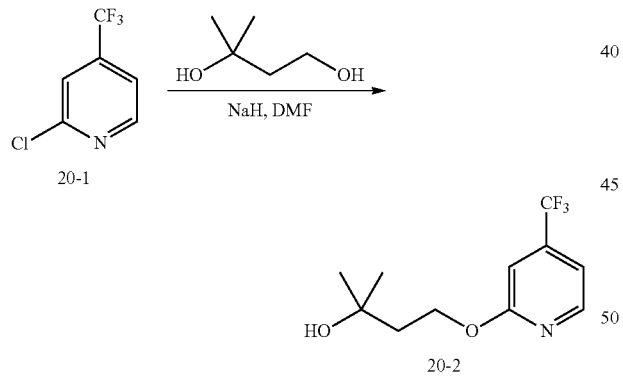

To a solution of 3-methyl-butane-1,3-diol (1.6 g, 15 mmol) in DMF (50 mL) was added NaH (1.2 g, 30 mmol) in portions, and the mixture was stirred at room temperature for 30 minutes. Then the mixture was poured into 300 mL of water, extracted with EtOAc (100 mL×2). The EtOAc layers were combined and concentrated, the resulting residue was purified by column chromatography on silica gel eluted with petroleum ether:ethyl acetate (2:1) to give compound 20-2.

Step B: 4-((5-bromo-4-(trifluoromethyl)pyridin-2-yl)oxy)-2-methylbutan-2-ol (20-3)

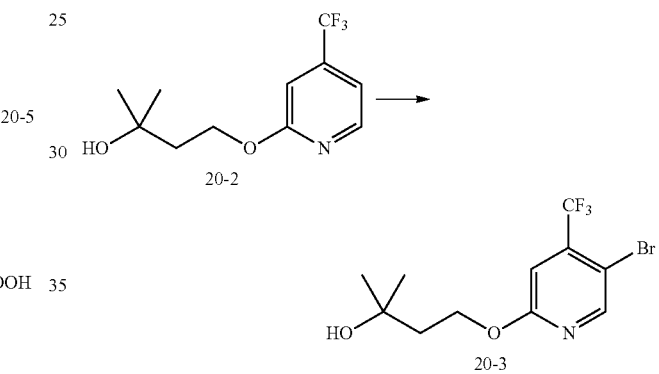

To a solution of compound 20-2 (100 mg, 0.4 mmol) in AcOH (0.5 mL) was added Br₂ (0.5 mL), and the mixture was stirred at room temperature for 2 hours. The mixture was then poured into 20 mL of NaHCO₃ aq. solution, and Na₂S₂O₃ was added until the solution turned colorless. The mixture was extracted with ethyl acetate (5 mL×3). The combined ethyl acetate layers were concentrated and purified by preparative TLC on silica gel eluted with petroleum ether:ethyl acetate (2:1) to give compound 20-3.

Step C: ethyl 3-((2-fluoro-5-(6-(3-hydroxy-3-methylbutoxy)-4-(trifluoromethyl) pyridin-3-yl) benzyl)oxy)-5,5a,6,6a-tetrahydrocyclopropa[4,5]cyclopenta[1,2-c]pyridine-6-carboxylate) (20-4)

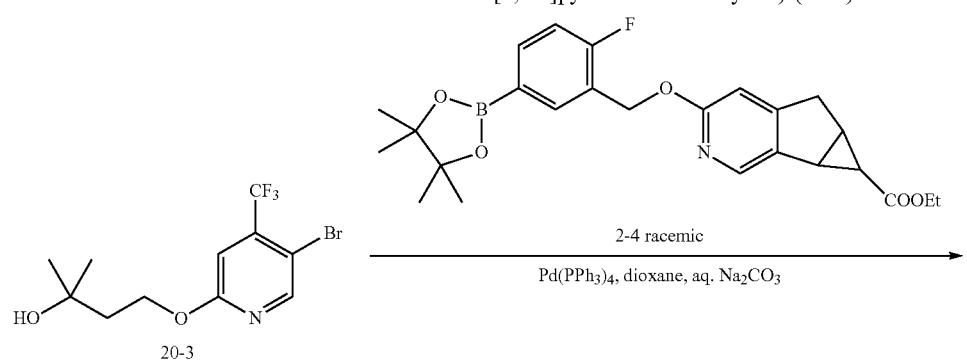

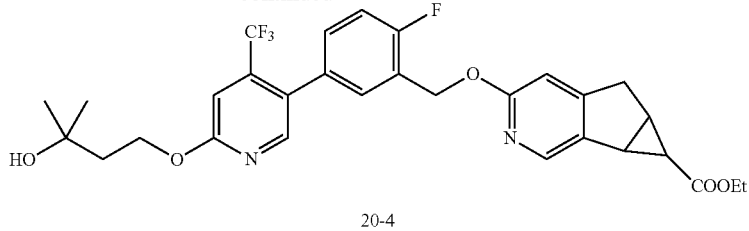

20-4

To a mixture of compound 20-3 (20 mg, 0.06 mmol) and Reference Example 2-4 (30 mg, 0.066 mmol) in dioxane (2 mL) and 2 M Na₂CO₃ aq. solution (1 mL) was added Pd(PPh₃)₄ (10 mg, 0.008 mmol) under N₂. The reaction was heated at 100° C. overnight. The dioxane layer was separated and purified by preparative TLC on silica gel eluted with petroleum ether:ethyl acetate (2:1) to give compound 20-4. MS (ESI) m/z: 575 (M+H)⁺.

Step D: 3-((2-fluoro-5-(6-(3-hydroxy-3-methylbutoxy)-4-(trifluoromethyl) pyridin-3-yl)benzyl)oxy)-5,5a,6,6a-tetrahydrocyclopropa[4,5]cyclopenta[1,2-c]pyridine-6-carboxylic acid (20-5)

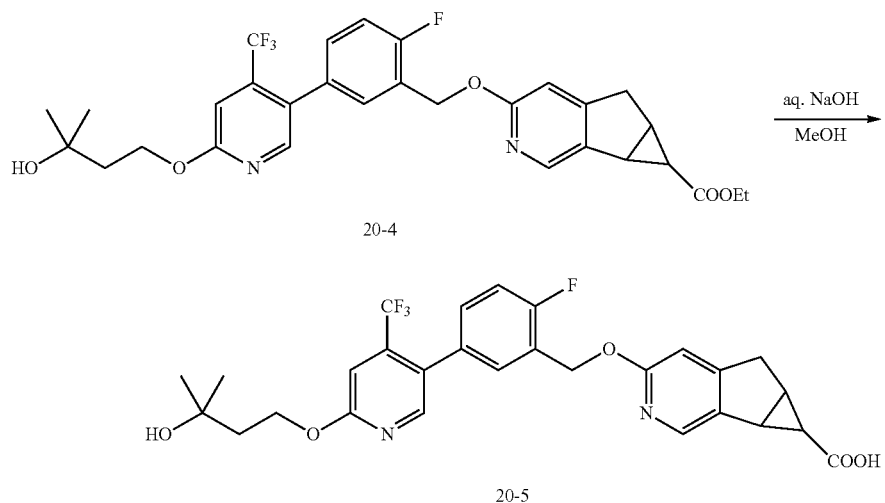

To a solution of compound 20-4 (10 mg, 0.017 mmol) in MeOH (2 mL) was added 2 M aq. NaOH solution (1 mL). The mixture was stirred at room temperature for 2 hours. The mixture was then poured into 10 mL of water, and acidified to pH 4 with dilute HCl. The mixture was extracted with ethyl acetate (5 mL×2), the combined ethyl acetate layers were concentrated in vacuo. The resulting residue was purified by preparative HPLC (preparative HPLC on a GILSON 281 instrument fitted with a Phenomenex Synergi C18 (150×30 mm×5 um) using water and acetonitrile as the eluents. Mobile phase A: water (containing 0.1% TFA, v/v), mobile phase B: acetonitrile. Gradient: 40-70% B, 0-10 min; 100% B, 10.5-12.5 min; 5% B, 13-15 min) to give compound 20-5. MS (ESI) m/z: 547 (M+H)⁺. ¹H-NMR (400 MHz, CD₃OD) δ: 8.11 (s, 1H), 8.09 (s, 1H), 7.44 (d, 1H, J=4.4 Hz), 7.29-7.32 (m, 1H), 7.19 (t, 1H, J=8.8 Hz), 7.09 (s, 1H), 6.84 (s, 1H), 5.42 (s, 2H), 4.51 (t, 2H, J=6.8 Hz), 3.28-3.29 (m, 1H), 3.08 (d, 1H, J=19.2 Hz), 2.94 (d, 1H, J=4.4 Hz), 2.43-2.47 (m, 1H), 1.98 (t, 2H, J=6.8 Hz), 1.27 (s, 6H), 1.17 (t, 1H, J=2.8 Hz).

The following Examples 47-49 (Compounds 20-6 to 20-8) were prepared in a similar manner to Compound 20-5 using the appropriate starting materials and Reference Example 2-4 or Reference Example 2-5.

| Example | Structure | M.W. | Compound Name | LC/MS (ESI) observed [M + 1]+ |
|---|---|---|---|---|
| 47 | (Compound 20-6) | 528 | (5aR,6S,6aS)-3-((3-(6-(3-hydroxy-3-methylbutoxy)-4-(trifluoromethyl)pyridin-3-yl)benzyl)oxy)-5,5a,6,6a-tetrahydrocyclopropa[4,5]cyclopenta[1,2-c]pyridine-6-carboxylic acid | 529 |
| 48 | (Compound 20-7) | 546 | (5aR,6S,6aS)-3-((2-fluoro-5-(6-(3-hydroxy-3-methylbutoxy)-4-(trifluoromethyl)pyridin-3-yl)benzyl)oxy)-5,5a,6,6a-tetrahydrocyclopropa[4,5]cyclopenta[1,2-c]pyridine-6-carboxylic acid | 547 |
| 49 | (Compound 20-8) | 546 | (5aR,6S,6aS)-3-((2-fluoro-5-(6-((4-(2-hydroxypropan-2-yl)cyclohexyl)oxy)-2-methylpyridin-3-yl)benzyl)oxy)-5,5a,6,6a-tetrahydrocyclopropa[4,5]cyclopenta[1,2-c]pyridine-6-carboxylic acid | 547 |

Example 50

Compound 21-7

3-((2-fluoro-5-(6-((4-hydroxy-4-methylpentyl)oxy)-4-(trifluoromethyl)pyridin-3-yl) benzyl)oxy)-5,5a,6,6a-tetrahydrocyclopropa[4,5]cyclopenta[1,2-c]pyridine-6-carboxylic acid (21-7)

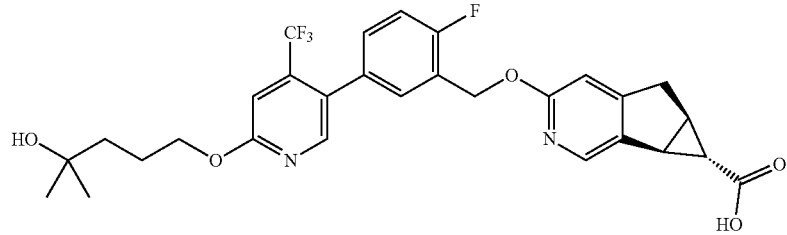

21-7

Step A: 4-(trifluoromethyl)pyridin-2-ol (21-2)

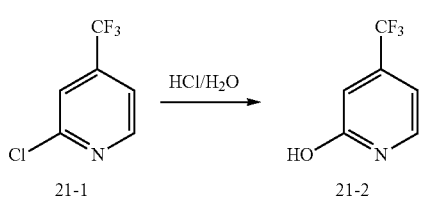 [SMILES: FC(F)(F)c1ccnc(Cl)c1 ; Oc1cc(C(F)(F)F)ccn1]

To a solution of compound 21-1 (8 g, 0.04 mol) in H₂O (30 mL) was added concentrated hydrochloric acid (30 mL). The resulting mixture was stirred at 110° C. for 18 hours. The solution was basified with NaHCO₃ to the precipitate a white solid. The white solid was filtered to give the compound 21-2.

Step B: methyl 4-((4-(trifluoromethyl)pyridin-2-yl)oxy)butanoate (21-3)

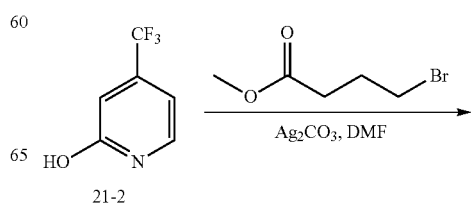

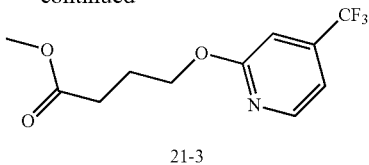

21-3

To a solution of compound 21-2 (1.0 g, 6.13 mmol) in DMF (10 mL) was added ethyl 4-bromobutyrate (2.3 g, 12.3 mmol) and Ag₂CO₃ (3.3 g, 12.3 mmol). The resulting mixture was stirred at 100° C. for 18 hours. Then H₂O was added and the solution was extracted with EtOAc (15 mL×3). The combined organic layers were washed with brine, dried and concentrated to give a residue, which was purified by column chromatography on silica gel eluted with petroleum ether:ethyl acetate (5:1) to give compound 21-3.

Step C: 2-methyl-5-((4-(trifluoromethyl)pyridin-2-yl)oxy)pentan-2-ol (21-4)

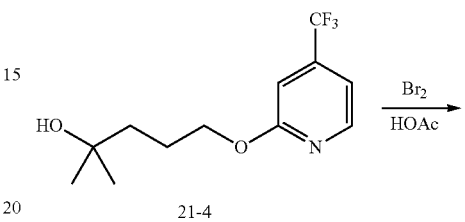

To a solution of compound 21-3 (1.1 g, 3.97 mmol) in THF (10.0 mL) was added dropwise methyl magnesium bromide (8 mL, 3 M) slowly at 0° C. The reaction mixture was warmed to rt. and stirred for 2 hours. Then the reaction was quenched with HCl (1 M), extracted with EtOAc (15 mL×3). The combined organic layers were washed with brine, dried, concentrated to give a residue, which was purified by column chromatography on silica gel eluted with petroleum ether: ethyl acetate (5:1) to give compound 21-4.

Step D: 5-((5-bromo-4-(trifluoromethyl)pyridin-2-yl)oxy)-2-methylpentan-2-ol (21-5)

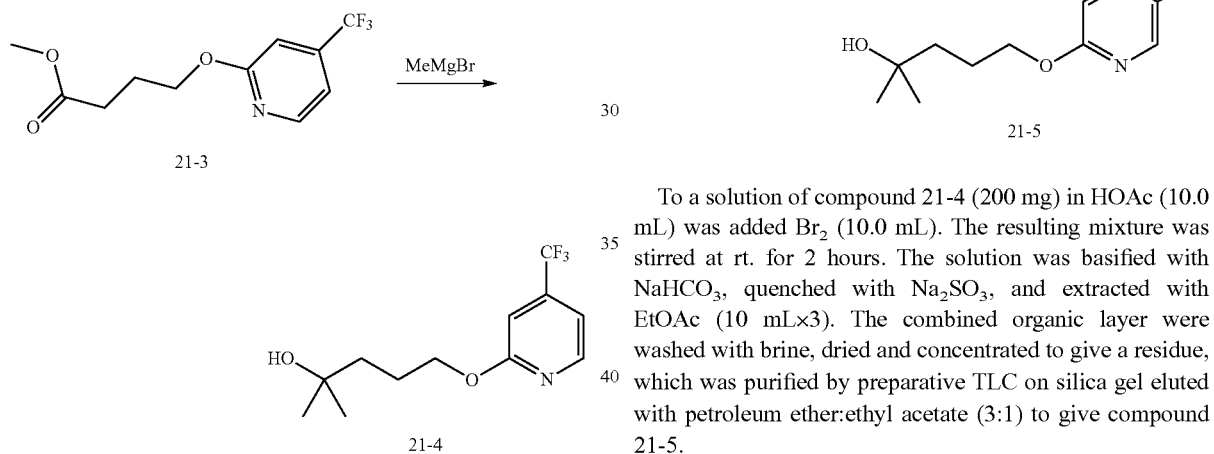

To a solution of compound 21-4 (200 mg) in HOAc (10.0 mL) was added Br₂ (10.0 mL). The resulting mixture was stirred at rt. for 2 hours. The solution was basified with NaHCO₃, quenched with Na₂SO₃, and extracted with EtOAc (10 mL×3). The combined organic layer were washed with brine, dried and concentrated to give a residue, which was purified by preparative TLC on silica gel eluted with petroleum ether:ethyl acetate (3:1) to give compound 21-5.

Step E: (5aR,6S,6aS)-ethyl 3-((2-fluoro-5-(6-((4-hydroxy-4-methylpentyl)oxy)-4-(trifluoromethyl)pyridin-3-yl) benzyl)oxy)-5,5a,6,6a-tetrahydro cyclopropa[4,5]cyclopenta[1,2-c]pyridine-6-carboxylate (21-6)

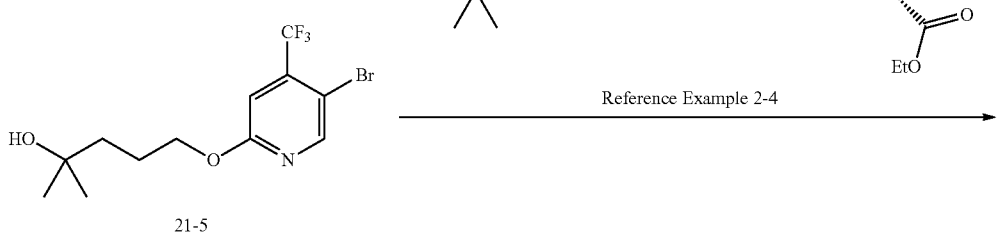

Reference Example 2-4

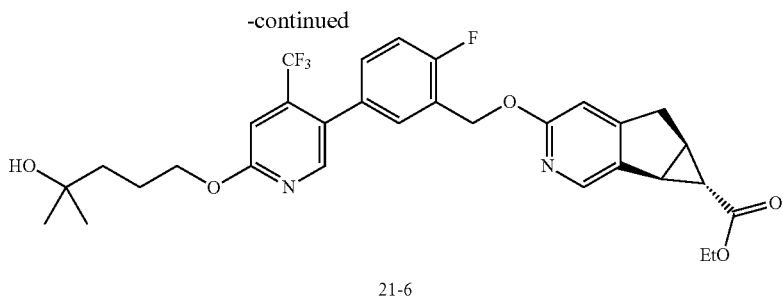

21-6

To a solution of compound 21-5 (15 mg, 0.04 mmol) in THF (5.0 mL) and H₂O (1 mL) was added the boronate from Reference Example 2-4 (24 mg, 0.05 mmol), Pd(dppf)Cl₂ (5 mg, 0.004 mmol) and K₃PO₄ (11 mg, 0.08 mmol). The resulting mixture was stirred at 100° C. for 2 hours. The mixture was filtered and the filtrate was extracted with EtOAc (15 mL×3). The combined organic layers were washed with brine, dried and concentrated to give a residue, which was purified by preparative TLC on silica gel eluted with DCM:MeOH (25:1) to give compound 21-6. MS (ESI) m/z: 589 (M+H)⁺.

Step F: 3-((2-fluoro-5-(6-((4-hydroxy-4-methylpentyl)oxy)-4-(trifluoromethyl)pyridin-3-yl) benzyl) oxy)-5,5a,6,6a-tetrahydrocyclopropa[4,5]cyclopenta [1,2-c]pyridine-6-carboxylic acid (2-2)

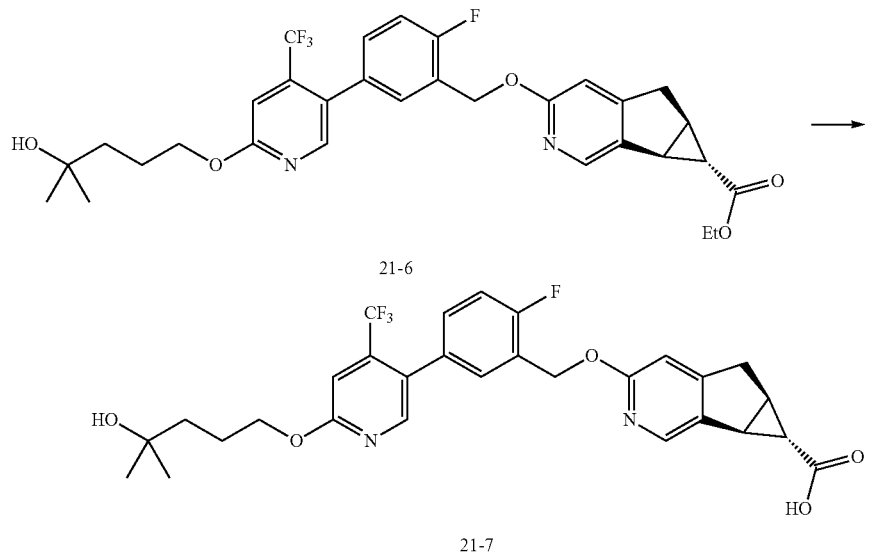

21-6

21-7

To a solution of compound 21-6 (10 mg, 0.02 mmol) in THF (3.0 mL), MeOH (1.0 mL) and H₂O (1.0 mL) was added LiOH.H₂O (4 mg, 0.08 mmol). The resulting mixture was stirred at rt. for 4 hours. Then H₂O was added and the solution was acidified with HCl (1M) to pH 2.5, and extracted with EtOAc (5 mL×3). The combined organic layers were washed with brine, dried and concentrated to give a residue, which was purified by preparative HPLC (preparative HPLC on a GILSON 281 instrument fitted with a Phenomenex Synergi C18 (150×30 mm×5 um) using water and acetonitrile as the eluents. Mobile phase A: water (containing 0.1% TFA, v/v), mobile phase B: acetonitrile. Gradient: 45-65% B, 0-10 min; 100% B, 10.5-12.5 min; 5% B, 13-15 min) to give Example 21-7. MS (ESI) m/z: 561 (M+H)⁺. ¹H-NMR (400 MHz, Methanol-d₄) δ: 8.11 (s, 2H), 7.45 (d, 1H, J=5.6 Hz), 7.31-7.32 (m, 1H), 7.21 (t, 1H, J=8.4 Hz), 7.10 (s, 1H), 6.91 (s, 1H), 5.44 (s, 2H) 4.38 (t, 2H, J=6.4 Hz), 3.29-3.30 (m, 1H), 3.08-3.13 (m, 1H), 2.95-2.97 (m, 1H), 2.45-2.49 (m, 1H), 1.84-1.92 (m, 2H), 1.59-1.63 (m, 2H), 121 (s, 7H).

The following Example 51 (Compound 21-8) was prepared in a similar manner to Compound 21-7 using the appropriate starting materials and the boronate from Reference Example 2-5.

| Example | Structure | M.W. | Compound Name | LC/MS (ESI) observed [M + 1]+ |
|---|---|---|---|---|
| 51 | (Compound 21-8) | 542 | (5aR,6S,6aS)-3-((3-(6-((4-hydroxy-4-methylpentyl)-oxy)-4-(trifluoromethyl)-pyridin-3-yl)benzyl)oxy)-5,5a,6,6a-tetrahydrocyclo-propa[4,5]cyclopenta[1,2-c]pyridine-6-carboxylic acid | 543 |

Example 52

Compound 22-2

(5aR,6S,6aS)-ethyl 3-((4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (22-2)

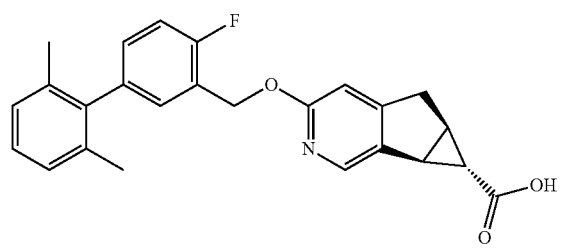

22-2

Step A: (5aR,6S,6aS)-ethyl 3-((4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (22-1)

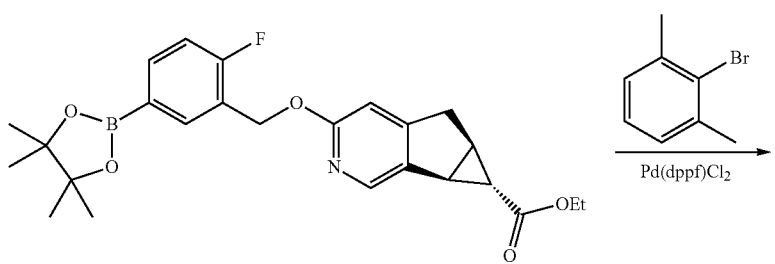

2-4

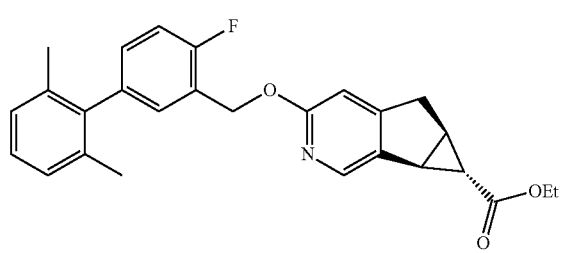

22-1

A suspension of compound Reference Example 2-4 (90 mg, 0.2 mmol), 2-bromo-1,3-dimethyl-benzene (36 mg, 0.2 mmol), Pd(dppf)Cl$_2$ (15 mg, 0.02 mmol), K$_3$PO$_3$ (120 g, 0.6 mmol) and in THF/H$_2$O (4:1, 2.5 mL) was heated at 100° C. for 30 min in a microwave under N$_2$. After cooling, the mixture was filtered and the filtrate was partitioned by ethyl acetate and water. The aqueous layer was extracted with ethyl acetate twice. The combined organic layers were washed with brine, dried over anhydrous sodium sulfate, and concentrated in vacuo. The resulting residue was purified by preparative TLC on silica gel eluted with DCM:MeOH (25:1) to afford compound 22-1. MS (ESI) m/e (M+H$^+$): 432.2 (M+H$^+$).

Step B: (5aR,6S,6aS)-ethyl 3-((4-fluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (22-2)

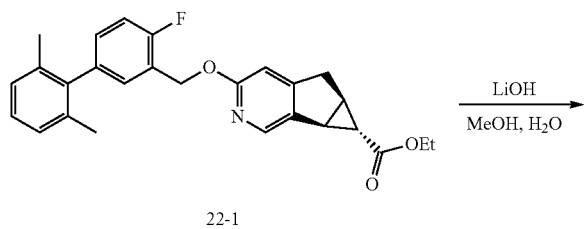

22-1

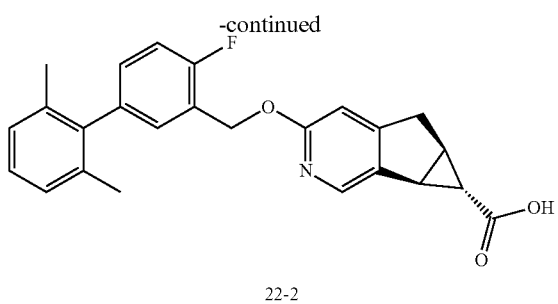

22-2

The mixture of compound 22-1 (71 mg, 0.16 mmol) and LiOH (32 mg, 0.8 mmol) in THF/H$_2$O/MeOH (1:1:1, 3 mL) was stirred at r.t for 5 hours. The mixture was acidified to pH 5-6 with 1N HCl. The resulting aqueous solution was extracted with ethyl acetate twice. The combined organic layers were washed with brine, dried over anhydrous Na$_2$SO$_3$, and concentrated. The resulting residue was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 65-85% B, 0-10 min; 100% B, 10.5-12.5 min; 5% B, 13-1 min) to give 22-2. MS (ESI) m/e (M+H$^+$): 404.2 (M+H$^+$). $^1$H-NMR (400 MHz, Methanol-d4) δ: 8.19 (s, 1H), 7.44 (d, 1H, J=7.2 Hz), 7.30 (t, 1H, J=7.6 Hz), 7.19 (br.s, 1H), 7.08-7.16 (m, 2H), 7.02 (d, 1H, J=7.6 Hz), 5.45 (s, 2H), 3.39-3.46 (m, 1H), 3.22 (d, 1H, J=19.2 Hz), 3.03 (d, 1H, J=6.4 Hz), 2.53 (m, 1H), 1.90 (s, 6H), 1.29 (m, 1H).

The following Examples 53-59 (Compounds 22-3 to 22-9) were prepared in a similar manner to Compound 22-2 using the appropriate starting materials and the boronates from Reference Example 2-4 or Reference Example 2-5.

| Example | Structure | M.W. | Compound Name | LC/MS (ESI) observed [M + 1]+ |
|---|---|---|---|---|
| 53 | (Compound 22-3) | 443.4 | 3-((4-fluoro-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 444.2 |
| 54 | (Compound 22-4) | 443.4 | 3-((4-fluoro-4'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 444.2 |

-continued

| Example | Structure | M.W. | Compound Name | LC/MS (ESI) observed [M + 1]+ |
|---|---|---|---|---|
| 55 | (Compound 22-5) | 443.4 | 3-((4-fluoro-3'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 444.2 |
| 56 | (Compound 22-6) | 461.4 | 3-((2',4-difluoro-6'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 462.2 |
| 57 | (Compound 22-7) | 477.8 | 3-((3'-chloro-4-fluoro-5'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 478.6 |
| 58 | (Compound 22-8) | 444.4 | 3-((2-fluoro-5-(2-(trifluoromethyl)pyridin-3-yl)benzyl)oxy)-5,5a,6,6a-tetrahydrocyclopropa[4,5]cyclopenta[1,2-c]pyridine-6-carboxylic acid | 445.2 |
| 59 | (Compound 22-9) | 444.4 | 3-((2-fluoro-5-(3-(trifluoromethyl)pyridin-2-yl)benzyl)oxy)-5,5a,6,6a-tetrahydrocyclopropa[4,5]cyclopenta[1,2-c]pyridine-6-carboxylic acid | 445.2 |

Example 60

Compound 23-8

4-{2-Fluoro-5-[6-(3-methanesulfonyl-propoxy)-4-methyl-pyridin-3-yl]-benzyloxy}-1,1a,6,6a-tetrahydro-3-aza-cyclopropa[a]indene-1-carboxylic acid (23-8)

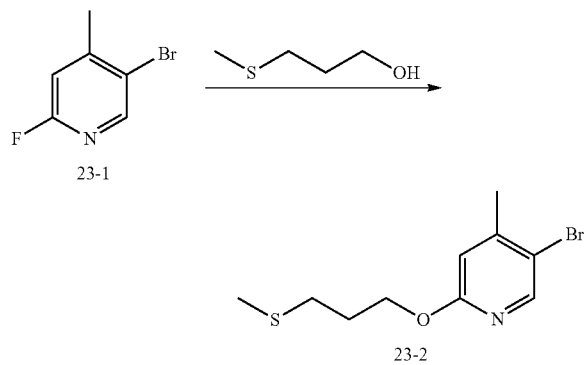

Step A: 5-bromo-4-methyl-2-(3-(methylthio)propoxy)pyridine (3-2)

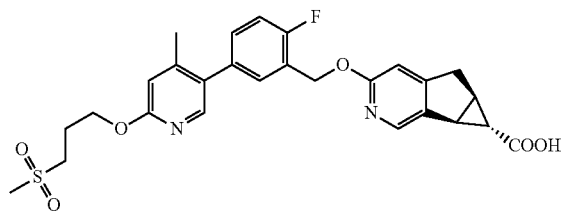

A mixture of compound 23-1 (6.30 g, 33 mmol), 3-methylsulfanyl-propan-1-ol (5.26 g, 49.5 mmol) and t-BuOK (5.54 g, 49.5 mmo) in anhydrous THF was heated at reflux for 4 hours. The mixture was then partitioned with water and EtOAc, and the layers were separated. The aqueous layer was extracted with EtOAc two times. The organic layers were combined and concentrated to afford a residue, which was purified by flash column chromatography on silica gel eluted with petroleum ether:ethyl acetate (10:1) to give compound 23-2. MS (ESI) m/e (M+H$^+$): 276.0/278.0.

Step B: 5-bromo-4-methyl-2-(3-(methylsulfonyl)propoxy)pyridine (23-3)

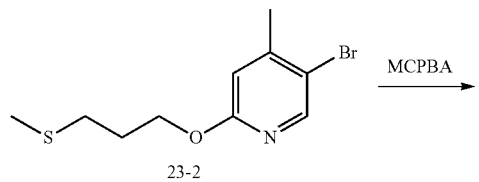

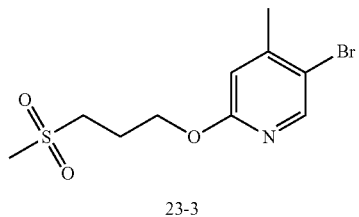

To a solution of 23-2 (9.23 g, 33 mmol) in dry DCM (150 mL) with ice-bath cooling was added MCPBA (80%, 15.15 g, 70.2 mmol). The resulting mixture was stirred at 0° C. for 2 hours, then an aqueous solution of NaHSO$_3$ was added. The DCM layer was separated, washed with Na$_2$CO$_3$ (aq.), water and then brine, and concentrated to afford a residue, which was purified by flash column chromatography on silica gel eluted with petroleum ether:ethyl acetate (20:1) to give compound 23-3. MS (ESI) m/e (M+H$^+$): 308.0/310.0.

Step C: 2-fluoro-5-(4-methyl-6-(3-(methylsulfonyl)propoxy)pyridin-3-yl)benzoic acid (23-4)

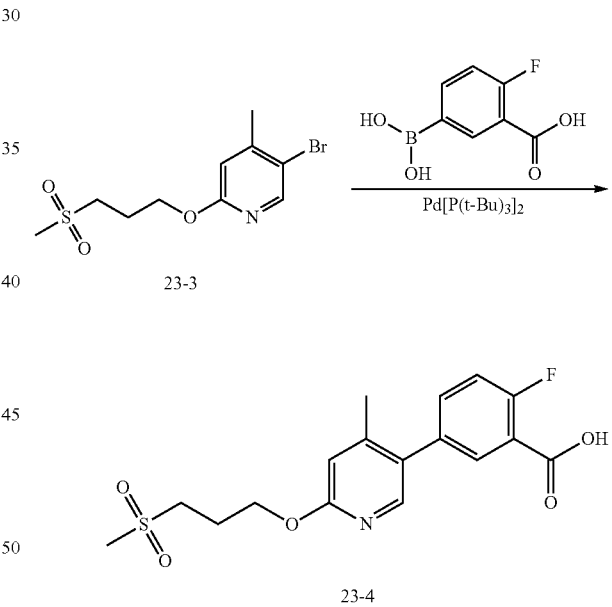

A mixture of 23-3 (924 mg, 3.0 mmol), 5-borono-2-fluorobenzoic acid (827 mg, 4.5 mmol), Cs$_2$CO$_3$ (2.94 g, 9.0 mmol) and Pd[P(t-Bu)$_3$]$_2$ (153 mg, 0.3 mmol) in a co-solvent of dioxane (12 mL)/H$_2$O (3 mL) was radiated by microwave to 100° C. for 30 min under a nitrogen atmosphere. The mixture was cooled to room temperature and filtered. The filtrate was extracted with EA, and the combined ethyl acetate layers were washed with water, dried and concentrated in vacuo to give crude 23-4. MS (ESI) m/e (M+H$^+$): 368.1

Step D: (2-fluoro-5-(4-methyl-6-(3-(methylsulfonyl)propoxy)pyridin-3-yl)phenyl)methanol (23-5)

Step E: 5-(3-(bromomethyl)-4-fluorophenyl)-4-methyl-2-(3-(methylsulfonyl)propoxy)pyridine (23-6)

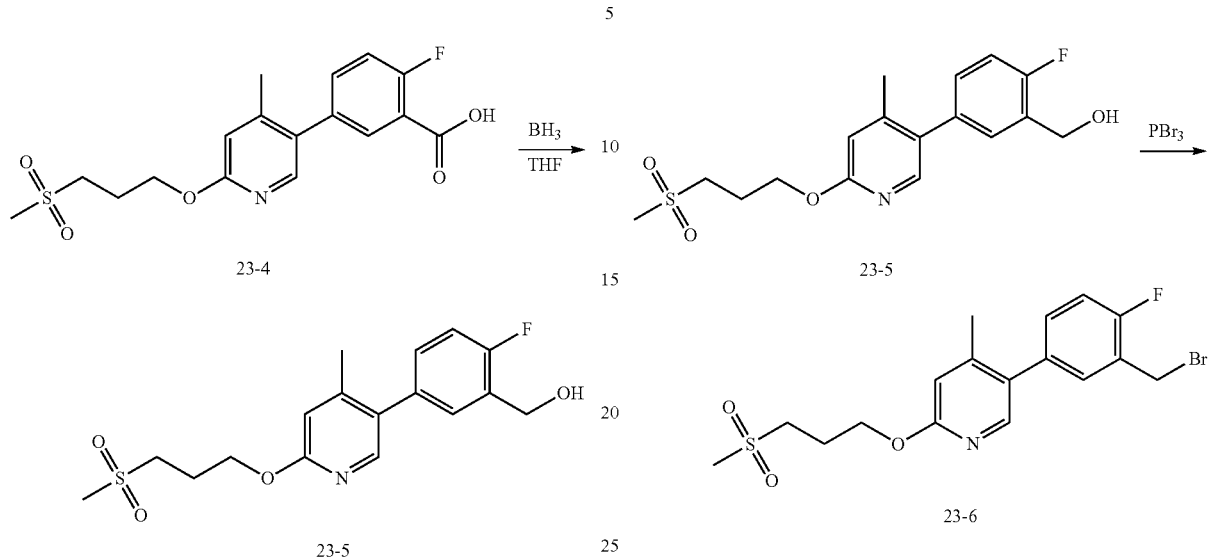

To a solution of crude compound 23-4 (2.45 g) in dry THF (50 mL), cooled in an ice bath, was added dropwise Me$_2$S—BH$_3$ (10 M, 6 mL). The reaction solution was stirred 0° C. for 1 h, and then warmed to 20° C. and stirred for 16 hrs. The mixture was re-cooled to 0° C., and MeOH was added to quench until there was no gas evolution. The mixture was concentrated to afford a residue, which was purified by flash column chromatography on silica gel eluted with petroleum ether:ethyl acetate (12:1) to give 23-5. MS (ESI) m/e (M+H$^+$): 354.1.

To a solution of crude compound 23-5 (353 mg, 1.0 mmol) in dry THF (5 mL), cooled in an ice bath, was added dropwise PBr$_3$ (216 mg, 0.8 mmol). The reaction mixture was stirred at 0° C. for 1 h and then warmed to 20° C. and stirred for 16 hrs. The reaction was quenched with water, and NaHCO$_3$ (aq) was added to adjust the pH of the mixture to pH 7. The reaction solution was concentrated to afford a residue, which was purified by flash column chromatography on silica gel eluted with petroleum ether:ethyl acetate (12:1) to give 23-6. MS (ESI) m/e (M+H$^+$): 416.0/418.0.

Step F: 4-{2-Fluoro-5-[6-(3-methanesulfonyl-propoxy)-4-methyl-pyridin-3-yl]-benzyloxy}-1,1a,6,6a-tetrahydro-3-aza-cyclopropa[a]indene-1-carboxylic acid ethyl ester (23-1)

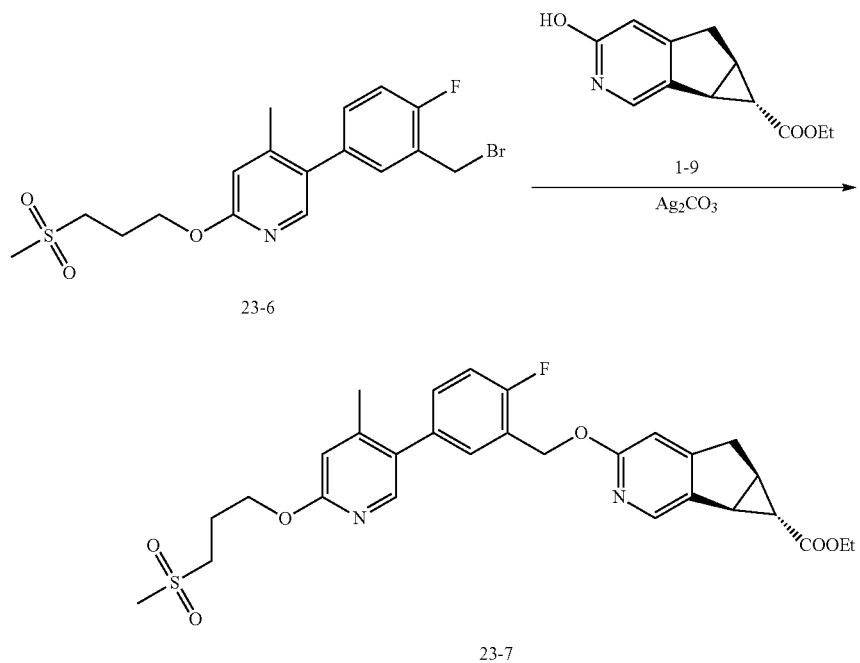 [SMILES: Cc1cc(OCCCS(C)(=O)=O)ncc1-c1ccc(F)c(CBr)c1 ; CCOC(=O)[C@H]1[C@@H]2Cc3cc(O)ncc3[C@@H]21 ; "Ag2CO3" ; CCOC(=O)[C@H]1[C@@H]2Cc3cc(OCc4cc(-c5cnc(OCCCS(C)(=O)=O)cc5C)ccc4F)ncc3[C@@H]21]

A mixture of compound 23-6 (227 mg, 0.54 mmol), compound 1-9 (120 mg, 1.64 mmol) and $Ag_2CO_3$ (451 mg, 1.64 mmol) in toluene (5 mL) was heated to 100° C. for 12 hrs. The mixture was filtered and the filtrate was concentrated to give a residue, which was purified by flash column chromatography on silica gel eluted with petroleum ether: ethyl acetate (5.7:1) to give compound 23-7. MS (ESI) m/e (M+H$^+$): 555.2

Step G: 4-{2-Fluoro-5-[6-(3-methanesulfonyl-propoxy)-4-methyl-pyridin-3-yl]-benzyloxy}-1,1a,6,6a-tetrahydro-3-aza-cyclopropa[a]indene-1-carboxylic acid (23-8)

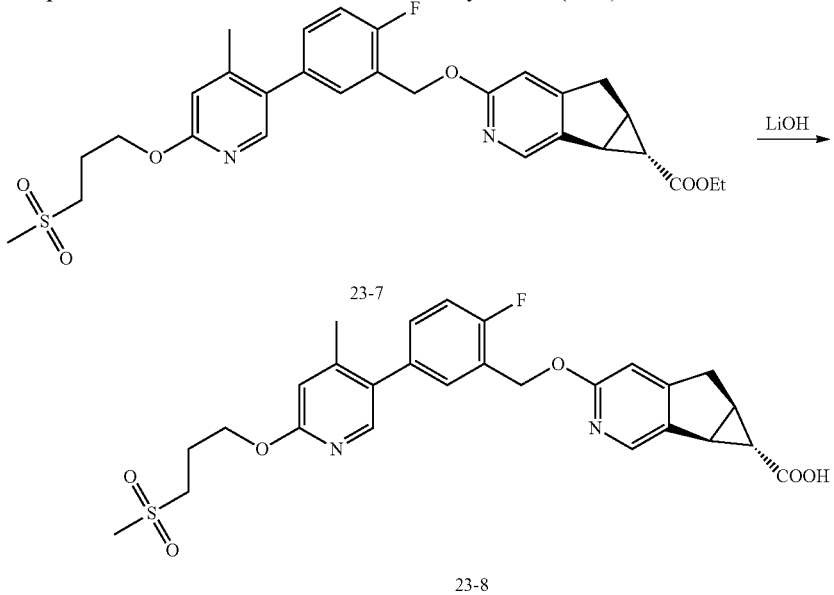

To a mixture of 23-7 (160 mg, 0.29 mmol) in a co-solvent THF (2 mL), MeOH (2 mL) and $H_2O$ (2 mL) was added NaOH (150 mg, 3.7 mmol), and the mixture was stirred at room temperature for 2 hrs. The resulting mixture was acidified by HCl (2 N) to pH 2, and extracted with ethyl acetate (10 mL) twice. The combined organic layers were washed with water, brine, dried over $Na_2SO_4$ and concentrated in vacuo to afford crude product, which was purified by prep-HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 20-70% B, 0-10 min; 100% B, 10.5-12.5 min; 5% B, 13-15 min) to give 23-8. MS (ESI) m/e (M+H$^+$): 527.2. $^1$H-NMR (400 MHz, Methanol-d4) δ: 8.07 (s, 1H), 7.87 (s, 1H), 7.40 (dd, 1H, J=7.8, 5.2 Hz), 7.26 (m, 1H, J=2 Hz), 7.19 (t, 1H, J=9.6 Hz), 6.74 (s, 1H), 6.70 (s, 1H), 5.41 (s, 2H), 4.40 (t, 2H, J=6.0 Hz), 3.32 (m, 2H), 3.23 (m, 1H, J=6.8 Hz), 3.02 (m, 1H, J=18.4 Hz), 3.00 (s, 3H) 2.92 (d, 1H, J=5.6 Hz), 2.41-2.44 (m, 1H), 2.24-2.31 (m, 2H), 2.17 (s, 3H), 1.13 (t, 1H, J=2.8 Hz).

The following Examples 61-70 (Compounds 23-9 to 23-18) were prepared in a similar manner to Compound 23-8 using the appropriate starting materials and boronates from Reference Example 2-4 or Reference Example 2-5.

| Example | Structure | M.W. | Compound Name | LC/MS (ESI) observed [M + 1]+ |
|---|---|---|---|---|
| 61 | (Compound 23-9) | 538.6 | 3-((5-(6-((1,1-dioxidotetrahydro-2H-thiopyran-4-yl)oxy)-2-methyl-pyridin-3-yl)-2-fluoro-benzyl)oxy)-5,5a,6,6a-tetrahydrocyclopropa[4,5]cyclopenta[1,2-c]pyridine-6-carboxylic acid | 539.4 |

| Example | Structure | M.W. | Compound Name | LC/MS (ESI) observed [M + 1]+ |
|---|---|---|---|---|
| 62 | (Compound 23-10) | 526.6 | (5aR,6S,6aS)-3-((2-fluoro-5-(2-methyl-6-(3-(methylsulfonyl)propoxy)pyridin-3-yl)benzyl)oxy)-5,5a,6,6a-tetrahydrocyclopropa[4,5]cyclopenta[1,2-c]pyridine-6-carboxylic acid | 527.4 |
| 63 | (Compound 23-11) | 522.6 | (5aR,6S,6aS)-3-((3-(2,4-dimethyl-6-(3-(methylsulfonyl)propoxy)pyridin-3-yl)benzyl)oxy)-5,5a,6,6a-tetrahydrocyclopropa[4,5]cyclopenta[1,2-c]pyridine-6-carboxylic acid | 523.4 |
| 64 | (Compound 23-12) | 540.6 | (5aR,6S,6aS)-3-((5-(2,4-dimethyl-6-(3-(methylsulfonyl)propoxy)pyridin-3-yl)-2-fluorobenzyl)oxy)-5,5a,6,6a-tetrahydrocyclopropa[4,5]cyclopenta[1,2-c]pyridine-6-carboxylic acid | 541.4 |
| 65 | (Compound 23-13) | 541.6 | 3-((5-(4,6-dimethyl-2-(3-(methylsulfonyl)propoxy)pyrimidin-5-yl)-2-fluorobenzyl)oxy)-5,5a,6,6a-tetrahydrocyclopropa[4,5]cyclopenta[1,2-c]pyridine-6-carboxylic acid | 542.4 |
| 66 | (Compound 23-14) | 532.6 | 3-((2-fluoro-5-(4-methyl-2-(3-(methylsulfonyl)propoxy)thiazol-5-yl)benzyl)oxy)-5,5a,6,6a-tetrahydrocyclopropa[4,5]cyclopenta[1,2-c]pyridine-6-carboxylic acid | 533.4 |
| 67 | (Compound 23-15) | 531.6 | 3-((2-fluoro-5-(2-methyl-6-(3-(2-oxopyrrolidin-1-yl)propoxy)pyridin-3-yl)benzyl)oxy)-5,5a,6,6a-tetrahydrocyclopropa[4,5]cyclopenta[1,2-c]pyridine-6-carboxylic acid | 532.3 |

-continued

| Example | Structure | M.W. | Compound Name | LC/MS (ESI) observed [M + 1]+ |
|---|---|---|---|---|
| 68 | (Compound 23-16) | 580.6 | (5aR,6S,6aS)-3-((2-fluoro-5-(6-(3-(methylsulfonyl)propoxy)-4-(trifluoromethyl)pyridin-3-yl)benzyl)oxy)-5,5a,6,6a-tetrahydrocyclopropa[4,5]cyclopenta[1,2-c]pyridine-6-carboxylic acid | 581.1 |
| 69 | (Compound 23-17) | 578.6 | (5aR,6S,6aS)-3-((5-(4-(difluoromethoxy)-6-(3-(methylsulfonyl)propoxy)pyridin-3-yl)-2-fluorobenzyl)oxy)-5,5a,6,6a-tetrahydrocyclopropa[4,5]cyclopenta[1,2-c]pyridine-6-carboxylic acid | 579.2 |
| 70 | (Compound 23-18) | 538.4 | 3-((2-fluoro-5-(2-methyl-6-(2,2,3,3,3-pentafluoropropoxy)pyridin-3-yl)benzyl)oxy)-5,5a,6,6a-tetrahydrocyclopropa[4,5]cyclopenta[1,2-c]pyridine-6-carboxylic acid | 539.2 |

Example 71

Compound 24-4

3-((2-fluoro-5-(2-methyl-6-(3-(methylsulfonyl)propoxy)pyridin-3-yl)benzyl)amino)-5,5a,6,6a-tetrahydrocyclopropa[4,5]cyclopenta[1,2-c]pyridine-6-carboxylic acid (24-4)

Step A: 2-fluoro-5-(2-methyl-6-(3-(methylsulfonyl)propoxy)pyridin-3-yl)benzaldehyde (24-2)

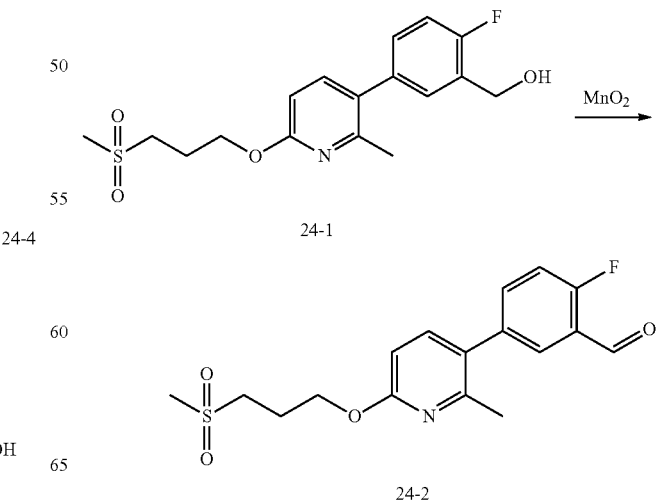

To a stirred solution of compound 24-1 (500 mg, 1.41 mmol, prepared using a procedure similar to the procedure for preparation of compound 13-5) in THF (10 ml) was added MnO$_2$ (1.23 g, 14.15 mmol). The reaction mixture was stirred at 60° C. for 1 h, then filtered, and washed with EA. The combined ethyl acetate layers were concentrated to give the pure product, which was used to the next step without further purification. MS (ESI) m/e (M+H$^+$) 352.1.

Step B: Ethyl 3-((2-fluoro-5-(2-methyl-6-(3-(methylsulfonyl)propoxy)pyridin-3-yl)benzyl)amino)-5,5a,6,6a-tetrahydrocyclopropa[4,5]cyclopenta[1,2-c]pyridine-6-carboxylate (24-3)

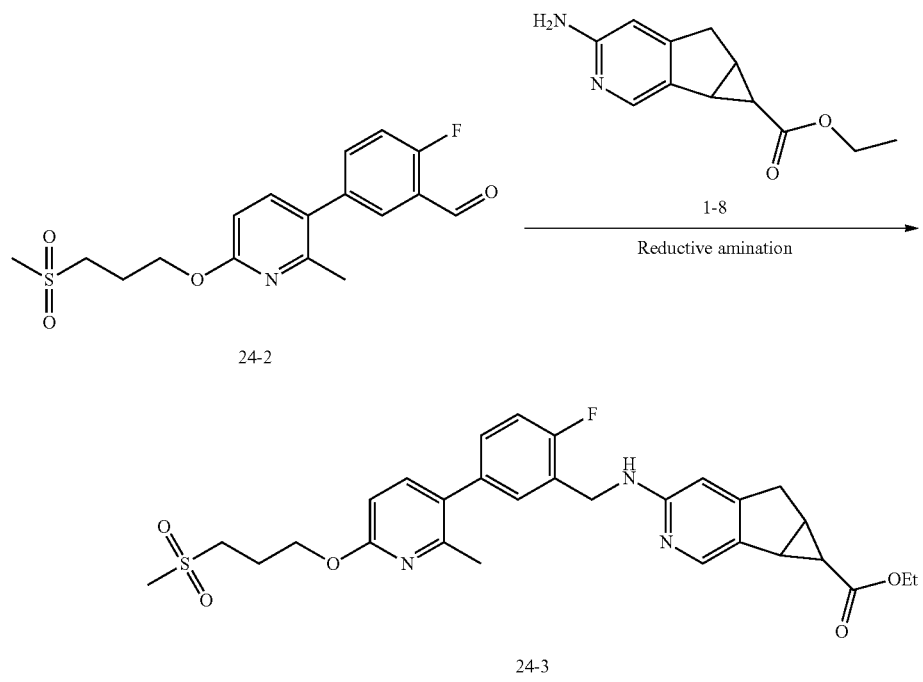

To a solution of amine 1-8 (28 mg, 128 μmol) in dry DCM (3 mL) was added triethylamine (34 mg, 341 μmol), and TiCl$_4$ (27 mg, 142 μmol). Then compound 24-2 (30 mg, 85 μmol) was carefully added at −40° C. The resulting suspension was stirred for 16 h at ambient temperature. Then the solvent was evaporated, and the remaining powder was crushed in ethyl acetate (20 mL). The resulting solid was filtered off and the filtrate was evaporated to dryness to give the crude product. The crude product was dissolved in EtOH (3 mL), and Na(AcO)$_3$BH (36 mg, 170 μmol) was added. The mixture was stirred at ambient temperature for 1 h, and the resulting reaction mixture was used directly in the next step. MS (ESI) m/e (M+H$^+$) 554.2.

Step C: 3-((2-fluoro-5-(2-methyl-6-(3-(methylsulfonyl)propoxy)pyridin-3-yl)benzyl)amino)-5,5a,6,6a-tetrahydrocyclopropa[4,5]cyclopenta[1,2-c]pyridine-6-carboxylic acid (24-4)

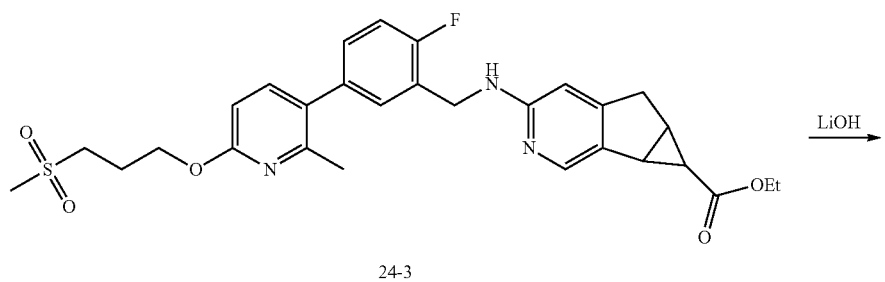

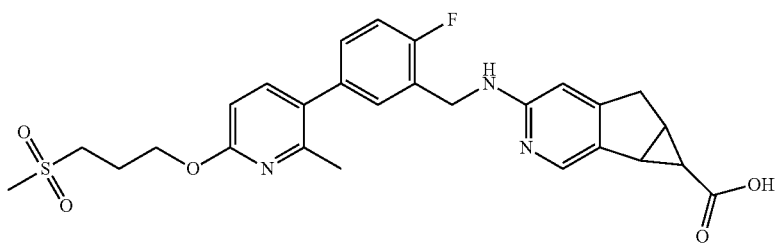

24-4

To a mixture of compound 24-3 (20 mg, 36 μmol) in THF (1 mL) and EtOH (0.5 mL) was added H₂O (0.5 mL) and LiOH (28 mg). The reaction mixture was stirred at ambient temperature overnight, then the pH was adjusted to pH 4 with HCl (1N). The reaction mixture was washed with brine (30 mL) and 50 mL of EA. The organic layer was separated, dried over Na₂SO₄, and concentrated. The resulting residue was purified by preparative HPLC (preparative HPLC on a GILSON 281 instrument fitted with a YMC-pack ODS-AQ C18 (150×30 mm×5 um) using water and acetonitrile as the eluents. Mobile phase A: water (containing 0.1% TFA, v/v), mobile phase B: acetonitrile. Gradient: 16-36% B, 0-10 min; 100% B, 10.5-12.5 min; 5% B, 13-15 min) to give the pure product 24-4. MS (ESI) m/e (M+H⁺) 526.2.

Example 72

Compound 25-2

4-[2-Fluoro-5-(2-trifluoromethyl-phenoxy)-benzyloxy]-1,1a,6,6a-tetrahydro-3-aza-cyclopropa[a]indene-1-carboxylic acid

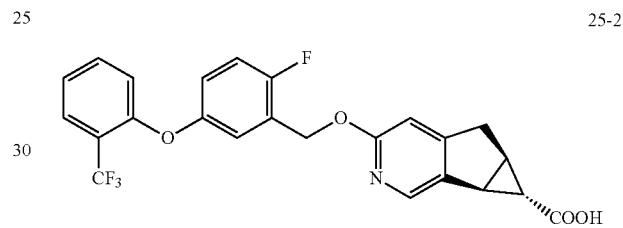

25-2

Step A: 4-[2-Fluoro-5-(2-trifluoromethyl-phenoxy)-benzyloxy]-1,1a,6,6a-tetrahydro-3-aza cyclopropa[a]indene-1-carboxylic acid ethyl ester (25-1)

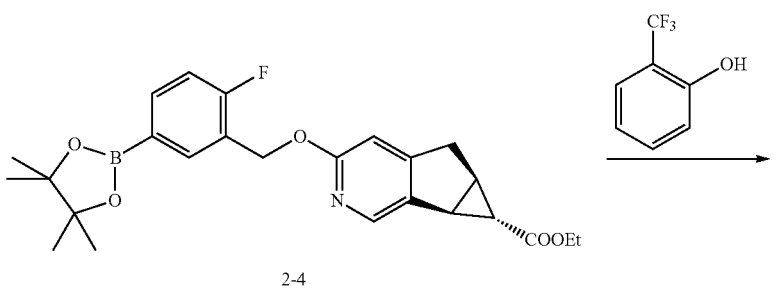

2-4

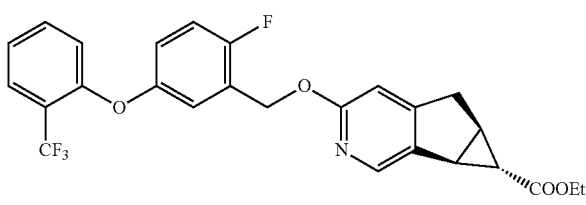

25-1

To a mixture of compound 2-4 (100 mg, 0.22 mmol) and 2-trifluoromethyl-phenol (71 mg, 0.44 mmol) in CH₃CN (3 mL) was added DMAP (54 mg, 0.33 mmol) and Cu(OAc)₂ (170 mg, 0.33 mmol). The mixture was degassed and refilled with N₂ three times. Then the mixture was heated to 80° C. and stirred over night. Then the mixture was cooled to room temperature and filtered. The filtrate was washed with a solution of sodium bicarbonate and brine, dried over anhydrous Na₂SO₄, and concentrated to give the crude product, which was purified by preparative HPLC to give crude compound 25-1. MS (ESI) m/e (M+H⁺): 488.0.

Step B: 4-[2-Fluoro-5-(2-trifluoromethyl-phenoxy)-benzyloxy]-1,1a,6,6a-tetrahydro-3-aza-cyclopropa[a]indene-1-carboxylic acid (25-2)

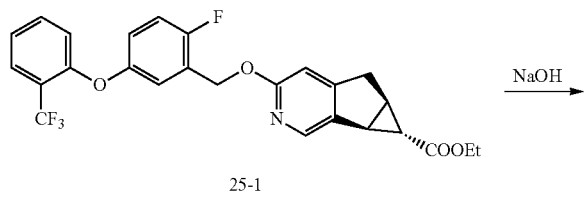

25-1

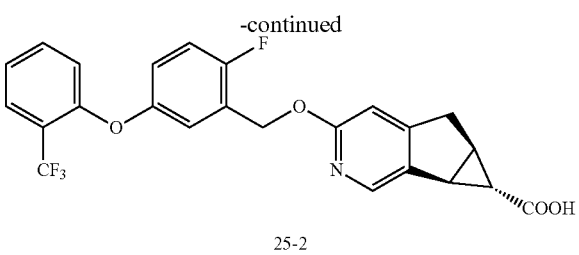

25-2

To a mixture of compound 25-1 (60 mg, 0.123 mmol) in a co-solvent THF (2 mL) MeOH (2 mL) and H₂O (2 mL) was added NaOH (25 mg, 0.62 mmol) at room temperature, and the mixture was stirred for 3 h. The resulting mixture was acidified with HCl (1 N) to pH 5-6, and extracted with ethyl acetate (10 mL) three times. The combined organic layer was washed with brine, dried over Na₂SO₄ and concentrated in vacuo to give crude product, which was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 45-75% B, 0-10 min; 100% B, 10.5-12.5 min; 5% B, 13-15 min) to give compound 25-2. MS (ESI) m/e (M+H⁺): 460.0. ¹H-NMR (400 MHz, Methanol-d4) δ: 8.09 (s, 1H), 7.69 (d, 1H, J=7.6 Hz), 7.51 (t, 1H, J=7.6 Hz), 7.15-7.25 (m, 3H), 6.99-7.03 (m, 1H), 6.92 (s, 1H), 6.88 (d, 1H, J=8.4 Hz), 5.39 (s, 2H), 3.33 (d, 1H, J=6.8 Hz), 3.11 (d, 1H, 19.2 Hz), 2.96 (d, 1H, J=4.4 Hz), 2.45-2.49 (m, 1H), 1.20 (t, 1H, J=2.8 Hz).

The following Examples 73 and 74 (Compounds 25-3 and 25-4) were prepared in a similar manner to Compound 25-2 using the appropriate starting materials.

| Example | Structure | M.W. | Compound Name | LC/MS (ESI) observed [M + 1]+ |
|---|---|---|---|---|
| 73 | (Compound 25-3) | 391.4 | 4-(2-Fluoro-5-phenoxy-benzyloxy)-1,1a,6,6a-tetrahydro-3-aza-cyclopropa[a]indene-1-carboxylic acid | 392.1 |
| 74 | (Compound 25-4) | 493.8 | 4-[5-(2-Chloro-4-trifluoromethyl-phenoxy)-2-fluoro-benzyloxy]-1,1a,6,6a-tetrahydro-3-aza-cyclopropa[a]indene-1-carboxylic acid | 494.1 |

Example 75

Compound 26-7

3-((6-(2,6-dimethylphenyl)-3-fluoropyridin-2-yl)methoxy)-5,5a,6,6a-tetrahydrocyclopropa[4,5]cyclopenta[1,2-c]pyridine-6-carboxylic acid (26-7)

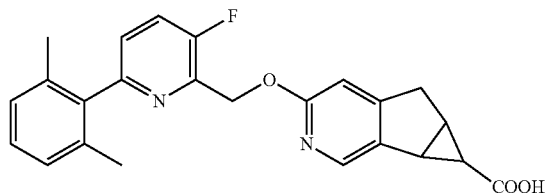

Step A: 6-(2,6-dimethylphenyl)-3-fluoro-2-methylpyridine (26-2)

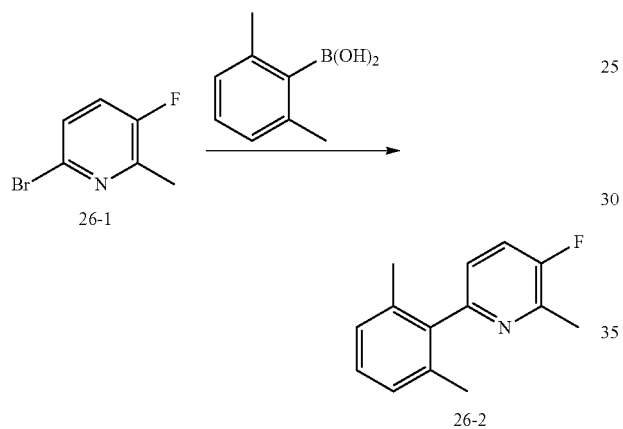

A mixture of 6-bromo-3-fluoro-2-methylpyridine 26-1 (570 mg, 3.0 mmol), 2,6-dimethyl phenylboronic acid (675 mg, 4.5 mmol)), $K_3PO_4$ (2.34 g, 9.0 mmol), $Pd_2(dba)_3$ (274 mg, 0.3 mmol), and s-phos (246 mg, 0.6 mmol) in a co-solvent of THF (10 mL)/$H_2O$ (2.5 mL) was radiated by microwave to 100° C. for 30 min under a nitrogen atmosphere. The mixture was cooled to room temperature, filtered, and the filtrate was extracted with EA. The ethyl acetate layer was washed with water, dried and concentrated in vacuo to give crude product, which was purified by flash column chromatography on silica gel eluted with petroleum ether:ethyl acetate (97:3) to give compound 26-2. MS (ESI) m/e (M+H$^+$): 216.1.

Step B: 6-(2,6-dimethylphenyl)-3-fluoropicolinaldehyde (26-3)

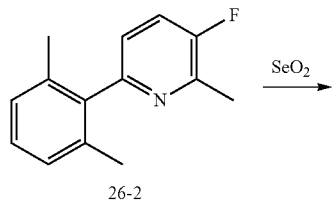

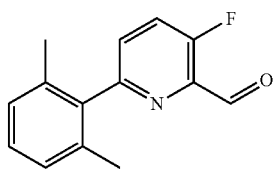

To a mixture of 26-2 (242 mg, 1.1 mmol) in 1,4-dioxane (3 mL) was added $SeO_2$ (276 mg, 2.4 mmol). The resulting mixture was stirred at 100° C. for 12 hrs, and then concentrated. The resulting residue was purified by flash column chromatography on silica gel eluted with petroleum ether: ethyl acetate (95:5) to give compound 26-3. MS (ESI) m/e (M+H$^+$): 230.1.

Step C: (6-(2,6-dimethylphenyl)-3-fluoropyridin-2-yl)methanol (26-4)

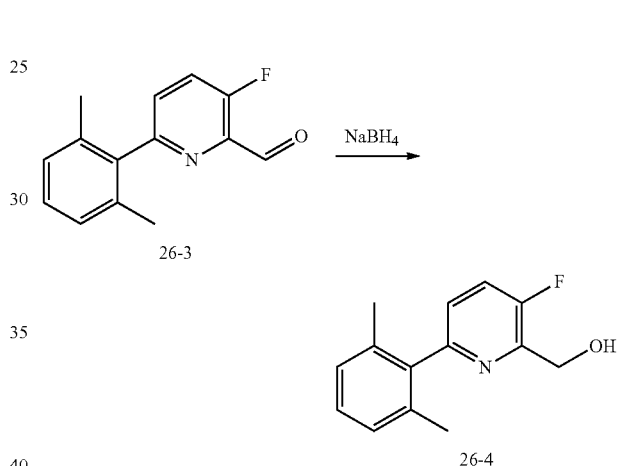

To a solution of crude compound 26-3 (166 mg) in MeOH (5 mL), cooled in an ice bath, was added NaBH$_4$ (76 mg, 2.0 mmol) in one portion. The reaction solution was stirred at 0° C. for 1 h. The reaction mixture was then quenched with water, and extracted with ethyl acetate three times. The combined organic layers were concentrated to afford a residue, which was purified by flash column chromatography on silica gel eluted with petroleum ether:ethyl acetate (92:8) to give compound 26-4. MS (ESI) m/e (M+H$^+$): 232.1.

Step D: 2-(bromomethyl)-6-(2,6-dimethylphenyl)-3-fluoropyridine (26-5)

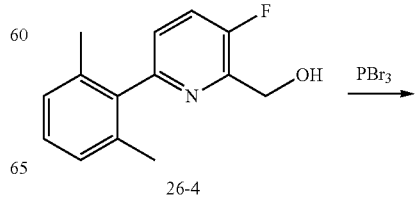

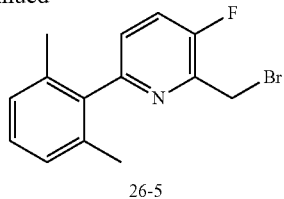

26-5

To a solution of crude compound 26-4 (113 mg, 0.49 mmol) in dry THF (3 mL), cooled in an ice bath, was added dropwise PBr₃ (106 mg, 0.39 mmol). The reaction solution was stirred at 0° C. for 1 h, and then warmed to 20° C. and stirred for 2 hours. The mixture was then quenched with water, and NaHCO₃ (aq) was added to neutralize the mixture to pH 7. The mixture was concentrated to afford a residue, which was purified by flash column chromatography on silica gel eluted with petroleum ether:ethyl acetate (95:5) to give compound 26-5. MS (ESI) m/e (M+H⁺): 294.0/296.0.

Step E: Ethyl 3-((6-(2,6-dimethylphenyl)-3-fluoro-pyridin-2-yl)methoxy)-5,5a,6,6a-tetrahydrocyclo-propa[4,5]cyclopenta[1,2-c]pyridine-6-carboxylate (26-6)

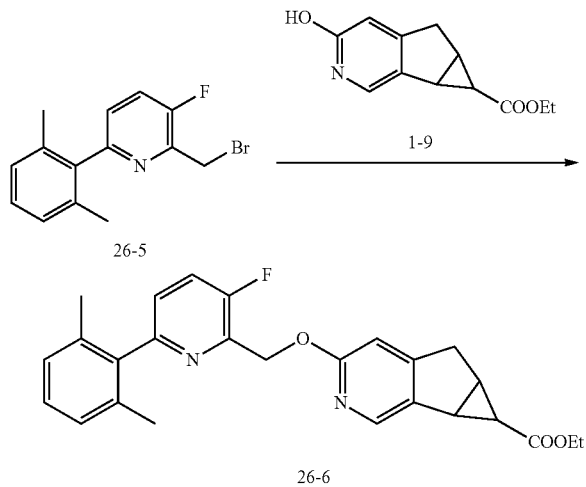

A mixture of compound 26-5 (90 mg, 0.3 mmol), compound 1-9 (66 mg, 0.3 mmol) and Ag₂CO₃ (249 mg, 0.9 mmol) in toluene (3 mL) was heated to 100° C. for 12 hrs. Then the mixture was filtered, and the filtrate was concentrated to give crude 26-6, which was used in the next step without purification. MS (ESI) m/e (M+H⁺): 433.2

Step F: 3-((6-(2,6-dimethylphenyl)-3-fluoropyridin-2-yl)methoxy)-5,5a,6,6a-tetrahydrocyclopropa[4,5]cyclopenta[1,2-c]pyridine-6-carboxylic acid (26-7)

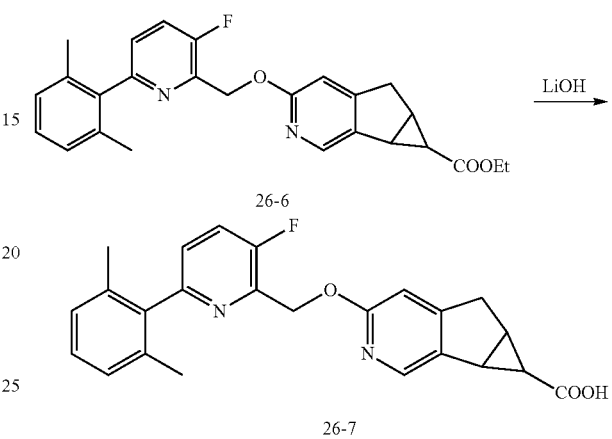

To a mixture of crude 26-6 (120 mg) in a co-solvent THF (2 mL), MeOH (2 mL) and H₂O (2 mL) was added NaOH (100 mg) and the mixture was stirred at room temperature for 2 hrs. The resulting mixture was acidified with HCl (2 N) to pH 3, and extracted with ethyl acetate (2×10 mL). The combined organic layers were washed with water, brine, dried over Na₂SO₄ and concentrated in vacuo to afford crude product, which was purified by preparative HPLC (preparative HPLC on a GILSON 281 instrument fitted with a YMC-pack ODS-AQ C18 (150×30 mm×5 um) using water and acetonitrile as the eluents. Mobile phase A: water (containing 0.1% TFA, v/v), mobile phase B: acetonitrile. Gradient: 40-70% B, 0-10 min; 100% B, 10.5-12.5 min; 5% B, 13-15 min) to give compound 26-7. MS (ESI) m/e (M+H⁺): 405.2. ¹H-NMR (400 MHz, Methanol-d4) δ: 8.10 (s, 1H), 7.80 (t, 1H, J=8.8 Hz), 7.40 (dd, 1H, J=8.4, 4.0 Hz), 7.20 (t, 1H, J=8.0 Hz), 7.10 (d, 2H, J=7.6 Hz), 7.04 (s, 1H), 5.58 (s, 2H), 3.35 (d, 1H, J=6.4 Hz), 3.13 (d, 1H, J=19.2 Hz), 2.98 (m, 1H), 2.47-2.51 (m, 1H), 1.94 (s, 6H), 1.20 (t, 1H, J=2.8 Hz)

The following Examples 76-78 (Compounds 26-8 to 26-10) were prepared in a similar manner to Compound 26-7 using the appropriate starting materials.

| Example | Structure | M.W. | Compound Name | LC/MS (ESI) observed [M + 1]+ |
|---------|-----------|------|---------------|-------------------------------|
| 76 | (Compound 26-8) | 404.4 | 3-((2-(2,6-dimethylphenyl)-5-fluoropyridin-4-yl)methoxy)-5,5a,6,6a-tetrahydrocyclopropa[4,5]cyclopenta[1,2-c]pyridine-6-carboxylic acid | 405.2 |

-continued

| Example | Structure | M.W. | Compound Name | LC/MS (ESI) observed [M + 1]+ |
|---|---|---|---|---|
| 77 | (Compound 26-9) | 580.6 | (5aR,6S,6aS)-3-((3-fluoro-6-(4-(3-(methylsulfonyl)-propoxy)-2-(trifluoromethyl)-phenyl)pyridin-2-yl)methoxy)-5,5a,6,6a-tetrahydrocyclo-propa[4,5]cyclopenta[1,2-c]pyridine-6-carboxylic acid | 581.4 |
| 78 | (Compound 26-10) | 553.6 | (5aR,6S,6aS)-3-((5-fluoro-2'-methyl-6'-(4-(methylsulfonyl)-piperazin-1-yl)-[2,3'-bipyridin]-6-yl)methoxy)-5,5a,6,6a-tetrahydrocyclo-propa[4,5]cyclopenta[1,2-c]pyridine-6-carboxylic acid | 554.2 |

Example 79

Compound 27-7

4-(2,2',6'-Trimethyl-biphenyl-3-ylmethoxy)-1,1a,6,6a-tetrahydro-3-aza-cyclopropa[a]indene-1-carboxylic acid (27-5)

27-5

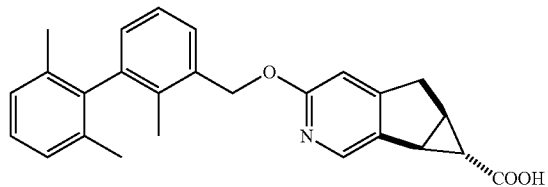

Step A: (2,2',6'-Trimethyl-biphenyl-3-yl)-methanol (27-2)

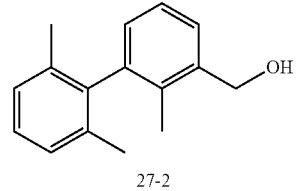

27-2

A mixture of 2-bromo-1,3-dimethyl-benzene (700 mg, 3.7 mmol), compound 27-1 (938 mg, 3.7 mmol), Na$_2$CO$_3$ (1.12 g, 11.1 mmol), Pd$_2$(dba)$_3$ (346 mg, 0.37 mmol), P(Cy)$_3$ (207 mg, 0.74 mmol) in a co-solvent of dioxane (12 mL)/H$_2$O (3 mL) was radiated by microwave to 100° C. for 30 min under a nitrogen atmosphere. The mixture was cooled to room temperature, filtered, and the filtrate was extracted with EA. The ethyl acetate layer was washed with water, dried and concentrated in vacuo to give crude compound 27-2. MS (ESI) m/e (M+H$^+$): 226.3/227.1.

Step B: 3-Bromomethyl-2,2',6'-trimethyl-biphenyl (27-3)

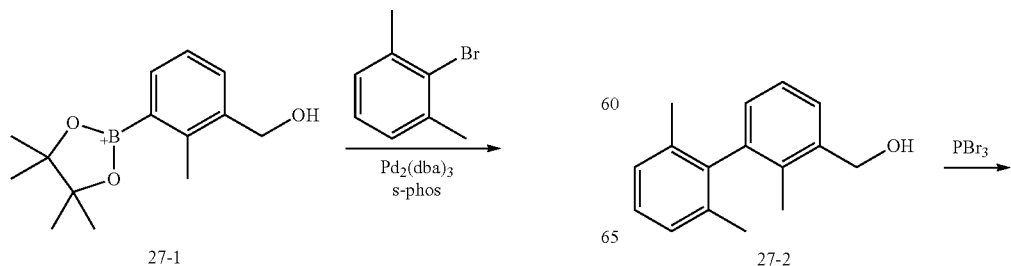

-continued

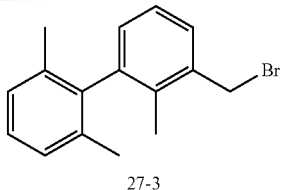

27-3

To a solution of crude compound 27-2 (200 mg, 0.88 mmol) in dry THF (5 mL), cooled in an ice bath, was added dropwise $PBr_3$ (191 mg, 0.70 mmol). The reaction solution was stirred 0° C. for 1 h and then warmed to 20° C. and stirred for 16 hrs. The mixture was then quenched with water, and $NaHCO_3$ (aq) was added to neutralize the mixture to pH 7. Then the mixture was concentrated to afford a residue, which was purified by flash column chromatography on silica gel eluted with petroleum ether:ethyl acetate (94:6) to give compound 27-3. MS (ESI) m/e (M+H$^+$): 289.2/289.1.

Step C: (2,2',6'-Trimethyl-biphenyl-3methoxy)-1,1a, 6,6a-tetrahydro-3-aza-cyclopropa[a]indene-1-carboxylic acid, ethyl ester (27-4)

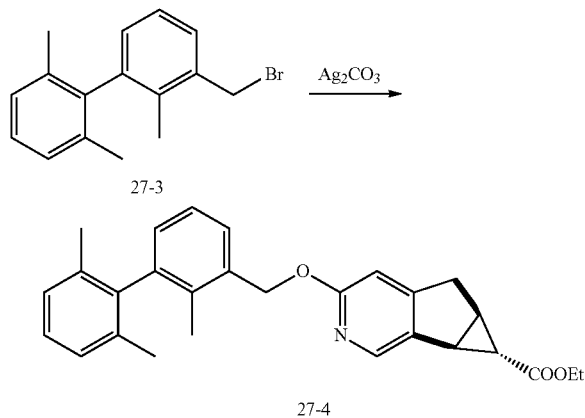

A mixture of compound 27-3 (50 mg, 0.18 mmol) and 1-9 (40 mg, 0.18 mmol) and $Ag_2CO_3$ (148 mg, 0.54 mmol) in toluene (5 mL) was heated to 100° C. for 12 hrs. The mixture was filtered and the filtrate was concentrated to give a residue, which was purified by flash column chromatography on silica gel eluted with petroleum ether:ethyl acetate (92:8) to give compound 27-4. MS (ESI) m/e (M+H$^+$): 427.5/428.2.

Step D: 4-(2,2',6'-Trimethyl-biphenyl-3-ylmethoxy)-1,1a,6,6a-tetrahydro-3-aza-cyclopropa[a]indene-1-carboxylic acid (27-5)

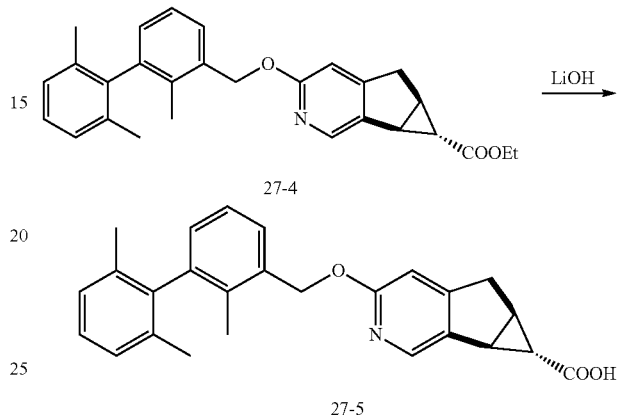

The mixture of compound 27-4 (50 mg, 0.11 mmol) and LiOH (40 mg, 1 mmol) in THF/$H_2O$/MeOH (3:3:3 mL) was stirred at r.t for 2 hours; then the mixture was acidified to pH 5-6, and extracted with EA. The ethyl acetate layer was washed with brine, dried over anhydrous $Na_2SO_4$ and concentrated. The resulting residue was purified by preparative HPLC (preparative HPLC on a GILSON281 instrument fitted with a Waters XSELECT C18 (150×30 mm×5 um) using water and acetonitrile as the eluents. Mobile phase A: water (containing 0.1% TFA, v/v), mobile phase B: acetonitrile. Gradient: 6-79% B, 0-10 min; 100% B, 10.5-12.5 min; 5% B, 13-15 min) to give 27-5. MS (ESI) m/e (M+H$^+$): 399.5/400.2. $^1$HNMR (400 MHz, Methanol-d4) δ: 8.19 (s, 1H), 7.44 (d, 1H, J=7.2 Hz), 7.30 (t, 1H, J=7.6 Hz), 7.19 (br.s, 1H), 7.08-7.16 (m, 3H), 7.02 (d, 1H, J=7.6 Hz), 5.45 (s, 2H), 3.39-3.46 (m, 1H), 3.22 (d, 1H, J=19.2 Hz), 3.03 (d, 1H, J=6.4 Hz), 2.53 (m, 1H), 1.99 (s, 3H), 1.90 (s, 6H), 1.29 (m, 1H).

The following Example 80 (Compound 27-6) was prepared in a similar manner to Compound 27-5 using the appropriate starting materials.

| Example | Structure | M.W. | Compound Name | LC/MS (ESI) observed [M + 1]+ |
|---|---|---|---|---|
| 80 | ![structure] (Compound 27-6) | 439.4 | 3-((2-methyl-2'-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 440.2 |

Example 81

Compound 28-6

(5aR,6S,6aR)-3-((4'-((4-cyano-4-methylpentyl)oxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

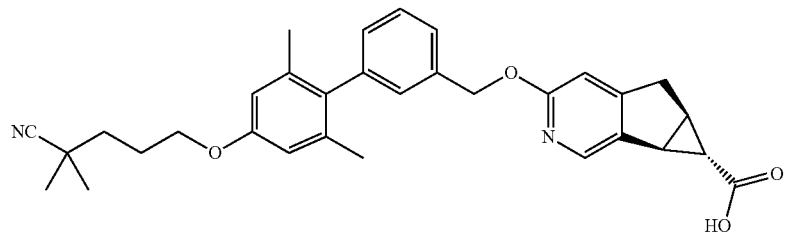

Step A: 1-(3-bromopropoxy)-3,5-dimethylbenzene (28-2)

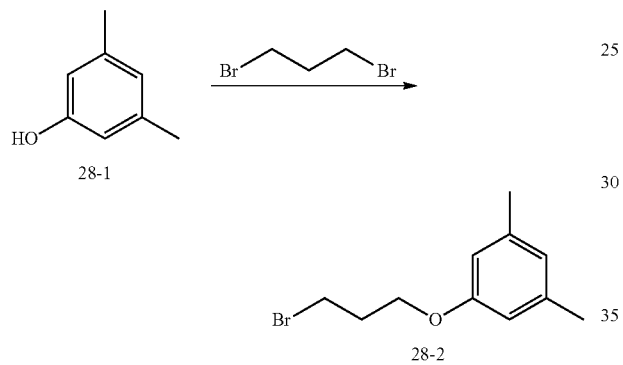

A mixture of compound 28-1 (3.6 g, 30 mmol), 1,3-dibromopropane (12 g, 60 mmol) and K$_2$CO$_3$ (8.4 g, 60 mmol) in 80 mL of acetone was refluxed for 18 h. Then the mixture was cooled to room temperature, filtered and purified by flash column chromatography on silica gel eluted with petroleum ether:ethyl acetate (15:1). MS (ESI) m/e (M+H$^+$): 243.0.

Step B: 5-(3,5-dimethylphenoxy)-2,2-dimethylpentanenitrile (28-3)

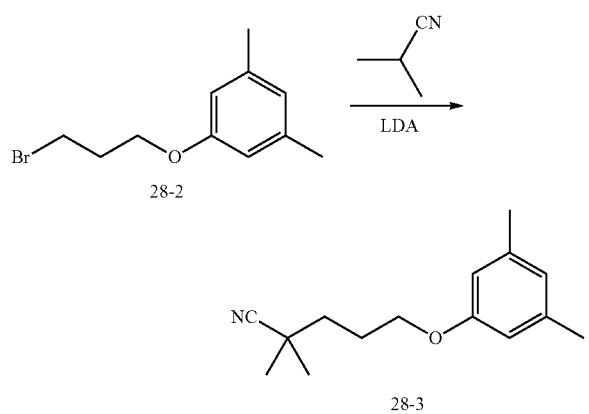

To a solution of compound 28-2 (6.55 g, 95 mmol) in dry THF (100 mL) at −78° C., was slowly added LDA (2 M, 10 mL, 70 mmol) under a N$_2$ atmosphere. After stirring for over 30 min, 1-(3-bromopropoxy)-3,5-dimethylbenzene (24 g, 95 mmol) was added dropwise into the reaction solution. The reaction was warmed to room temperature, stirred overnight, and quenched by the addition of 150 mL of NH$_4$Cl (aq). The mixture was extracted with ethyl acetate (3×60 mL), and the combined organic layers were washed with brine (60 mL), dried over Na$_2$SO$_4$, and concentrated. The resulting crude product was purified by flash column chromatography on silica gel eluted with petroleum ether:ethyl acetate (10:1) to afford 28-3. MS (ESI) m/e (M+H$^+$): 232.1

Step C: 5-(4-bromo-3,5-dimethylphenoxy)-2,2-dimethylpentanenitrile (28-4)

A mixture of compound 28-3 (690 mg, 3 mmol) and NBS (564 mg, 3.15 mmol) in 8 mL of DCM was stirred at 15° C. for 18 h. Then the mixture was concentrated directly to give crude product, which was purified by flash column chromatography on silica gel eluted with petroleum ether:ethyl acetate (10:1) to give compound 28-4. MS (ESI) m/e (M+H$^+$): 310.1.

Step D: Ethyl (5aR,6S,6aR)-ethyl 3-((4'-((4-cyano-4-methylpentyl)oxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (28-5)

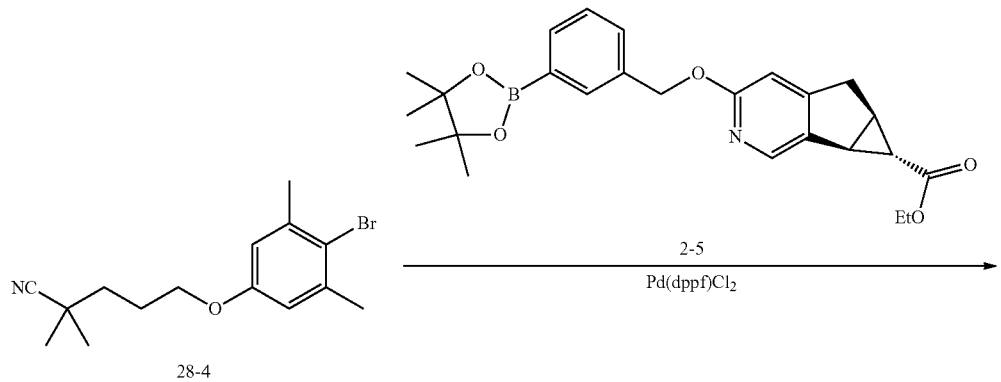

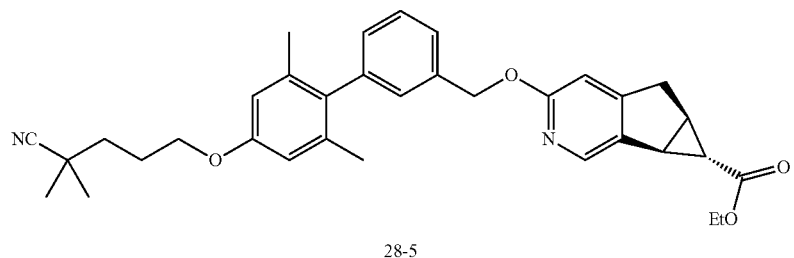

A mixture of compound 28-4 (30 mg, 0.1 mmol), Reference Example 2-5 (43 mg, 0.1 mmol), Na$_2$CO$_3$ (32 mg, 0.3 mmol), Pd(dppf)Cl$_2$ (7 mg, 0.01 mmol), THF (2 mL) and water (0.5 mL) was heated under N$_2$ atmosphere at 100° C. for 18 h. Then water (20 mL) was added, and the mixture was extracted with ethyl acetate (3×20 mL). The combined organic layers were washed with brine (20 mL), dried over anhydrous Na$_2$SO$_4$, concentrated to give compound 28-5, which was used in the next step without further purification. MS (ESI) m/e (M+H$^+$): 539.3.

Step E: (5aR,6S,6aR)-3-((4'-((4-cyano-4-methylpentyl)oxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (28-6)

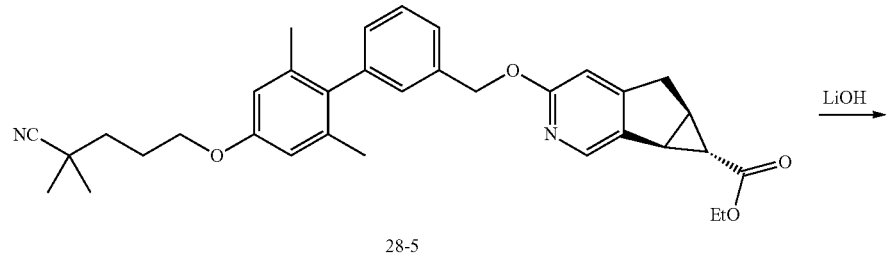

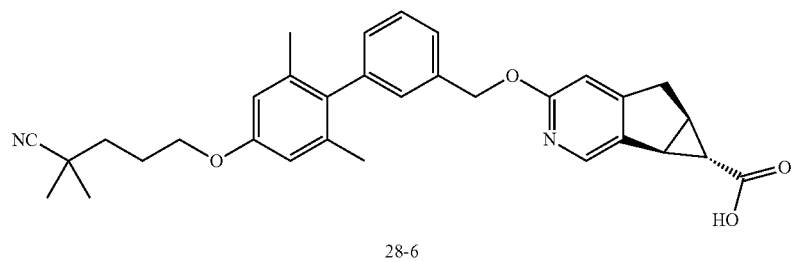

The mixture of compound 28-5 (27 mg, 0.05 mmol) and LiOH (12 mg, 0.5 mmol) in THF/MeOH/H₂O (3/0.5/0.5 mL) was stirred at room temperature for 1 h, then NH₄Cl (aq) was added to adjust the pH to pH 5. The mixture was extracted with DCM (3×10 mL), and the combined organic layers were washed with brine (10 mL), dried over Na₂SO₄, and concentrated. The resulting crude compound was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 50-70% B, 0-10 min; 100% B, 10.5-12.5 min; 5% B, 13-15 min) to give compound 28-6. MS (ESI) m/e (M+H⁺): 511.2. ¹HNMR (400 MHz, Methanol-d4) δ: 8.15 (s, 1H), 7.42-7.44 (m, 2H), 7.19 (s, 1H), 7.07-7.10 (m, 2H), 6.65 (s, 2H), 5.40 (s, 2H), 4.01 (t, 2H, J=6.0 Hz), 3.34-3.40 (m, 1H), 3.20 (d, 1H, J=19.2 Hz), 3.00 (d, 1H, J=4.4 Hz), 2.48-2.52 (m, 1H), 1.93 (m, 8H), 1.72-1.76 (m, 2H), 1.38 (s, 6H), 1.20 (s, 1H).

The following Example 82 (Compound 28-7) was prepared in a similar manner to Compound 28-6 using the appropriate starting materials.

Step A: 3-cyanocyclobutyl methanesulfonate (29-2)

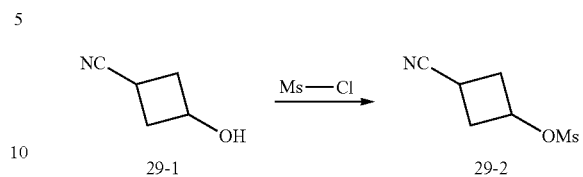

To a solution of compound 29-1 (200 mg, 2 mmol) in DCM (4 mL), was added TEA (606 mg, 6 mmol) in one portion at 0° C. Then MsCl (273 mg, 2.4 mmol) was added. The mixture was stirred at this temperature for 2 h, and then quenched by the addition of 10 mL of H₂O and extracted with ethyl acetate (3×10 mL). The combined organic layers were washed with brine (30 mL), dried over Na₂SO₄, then concentrated to give crude product 29-2, which was used directly in the next step.

| Example | Structure | M.W. | Compound Name | LC/MS (ESI) observed [M + 1]+ |
|---|---|---|---|---|
| 82 | (Compound 28-7) | 508.6 | (5aR,6S,6aR)-3-((4'-(3-(1-cyanocyclopropyl)propoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 509.2 |

Example 83

Compound 29-7

(5aR,6S,6aR)-3-((4'-((1s,3s)-3-cyano-3-methylcyclobutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid (29-7)

29-7

Step B: 3-(3,5-dimethylphenoxy)cyclobutanecarbonitrile (29-3)

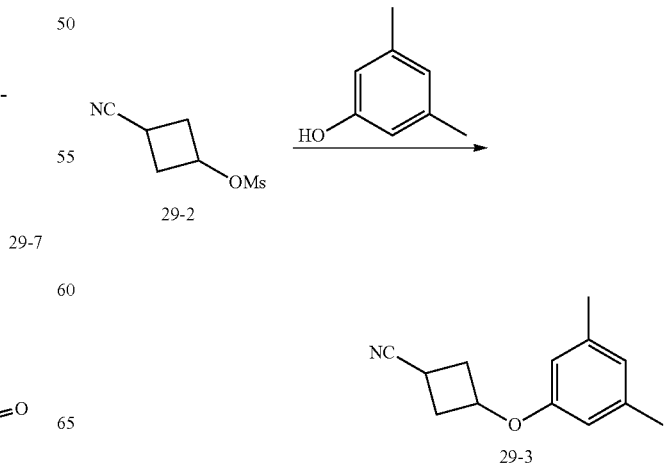

A mixture of compound 29-2 (350 mg, 2 mmol), 3,5-dimethylphenol (244 mg, 2 mmol) and $K_2CO_3$ (834 mg, 6 mmol) in 5 mL of DMSO was stirred at 120° C. for 18 h. The mixture was cooled to room temperature, then 10 mL of $H_2O$ was added and the mixture was extracted with ethyl acetate (3×10 mL). The combined organic layers were washed with brine (30 mL), dried over $Na_2SO_4$, and concentrated to give crude product. The crude product was purified by flash column chromatography on silica gel eluted with petroleum ether:ethyl acetate (10:1) to give 29-3. MS (ESI) m/e (M+H$^+$): 202.1.

Step C: (1s,3s)-3-(3,5-dimethylphenoxy)-1-methyl-cyclobutanecarbonitrile (29-4)

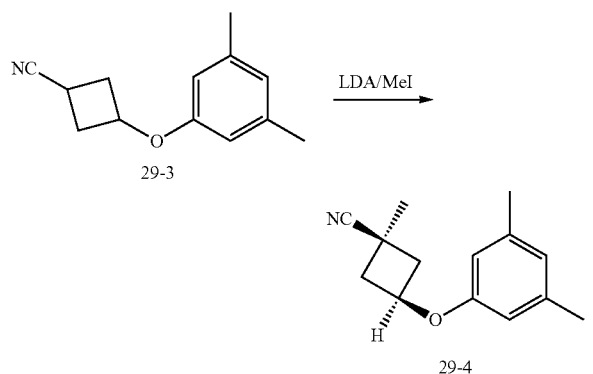

To a solution of compound 29-3 (200 mg, 1 mmol) in dried THF (5 mL) at −78° C., was slowly added LDA (2 M, 1 mL, 2 mmol) under a $N_2$ atmosphere. After stirring for 30 min, iodomethane (284 mg, 2 mmol) was added dropwise, then the reaction was warmed to room temperature, and stirred overnight. Then the reaction was quenched by the addition of 10 mL of $NH_4Cl$ (aq) and extracted with ethyl acetate (3×10 mL). The combined organic layers were washed with brine (10 mL), dried over $Na_2SO_4$, concentrated and purified by flash column chromatography on silica gel eluted with petroleum ether:ethyl acetate (10:1) to give 29-4. MS (ESI) m/e (M+H$^+$): 216.0.

Step D: ((1s,3s)-3-(4-bromo-3,5-dimethylphenoxy)-1-methylcyclobutanecarbonitrile (29-5)

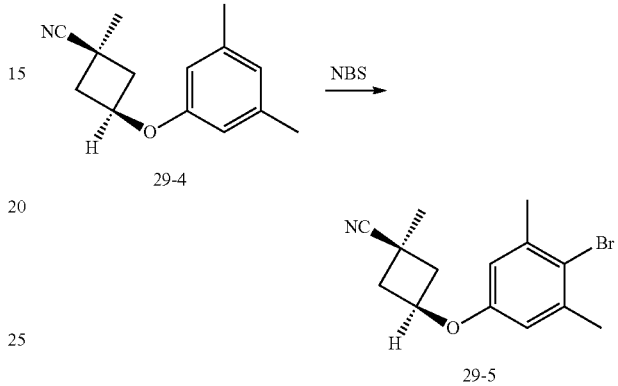

A mixture of compound 29-4 (60 mg, 0.3 mmol) and NBS (54 mg, 0.3 mmol) in 3 mL of DCM was stirred at 15° C. for 18 h, then the mixture was concentrated directly and the crude product was purified by flash column chromatography on silica gel eluted with petroleum ether:ethyl acetate (8:1) MS (ESI) m/e (M+H$^+$): 294.1.

Step E: (5aR,6S,6aR)-ethyl 3-((4'-((1s,3s)-3-cyano-3-methylcyclobutoxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylate (29-6)

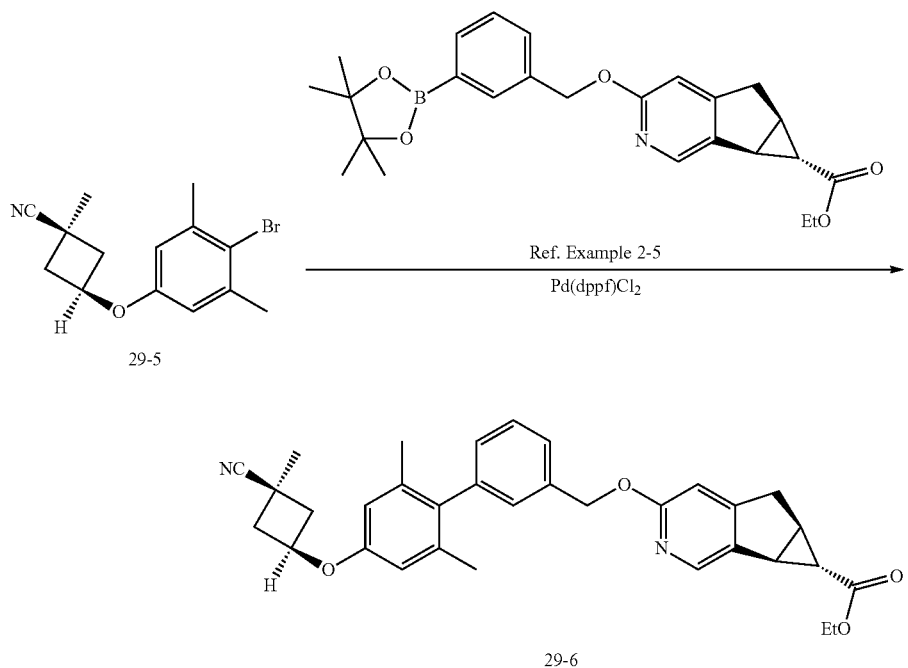 [SMILES: Cc1cc(O[C@H]2C[C@@](C)(C#N)C2)cc(C)c1Br ; CCOC(=O)[C@H]1[C@@H]2Cc3cc(OCc4cccc(B5OC(C)(C)C(C)(C)O5)c4)ncc3[C@@H]21 ; CCOC(=O)[C@H]1[C@@H]2Cc3cc(OCc4cccc(-c5c(C)cc(O[C@H]6C[C@@](C)(C#N)C6)cc5C)c4)ncc3[C@@H]21]

A mixture of compound 29-5 (29 mg, 0.1 mmol), Reference Example 2-5 (43 mg, 0.1 mmol), Na₂CO₃ (32 mg, 0.3 mmol), Pd(dppf)Cl₂ (7 mg, 0.01 mmol), THF (2 mL) and water (0.5 mL) was heated under a N₂ atmosphere at 100° C. for 18 h. Then water (20 mL) was added, and the mixture was extracted with ethyl acetate (3×20 mL). The combined organic layers were washed with brine (20 mL), dried over anhydrous Na₂SO₄, concentrated to give the crude product, which was used in the next step without further treatment. MS (ESI) m/e (M+H⁺): 523.0.

Step F: (5aR,6S,6aR)-3-((4'-((1s,3s)-3-cyano-3-methylcyclobutoxy)-2',6'-dimethyl-[1,1'-biphenyl]-3-yl) methoxy)-5,5a,6,6a-tetrahydrocyclopropa[4,5]cyclopenta[1,2-c]pyridine-6-carboxylic acid (29-7)

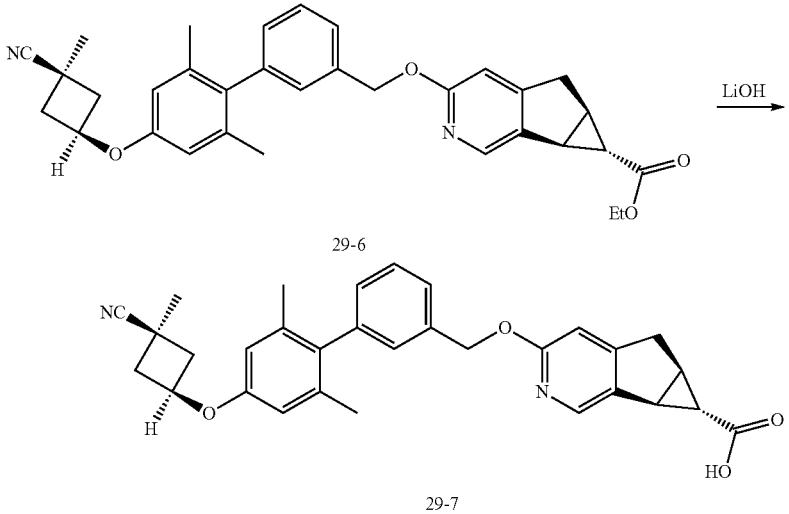

The mixture of compound 29-6 (26 mg, 0.05 mmol) and LiOH (12 mg, 0.5 mmol) in THF/MeOH/H₂O (3/0.5/0.5 mL) was stirred at room temperature for 1 h, then NH₄Cl (aq) was added to reach pH 5. The resulting mixture was extracted with DCM (3×10 mL). The combined organic layers were washed with brine (10 mL), dried over Na₂SO₄, and concentrated. The resulting crude product was purified by preparative HPLC (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 47-67% B, 0-10 min; 100% B, 10.5-12.5 min; 5% B, 13-15 min) to give compound 29-7. MS (ESI) m/e (M+H⁺): 495.0. ¹H-NMR (400 MHz, Methanol-d4) δ: 8.16 (s, 1H), 7.43-7.46 (m, 2H), 7.19 (s, 1H), 7.15 (s, 1H), 7.08 (d, 1H, J=6.8 Hz), 6.56 (s, 2H), 5.41 (s, 2H), 4.83-4.86 (m, 1H), 3.35-3.42 (m, 1H), 3.19 (d, 1H, J=19.6 Hz), 3.01 (d, 1H, J=4.8 Hz), 2.66-2.71 (m, 2H), 2.57-2.64 (m, 2H), 2.49-2.53 (m, 1H), 1.92 (s, 6H), 1.58 (s, 3H), 1.26 (m, 1H).

Example 84

Compound 30-5

(5aR,6S,6aS)-3-(1-(4-fluoro-2',6'-dimethyl-4'-(3-(methylsulfonyl)propoxy)-[1,1'-biphenyl]-3-yl) ethoxy)-5,5a,6,6a-tetrahydrocyclopropa[4,5]cyclopenta[1,2-c]pyridine-6-carboxylic acid (30-5)

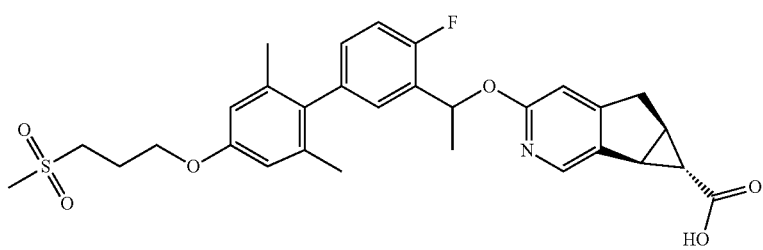

30-5

Step A: 4-bromo-2-(1-bromo ethyl)-1-fluorobenzene (30-2)

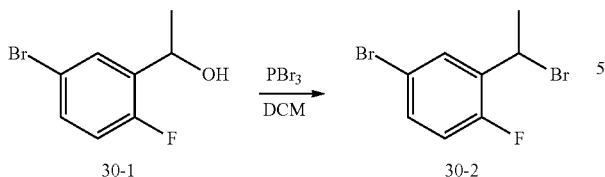

To a stirred solution of 1-(5-bromo-2-fluorophenyl)ethanol 30-1 (1.2 g, 5.48 mmol) in DCM (15 ml) was added tribromophosphine (0.26 mL, 2.74 mmol). The reaction mixture was stirred at 0° C. for 1 h, and then diluted with DCM (50 mL). Then saturated NaHCO₃ solution was added dropwise to the mixture, and the layers were separated. The organic layer was washed with saturated NaHCO₃ solution (30 mL), brine (30 mL), and then dried over Na₂SO₄, and concentrated to give the crude product 30-2, which was used in the next step without purification.

Step B: (5aR,6S,6aS)-ethyl 3-(1-(5-bromo-2-fluorophenyl)ethoxy)-5,5a,6,6a-tetrahydrocyclopropa[4,5]cyclopenta[1,2-c]pyridine-6-carboxylate (30-3)

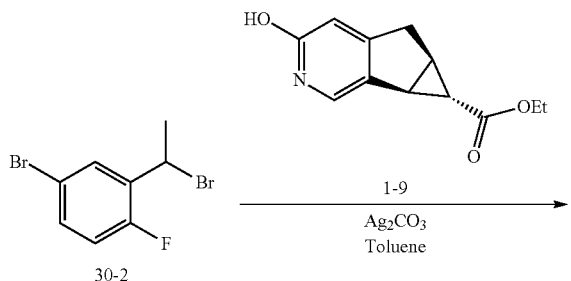

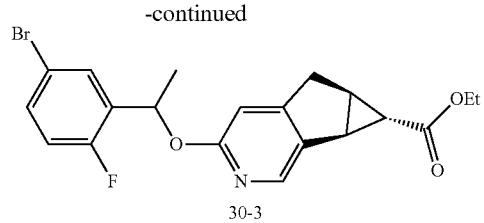

To a solution of compound 30-2 (150 mg, 533 μmol) in toluene (3 ml) was added compound 1-9 (209 mg, 2.98 mmol) and Ag₂CO₃ (294 mg, 1.07 mmol). The reaction mixture was stirred at 110° C. for 16 h, then diluted with DCM (30 mL), and filtered. The filtrate was concentrated, and the resulting residue was purified by preparative TLC on silica gel eluted with petroleum ether:ethyl acetate (2:1) to give pure product 30-3. MS (ESI) m/e (M+H⁺) 421.

Step C: (5aR,6S,6aS)-3-(1-(4-fluoro-2',6'-dimethyl-4'-(3-(methylsulfonyl)propoxy)-[1,1'-biphenyl]-3-yl)ethoxy)-5,5a,6,6a-tetrahydrocyclopropa[4,5]cyclopenta[1,2-c]pyridine-6-carboxylic acid (30-4)

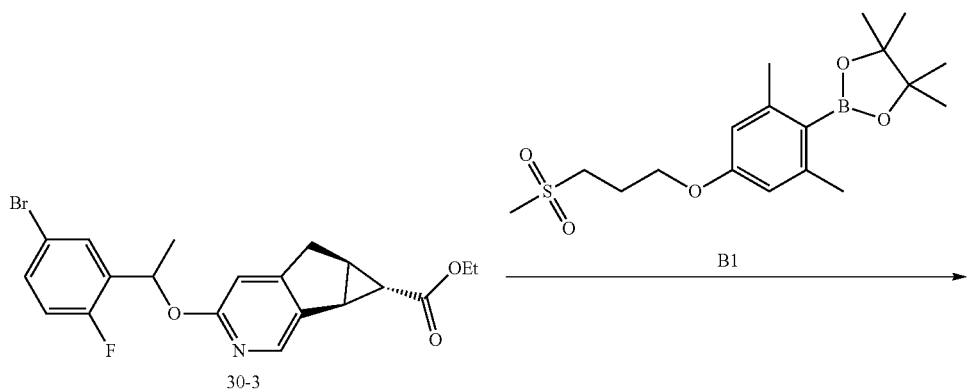

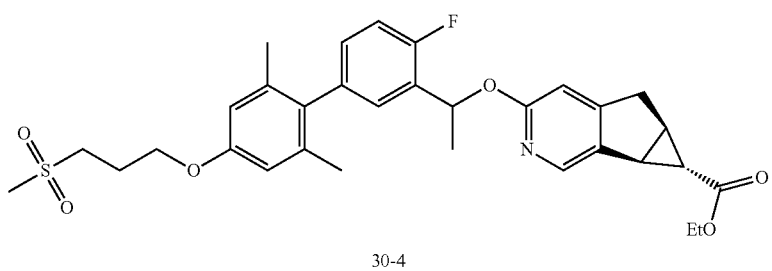

A 40 mL bottle was charged with compound 30-3 (57 mg, 135.7 μmol), the borate B1 (50 mg, 135.7 μmol, was prepared from the bromide using the traditional Miyaura boranation method), Na$_2$CO$_3$ (28 mg, 271.5 dioxane (1.5 mL), H$_2$O (0.5 mL), and PdCl$_2$dppf CH$_2$Cl$_2$ (5 mg).

The bottle was placed on a 100° C. shaker overnight, and then cooled to ambient temperature. The reaction mixture was diluted with ethyl acetate (30 mL), then the organic layer was separated, washed with brine, and concentrated to give crude product 30-4, which was used in the next step without further purification. MS (ESI) m/e (M+H$^+$) 582.

Step D: (5aR,6S,6aS)-3-(1-(4-fluoro-2',6'-dimethyl-4'-(3-(methylsulfonyl)propoxy)-[1,1'-biphenyl]-3-yl)ethoxy)-5,5a,6,6a-tetrahydrocyclopropa[4,5]cyclopenta[1,2-c]pyridine-6-carboxylic acid (30-5)

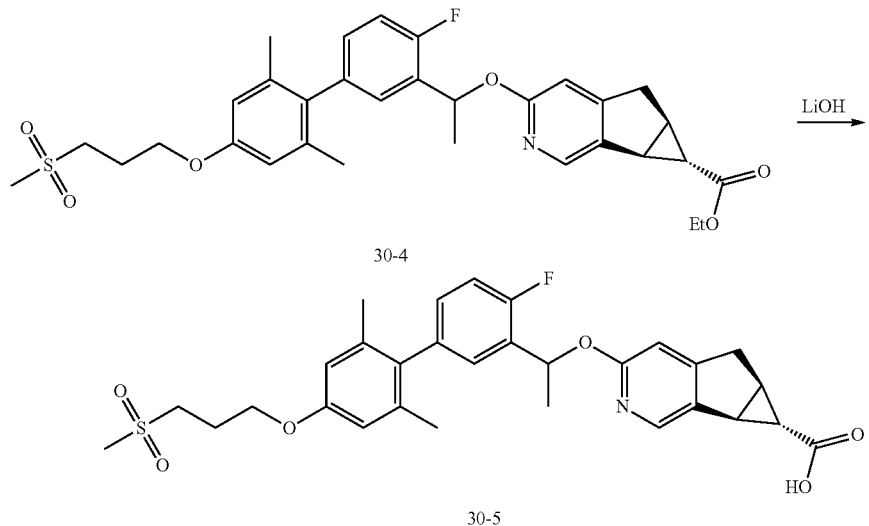

To a mixture of compound 30-4 (50 mg, 86 μmol) in THF (1 mL) and EtOH (0.5 mL), was added H$_2$O (0.5 mL) and LiOH (10 mg, 429 μmol). The reaction mixture was stirred at ambient temperature overnight, then the pH was adjusted to pH 4 with HCl (1N). The reaction mixture was washed with brine (30 mL) and 50 mL of EA, and the organic layer was separated, dried over Na$_2$SO$_4$, and concentrated. The resulting residue was purified by preparative HPLC (preparative HPLC on a GILSON 281 instrument fitted with a YMC-pack ODS-AQ (150×30 min×5 um) using water and acetonitrile as the eluents. Mobile phase A: water (containing 0.1% TFA, v/v), mobile phase B: acetonitrile. Gradient: 41-61% B, 0-10 min; 100% B, 10.5-12.5 min; 5% B, 13-15 min) to give the pure product 30-5. MS (ESI) m/e (M+H$^+$) 537. $^1$H-NMR (400 MHz, Methanol-d4) δ: 8.07-8.11 (m, 1H), 7.11-7.18 (m, 2H), 6.90-7.04 (m, 2H), 6.44 (d, 2H, J=17.6 Hz), 6.22 (m, 1H), 4.12 (m, 2H), 3.33-3.38 (m, 3H), 3.10 (d, 1H, J=19.2 Hz), 2.95-2.99 (m, 4H), 2.46-2.48 (m, 1H), 2.22-2.26 (m, 2H), 1.92-1.95 (m, 3H), 1.60-1.71 (m, 6H), 1.15-1.20 (m, 1H).

Example 85

Compound 31-8

(5aR,6S,6aS)-3-((2-fluoro-5-(2-methyl-6-(3-((methylsulfonyl)methyl)azetidin-1-yl)pyridin-3-yl)benzyl)oxy)-5,5a,6,6a-tetrahydrocyclopropa[4,5]cyclopenta[1,2-c]pyridine-6-carboxylic acid (31-8)

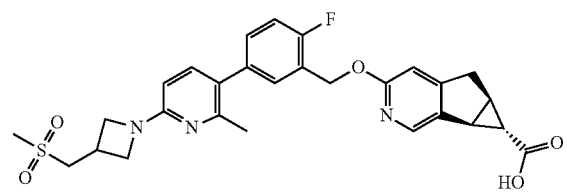

Step A: tert-butyl 3-((methylsulfonyloxy)methyl)azetidine-1-carboxylate (31-2)

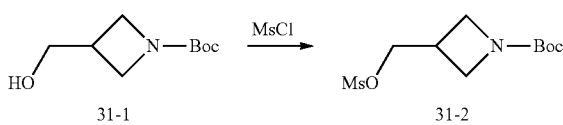 [SMILES: "MsCl" ; CC(C)(C)OC(=O)N1CC(CO)C1 ; CC(C)(C)OC(=O)N1CC(COS(C)(=O)=O)C1]

To a stirred solution of compound 31-1 (1.0 g, 5.34 mmol) in DCM (10 mL) was added triethylamine (810 mg, 8.01 mmol), and then methanesulfonyl chloride (734 mg, 6.41 mmol) was added dropwise. The reaction mixture was stirred at ambient temperature for 1 h and diluted with DCM (50 mL). The mixture was washed with water (20 mL), diluted HCl solution (20 mL×3) and brine, then dried over Na$_2$SO$_4$, and concentrated to give the crude product 31-2, which was used in the next step without purification.

Step B: tert-butyl 3-(methylthiomethyl)azetidine-1-carboxylate (31-3)

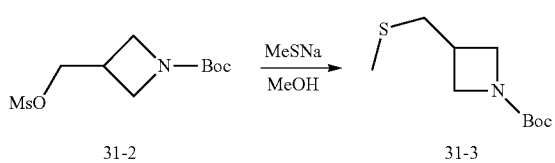 [SMILES: "MeSNa" ; "MeOH" ; CC(C)(C)OC(=O)N1CC(COS(C)(=O)=O)C1 ; CSCC1CN(C(=O)OC(C)(C)C)C1]

To a stirred solution of compound 31-2 (800 mg, 3.02 mmol) in EtOH (10 mL) was added sodium methanethiolate (317 mg, 4.52 mmol). The bottle was place on a 100° C. shaker for 1 h, monitored by TLC (PE/EA=2/1). Then the reaction mixture was cooled to RT, and diluted with ethyl acetate (60 mL). The mixture was washed with water (20 mL×3) and brine (30 mL), dried over Na₂SO₄, and concentrated to give the crude product, which was used in the next step without purification.

Step C: 3-(methylthiomethyl)azetidine (31-4)

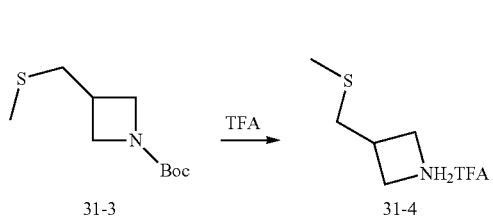

To a solution of compound 31-3 (500 mg, 2.46 mmol) in DCM (2 mL) was added TFA (2 mL). The reaction mixture was stirred at RT for 10 min. and then concentrated to give the crude azetidine 31-4 as a trifluoroacetic acid salt.

Step D: 3-bromo-2-methyl-6-(3-(methylthiomethyl)azetidin-1-yl)pyridine (31-5)

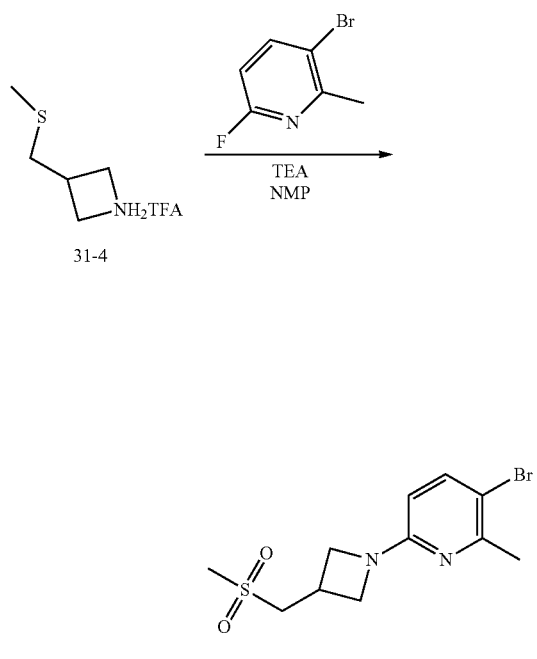

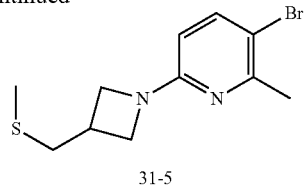

To a solution of compound 31-4 (500 mg, 2.16 mmol) in NMP (5 mL) was added TEA (656 mg, 6.49 mmol), and 3-bromo-6-fluoro-2-methylpyridine (410 mg, 2.16 mmol). The reaction mixture was stirred at 120° C. under a nitrogen atmosphere overnight. The reaction mixture was diluted with ethyl acetate (50 mL), washed with water (10 mL×3) and brine (20 mL), dried over Na₂SO₄, and concentrated to give the crude product 31-5, which was purified by flash column chromatography on silica gel eluted with petroleum ether:ethyl acetate (5:1) to give the pure product. MS (ESI) m/e (M+H+) 288

Step E: 3-Bromo-2-methyl-6-(3-(methylsulfonylmethyl)azetidin-1-yl)pyridine (31-6)

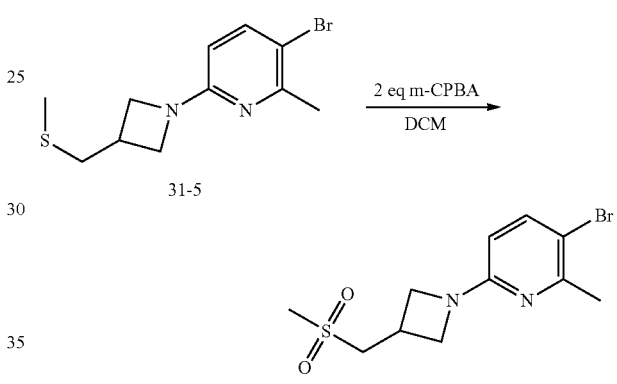

To an ice cooled solution of compound 31-5 (200 mg, 696.3 μmol) in dry DCM (10 mL) was added m-CPBA (85%, 89 mg, 439 μmol) in portions. The reaction mixture was stirred at 0° C. for 1 h, and then diluted with DCM (50 mL). The mixture was washed with saturated Na₂SO₃ solution (20 mL), NaHCO₃ (20 mL) solution, and brine (20 mL), then dried over Na₂SO₄, and concentrated to give the crude product, which was purified by preparative TLC on silica gel eluted with petroleum ether:ethyl acetate (3:1) to give the pure product 31-6. MS (ESI) m/e (M+H+) 522

Step F: (5aR,6 S,6aS)-ethyl 3-((2-fluoro-5-(2-methyl-6-(3-((methylsulfonyl)methyl)azetidin-1-yl)pyridin-3-yl)benzyl)oxy)-5,5a,6,6a-tetrahydrocyclopropa[4,5]cyclopenta[1,2-c]pyridine-6-carboxylate (31-7)

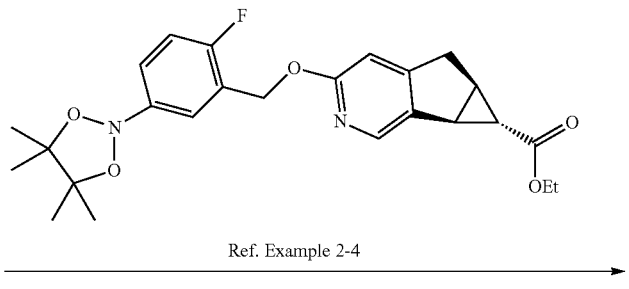

Ref. Example 2-4

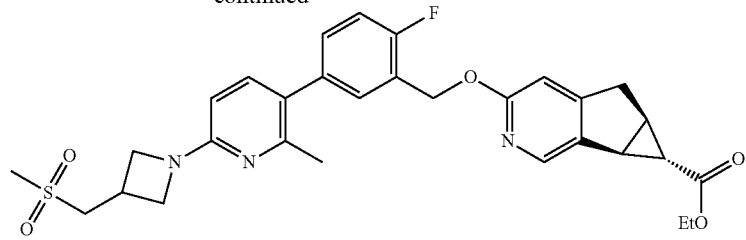

31-7

A 40 mL bottle was charged with compound 31-6 (20 mg, 62 μmol), the boronate from Reference Example 2-4 (28 mg, 62 μmol), Na$_2$CO$_3$ (13 mg, 124 μmol), dioxane (1.5 mL), H$_2$O (0.5 mL), and PdCl$_2$dppfCH$_2$Cl$_2$ (5 mg). The bottle was placed on a 100° C. shaker overnight, cooled to ambient temperature, and diluted with ethyl acetate (30 mL). The mixture was washed with brine, and concentrated to give the crude product, which was used in the next step without further purification. MS (ESI) m/e (M+H$^+$) 566.

Step F: (5aR,6S,6aS)-3-((2-fluoro-5-(2-methyl-6-(3-((methylsulfonyl)methyl)azetidin-1-yl)pyridin-3-yl)benzyl)oxy)-5,5a,6,6a-tetrahydrocyclopropa[4,5]cyclopenta[1,2-c]pyridine-6-carboxylic acid (31-8)

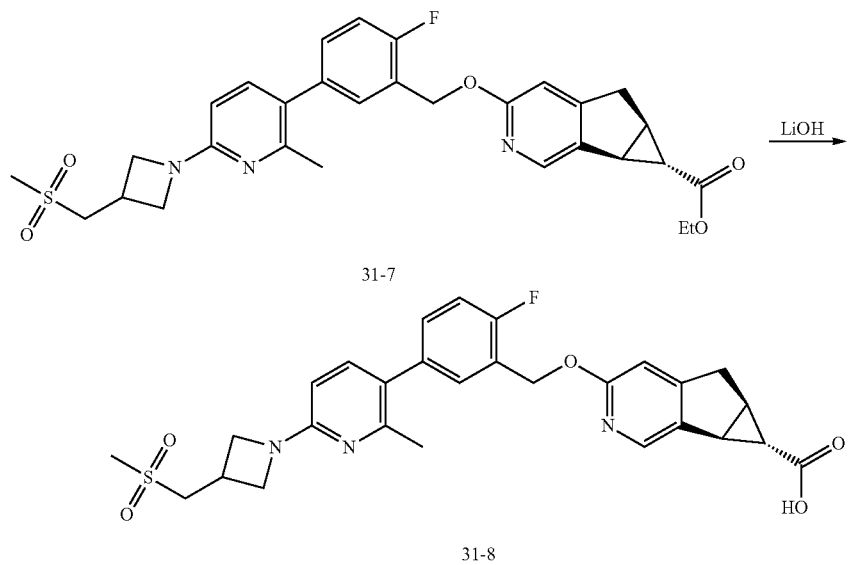

To a mixture of compound 31-7 (35 mg, 62 μmol) in THF (2 mL) and EtOH (1 mL) was added H$_2$O (1 mL) and LiOH (15 mg). The reaction mixture was stirred at ambient temperature overnight, then the pH was adjusted to pH 4 with HCl (1N). The reaction mixture was washed with brine (30 mL) and ethyl acetate (50 mL), and the organic layer was separated, dried over Na$_2$SO$_4$, and concentrated. The resulting residue was purified by preparative HPLC (preparative HPLC on a GILSON 215 instrument fitted with a Diamonsil C18 (150×20 mm×5 um) using water and acetonitrile as the eluents. Mobile phase A: water (containing 0.1% TFA, v/v), mobile phase B: acetonitrile. Gradient: 25-55% B, 0-10 min; 100% B, 10.5-12.5 min; 5% B, 13-15 min) to give the pure product 31-8. MS (ESI) m/e (M+H$^+$) 538. $^1$H-NMR (400 MHz, Methanol-d4) δ: 8.07 (s, 1H), 7.80 (d, 1H, J=9.2 Hz), 7.45-7.47 (m, 1H), 7.31-7.34 (m, 1H), 7.21-7.26 (m, 1H), 6.73 (d, 1H, J=9.2 Hz), 5.41 (m, 2H), 4.54-4.59 (m, 2H), 4.25-4.29 (m, 2H), 3.62 (d, 2H, J=7.6 Hz), 3.48-3.54 (m, 1H), 3.29 (s, 1H), 3.07 (m, 4H), 2.92 (d, 1H, J=4.8 Hz), 2.42-2.45 (m, 1H), 2.381 (s, 3H), 0.96 (m, 1H).

Examples 86-90 (compounds 31-9 to 31-13) were prepared in a similar manner to Compound 31-8 using the appropriate commercially available starting materials.

| Example | Structure | M.W. | Compound Name | LC/MS (ESI) observed [M + 1]+ |
|---|---|---|---|---|
| 86 | (Compound 31-9) | 551.6 | 3-((2-fluoro-5-(2-methyl-6-(3-((methylsulfonyl)methyl)pyrrolidin-1-yl)pyridin-3-yl)benzyl)oxy)-5,5a,6,6a-tetrahydrocyclopropa[4,5]cyclopenta[1,2-c]pyridine-6-carboxylic acid | 552.4 |
| 87 | (Compound 31-10) | 490.5 | 3-((5-(4,6-dimethyl-2-morpholinopyrimidin-5-yl)-2-fluorobenzyl)oxy)-5,5a,6,6a-tetrahydrocyclopropa[4,5]cyclopenta[1,2-c]pyridine-6-carboxylic acid | 491.3 |
| 88 | (Compound 31-11) | 558.7 | 3-((5-(4,6-dimethyl-2-(spiro[indene-1,4'-piperidin]-1'-yl)pyrimidin-5-yl)-2-fluorobenzyl)oxy)-5,5a,6,6a-tetrahydrocyclopropa[4,5]cyclopenta[1,2-c]pyridine-6-carboxylic acid | 559.5 |
| 89 | (Compound 31-12) | 552.6 | 3-((2-fluoro-5-(2-methyl-6-(3-(methylsulfonamido)pyrrolidin-1-yl)pyridin-3-yl)benzyl)oxy)-5,5a,6,6a-tetrahydrocyclopropa[4,5]cyclopenta[1,2-c]pyridine-6-carboxylic acid | 553.4 |

| Example | Structure | M.W. | Compound Name | LC/MS (ESI) observed [M + 1]+ |
|---|---|---|---|---|
| 90 | 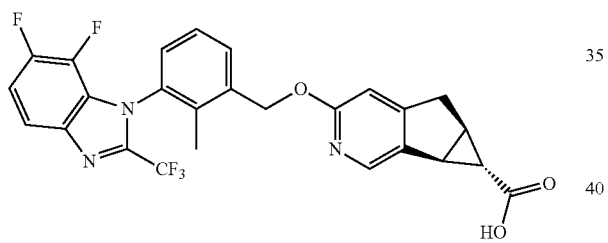<br>(Compound 31-13) | 552.6 | (5aR,6S,6aS)-3-((2-fluoro-5-(2-methyl-6-(4-(methyl-sulfonyl)piperazin-1-yl)pyridin-3-yl)benzyl)oxy)-5,5a,6,6a-tetrahydrocyclo-propa[4,5]cyclopenta[1,2-c]pyridine-6-carboxylic acid | 553.4 |

Example 91

Compound 32-8

((5aR,6S,6aS)-3-((3-(6,7-difluoro-2-(trifluorom-ethyl)-1H-benzo[d]imidazol-1-yl)-2-methylbenzyl)oxy)-5,5a,6,6a-tetrahydrocyclopropa[4,5]cyclopenta[1,2-c]pyridine-6-carboxylic acid (32-8)

32-8

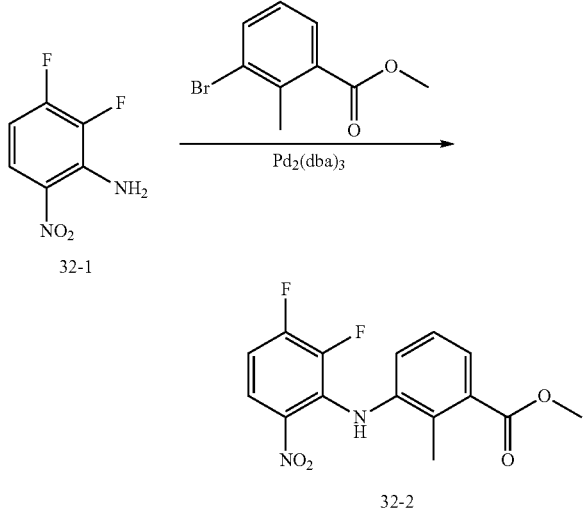

Step A: methyl 3-(2,3-difluoro-6-nitrophe-nylamino)-2-methylbenzoate (32-2)

A mixture of compound 32-1 (7 g, 40 mmol), methyl 3-bromo-2-methylbenzoate (11 g, 48 mmol), $K_3PO_4$ (25 g, 120 mmol), $Pd_2(dba)_3$ (915 mg, 1 mmol), X-phos (952 mg, 2 mmol) in 100 mL of dried toluene was heated under a $N_2$ atmosphere at 100° C. for 18 h. Then water (200 mL) was added, and the mixture was extracted with ethyl acetate (3×100 mL). The combined organic layers were washed with brine (100 mL), dried over anhydrous $Na_2SO_4$ and concentrated to give the crude product. The crude product was purified by flash column chromatography on silica gel eluted with petroleum ether:ethyl acetate (3:1) to give 32-2. MS (ESI) m/e (M+H$^+$): 323.1.

Step B: Methyl 3-(6-amino-2,3-difluorophe-nylamino)-2-methylbenzoate (32-3)

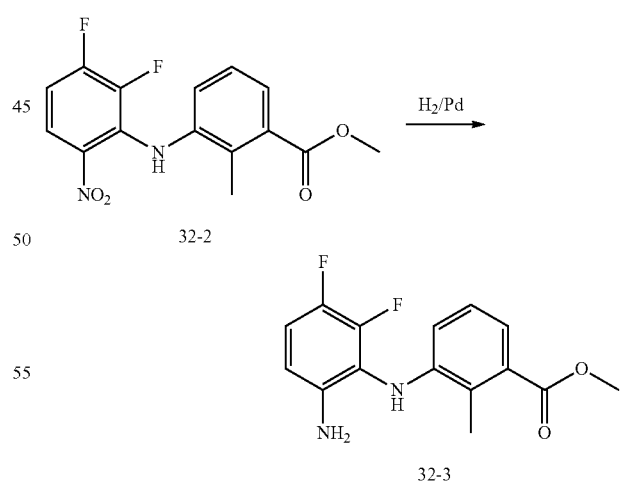

The mixture of compound 32-2 (5 g, 15.5 mmol) in THF/MeOH (20/40 mL) was stirred under a $H_2$ atmosphere (50 psi) at 25° C. Then the mixture was filtered through Celite™, and concentrated. The resulting crude product was used directly in the next step without further purification. MS (ESI) m/e (M+H$^+$): 293.0.

Step C: Methyl 3-(6,7-difluoro-2-(trifluoromethyl)-1H-benzo[d]imidazol-1-yl)-2-methylbenzoate (32-4)

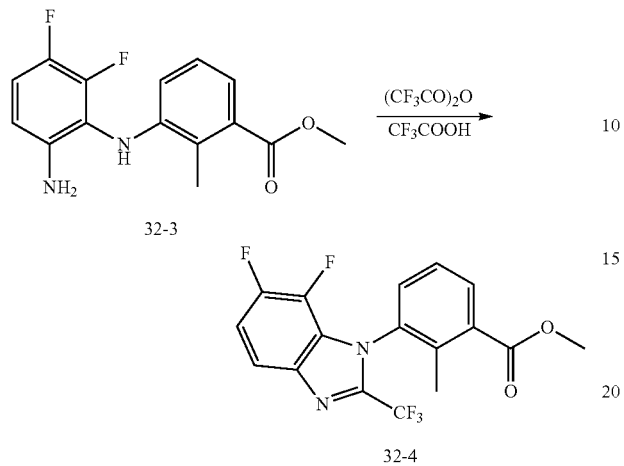

The mixture of compound 32-3 (1.1 g, 3.8 mmol) in (CF$_3$CO)$_2$O/CF$_3$COOH (2/8 mL) was refluxed 18 h, and then concentrated. The resulting residue was re-dissolved in 20 mL of EA, washed with NaHCO$_3$ (aq, 20 mL) and brine (20 mL), then dried over anhydrous Na$_2$SO$_4$ and concentrated to give the crude product. The desired product was purified by flash column chromatography on silica gel eluted with petroleum ether:ethyl acetate (5:1). MS (ESI) m/e (M+H$^+$): 371.2.

Step D: (3-(6,7-difluoro-2-(trifluoromethyl)-1H-benzo[d]imidazol-1-yl)-2-methylphenyl)methanol (32-5)

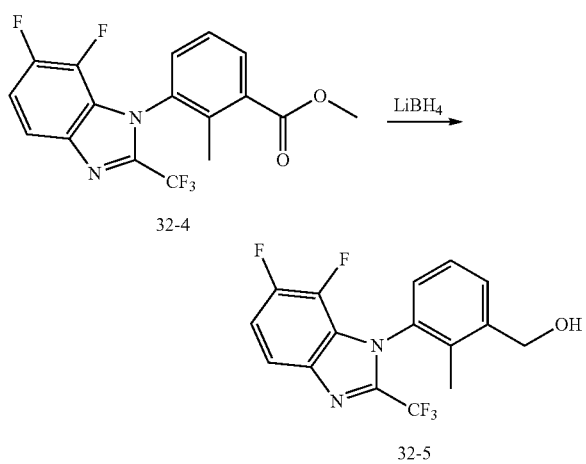

To a solution of compound 32-4 (1.15 g, 3.1 mmol) in dried THF (30 mL) was added slowly LiBH$_4$ (136 mg, 6.2 mmol) at 0° C. After stirring for 3 h at rt, MeOH (10 mL) was added at 0° C., and then the solvent was removed. The crude product was re-dissolved in ethyl acetate (20 mL), washed with water (10 mL) and then brine (10 mL), dried over Na$_2$SO$_4$, and concentrated to afford compound 32-5. MS (ESI) m/e (M+H$^+$): 343.1.

Step E: 1-(3-(bromomethyl)-2-methylphenyl)-6,7-difluoro-2-trifluoromethyl)-1H-benzo[d]imidazole (32-6)

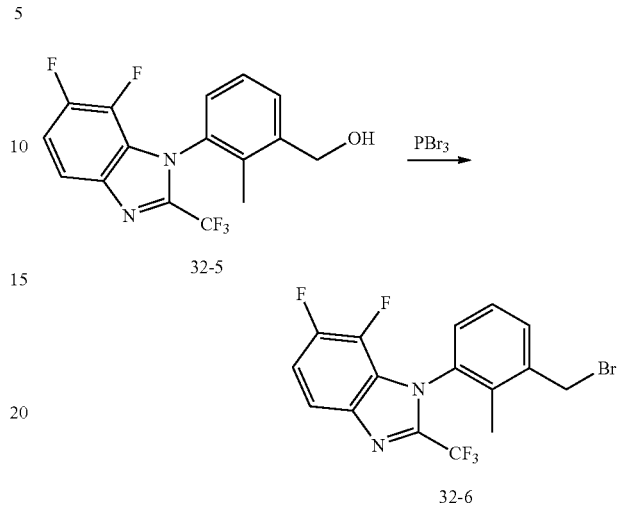

To a solution of compound 32-5 (684 mg, 2 mmol) in dried THF (10 mL) was added tribromophosphine (427 mg, 1.6 mmol). After stirring for 180 min, ethyl acetate (20 mL) was added. The mixture was washed with NaHCO$_3$ (aq, 20 mL) and brine (20 mL), dried over anhydrous Na$_2$SO$_4$ and concentrated to give the crude product. The pure product was purified by flash column chromatography on silica gel eluted with petroleum ether:ethyl acetate (10:1). MS (ESI) m/e (M+H$^+$): 404.8.

Step F: (5aR,6S,6aS)-ethyl 3-((3-(6,7-difluoro-2-(trifluoromethyl)-1H-benzo[d]imidazol-1-yl)-2-methylbenzyl)oxy)-5,5a,6,6a-tetrahydrocyclopropa[4,5]cyclopenta[1,2-c]pyridine-6-carboxylate (2-7)

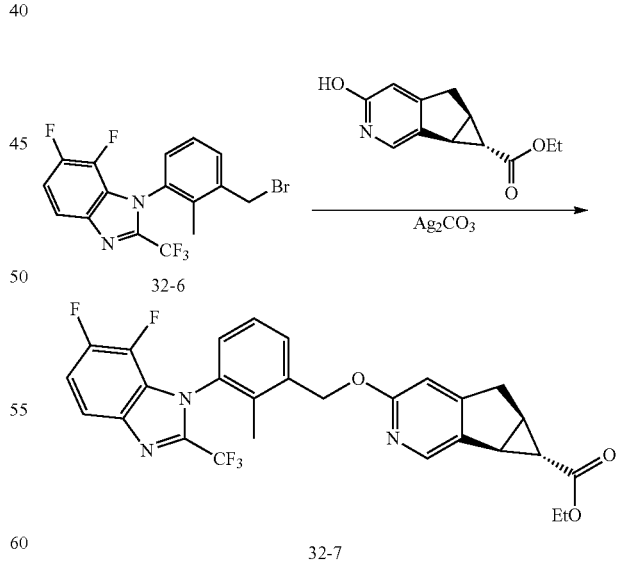

A mixture of compound 32-6 (419 mg, 1.04 mmol), Reference Example 1-9 (227 mg, 1.04 mmol), Ag$_2$CO$_3$ (1.0 g, 3.69 mmol) and toluene (6 mL) was heated under N$_2$ atmosphere at 100° C. for 18 h. Then the mixture was cooled to room temperature and filtered through Celite™ and concentrated to give the crude product. The pure product was afforded by purified by preparative TLC on silica gel eluted with petroleum ether:ethyl acetate (3:1). MS (ESI) m/e (M+H⁺): 544.2.

Step G: ((5aR,6S,6aS)-3-43-(6,7-difluoro-2-(trifluoromethyl)-1H-benzo[d]imidazol-1-yl)-2-methylbenzyl)oxy)-5,5a,6,6a-tetrahydrocyclopropa[4,5]cyclopenta[1,2-c]pyridine-6-carboxylic acid (32-8)

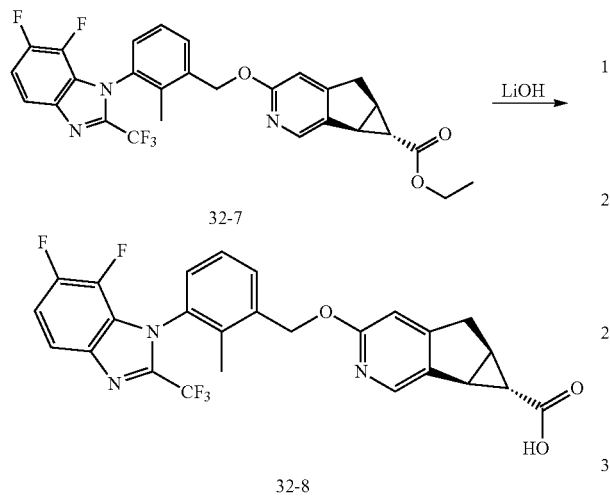

The mixture of compound 32-7 (54 mg, 0.1 mmol) and LiOH (23 mg, 1 mmol) in THF/MeOH/H₂O (3/0.5/0.5 mL) was stirred at room temperature for 1 h, then NH₄Cl (aq) was added to reach pH 5. The mixture was extracted with DCM (3×10 mL). The combined organic layers were washed with brine (10 mL), dried over Na₂SO₄, concentrated to give the crude product. The pure product 32-8 was afforded by preparative HPLC separation (preparative HPLC on a GILSON 281 instrument fitted with a YMC-Actus Triart C18 (150×30 mm×5 um) using water and acetonitrile as the eluents. Mobile phase A: water (containing 0.1% TFA, v/v), mobile phase B: acetonitrile. Gradient: 42-82% B, 0-10 min; 100% B, 10.5-12.5 min; 5% B, 13-15 min) MS (ESI) m/e (M+H⁺): 516.0. ¹H-NMR (400 MHz, Methanol-d4) δ: 8.17 (s, 1H), 7.70-7.56 (m, 1H), 7.67-7.69 (m, 1H), 7.53-7.55 (m, 1H), 7.40-7.46 (m, 1H), 7.33-7.38 (m, 1H), 7.16 (s, 1H), 5.50 (s, 2H), 3.36-3.43 (m, 1H), 3.17-3.22 (m, 1H), 3.01 (d, 1H, J=4.8 Hz), 2.49-2.53 (m, 1H), 2.01 (s, 3H), 1.26 (m, 1H).

The following Example 92 (Compound 32-9) was prepared in a similar manner to Compound 32-8 using the appropriate starting materials.

| Example | Structure | M.W. | Compound Name | LC/MS (ESI) observed [M + 1]+ |
|---|---|---|---|---|
| 92 | (Compound 32-9) | 475.5 | (5aR,6S,6aS)-3-((3-(2-ethyl-6,7-difluoro-1H-benzo[d]imidazol-1-yl)-2-methylbenzyl)oxy)-5,5a,6,6a-tetrahydrocyclopropa[4,5]cyclopenta[1,2-c]pyridine-6-carboxylic acid | 476.3 |

Example 93

Compound 33-5

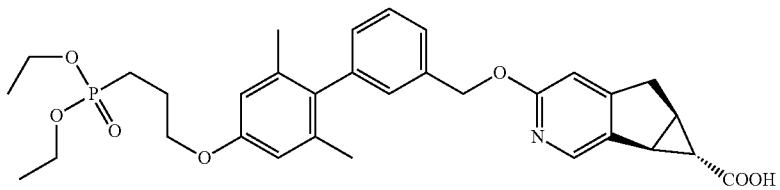

Step A: (3-Bromo-propyl)-phosphonic acid diethyl ester (33-2)

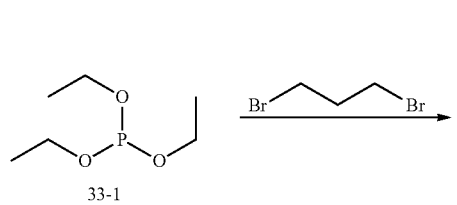

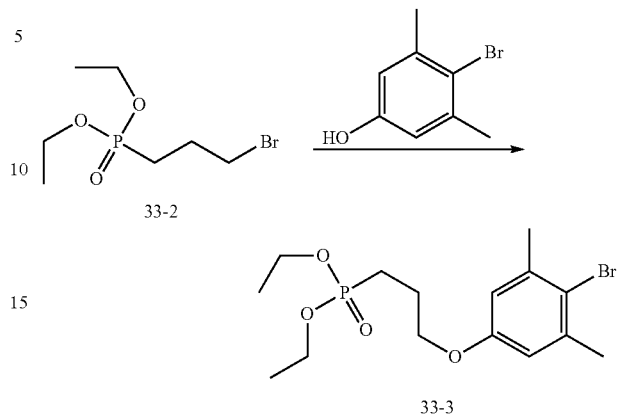

A stirred mixture of compound 33-1 (10 g, 0.06 mol) and 1,3-dibromo-propane (18.2 g, 0.09 mol) was heated at 140° C. overnight. Then the reaction was cooled to R.T. and concentrated in vacuo to give the crude product, which was purified by column chromatography on silica gel (Eluting with PE/EA=50/1) to give compound 33-2. as a colorless oil. (ESI) m/e (M+H⁺): 259.0/261.0.

Step B: [3-(4-Bromo-3,5-dimethyl-phenoxy)-propyl]-phosphonic acid diethyl ester (33-3)

To a solution of 4-Bromo-3,5-dimethyl-phenol (0.3 g, 1.5 mmol) in anhydrous THF (3 mL) was added NaH (60% in oil, 80 mg, 2.0 mmol) at 0° C. and the mixture was stirred at this temperature for 10 min Then a solution of compound 33-2 (520 mg, 2.0 mmol) in THF (0.5 mL) was added dropwise and the resulting mixture was allowed to stir at room temperature for 5 h. The reaction was then quenched with NH₄Cl and extracted with EtOAc three times. The combined organic layers were washed with brine, dried over anhydrous Na₂SO₄ and concentrated. The resulting residue was purified by flash chromatography on silica gel (5% EA in PE) to afford compound 33-3. (ESI) m/e (M+H⁺): 379.1/381.1.

Step C: Compound (33-4)

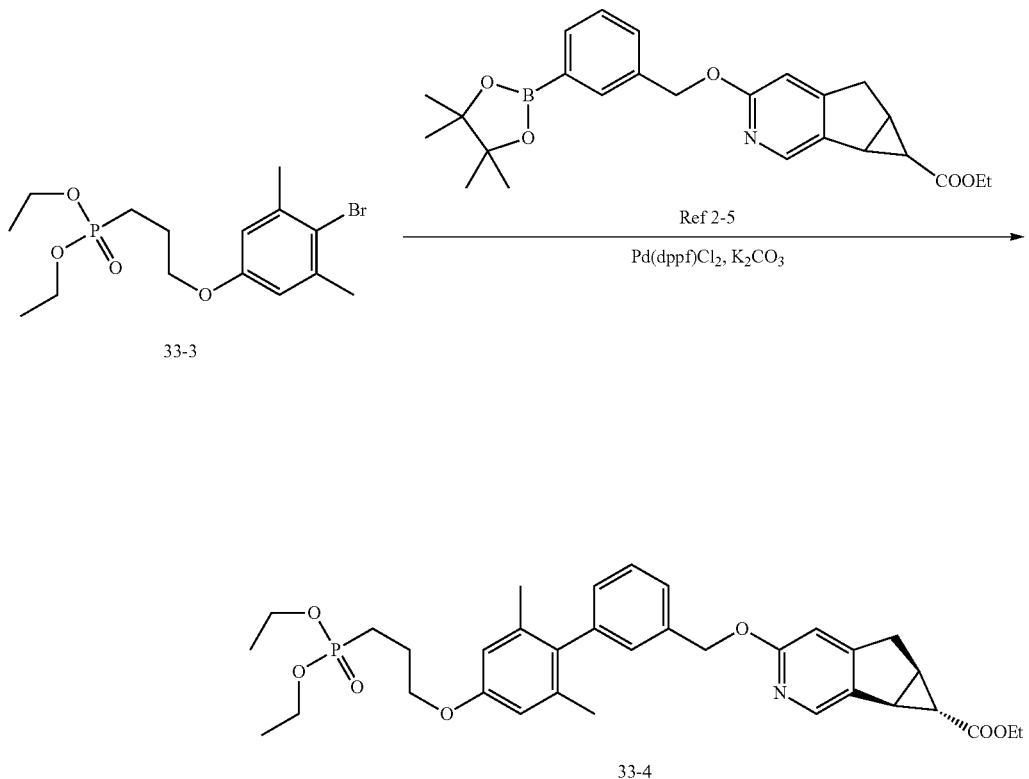

A mixture of compound 33-3 (80 mg, 0.211 mmol), reference compound 2-5 (110 mg, 1.2 eq), Pd(dppf)Cl₂ (15 mg, 0.1 eq) and K₃PO₄ (110 mg, 3 eq) in THF/H₂O (2/0.4 mL) was refluxed at 110° C. under a N₂ atmosphere overnight. Then the mixture was cooled to room temperature and diluted with ethyl acetate (15 mL). The mixture was then washed with water and brine, dried over anhydrous Na₂SO₄, and concentrated to give the crude product, which was purified by preparative. silica TLC (CH₂Cl₂/MeOH=20/1) to give compound 33-4. (ESI) m/e (M+H⁺): 625.1.

Step D: Compound (33-5)

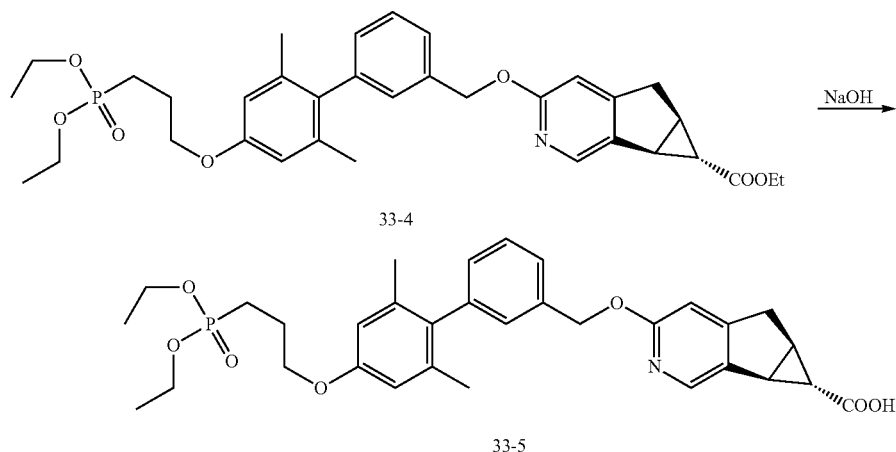

To a mixture of compound 33-4 (50 mg, 0.082 mmol) in a co-solvent THF (1.0 mL), MeOH (1.0 mL) and H₂O (0.5 mL) was added NaOH (17 mg, 0.412 mmol) at room temperature. The reaction was stirred overnight at room temperature. The resulting mixture was acidified with HCl (1 N) to pH=5-6, and extracted with ethyl acetate (10 mL) three times. The combined organic layers were washed with brine, dried over Na₂SO₄ and concentrated in vacuo to give the crude product, which was purified by preparative-HPLC to obtain compound 33-5. (ESI) m/e (M+H+): 597.1.

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µL medium/well. The cells were incubated with 20 µl well of the assay buffer (HBSS, 0.1% BSA, 20 mM HEPES, 2.5 mM probenecid, pH 7.4) containing 8 µM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added. The compounds in Examples 1-93 have EC₅₀ values less than 100 nanomolar (nM) in the FLIPR assay described above and are listed in Table 1.

Inositol Phosphate Turnover (IP1) Assay:

The assay is performed in 96-well format. HEK cells stably expressing human GPR40 are plated to be 60-80% confluent within 72 h. After 72 h, the plates are aspirated and the cells washed with inositol-free DMEM (ICN). The wash media is replaced with 150 µL of 3H-inositol labeling media (inositol-free media containing 0.4% human albumin or 0.4% mouse albumin, 1× pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 µCi/150 µL). Alternatively, the human and mouse albumin can be added after the overnight labeling step before the addition of LiCl.

The assay is typically run the next day after 18 h labeling. On the day of the assay, 5 µL of 300 mM LiCl is added to all wells and incubated at 37 degrees for 20 min. 0.75 µL of 200× compounds are added and incubated with the cells for 60 min at 37 degrees. The media is then aspirated off and the assay terminated with the addition of 60 µL 10 mM formic acid. The cells are lysed for 60 min at room temperature. 15-30 µL of lysate is mixed with 70 µL mg YSi SPA beads (Amersham) in clear bottom Isoplates. The plates are shaken for 2 h at room temperature. Beads are allowed to settle and the plates are counted in the Wallac Microbeta. The compounds in Examples 1-93 have EC₅₀ values less than 3000 nanomolar (nM) in the Inositol Phophate Turnover (IP1) assay described above and are listed in Table 1.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

TABLE 1

$EC_{50}$ values (nM) for Examples in the GPR40 FLIPR and IP1 Assays.

| Compound # | hGPR40 FLIPR $EC_{50}$ (nM) | hGPR40 IP1 $EC_{50}$ (0% serum) (nM) |
|---|---|---|
| 3-4 | 43 | 18 |
| 3-5 | 27 | 9.1 |
| 4-5 | 27 | 8.6 |
| 4-6 | 30 | 12 |
| 5-3 | 22 | 6.1 |
| 5-4 | 21 | 5.6 |
| 5-5 | 15 | 10 |
| 5-6 | 14 | 9.5 |
| 6-4 | 40 | 8.4 |
| 7-4 | 42 | 28 |
| 7-5 | 65 | 21 |
| 7-6 | 15 | 7.5 |
| 7-8 | 35 | 32 |
| 7-7 | 23 | 6.5 |
| 8-5 | 26 | 7.6 |
| 8-6 | 41 | 22 |
| 9-7 | 19 | 9.9 |
| 9-8 | 23 | 14 |
| 10-5 | 18 | 12 |
| 10-6 | 42 | 4.5 |
| 10-7 | 78 | ND |
| 10-8 | 25 | 4.0 |
| 10-9 | 43 | 8.7 |
| 10-10 | 19 | 3.8 |
| 10-11 | 34 | 280 |
| 10-12 | 64 | 14 |
| 14-4 | 32 | 6.2 |
| 11-6 | 13 | 7.5 |
| 12-7 | 17 | 50 |
| 12-8 | 27 | 79 |
| 12-9 | 26 | 3.7 |
| 12-10 | 36 | 19 |
| 13-7 | 78 | 14 |
| 13-8 | 59 | 3.7 |
| 15-6 | 46 | 14 |
| 16-10 | 15 | 57 |
| 16-8 | 20 | 55 |
| 16-9 | 19 | 45 |
| 17-5 | 13 | 98 |
| 17-6 | 13 | 29 |
| 18-4 | 16 | 26 |
| 19-16 | 160 | 7.3 |
| 19-19 | 36 | 5.5 |
| 19-6 | 20 | 4.0 |
| 20-5 | 76 | 15 |
| 20-6 | 19 | 4.9 |
| 20-7 | 23 | 6.7 |
| 20-8 | 99 | 175 |
| 21-7 | 11 | 6.2 |
| 21-8 | 15 | 6.2 |
| 22-2 | 49 | 26 |
| 22-3 | 36 | 35 |
| 22-4 | 54 | 240 |
| 22-5 | 47 | 310 |
| 22-6 | 87 | 100 |

TABLE 1-continued $EC_{50}$ values (nM) for Examples in the GPR40 FLIPR and IP1 Assays.

| Compound # | hGPR40 FLIPR $EC_{50}$ (nM) | hGPR40 IP1 $EC_{50}$ (0% serum) (nM) |
|---|---|---|
| 22-7 | 67 | 400 |
| 22-8 | 48 | 75 |
| 22-9 | 95 | 850 |
| 23-10 | 46 | 15 |
| 23-11 | 50 | 25 |
| 23-12 | 35 | 12 |
| 23-13 | 77 | 110 |
| 23-14 | 18 | 34 |
| 23-15 | 38 | 27 |
| 23-17 | 58 | 82 |
| 23-18 | 10 | 56 |
| 23-6 | 23 | 3.5 |
| 23-8 | 26 | 4.8 |
| 23-9 | 97 | ND |
| 24-4 | 96 | 90 |
| 25-2 | 35 | 56 |
| 25-3 | 34 | 85 |
| 25-4 | 49 | 300 |
| 26-10 | 90 | 300 |
| 26-7 | 42 | 120 |
| 26-8 | 28 | 100 |
| 26-9 | 70 | 53 |
| 27-5 | 8.1 | 6.7 |
| 27-6 | 30 | 85 |
| 28-6 | 24 | 66 |
| 28-7 | 40 | 40 |
| 29-7 | 54 | 21 |
| 30-5 | 45 | 300 |
| 30-6 | 19 | 170 |
| 31-10 | 86 | 45 |
| 31-11 | 45 | 180 |
| 31-12 | 44 | 51 |
| 31-13 | 69 | 32 |
| 31-8 | 51 | 28 |
| 31-9 | 76 | 69 |
| 32-8 | 34 | 3.5 |
| 32-9 | 30 | 4.9 |

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:
1. A compound of structural formula I:

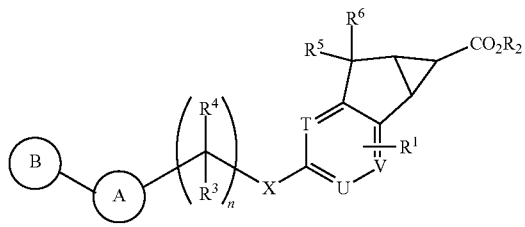

wherein
n is 1;
X is oxygen;
T is CH;
U is N;
V is CH;
A is selected from the group consisting of: phenyl and pyridine, wherein A is unsubstituted or substituted with one to five substituents selected from $R^a$;
B is selected from the group consisting of: phenyl, pyridine, pyrimidine, thiazole, benzimidazole, benzthiazole, benzoxazole, and benzisoxazole, wherein B is unsubstituted or substituted with one to five substituents selected from $R^b$;
$R^1$, $R^2$, $R^5$ and $R^6$ are hydrogen;
$R^3$ and $R^4$ are selected from the group consisting of: hydrogen, halogen, and —$C_{1-6}$alkyl, wherein each $C_{1-6}$alkyl is unsubstituted or substituted with one to three substituents selected from $R^L$;
$R^a$ is selected from the group consisting of:
(1) halogen,
(2) —$OR^e$,
(3) —$NR^cS(O)_mR^e$,
(4) —$S(O)_mR^e$,
(5) —$S(O)_mNR^cR^d$,
(6) —$NR^cR^d$,
(7) —$C(O)R^e$,
(8) —$OC(O)R^e$,
(9) —$CO_2R^e$,
(10) —CN,
(11) —$C(O)NR^cR^d$,
(12) —$NR^cC(O)R^e$,
(13) —$NR^cC(O)OR^e$,
(14) —$NR^cC(O)NR^cR^d$,
(15) —$CF_3$,
(16) —$OCF_3$, and,
(17) —$OCHF_2$;
$R^b$ is independently selected from the group consisting of:
(1) —$C_{1-10}$alkyl,
(2) halogen,
(3) —OH,
(4) —$OC_{1-10}$alkyl,
(5) —$O(CH_2)pOC_{1-10}$alkyl,
(6) —$O(CH_2)_pC_{3-6}$cycloalkyl,
(7) —$O(CH_2)pC_{2-10}$cycloheteroalkyl,
(8) —$O(CH_2)pO-C_{3-6}$cycloalkyl,
(9) —$O(CH_2)pO-C_{2-10}$cycloheteroalkyl,
(10) —$CF_3$,
(11) —$OCF_3$,
(12) —$OCHF_2$,
(13) —$(CH_2)p-C_{2-10}$cycloheteroalkyl, and
(14) —$S(O)_2C_{1-10}$alkyl, wherein each $R^b$ is unsubstituted or substituted with one to five substituents selected from $R^k$;
$R^c$ and $R^d$ are each independently selected from the group consisting of:
(1) hydrogen,
(2) —$C_{1-10}$alkyl, and
(3) —$C_{2-10}$alkenyl,
wherein each $R^c$ and $R^d$ is unsubstituted or substituted with one to three substituents independently selected from $R^f$;
each $R^e$ is independently selected from the group consisting of:
(1) hydrogen, and
(2) —$C_{1-10}$alkyl,
wherein each $R^e$ is unsubstituted or substituted with one to three substituents selected from $R^h$;
each $R^f$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each $C_{1-10}$ alkyl is unsubstituted or substituted with one to three substituents independently selected from: —OH, halogen, cyano, and —$S(O)_2CH_3$;
each $R^g$ is selected from the group consisting of:
(1) hydrogen,
(2) —$C(O)R^e$, and
(3) —$C_{1-10}$alkyl,
wherein —$C_{1-10}$alkyl is unsubstituted or substituted with one to five fluorines;
each $R^h$ is selected from the group consisting of:
(1) halogen,
(2) $C_{1-10}$alkyl,
(3) —OH,
(4) —O—$C_{1-4}$alkyl,
(5) —$S(O)_m$—$C_{1-4}$alkyl,
(6) —CN,
(7) —$CF_3$,
(8) —$OCHF_2$, and
(9) —$OCF_3$,
wherein each $C_{1-10}$ alkyl is unsubstituted or substituted with one to three substituents independently selected from: —OH, halogen, cyano, and —$S(O)_2CH_3$;
each $R^k$ is independently selected from the group consisting of:
(1) halogen,
(2) —$C_{1-10}$alkyl,
(3) —OH,
(4) oxo,
(5) halogen,
(6) —O—$C_{1-4}$ alkyl,
(7) —$SO_2$—$C_{1-6}$ alkyl,
(8) —$C_{1-6}$ alkyl-$SO_2C_{1-6}$alkyl,
(9) —CN,
(10) —$CF_3$,
(11) —$OCHF_2$,
(12) —$OCF_3$,
(13) —$NH_2$,
(14) —$NHSO_2C_{1-6}$alkyl,
(15) —$NHCOC_{1-6}$alkyl,
(16) =$N(OCH_3)$,
(17) —$P(O)(OH)_2$, and
(18) —$P(O)(OC_{1-6}alkyl)_2$, wherein each $C_{1-10}$ alkyl is unsubstituted or substituted with one to three substituents independently selected from: —OH, —$OC_{1-6}$alkyl, halogen, cyano, and —$S(O)_2C_{1-6}$ alkyl;

$R^L$ is selected from the group consisting of:
(1) —$C_{1-6}$alkyl,
(2) halogen,
(3) —$OR^e$,
(4) —$NR^cR^d$,
(5) —$C(O)R^e$,
(6) —$OC(O)R^e$,
(7) —$CO_2R^e$,
(8) —CN,
(9) —$CF_3$,
(10) —$OCF_3$, and
(11) —$OCHF_2$;

each m is independently selected from: 0, 1 or 2; and
each p is independently selected from: 0, 1, 2, 3, 4, 5, 6, 7, 8, 9 or 10;
or a pharmaceutically acceptable salt thereof.

2. A compound of structural formula I:

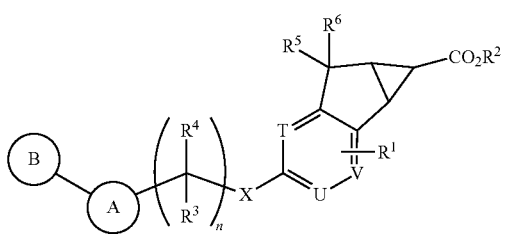

wherein:
n is 1;
X is oxygen;
T is CH;
U is N;
V is CH;
A is selected from the group consisting of: phenyl and pyridine, wherein A is unsubstituted or substituted with one to five substituents selected from $R^a$;
B is selected from the group consisting of: phenyl, pyridine, pyrimidine, thiazole, benzimidazole, benzthiazole, benzoxazole, and benzisoxazole, wherein B is unsubstituted or substituted with one to five substituents selected from $R^b$;
$R^1$, $R^2$, $R^3$, $R^4$, $R^5$ and $R^6$ are hydrogen;
$R^a$ is selected from the group consisting of: —$C_{1-6}$alkyl, halogen, and —$CF_3$;
$R^b$ is independently selected from the group consisting of:
(1) —$C_{1-10}$alkyl,
(2) halogen,
(3) —OH,
(4) —$OC_{1-10}$alkyl,
(5) —$O(CH_2)pOC_{1-10}$alkyl,
(6) —$O(CH_2)pC_{3-6}$cycloalkyl,
(7) —$O(CH_2)pC_{2-10}$cycloheteroalkyl,
(8) —$O(CH_2)pO$-$C_{3-6}$cycloalkyl,
(9) —$O(CH_2)pO$-$C_{2-10}$cycloheteroalkyl,
(10) —$CF_3$,
(11) —$OCF_3$,
(12) —$OCHF_2$,
(13) —$(CH_2)p$-$C_{2-10}$cycloheteroalkyl, and
(14) —$S(O)_2C_{2-10}$alkyl, wherein each $R^b$ is unsubstituted or substituted with one to five substituents selected from $R^k$; and
each $R^k$ is independently selected from the group consisting of:
(1) —$C_{1-10}$alkyl,
(2) —O—$C_{1-4}$ alkyl,
(3) —OH,
(4) halogen,
(5) —$SO_2$—$C_{1-6}$ alkyl,
(6) —$C_{1-6}$ alkyl-$SO_2C_{1-6}$alkyl,
(7) —CN,
(8) —$NHSO_2C_{1-6}$alkyl,
(9) =$N(OCH_3)$, and
(10) —$P(O)(OC_{1-6}$alkyl$)_2$, wherein each $C_{1-10}$ alkyl is unsubstituted or substituted with one to three substituents independently selected from: —OH, —$OC_{1-6}$alkyl, halogen, cyano, and —$S(O)_2C_{1-6}$alkyl; and
each p is independently selected from: 0, 1, 2, 3, 4, 5, 6, 7, 8, 9 or 10;
or a pharmaceutically acceptable salt thereof.

3. A compound of structural formula I:

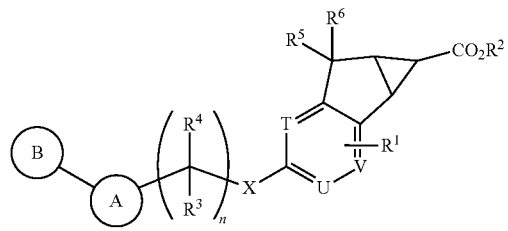

wherein:
n is 1;
X is oxygen;
T is CH;
U is N;
V is CH;
A is phenyl, wherein phenyl is unsubstituted or substituted with one to five substituents selected from $R^a$;
B is selected from the group consisting of: phenyl and pyridine, wherein B is unsubstituted or substituted with one to five substituents selected from $R^b$;
$R^1$, $R^2$, $R^3$, $R^4$, $R^5$ and $R^6$ are hydrogen;
$R^a$ is selected from the group consisting of: —$C_{1-6}$alkyl, halogen, and —$CF_3$;
$R^b$ is independently selected from the group consisting of:
(1) —$C_{1-10}$alkyl,
(2) halogen,
(3) —OH,
(4) —$OC_{1-10}$alkyl,
(5) —$O(CH_2)pC_{2-10}$cycloheteroalkyl,
(6) —$CF_3$, and
(7) —$(CH_2)p$-$C_{2-10}$cycloheteroalkyl, wherein each $R^b$ is unsubstituted or substituted with one to five substituents selected from $R^k$; and
each $R^k$ is independently selected from the group consisting of:
(1) —$C_{1-10}$alkyl,
(2) —OH,
(3) halogen,
(4) —$SO_2$—$C_{1-6}$ alkyl,
(5) —$C_{1-6}$ alkyl-$SO_2C_{1-6}$alkyl, and
(6) —CN, wherein each C$_{1-10}$alkyl is unsubstituted or substituted with one to three substituents independently selected from: —OH, —OC$_{1-6}$alkyl, halogen, cyano, and —S(O)$_2$C$_{1-6}$alkyl; and
each p is independently selected from: 0, 1, 2, 3, 4, 5, 6, 7, 8, 9 or 10;
or a pharmaceutically acceptable salt thereof.
4. A compound selected from:
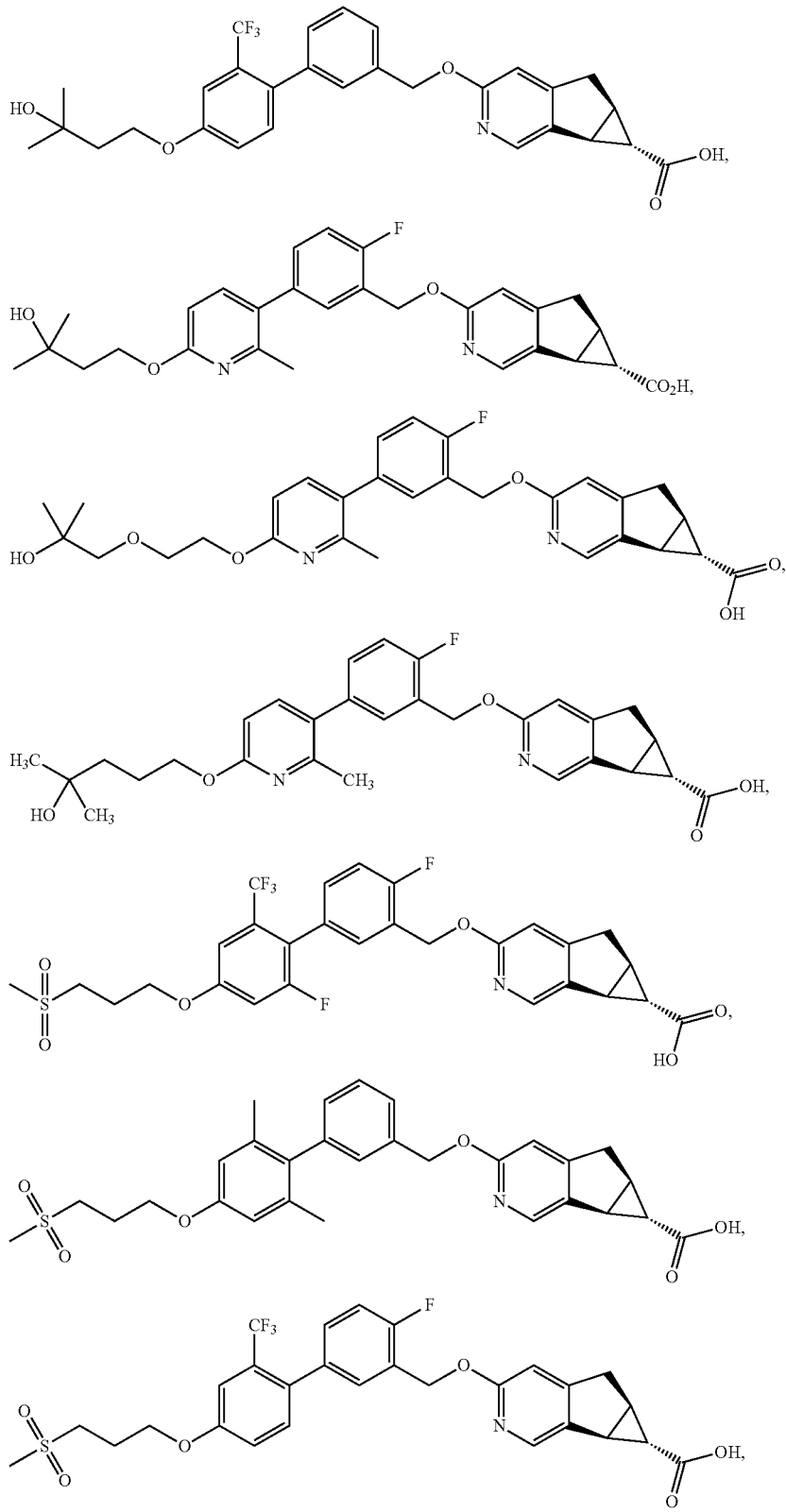

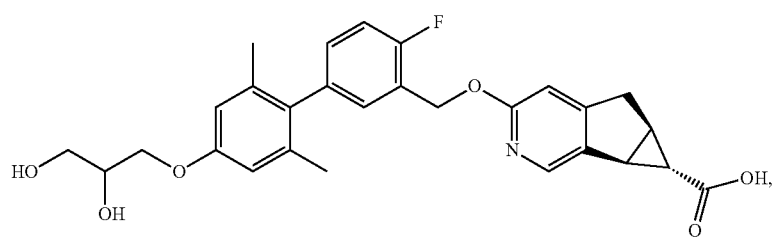
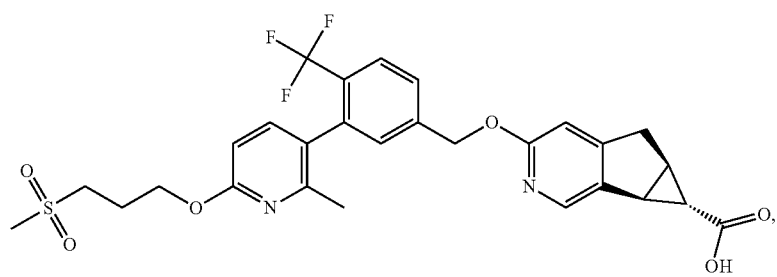
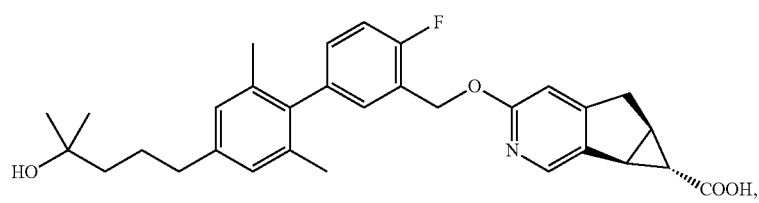
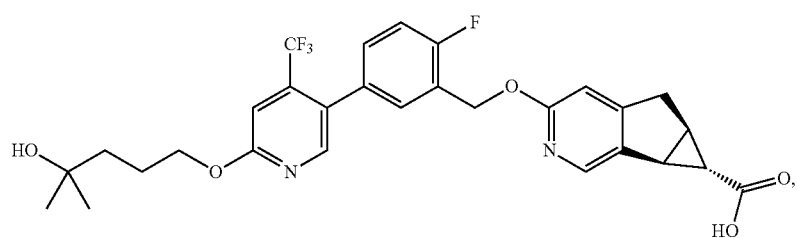
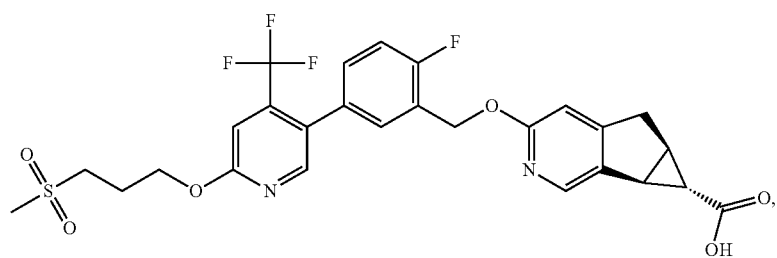
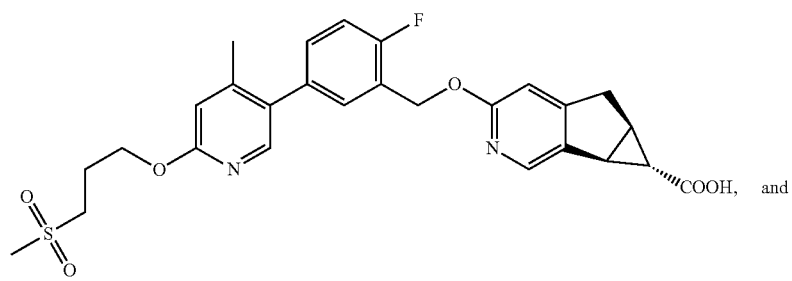

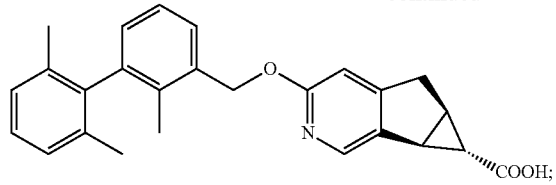

or a pharmaceutically acceptable salt thereof.

5. A pharmaceutical composition comprising a compound of 1, or a pharmaceutically acceptable salt thereof, and a pharmaceutically acceptable carrier.

6. A pharmaceutical composition comprising
(1) a compound of claim 1 or a pharmaceutically acceptable salt thereof;
(2) one or more compounds selected from the group consisting of:
 (a) PPAR gamma agonists and partial agonists;
 (b) biguanides;
 (c) protein tyrosine phosphatase-1B (PTP-1B) inhibitors;
 (d) dipeptidyl peptidase IV (DP-IV) inhibitors;
 (e) insulin or an insulin mimetic;
 (f) sulfonylureas;
 (g) α-glucosidase inhibitors;
 (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA: cholesterol acyltransferase (ACAT) inhibitors, (vii) CETP inhibitors, and (viii) phenolic anti-oxidants;
 (i) PPARα/γ dual agonists,
 (j) PPARδ agonists,
 (k) antiobesity compounds,
 (l) ileal bile acid transporter inhibitors;
 (m) anti-inflammatory agents;
 (n) glucagon receptor antagonists;
 (o) GLP-1;
 (p) GIP-1;
 (q) GLP-1 analogs;
 (r) HSD-1 inhibitors;
 (s) SGLT 1 inhibitors; and
 (t) SGLT 2 inhibitors; and
(3) a pharmaceutically acceptable carrier.

7. A pharmaceutical composition comprising a compound according to claim 1, or a pharmaceutically acceptable salt thereof, and a compound selected from simvastatin, ezetimibe and sitagliptin; and a pharmaceutically acceptable carrier.

8. The compound according to claim 4 selected from:

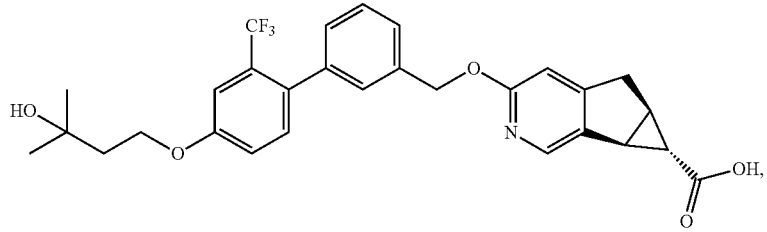 [SMILES: CC(C)(O)CCOc1ccc(-c2cccc(COc3cc4c(cn3)[C@H]3[C@@H](C4)[C@@H]3C(=O)O)c2)c(C(F)(F)F)c1]

or a pharmaceutically acceptable salt thereof.

9. The compound according to claim 4 selected from:

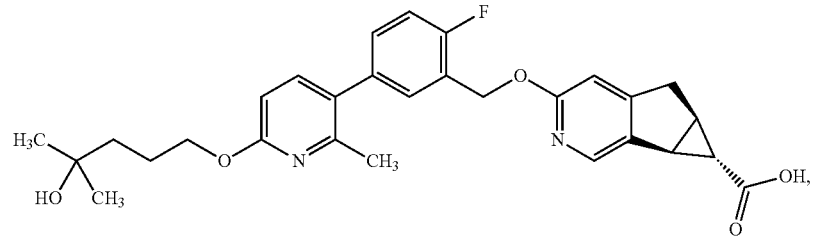 [SMILES: Cc1nc(OCCCC(C)(C)O)ccc1-c1ccc(F)c(COc2cc3c(cn2)[C@H]2[C@@H](C3)[C@@H]2C(=O)O)c1]

or a pharmaceutically acceptable salt thereof.

10. The compound according to claim 4 selected from:

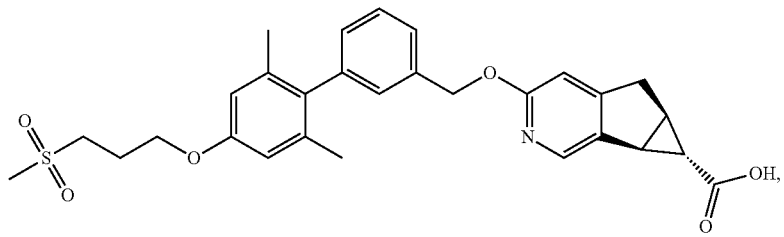 [SMILES: Cc1cc(OCCCS(C)(=O)=O)cc(C)c1-c1cccc(COc2cc3c(cn2)[C@H]2[C@@H](C3)[C@@H]2C(=O)O)c1]

or a pharmaceutically acceptable salt thereof.

11. The compound according to claim 4 selected from:
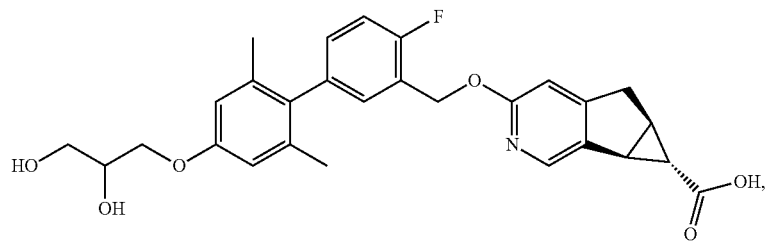 [SMILES: Cc1cc(OCC(O)CO)cc(C)c1-c1ccc(F)c(COc2cc3c(cn2)[C@H]2[C@@H](C3)[C@@H]2C(=O)O)c1]
or a pharmaceutically acceptable salt thereof.
12. The compound according to claim 4 selected from:
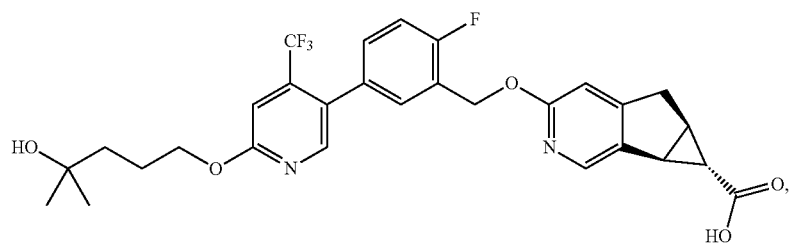 [SMILES: CC(C)(O)CCCOc1cc(C(F)(F)F)c(-c2ccc(F)c(COc3cc4c(cn3)[C@H]3[C@@H](C4)[C@@H]3C(=O)O)c2)cn1]
or a pharmaceutically acceptable salt thereof.
13. The compound according to claim 4 selected from:
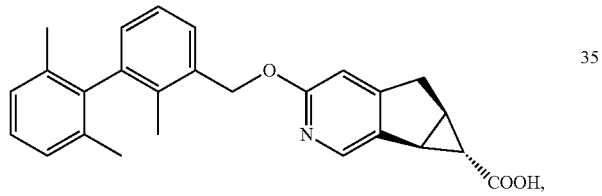
or a pharmaceutically acceptable salt thereof.
* * * * *